(12) United States Patent
Luo et al.

(10) Patent No.: US 11,369,614 B2
(45) Date of Patent: Jun. 28, 2022

(54) TELODENDRIMERS WITH RIBOFLAVIN MOIETIES AND NANOCARRIERS AND METHODS OF MAKING AND USING SAME

(71) Applicant: The Research Foundation for the State University of New York, Syracuse, NY (US)

(72) Inventors: Juntao Luo, Jamesville, NY (US); Dandan Guo, Syracuse, NY (US); Changying Shi, Jamesville, NY (US)

(73) Assignee: The Research Foundation for the State University of New York, Syracuse, NY (US)

( * ) Notice: Subject to any disclaimer, the term of this patent is extended or adjusted under 35 U.S.C. 154(b) by 0 days.

(21) Appl. No.: 16/478,789

(22) PCT Filed: Jan. 19, 2018

(86) PCT No.: PCT/US2018/014492
§ 371 (c)(1),
(2) Date: Jul. 17, 2019

(87) PCT Pub. No.: WO2018/136778
PCT Pub. Date: Jul. 26, 2018

(65) Prior Publication Data
US 2019/0328742 A1 Oct. 31, 2019

Related U.S. Application Data

(60) Provisional application No. 62/448,318, filed on Jan. 19, 2017.

(51) Int. Cl.
| | | |
|---|---|---|
| *A61K 31/525* | (2006.01) |
| *A61K 9/14* | (2006.01) |
| *A61K 47/34* | (2017.01) |
| *A61K 47/56* | (2017.01) |
| *A61K 9/00* | (2006.01) |
| *A61K 31/704* | (2006.01) |
| *A61K 31/75* | (2006.01) |

(52) U.S. Cl.
CPC .......... *A61K 31/525* (2013.01); *A61K 9/0014* (2013.01); *A61K 9/0019* (2013.01); *A61K 9/0043* (2013.01); *A61K 9/146* (2013.01); *A61K 31/704* (2013.01); *A61K 31/75* (2013.01); *A61K 47/34* (2013.01); *A61K 47/56* (2017.08)

(58) Field of Classification Search
None
See application file for complete search history.

(56) References Cited

U.S. PATENT DOCUMENTS

| | | |
|---|---|---|
| 10,947,350 B2 | 3/2021 | Luo et al. |
| 2009/0053139 A1 | 2/2009 | Shi et al. |
| 2011/0286915 A1 | 11/2011 | Lam et al. |
| 2013/0164369 A1 | 6/2013 | Lam et al. |
| 2013/0165636 A1 | 6/2013 | Luo et al. |
| 2014/0363371 A1 | 12/2014 | Luo et al. |
| 2015/0056139 A1 | 2/2015 | Luo et al. |
| 2015/0224206 A1 | 8/2015 | Van |
| 2017/0252456 A1 | 9/2017 | Luo et al. |
| 2017/0266292 A1 | 9/2017 | Luo et al. |
| 2017/0290921 A1 | 10/2017 | Lam et al. |
| 2018/0079829 A1 | 3/2018 | Luo et al. |
| 2019/0112423 A1 | 4/2019 | Lam et al. |
| 2019/0292328 A1 | 9/2019 | Luo et al. |
| 2020/0009069 A1 | 1/2020 | Luo et al. |
| 2020/0254012 A1 | 8/2020 | Luo et al. |
| 2021/0060232 A1 | 3/2021 | Luo et al. |
| 2021/0269601 A1 | 9/2021 | Luo et al. |
| 2021/0317234 A1 | 10/2021 | Luo et al. |

OTHER PUBLICATIONS

Beztsinna et al. (Biomaterials, 80, 121-133, 2016) Bioengineered riboflavin in nanotechnology.*
Singh, P., Amino Acid Based Dendrimer Peptide: Synthesis, Characterization and Applications, Masters Thesis, National University of Singapore, 2013, pp. 1-87.
Thomas, T.P., et al., Design of riboflavin-presenting PAMAM dendrimers as a new nanoplatform for cancer-targeted delivery, Bioorganic Medicinal Chemistry Letters, Sep. 1, 2010, vol. 20, No. 17, pp. 1-9.
Zhang, Peng, et al., A PEG-Fmoc conjugate as a nanocarrier for paclitaxel, Biomaterials, Aug. 2014, 35(25), pp. 7146-7156.

* cited by examiner

*Primary Examiner* — Tigabu Kassa
(74) *Attorney, Agent, or Firm* — Michael Krenicky; Lance Reich; Steven A. Wood, Jr.

(57) ABSTRACT

Provided herein are compositions and nanocarriers comprising linear-dendritic telodendrimers (TD) containing riboflavin. The nanocarriers and compositions have desirable loading properties and stabilized structure and can be used for efficient in vivo delivery.

15 Claims, 69 Drawing Sheets

A

Blank TD-1

B

Blank TD-2

C

1:1 DOX-TD-1

D

1:1 DOX-TD-2

A

B

A

B

C

D

C

D

A

B

C

D

A

DiD-DOX-TD-1

B

DiD-DOX-TD-2

A

B

E

Cell Viability

| Cell | Tumor Type | IC$_{50}$ (ng/mL) | | | | | | | |
|---|---|---|---|---|---|---|---|---|---|
| | | Free DOX | Doxil | 1:10 DOX-TD-1 | 1:10 DOX-TD-2 | 1:1 DOX-TD-1$^c$ | 1:1 DOX-TD-2$^c$ | 1:1 DOX-TD-1$^p$ | 1:1 DOX-TD-2$^p$ |
| MDA-MB-231 | Breast cancer | 45 | 434 | 37 | 60 | 67 | 60 | 52 | 42 |
| SKOV3 | Ovarian cancer | 31 | 164 | 44 | 52 | 47 | 51 | 50 | 51 |
| Raji | B-cell Lymphoma | 44 | 413 | 53 | 61 | 58 | 59 | 57 | 61 |
| Jurkat | T-cell Lymphoma | 39 | -- | -- | -- | 47 | 34 | -- | -- |
| K562 | Leukemia | 34 | -- | -- | -- | 37 | 38 | -- | -- |
| H929 | Myeloma | 75 | -- | -- | -- | 101 | 119 | -- | -- |

Figure 31

A 0.5:5 MTX-PEG5kCA8 fresh

17±4 nm

B 0.5:5 MTX-PEG5kCA8 1h later 1762 nm 47.2%
350 nm 47.3%
116 nm 5.5%

| Formulations | Loading efficiency in $H_2O$ |
|---|---|
| MTX-PEG5kCA8 | 9% |
| MTX-PEG5kRF8 | 70% |

- Rf is required for MTX loading in telodendrimer systems

TELODENDRIMERS WITH RIBOFLAVIN MOIETIES AND NANOCARRIERS AND METHODS OF MAKING AND USING SAME

CROSS REFERENCE TO RELATED APPLICATIONS

This application claims priority U.S. Provisional Application No. 62/448,318, filed on Jan. 19, 2017, the disclosure of which is hereby incorporated by reference.

STATEMENT REGARDING FEDERALLY SPONSORED RESEARCH

This invention was made with government support under contract no. EB019607 awarded by the National Institutes of Health. The government has certain rights in the invention.

FIELD OF DISCLOSURE

The disclosure generally relates to telodendrimers for drug delivery. More particularly the telodendrimers with riboflavin groups for drug delivery.

BACKGROUND OF THE DISCLOSURE

Doxorubicin (DOX) is one of the most popular anthracycline chemo drugs used for the treatment of many cancers, e.g. acute myeloid leukemia, ovarian cancer, Hodgkin lymphoma, and also for the patients who had previous taxane-based or platinum-based treatment. However, many tumors have either intrinsic or acquired resistance to DOX treatment through increased expression of ATP-dependent drug-efflux proteins. The combinational drug regiments and the escalating dose may overcome drug resistance, which are, however, hindered by the dose-limiting cardiotoxicity for DOX as well as tissue necrosis and severe myelosuppression.

To solve these problems, drug delivery systems have been developed to enhance drug accumulation at the tumor site while moderating its systemic toxicities. The emergence of Doxil®, a PEGylated liposomal DOX nanoformulation dramatically improves the pharmacokinetics (PK), reduces the cardiotoxicity and increases the DOX accumulation in tumor sites by the enhanced permeable and retention (EPR) effect. Doxil® has a particle size around 100 nm with very stable DOX encapsulation, which in turn hinders the intratumoral penetration and the availability of released drug at tumor sites. As a result in clinic outcome, Doxil has only marginally improved tumor treatment efficiency, although significantly improved PK and toxicity profiles in comparison with free DOX when used in the treatment of metastatic breast cancer and progressive ovarian cancer. In addition, up to 48% of patients receiving Doxil® treatment were found to have a formulation-associated hand-foot syndrome (Palmar-Plantar Erythrodysesthesia), which is due to the peripheral accumulation of the long-circulating large-sized Doxil® particles. Therefore, the development of nanoformulations with optimal particle sizes and drug release profile is important to improve the efficacy and reduce the toxicity of DOX as well as for other chemo drugs.

Up to date, many nanocarriers based on amphiphilic block copolymers, liposome, gold nanoparticle, carbon nanotube and other materials have been successfully developed for the delivery of chemo drugs. Among them, polymer-based nanocarriers have drawn significant attentions as drug delivery vehicles due to their highly engineerable macromolecular core-shell architectures, which are critical for tailoring the physicochemical properties of nanocarriers for efficient drug delivery. The use of polymer-based materials as nanocarriers for DOX delivery has been well studied by the work of Kataoka group and others. DOX can be incorporated into the core of the micelles by either chemical conjugation via amidation reactions or physical encapsulation through $\pi$-$\pi$ interaction, hydrogen-bonding and hydrophobic interactions. The chemical conjugation strategy usually yield high drug loading capacity, but hinder the total amount of bioactive drugs due to inefficient drug release, even when using the acid-cleavable linkage-hydrazine bond. Compared to chemical conjugation, physical encapsulation of drugs in the core of the micelle would be advantageous for favorable drug bioavailability, convenient polymer preparation, and simple nanocarrier fabrication. However, existing nanocarriers designed for DOX delivery always suffer from low drug loading capacity (less than 5%), fair loading efficiency and burst drug release, which results in safety concerns of applying large amount of vehicle materials and suboptimal efficacy.

SUMMARY OF THE DISCLOSURE

This disclosure provides nanocarriers comprising linear-dendritic telodendrimers (TD) containing Rf as a peripheral group. These nanocarriers can be used for delivery of agents, including therapeutic, diagnostic, and/or monitoring agents. These nanocarriers have desirable loading properties and have a stabilized structure for efficient in vivo drug delivery. Data is provided herein to demonstrate that Rf-TDs formed stable nanoparticles for at least several months. The nanoparticles majority of particles exhibit particle sizes of 20-40 nm (e.g., at least 90% of the nanoparticles are between 20-40 nm and/or 95% are less than 40 nm), exhibiting loading properties of up to 1:1.6 mass ratio (e.g., loading properties of a 1:1 to 1:1.6 mass ratio), and sustained drug release profiles without initial burst release. In vivo indicate that the TD provide prolonged the drug blood circulation time, increased the maximum tolerated doses (~2.5-fold increase), and improved tumor growth inhibition in comparison to both free drug.

The present disclosure provides telodendrimers (e.g., charged telodendrimers). The telodendrimers (e.g., charged telodendrimers) are linear-dendritic copolymers. The telodendrimers are functionally segregated telodendrimers having, for example, one or two functional segments. In an embodiment, the functional segments are a hydrophilic segment (e.g., a PEG group) and a hydrophobic segment. The hydrophilic segment can comprise one or more charged groups and/or a PEG group. The hydrophobic segment can comprise riboflavin or riboflavin and cholic acid.

The present disclosure provides nanocarriers comprising telodendrimers. Nanocarriers can also be referred to herein as nanoparticles. This disclosure provides nanocarriers comprising a self-assembled plurality of the telodendrimers that form a nanocarrier having a hydrophobic core and a hydrophilic exterior.

The telodendrimers of the present disclosure can self-assemble to form nanocarriers with a hybrid hydrophobic/polyelectrolic core and a hydrophilic exterior. In an embodiment, a plurality of telodendrimers self-assemble to form nanocarriers with a hydrophobic and polyelectrolic core and a hydrophilic exterior. In an embodiment, the disclosure provides a nanocarrier having an interior and an exterior, the nanocarrier comprising a plurality of the telodendrimer conjugates of the disclosure, wherein each compound self-assembles in an aqueous solvent to form the nanocarrier such that a hydrophobic pocket is formed in the interior of the nanocarrier, and wherein the hydrophilic segment (e.g., PEG group) of each compound is on the exterior of the nanocarrier. The telodendrimers may encapsulate (e.g., sequester in the hydrophobic core) one or more drug (e.g., an anthracycline (e.g., doxorubicin), and/or methotrexate).

The present disclosure provides methods of using the telodendrimers. The telodendrimers can be used, for example, in methods of administering a drug (e.g., methotrexate and/or an anthracycline (e.g., doxorubicin)) to a subject in need of treatment.

The compositions or nanocarriers of the present disclosure can be used administer to subject in need of treatment a treatment to any disease requiring the administration one or more drug, such as, for example, by sequestering a drug or drugs (e.g., an anthracycline (e.g., doxorubicin) and/or methotrexate) in the interior of the nanocarrier, and delivering said drug to a target. The drug(s) can be delivered systemically or intracellularly. In an embodiment, compositions comprising the telodendrimers are used in a method for treating a disease. A composition for administration can comprise a plurality of nanocarriers, where each nanocarrier is sequestering a drug or drugs (e.g., methotrexate and/or an anthracycline (e.g., doxorubicin)) in the interior of the nanocarrier.

In some embodiments, the present disclosure provides a method of treating a disease, including administering to a subject in need of such treatment a therapeutically effective amount of a composition or nanocarrier of the present disclosure, where the nanocarrier comprises a drug.

BRIEF DESCRIPTION OF THE DRAWINGS

For a fuller understanding of the nature and objects of the disclosure, reference should be made to the following detailed description taken in conjunction with the accompanying figures.

FIG. 31 shows cell viability of various cell lines with various nanocarriers. Nanoformulations of the instant disclosure kept the same potency as free DOX during 72 hour (h) incubation. DOXIL® was less potent than free DOX and the nanoformulations of the instant disclosure.

DETAILED DESCRIPTION OF THE DISCLOSURE

Figure 1:
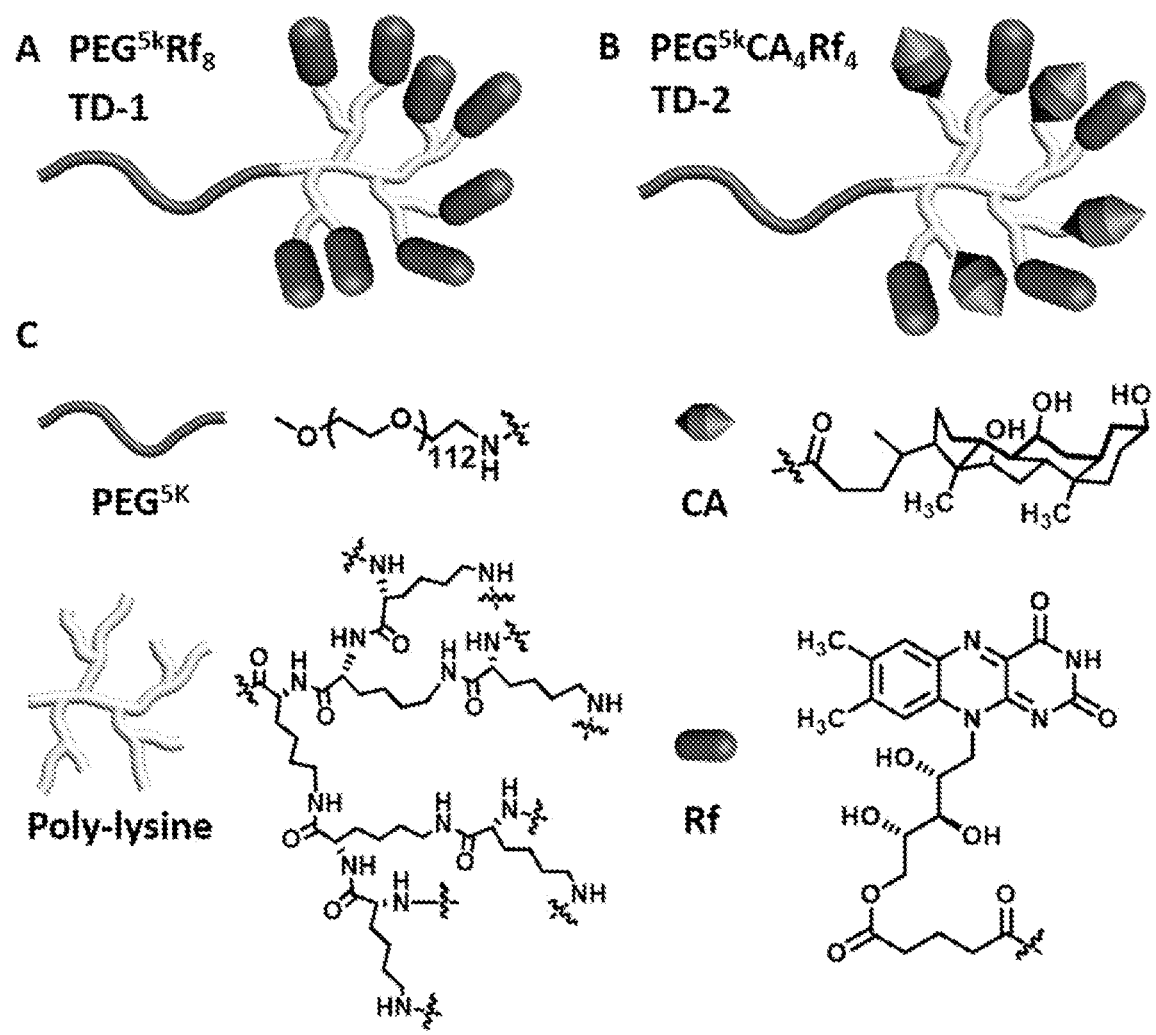
FIG. 1 shows (A, B) structures of $PEG^{5k}Rf_8$ (TD-1, A) and $PEG^{5k}CA_4Rf_4$ (TD-2, B). (C) The chemical structures of TD components.

Although claimed subject matter will be described in terms of certain embodiments and examples, other embodiments and examples, including embodiments and examples that do not provide all of the benefits and features set forth herein, are also within the scope of this disclosure. Various structural, logical, process step, and electronic changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

This disclosure provides nanocarriers comprising linear-dendritic telodendrimers (TD) containing Rf as a peripheral group. These nanocarriers can be used for delivery of agents, including therapeutic, diagnostic, and/or monitoring agents. These nanocarriers have desirable loading properties and have a stabilized structure for efficient in vivo drug delivery. Data is provided herein to demonstrate that Rf-TDs formed stable nanoparticles for at least several months. The nanoparticles exhibit particle sizes with the majority being from 20-40 nm (e.g., at least 90% of the nanoparticles are between 20-40 nm and/or 95% are less than 40 nm) (see FIG. 14), exhibiting loading properties of up to 1:1.6 mass ratio (e.g., loading properties of a 1:1 to 1:1.6 mass ratio), and sustained drug release profiles without initial burst release. In vivo indicate that the TD provide prolonged the drug blood circulation time, increased the maximum tolerated doses (~2.5-fold increase), and improved tumor growth inhibition in comparison to both free drug.

The telodendrimers can comprise multiple segments. Examples of segments include linear hydrophilic polymer segments, adjacent branched functional segments, charged segments. The telodendrimers can form nanocarriers (e.g., telodendrimer micelle structures).

Definitions

As used herein, the term "moiety" refers to a part (substructure) or functional group of a molecule that is part of the telodendrimer structure. For example,

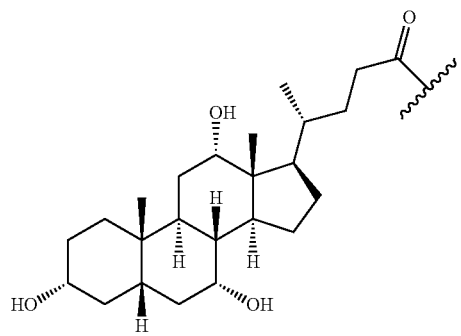

refers to a cholic acid moiety,

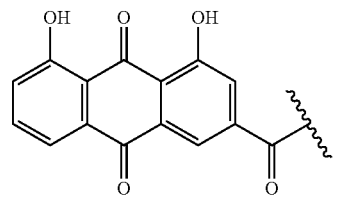 [SMILES: *C(=O)c1cc(O)c2c(c1)C(=O)c1cccc(O)c1C2=O]

refers to a rhein moiety,

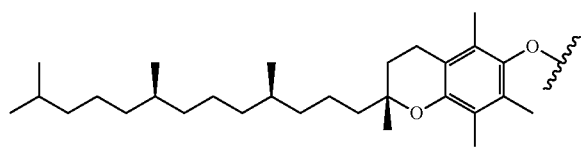 [SMILES: *Oc1c(C)c(C)c2c(c1C)CC[C@@](C)(CCC[C@H](C)CCC[C@H](C)CCCC(C)C)O2]

refers to a vitamin E moiety,

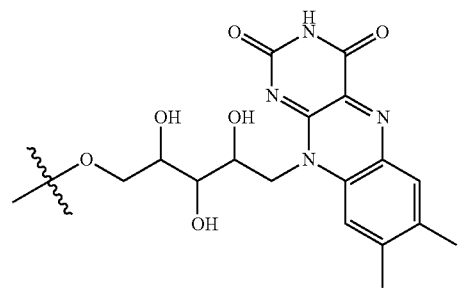 [SMILES: *OCC(O)C(O)C(O)Cn1c2nc(=O)[nH]c(=O)c-2nc2cc(C)c(C)cc21]

refers to a riboflavin (Rf) moiety.

As used herein, the terms "dendritic polymer" or "dendritic polymer moiety" refer to branched polymers containing a focal point, a plurality of branched monomer units, and a plurality of end groups. The monomers are linked together to form arms (or "dendritic polymer moiety") extending from the focal point and terminating at the end groups. The focal point of the dendritic polymer can be attached to other segments of the compounds of the disclosure, and the end groups may be further functionalized with additional chemical moieties. The dendritic polymer can be composed of, for example, branched lysine and/or branched arginine moieties.

As used herein, the term "nanocarrier" refers to a micelle resulting from aggregation of telodendrimer conjugates of the present disclosure. The nanocarrier has a hydrophobic core and a hydrophilic exterior.

As used herein, the terms "monomer" and "monomer unit" refer to a diamino carboxylic acid, a dihydroxy carboxylic acid, or a hydroxyl amino carboxylic acid. Examples of diamino carboxylic acid groups of the present disclosure include, but are not limited to, 2,3-diamino propanoic acid, 2,4-diaminobutanoic acid, 2,5-diaminopentanoic acid (ornithine), 2,6-diaminohexanoic acid (lysine), (2-aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid. Examples of dihydroxy carboxylic acid groups of the present disclosure include, but are not limited to, glyceric acid, 2,4-dihydroxybutyric acid, glyceric acid, 2,4-dihydroxybutyric acid, 2,2-bis(hydroxymethyl)propionic acid, and 2,2-bis(hydroxymethyl)butyric acid. Examples of hydroxyl amino carboxylic acids include, but are not limited to, serine and homoserine. One of skill in the art will appreciate that other monomer units can be used in the present disclosure. Monomers of the present disclosure can have a bond connectivity of, for example,

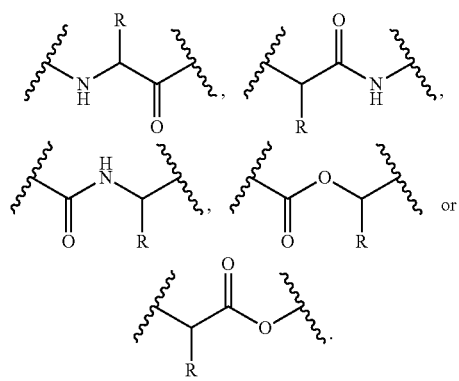

For example, when a monomer is defined as a lysine moiety, with a bond connectivity of A-Lys-B, where A and B are generic appendages, then it can be assumed that the structure can be any one of the following:

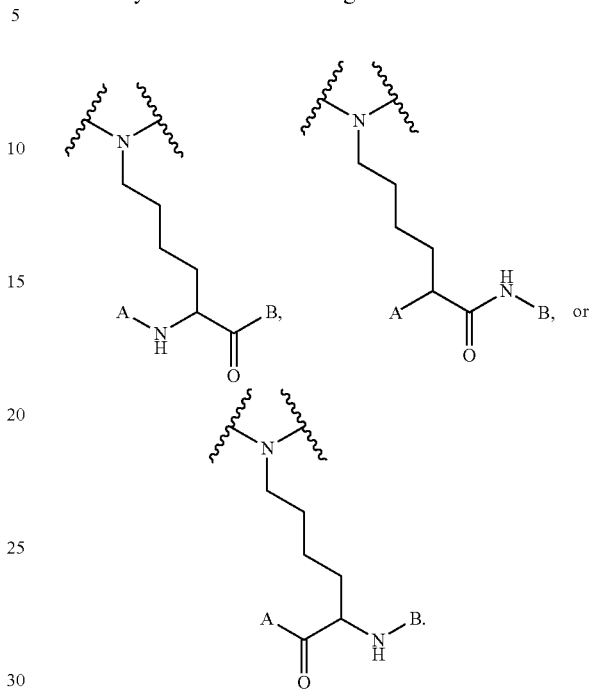

As used herein, the term "linker" refers to a chemical moiety that links (e.g., via covalent bonds) one segment of a dendritic conjugate to another segment of the dendritic conjugate. The types of bonds used to link the linker to the segments of the telodendrimers include, but are not limited to, amides, amines, esters, carbamates, ureas, thioethers, thiocarbamates, thiocarbonate, and thioureas. For example, the linker (L, $L^2$, and/or $L^4$), individually at each occurrence in the telodendrimer, can be a polyethylene glycol moiety, polyserine moiety, polyglycine moiety, poly(serine-glycine) moiety, aliphatic amino acid moieties, 6-amino hexanoic acid moiety, 5-amino pentanoic acid moiety, 4-amino butanoic acid moiety, and beta-alanine moiety. The linker can also be a cleavable linker. In certain embodiments, combinations of linkers can be used. For example, the linker can be an enzyme cleavable peptide moiety, disulfide bond moiety or an acid labile moiety. One of skill in the art will appreciate that other types of bonds can be used in the present disclosure. In certain embodiments, the linker L, $L^2$, and/or $L^4$ can be:

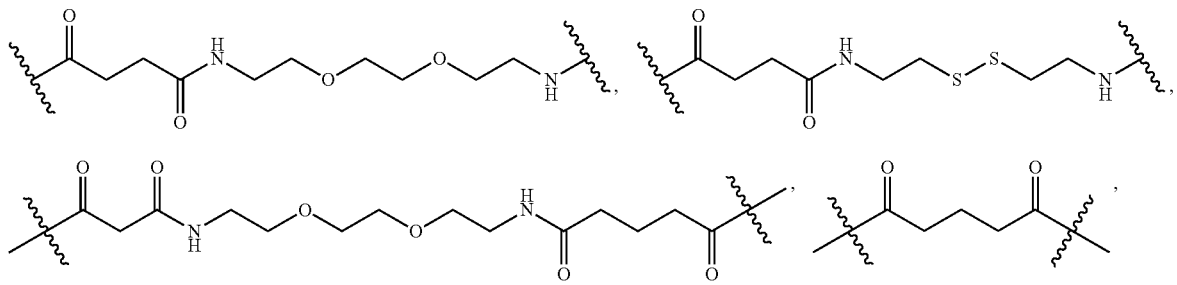

or a combination thereof, or other peptide sequence or spacer molecules.

As used herein, PEG group refers to polyethylene glycol. For example, the structure of PEG is

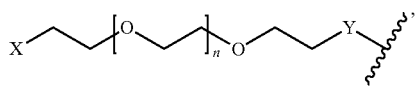

where X is selected from the group consisting of —NH$_2$, —OH, —SH, —COOH, —OMe, —N$_3$, —C═CH$_2$, or —≡CH, Y is selected from the group consisting of —C(═O)O—, —OC(═O)—, —OC(═O)NH—, —NHC(═O)—, —NHC(═O)O—, —NH—, —O—, —S—,

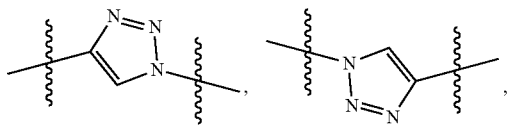 [SMILES: *c1cn(*)nn1 ; *c1cn(*)nn1]

—N(PEG)-, —NHCOLys(PEG)-, —NHCO[branched Lys (PEG)]$_n$NH—, -Lys-, -Lys(PEG)-, -Lys(PEG)-Lys, -Lys(PEG)-Lys(PEG)-, Lys(PEG-Lys-Lys(PEG), and -Lys(PEG)-Lys(Lys(PEG)$_2$)-Lys- and n is the number of repeating unit in a range of 1 to 72736. For example, the PEG group has the following structure:

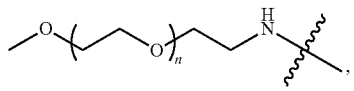

wherein n is 10-500.

As used herein, the term "reversible crosslinking group" refers to a chemical moiety that can be reversible reacted with another chemical moiety that will crosslink and decrosslink when exposed to certain conditions (e.g., different pH condition, chemical environments (e.g. sugar level), redox environments (concentration of glutathione) and UV light of varying wavelength). For example, a coumarin derivative moiety, can be photocrosslinked at >300 nm and decrosslinked at ~265 nm. Another example is catechol and boronic acid which form a boronate crosslinkage, which can be cleaved at acidic pH or with cis-diol containing sugar. Another example is disulfide formation, which can be cleaved under higher concentration of glutathione in vivo. The degree of crosslinking can be controlled by the density of crosslinking moieties and crosslinking conditions, e.g., the time of reversible photocrosslinkable groups are exposed to UV light.

As used herein, the term "oligomer" or "oligomer moiety" refers to fifteen or fewer monomers, as described above, covalently linked together. The monomers may be linked together in a linear or branched fashion. The oligomer may function as a focal point for a branched segment of a telodendrimer.

As used herein, the term "hydrophobic group" refers to a chemical moiety that is water-insoluble or repelled by water. Examples of hydrophobic groups include, but are not limited to, long-chain alkanes and fatty acids, lipids, vitamins, natural compounds, herbal extracts, fluorocarbons, silicones, certain steroids such as cholesterol, bile acids, and certain polymers such as, for example, polystyrene and polyisoprene.

As used herein, the term "hydrophilic group" refers to a chemical moiety that is water-soluble or attracted to water. Examples of hydrophilic groups include, but are not limited to, alcohols, short-chain carboxylic acids, quaternary amines, sulfonates, phosphates, sugars, and certain polymers such as, for example, PEG, PVA.

As used herein, the term "amphiphilic compound" refers to a compound having both hydrophobic portions and hydrophilic portions. For example, the amphiphilic compounds of the present disclosure can have one hydrophilic part of the compound and one hydrophobic part of the compound, for example, bile acids, cholic acids, riboflavin, chlorogenic acid, etc.

As used herein, the term "polar compound" refers to a compound having a non-zero vector sum of its bond dipoles.

As used herein, the terms "treat", "treating" and "treatment" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "subject" refers to animals such as mammals. Suitable examples of mammals include, but are not limited to, primates (e.g., humans), cows, sheep, goats, horses, dogs, cats, rabbits, rats, mice, and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non-sensitized cells.

Telodendrimers. In an aspect, the present disclosure provides telodendrimers (e.g., charged telodendrimers). The telodendrimers (e.g., charged telodendrimers) are linear-dendritic copolymers. The telodendrimers are functionally segregated telodendrimers having, for example, one or two functional segments. In an embodiment, the functional segments are a hydrophilic segment (e.g., a PEG group) and a hydrophobic segment. The hydrophilic segment can comprise one or more charged groups and/or a PEG group. The hydrophobic segment can comprise riboflavin or riboflavin and cholic acid. The telodendrimers may have one or more crosslinking groups (e.g., boronic acid/catechol reversible crosslinking groups).

The telodendrimers may comprise PEG groups. For example, the PEG group has the following structure:

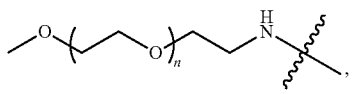

where n is 10-500.

In an embodiment, the present disclosure provides telodendrimers that are functional and spatially segregated telodendrimers having 1 to 128 charged moieties and/or groups. In an embodiment, the telodendrimers may have one or more crosslinking groups (e.g., reversible boronate crosslinking groups). In an embodiment, the telodendrimers are functional segregated telodendrimers having one or two functional segments.

In an embodiment, the telodendrimer comprises eight riboflavin moieties. In an embodiment, the telodendrimer is a charged telodendrimer comprising four riboflavin moieties and four arginine moieties. In an embodiment, the telodendrimer is a charged telodendrimer comprising four riboflavin moieties and eight arginine moieties. In an embodiment, the telodendrimer comprises eight riboflavin moieties and eight arginine moieties, where there is a linker between the riboflavin and arginine moieties. In an embodiment, the telodendrimers of any of the preceding embodiments further comprise one or more PEG moieties having, individually at each occurrence in the telodendrimer, a molecular weight of 4,000 to 6,000 g/mol (e.g., 5,000 g/mol). In embodiment, a composition comprises one or more telodendrimers of these preceding embodiments (e.g., where at least one of the telodendrimers is a charged telodendrimer) and one or more drugs such as, for example, methotrexate or an analog thereof. At least a portion or all of the methotrexate or an analog thereof is non-covalently bound (e.g., via hydrogen bonding and/or pi-pi stacking) to one or more riboflavin moieties and, where the telodendrimers comprise one or more arginine moieties, the methotrexate or an analog thereof electrostatically (e.g., ionically) interacts with one or more arginine moieties.

Methotrexate has the following structure:

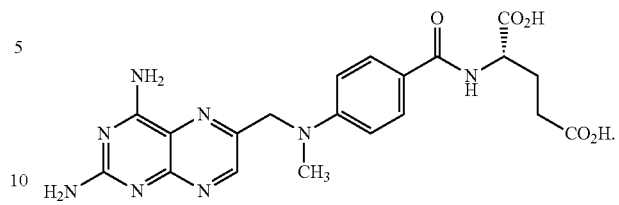

In an embodiment, the telodendrimer comprises eight riboflavin moieties. In an embodiment, the telodendrimer is a charged telodendrimer comprising four riboflavin moieties and four cholic acid moieties. In an embodiment, the telodendrimers of any of the preceding embodiments further comprise one or more PEG moieties having, individually at each occurrence in the telodendrimer, a molecular weight of 4,000 to 6,000 g/mol (e.g., 5,000 g/mol). In embodiment, a composition comprises one or more telodendrimers of these preceding embodiments and one or more drugs such as, for example, doxorubicin or an analog thereof.

Doxorubicin has the following structure:

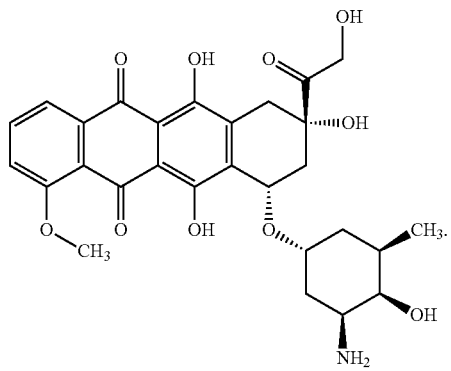 [SMILES: COc1cccc2c1C(=O)c1c(O)c3c(c(O)c1C2=O)C[C@@](O)(C(=O)CO)C[C@@H]3O[C@@H]1C[C@@H](C)[C@@H](O)[C@@H](N)C1]

Doxorubicin can also refer to herein as its corresponding HCl salt.

In an embodiment, the disclosure provides a compound of formula (I):

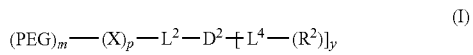

where PEG is optionally present and is a polyethylene glycol moiety, where PEG has a molecular weight of 44 Da to 100 kDa; X is optionally present and is a branched monomer unit or a group connecting one or PEG groups to $L^2$ or $D^2$; each $L^2$ is independently optional and is a linker group; each $L^4$ is independently optional and is a linker group; $D^2$ is a dendritic polymer moiety having one or more branched monomer units (X), and a plurality of end groups; $R^2$ is an end group of the dendritic polymer and is independently at each occurrence in the compound selected from the group consisting of positively or negatively charged groups (e.g., arginine, lysine, guanidine, amine, amidine, tetrazole, hydroxyl, carboxyl, phosphate, sulfonate, methanesulfonamide, sulfonamide, or oxalic acid functional groups) and neutral groups (e.g., polar groups, such as sugars, peptides, and hydrophilic polymers), or hydrophobic groups, such as long-chain alkanes ($C_1$-$C_{50}$) and fatty acids ($C_1$-$C_{50}$), lipids, vitamins, natural compounds, herbal extracts, aromatic molecules, esters, halogens, nitrocompounds, anthracyclines, fluorocarbons, silicones, certain steroids such as cholesterol, terpenoids, vitamins, and polymers (e.g., PLGA, polycaprolactone, polylactic acid, polyglycolic acid, polystyrene and polyisoprene, polyvinyl pyridine)), or amphiphilic groups (e.g. cholic acid, riboflavin, chlorogenic acid). The $R^2$ group(s) include at least one riboflavin group. In an example, all of the $R^2$ groups are riboflavin (e.g., all of the $R^2$ groups are riboflavin and there are eight $R^2$ groups). Subscript y is an integer from 1 to 64, where subscript y is equal to the number of end groups on the dendritic polymer. Subscript p is an integer from 0 to 32. Subscript m is an integer from 0 to 32. In the case of charged telodendrimers, when $D^2$ is present and, for example, a branched arginine dendritic moiety, the guanidine portion of the arginine subunits are not part of $D^2$, but rather, the guanidine moiety is an $R^2$ group. In various examples, the $D^2$ is a dendritic polymer moiety having one or more branched monomer units (X) has one or more terminal point that are not functionalized (e.g., with an $R^2$ group or -$L^4$-$R^2$ group); for example, the $D^2$ dendritic polymer moiety has one or more branched monomer units (X) having one or more unfunctionalized terminal points (e.g., one or more terminal —$NH_2$ group of a lysine branched monomer unit).

In an example, all of terminal points of the $D^2$ dendritic polymer moiety are $R^2$ groups and/or moieties. In another example, all of terminal points of the $D^2$ dendritic polymer moiety are riboflavin $R^2$ groups (e.g., there are eight $R^2$ groups and each is a riboflavin moiety). In another example, all of terminal points of the $D^2$ dendritic polymer moiety are $R^2$ groups and one or more or all (e.g., half) of the $R^2$ groups are riboflavin moieties and the remainder of the $R^2$ groups are cholic acid moieties or arginine moieties (e.g., there are eight $R^2$ groups and four $R^2$ groups are riboflavin moieties and four $R^2$ groups are cholic acid moieties or arginine moieties or there are twelve $R^2$ groups and four $R^2$ groups are riboflavin moieties and eight $R^2$ groups are arginine moieties). $D^2$ is also referred to as D herein.

When X is present, in an embodiment, at each occurrence in the compound, the branched monomer unit (X) is independently selected from the group consisting of a diamino carboxylic acid moiety, a dihydroxy carboxylic acid moiety, and a hydroxyl amino carboxylic acid moiety.

$R^2$ is covalently bonded to a dendritic polymer or linker. The $R^2$ groups may be end groups. The $R^2$ groups may be linked to another $R^2$ group/moiety or $R^2$ end groups. The $R^2$ group(s)/moiety(ies) is/are independently at each occurrence in the compound selected from the group consisting of positively or negatively charged groups (e.g., arginine, lysine, guanidine, amine (e.g., secondary, tertiary or quaternary amines), amidine, tetrazole, hydroxyl, carboxyl, phosphate, sulfonate, methanesulfonamide, sulfonamide, or oxalic acid functional groups) and neutral groups (e.g., polar groups: sugars, peptides, hydrophilic polymers, or hydrophobic groups: long-chain alkanes ($C_1$-$C_{50}$) and fatty acids ($C_1$-$C_{50}$), lipids, vitamins, natural compounds, herbal extracts, aromatic molecules, esters, halogens, nitrocompounds, anthracyclines, fluorocarbons, silicones, certain steroids such as cholesterol, terpenoids, vitamins, and polymers (e.g., PLGA, polycaprolactone, polylactic acid, polyglycolic acid, polystyrene and polyisoprene, polyvinyl pyridine); or amphiphilic groups, cholic acid, riboflavin, chlorogenic acid) where at least one riboflavin group is present as an $R^2$ group/moiety. $R^2$ groups/moieties may be directly bonded to the dendritic moiety (e.g. a lysine moiety or the guanidine portion of an arginine moiety), or they may be attached through a linker. In an example, when $R^2$ is not an end group each $R^2$ is linked to one of the end $R^2$ groups. In an embodiment, at least one hydrophobic group/moiety is an $R^2$ group. $R^2$ is also referred to as R herein.

In an example, a telodendrimer of the present disclosure has the following structure:

(formula (II))

where PEG is polyethylene glycol group; L is optional and independently at each occurrence a linking group, D is a dendritic polymer moiety having one or more branched monomer units (e.g., lysine, arginine, or a combination thereof), and R is an end group of the dendritic polymer and is independently at each occurrence in the compound (e.g., a cholic acid moiety, a riboflavin moiety, or a combination thereof).

More specifically, a telodendrimer of the present disclosure has the following structure:

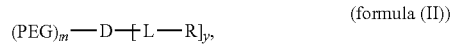

(formula (II))

where PEG is polyethylene glycol group; L is optional and independently at each occurrence selected from the group consisting of

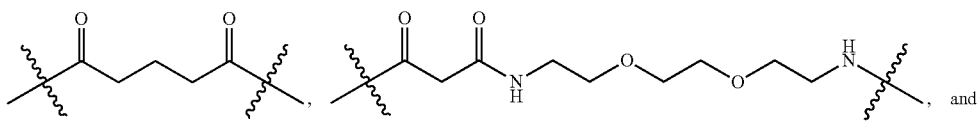

, and

-continued

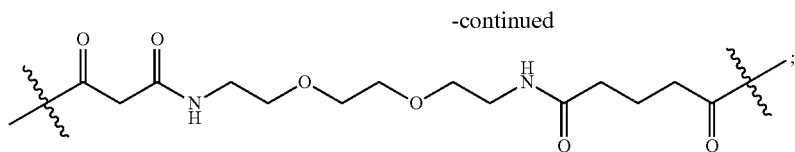

D is a dendritic polymer moiety having one or more branched monomer units selected from the group consisting of a lysine moiety, an arginine moiety, and combinations thereof; R is independently at each occurrence in the compound

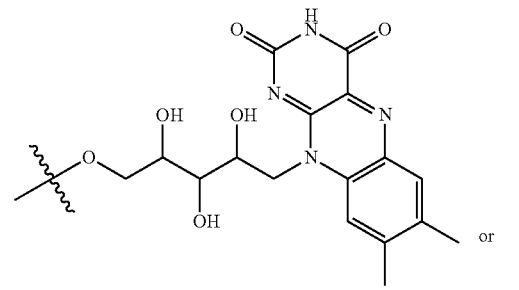

or

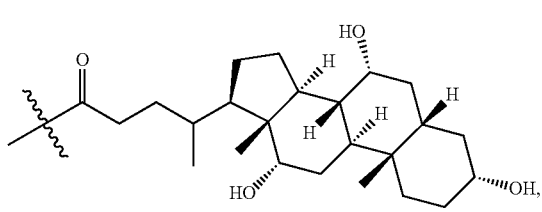

where at least one occurrence is

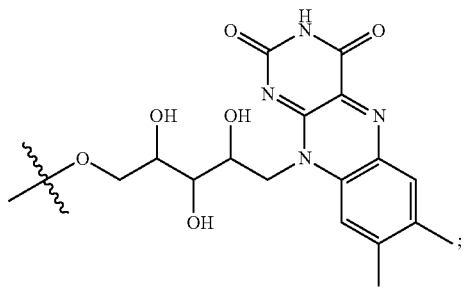

m is 1; and y is 1-20, including all integer values and ranges therebetween (e.g., 1, 2, 3, 4, 5, 6, 7, 8, 9, 10, 11, 12, 13, 14, 15, 16, 17, 18, 19, or 20).

In various embodiments, the telodendrimer compound of the present disclosure has the following structure:

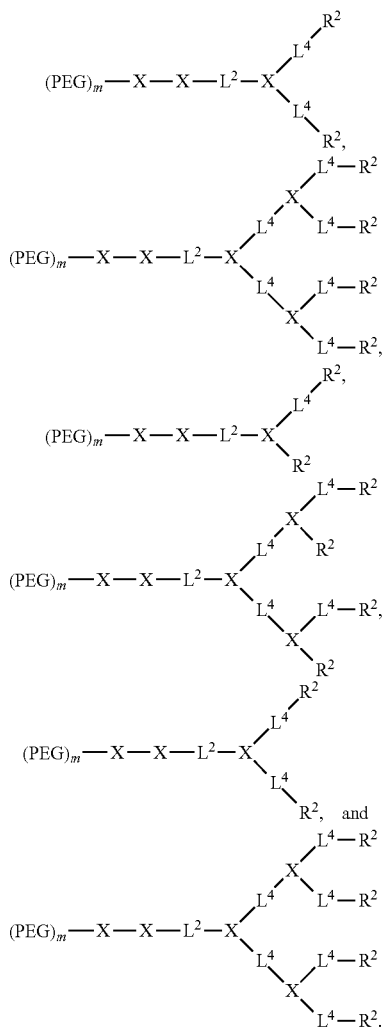

For example, each branched monomer unit is a lysine moiety or an arginine moiety or selected from a lysine moiety and an arginine moiety.

In an embodiment, at each occurrence in the compound the linker (e.g., L, $L^2$ and/or $L^4$) are independently selected from the group consisting of:

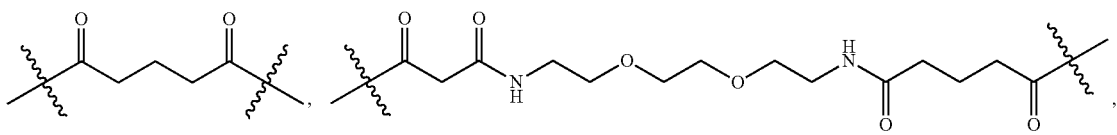

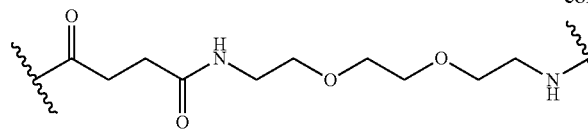 and 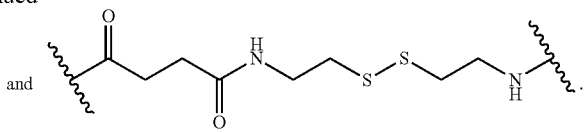

In an embodiment, at each occurrence in the compound the linker (e.g., L, $L^2$ and/or $L^4$) or a combination thereof comprises a cleavable group. In a specific embodiment, the cleavable group is a disulfide cleavable moiety.

In an embodiment, the PEG portion of the compound is selected from the group consisting of:

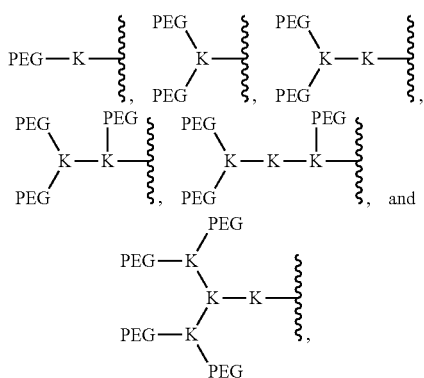

where each K is lysine in the compound of formula (I) and/or formula (II).

In an embodiment, the reversible crosslinking group, if present, is a coumarin moiety, 4-methylcoumarin moiety, boronic acid moiety or derivative or analog thereof, catechol moiety or derivative or analog thereof, cis-diol moiety or derivative or analog thereof, cinnamic acid moiety or derivative or analog thereof, chlorogenic acid moiety or derivative or analog thereof, amine moiety or a derivative thereof, carboxylic acid or a derivative thereof, acyl group, or a derivative thereof, epoxide or a derivative thereof, thiol group or a derivative thereof, malaimide or a derivative thereof, alkene or a derivative thereof, azide or a derivative thereof, alkyne or a derivative thereof, comarin or a derivative thereof, or a combination thereof.

The charged group can be any group/moiety with a positive or negative charge. For example, the charged group has a positive or negative charge in aqueous solution at a certain pH. In an embodiment, the charged group (e.g., R and/or $R^2$) is a moiety or derivative or analog of arginine, lysine, or guanidine. In an embodiment, the charged group (e.g., R and/or $R^2$) is a moiety or derivative or analog of an amine, amidine, tetrazole, hydroxyl, carboxyl, phosphate, sulfonate, sulfonamide (e.g., methanesulfonamide), oxalic acid, or similar functional groups.

In an embodiment, the neutral group is the moiety or derivative or analog of sugars, peptides, hydrophilic polymers, long-chain alkanes ($C_1$-$C_{50}$) and fatty acids ($C_1$-$C_{50}$), aromatic molecules, esters, halogens, nitrocompounds, anthracyclines, fluorocarbons, silicones, certain steroids such as cholesterol, terpenoids, vitamins, and polymers (e.g., PLGA, polycaprolactone, polylactic acid, polyglycolic acid, polystyrene and polyisoprene, polyvinyl pyridine); amphiphilic groups, cholic acid, riboflavin, chlorogenic acid and natural compound extract and synthetic compounds.

The telodendrimers can have various combinations of functional groups (e.g., R and/or $R^2$ groups). The functional groups can be end groups or linked to end groups.

The dendritic moiety may comprise one or more amino acid moieties (e.g., lysine and/or arginine moieties). For example, it is a polylysine or polyarginine moiety. Amino acid side chains may further provide additional branches or an R or $R^2$ group (e.g., a terminal R or $R^2$ group). For example, in the case of a polylysine dendritic moiety, the nitrogen of the lysine side chain may further react to form additional branches, or may be an $R^2$ group or R group. Different moieties (e.g., functional groups) may be selectively installed at selected end groups of the dendritic moiety using orthogonal protecting group strategies.

The telodendrimers may be used to binds drugs such as, for example, methotrexate or an analog thereof and doxorubicin or an analog (e.g., an anthracycline) thereof for delivery to an individual.

Nanocarriers. In an aspect, the present disclosure provides nanocarriers comprising telodendrimers. Nanocarriers can also be referred to herein as nanoparticles. This disclosure provides nanocarriers comprising a self-assembled plurality of the telodendrimers that form a nanocarrier having a hydrophobic core and a hydrophilic exterior.

Figure 5:
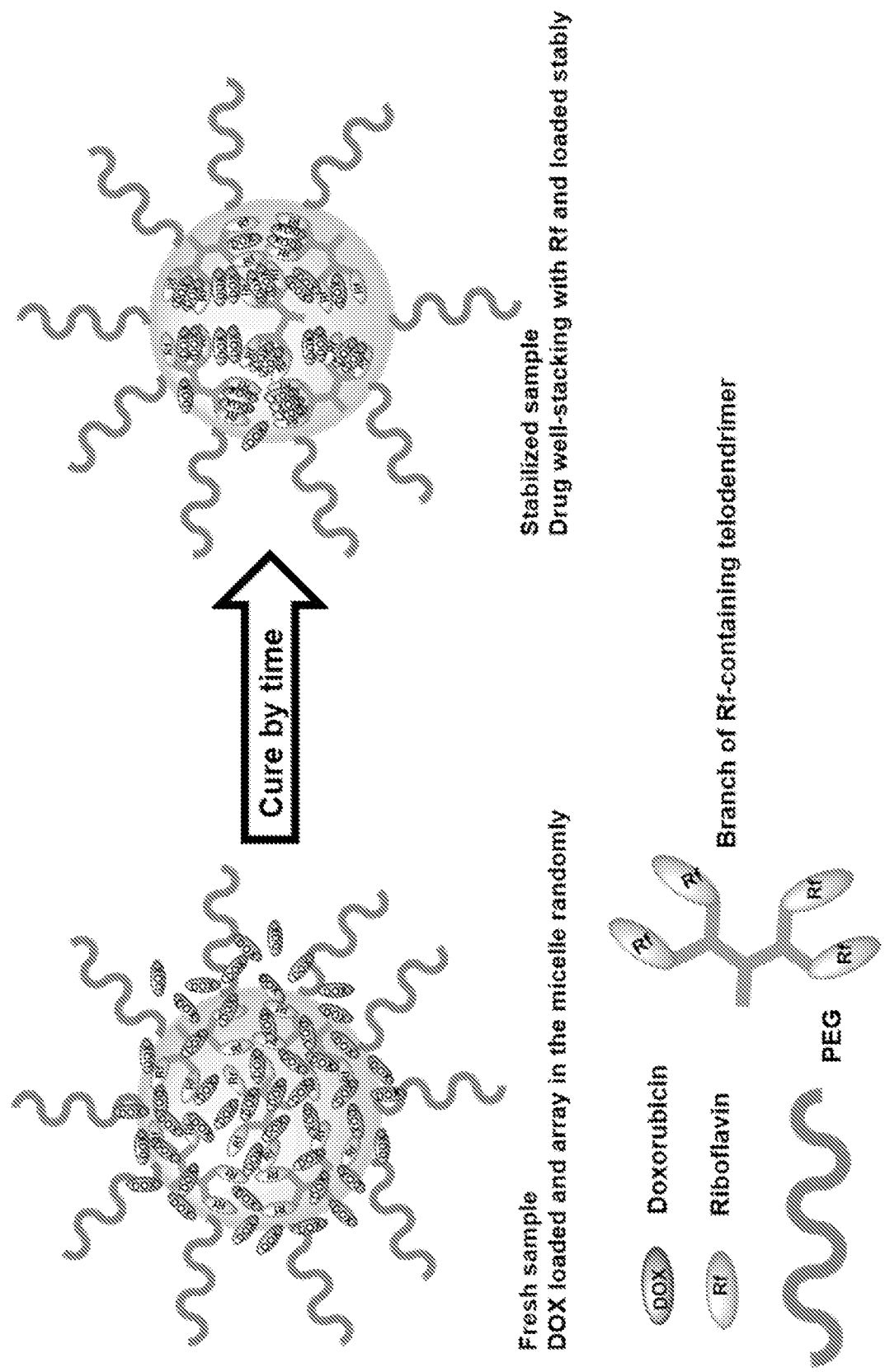
FIG. 5 shows a dynamic process from fresh DOX-loaded Rf-containing micelles to cured micelles. This phenomenon indicates a dynamic molecular rearrangement within the core of the nanocarriers, where the loosely bounded and randomly dispersed DOX molecules (highly fluorescent) start to anneal to form stacking with Rf and DOX (quenched) within the core of a micelle.

The nanocarrier may be a telodendrimer micelle. A telodendrimer micelle is a nanoconstruct formed by the self-assembly of a plurality of telodendrimers in aqueous solution. The telodendrimer micelle can serve as a nanocarrier to load various types of drugs. FIG. 5 shows a nanocarrier of the present disclosure carrying a drug (e.g., an anthracycline (e.g., doxorubicin) and/or methotrexate).

The nanocarrier has a PEG layer. Without intending to be bound by any particular theory, it is considered that the PEG layer serves as a stealth hydrophilic shell (e.g., hydrophilic layer) to stabilize the nanoparticle and to avoid systemic clearance by the reticuloendothelial system (RES). The interior layer (i.e., hydrophobic layer) comprises one or more riboflavin moieties and, optionally, one or more cholic acid moieties and/or positively or negatively charged moieties. The interior layer may also comprise, for example, protein-binding building blocks, such as vitamins (e.g., α-tocopherol, folic acid, retinoic acid, etc.), functional lipids (ceramide), and chemical extracts (e.g., rhein, coumarin, curcurmine, etc.), from herbal medicine to increase the affinity to drug molecules. The interior layer may also comprise one or more protecting groups such as, for example, FMOC or BOC.

The nanocarriers (e.g., telodendrimer micelles) have a multiple layer (e.g., a two-layer) structure. For example, one layer is a hydrophilic layer (e.g., the PEG layer) and a second layer is a hydrophobic layer (e.g., hydrophobic core).

The empty nanocarriers were examined to be nontoxic in cell culture and the drug-loaded nanoformulations exhibited the similar potency in killing cancer cells in vitro. The resulting nanocarriers exhibit superior drug loading capacity and stability. The nanoparticle is able to deliver payload drug(s) to a cancer site.

In an embodiment, the nanocarrier comprises one or more drugs (e.g., an anthracycline (e.g., doxorubicin) and/or methotrexate). The nanocarriers comprising one or more drug may have a diameter of 5 nm to 50 nm, including all integer nm values and ranges therebetween. In an embodiment, the nanocarriers comprising one or more drug may have a diameter of 10 nm to 30 nm.

The telodendrimers of the present disclosure can self-assemble to form nanocarriers with a hybrid hydrophobic/polyelectrolic core and a hydrophilic exterior. In an embodiment, a plurality of telodendrimers self-assemble to form nanocarriers with a hydrophobic and polyelectrolic core and a hydrophilic exterior. In an embodiment, the disclosure provides a nanocarrier having an interior and an exterior, the nanocarrier comprising a plurality of the telodendrimer conjugates of the disclosure, wherein each compound self-assembles in an aqueous solvent to form the nanocarrier such that a hydrophobic pocket is formed in the interior of the nanocarrier, and wherein the hydrophilic segment (e.g., PEG group) of each compound is on the exterior of the nanocarrier. The telodendrimers may encapsulate one or more drug. The telodendrimers may encapsulate (e.g., sequester in the hydrophobic core) one or more drug (e.g., an anthracycline (e.g., doxorubicin), and/or methotrexate).

The nanocarrier may comprise two or more different telodendrimer/drug constructs. Each of the two or more different telodendrimer polymers can each be designed for a different drug combinations (i.e., the affinity layer of each telodendrimer can be tuned to different drugs).

For example, each of the telodendrimers can be associated with (e.g., encapsulate) a different drug (e.g., methotrexate or an analog thereof or doxorubicin or an analog thereof) in separate reactions. Subsequently, the two or more telodendrimer/drug combinations can be combined under such conditions that they form micelles containing a mix of telodendrimer/drug constructs. If, for example, the micelles contain 100 or so individual telodendrimers, it is expected that the "mixed" micelles will contain stochiastic mix of the two or more drugs. The average composition will depend upon the ratio of the 2 or more telodendrimer polymer/drug constructs in the mixture.

For example, a nanocarrier of the present disclosure has a nanocarrier:drug (e.g., methotrexate, anthracycline, or a combination thereof) mass ratio of 1:1 to 1:1.6, including all 0.1 values and ranges therebetween. More specifically, the nanocarrier:drug mass ratio is 1:0.5, 1:0.6, 1:0.7, 1:0.8, 1:0.9, 1:1, 1:1.1, 1:1.2, 1:1.3, 1:1.4, 1:1.5, or 1.6.

The telodendrimers can be present in a composition. In an embodiment, the composition comprises one or more telodendrimers. The composition may comprise a mixture of telodendrimers. In an embodiment the composition further comprises one or more drugs. The composition can have a formulation as disclosed herein. For example, the composition can be a pharmaceutical composition as described herein.

The nanocarriers may comprise one or more drugs. The drugs can be therapeutic agents. The drugs may be sequestered in the nanocarriers (e.g., sequestered in one or more of the layers (e.g., the hydrophobic core) of a telodendrimer) or linked to the conjugates of the present disclosure. In an example, a drug is methotrexate or an analog thereof and/or an anthracycline (e.g., doxorubicin) or an analog thereof. The composition may comprise additional drugs. Examples of additional drugs include, but are not limited to, cytostatic agents, cytotoxic agents (such as for example, but not limited to, DNA interactive agents (such as cisplatin)); taxanes (e.g., taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites; alkylating agents (such as temozolomide (TEMODAR™ from Schering-Plough Corporation, Kenilworth, N.J.), cyclophosphamide); aromatase combinations; ara-C, adriamycin, cytoxan, and gemcitabine. Other drugs useful in the nanocarrier of the present disclosure include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Epirubicin, Idarubicin, Mithramycin, Deoxycoformycin, Mitomycin-C, L-Asparaginase, Teniposide 17alpha-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine. Prodrug forms are also useful in the disclosure.

Examples of anthracyclines include, but are not limited to: daunorubicin, doxorubicin, epirubicin, idarubicin, and combinations thereof.

For example, 100% of the methotrexate and/or an anthracycline (e.g., doxorubicin) is sequestered in the nanocarrier (e.g., sequestered in the hydrophobic core of the nanocarrier). In an embodiment, there is no observable methotrexate and/or an anthracycline (e.g., doxorubicin) that is not in the nanocarrier. Methods for detecting free (e.g., non-sequestered) methotrexate and/or an anthracycline (e.g., doxorubicin) are known in the art. Non-limiting examples of methods for detecting free methotrexate and/or an anthracycline (e.g., doxorubicin) are electrophoresis and size exclusion chromatography.

In an aspect, the present disclosure provides methods of using the telodendrimers. The telodendrimers can be used, for example, in methods of treatment.

Method of treating. The compositions or nanocarriers of the present disclosure can be used administer to subject in need of treatment a treatment to any disease requiring the administration one or more drug, such as, for example, by sequestering a drug or drugs (e.g., an anthracycline (e.g., doxorubicin) and/or methotrexate) in the interior of the nanocarrier, and delivering said drug to a target. The drug(s) can be delivered systemically or intracellularly. In an embodiment, compositions comprising the telodendrimers are used in a method for treating a disease. A composition for administration can comprise a plurality of nanocarriers, where each nanocarrier is sequestering a drug or drugs (e.g., methotrexate and/or an anthracycline (e.g., doxorubicin)) in the interior of the nanocarrier (e.g., sequestered in the nanocarrier).

In some embodiments, the present disclosure provides a method of treating a disease, including administering to a subject in need of such treatment a therapeutically effective amount of a composition or nanocarrier of the present disclosure, where the nanocarrier comprises a drug.

The compositions or nanocarriers of the present disclosure can be administered to a subject for treatment, e.g., of hyperproliferative disorders including cancer.

For example, doxorubicin or an analog thereof (e.g., an anthracycline) can be administered using compositions or nanocarriers of the present disclosure to an subject for treatment of conditions such as, for example, bladder, brain, bone, breast, colorectal, endometrial, gastrointestinal, head and neck, kidney, liver, lymphocytic, small cell lung, ovarian, pancreatic, prostate, thyroid cancers and leukemia (acute and acute myeloid), soft tissue sarcoma, solid tumors, Kaposi sarcoma, melanoma, AIDS, bacterial infections, and lymphoma.

For example, methotrexate or an analog thereof can be administered using compositions or nanocarriers of the present disclosure to an subject for treatment of conditions such as, for example, rheumatoid arthritis, autoimmune diseases, solid tumors, bone cancer, breast cancer, leukemia, acute lymphocytic, psoriasis, rheumatoid arthritis, psoriasis, inflammatory diseases, breast cancer, head and neck cancer, leukemia, lung cancer, lymphoma, non-Hodgkin's lymphoma, arthritis, hematological cancer, cervical cancer, bladder cancer, ovarian cancer, irritable bowel syndrome, acute lymphocytic, and fungal infections.

In various examples, compositions or nanocarriers of the present disclosure are cured and/or dialyzed prior to administration to a subject. For example, a composition or nanocarriers of the present disclosure are cured for a period of 5 days or more prior to administration to a subject.

Curing a composition or nanocarrier of the present disclosure is the molecular rearrangement within the core of the composition or nanocarrier. Uncured compositions and nanocarriers have loosely bound and randomly dispersed drugs (e.g., methotrexate, an anthracycline, or combination thereof) in the hydrophobic core of the micelle, whereas cured compositions or nanocarrier have ordered (e.g., stacked on and/or aligned with Rf moieties) drugs such that the drugs are more organized in the cured composition or nanocarrier than in an uncured composition or nanocarrier.

Formulations. The nanocarriers of the present disclosure can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present disclosure (see, e.g., Remington's Pharmaceutical Sciences, $20^{th}$ ed., 2003, supra). Effective formulations include oral and nasal formulations, formulations for parenteral administration, and compositions formulated for with extended release.

Formulations suitable for oral administration can consist of (a) liquid solutions, such as an effective amount of a compound of the present disclosure suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above can be sterile solutions. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the disclosure in a sustained release formulation.

Pharmaceutical preparations useful in the present disclosure also include extended-release formulations. In some embodiments, extended-release formulations useful in the present disclosure are described in U.S. Pat. No. 6,699,508, which can be prepared according to U.S. Pat. No. 7,125,567, both patents are incorporated herein by reference.

The pharmaceutical preparations are typically delivered to a mammal, including humans and non-human mammals. Non-human mammals treated using the present methods include domesticated animals (e.g., canine, feline, murine, rodentia, and lagomorpha) and agricultural animals (e.g., bovine, equine, ovine, porcine).

In practicing the methods of the present disclosure, the pharmaceutical compositions can be used alone, or in combination with other therapeutic or diagnostic agents.

Administration. The nanocarriers or compositions of the present disclosure can be administered as frequently as necessary, including hourly, daily, weekly or monthly. The compounds utilized in the pharmaceutical method of the disclosure are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present disclosure should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch or pump. Individual doses (e.g., consecutive doses) may be interrupted by rest periods of no administration. Rest periods can be regular or irregularly spaced and/or of regular or irregular duration. For example, administration of individual or multiple doses is/are interrupted by short independent rest period(s) (e.g., one to six days) followed by further administration of individual or multiple doses interrupted by longer independent rest period(s) (e.g., two to ten times the length of a short rest period).

In the case of doxorubicin or an analog thereof (e.g., an anthracycline), compositions or nanocarriers comprising doxorubicin or an analog thereof are administered as described herein to provide a dose of 30 to 75 mg/m$^2$ (e.g., by IV) every 21 to 28 days; approximately equivalent to 10 to 25 mg/kg in mouse for one injection every four days. In an example, the compositions or nanocarriers comprising doxorubicin or an analog thereof are administered to provide a dose of 10 to 200 mg/m$^2$ (e.g., by IV) daily to every 2 to 35 days. In other examples, the compositions or nanocarriers comprising doxorubicin or an analog thereof are administered to provide a dose of 30 to 160, 40 to 120, 40 to 130, or 40 to 150, 50 to 150, 75 to 125, 75 to 150, 90 to 125 mg/m$^2$, (e.g., by IV) daily or every 2 to 35 days. In various examples, compositions or nanocarriers comprising doxorubicin or an analog thereof are administered as described herein to provide a dose that is 1.5 to 3 times the recommended dose of a doxorubicin drug or formulation (e.g., liposomal doxorubicin drug formulations such as, for example, DOXIL®). In various examples, doxorubicin or an analog thereof has a recommended dose of 65 to 75 mg/m$^2$ every 21 days by IV, 60 mg/m$^2$ every 14 days by IV, 40 to 60 mg/m$^2$ every 21 to 28 days by IV, or 20 mg/m$^2$ every week. For example, DOXIL® has a recommended dose of 50 mg/m$^2$ every 28 days. In various examples, compositions or nanocarriers comprising doxorubicin or an analog thereof or an analog thereof are administered as described herein to provide a total cumulative dose of 450 or greater, 500 or greater, or 550 mg/m$^2$ (e.g., by IV).

In the case of methotrexate or an analog thereof, compositions or nanocarriers comprising methotrexate or an analog thereof are administered in an antineoplastic dosage range (e.g., 30 to 40 mg/m$^2$/week); equivalent to 10-13 mg/kg in mouse maybe every other day.

The pharmaceutical compositions can be administered to the patient in a variety of ways, including topically, parenterally, intravenously, intradermally, subcutaneously, intramuscularly, colonically, rectally or intraperitoneally. Preferably, the pharmaceutical compositions are administered parenterally, topically, intravenously, intramuscularly, subcutaneously, orally, or nasally, such as via inhalation.

In practicing the methods of the present disclosure, the pharmaceutical compositions can be used alone, or in combination with other therapeutic or diagnostic agents. The additional therapeutic or diagnostic agents used in the combination protocols of the present disclosure can be administered separately or one or more of the drugs used in the combination protocols can be administered together, such as in an admixture. Where one or more drugs are administered separately, the timing and schedule of administration of each drug and, optionally, additional therapeutic or diagnostic agents, can vary.

Method of imaging. In an aspect, compositions or nanocarriers comprising telodendrimers are used in imaging methods. In an embodiment, a composition or nanocarrier comprises an imaging agent.

In an embodiment, the present disclosure provides a method of imaging, including administering to a subject to be imaged, an effective amount of a composition or nanocarrier of the present disclosure, wherein the composition or nanocarrier includes an imaging agent. In other embodiments, the method of treating and the method of imaging are accomplished simultaneously using a nanocarrier comprising a drug, and/or an imaging agent.

Exemplary imaging agents include paramagnetic agents, optical probes, and radionuclides. Paramagnetic agents imaging agents that are magnetic under an externally applied field. Examples of paramagnetic agents include, but are not limited to, iron particles including nanoparticles. Optical probes are fluorescent compounds that can be detected by excitation at one wavelength of radiation and detection at a second, different, wavelength of radiation. Optical probes useful in the present disclosure include, but are not limited to, Cy5.5, Alexa 680, Cy5, DiD (1,1'-dioctadecyl-3,3,3,3', 3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo radioactive decay. Radionuclides useful in the present disclosure include, but are not limited to, $^{3}$H, $^{11}$C, $^{13}$N, $^{18}$F, $^{19}$F, $^{60}$Co, $^{64}$Cu, $^{67}$Cu, $^{68}$Ga, $^{82}$Rb, $^{90}$Sr, $^{90}$Y, $^{99}$Tc, $^{99m}$Tc, $^{111}$In, $^{123}$I, $^{124}$I, $^{125}$I, $^{129}$I, $^{131}$I, $^{137}$Cs, $^{177}$Lu, $^{186}$Re, $^{188}$Re, $^{211}$At, Rn, Ra, Th, U, Pu and $^{241}$Am.

The steps of the method described in the various embodiments and examples disclosed herein are sufficient to carry out the methods of the present disclosure. Thus, in an example, the method consists essentially of a combination of the steps of the methods disclosed herein. In another example, the method consists of such steps.

The following Statements describe various examples/embodiments of the compounds (telodendrimers), compositions, nanocarriers, and methods of the present disclosure:

Statement 1. A compound having the following structure:

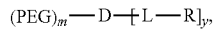

where PEG is polyethylene glycol group; L is optional and independently at each occurrence selected from the group consisting of

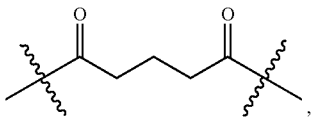

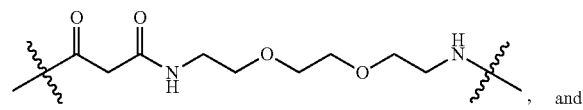, and

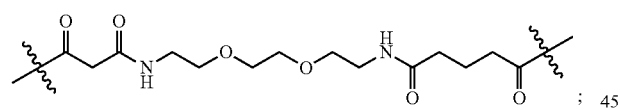;

D is a dendritic polymer moiety having one or more branched monomer units selected from the group consisting of a lysine moiety, an arginine moiety, and combinations thereof; R is independently at each occurrence in the compound

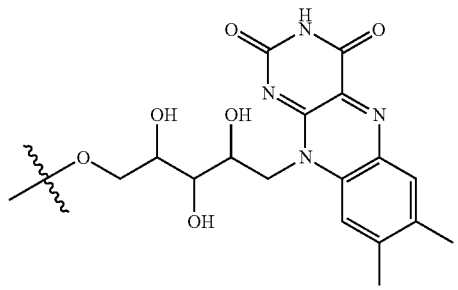

or

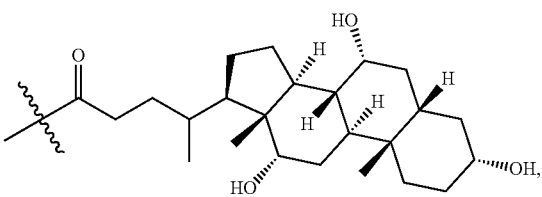

where at least one occurrence is

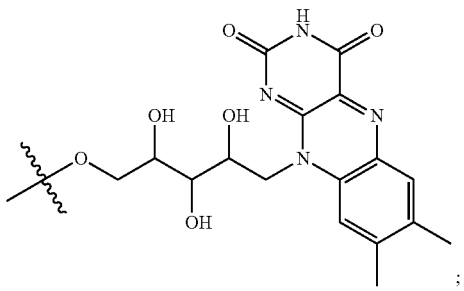;

m is 1; and y is 1-20, including all integer values and ranges therebetween.

Statement 2. The compound of Statement 1, wherein the PEG group has the following structure:

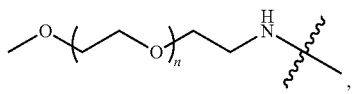

wherein n is 10-500.

Statement 3. The compound of Statement 1 or 2, wherein D comprises 4 or 8 arginine moieties and each R is

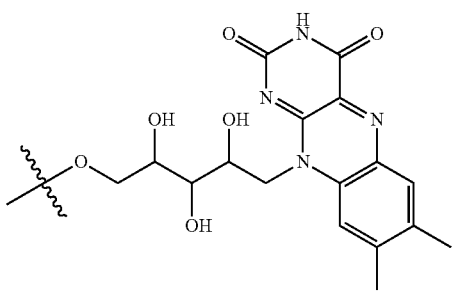

Statement 4. The compound of any one of the preceding Statements, wherein the compound is selected from the group consisting of:
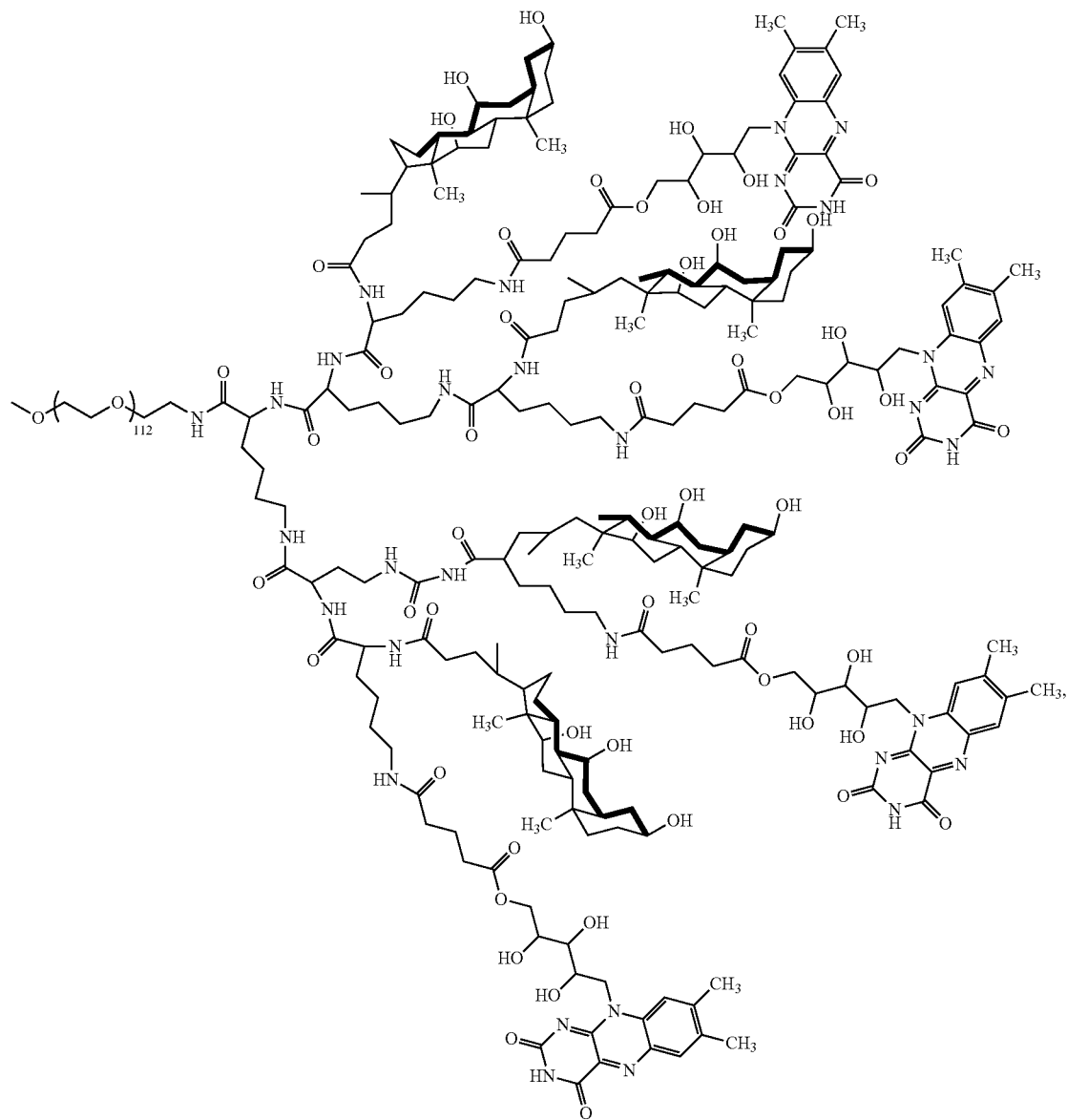

-continued
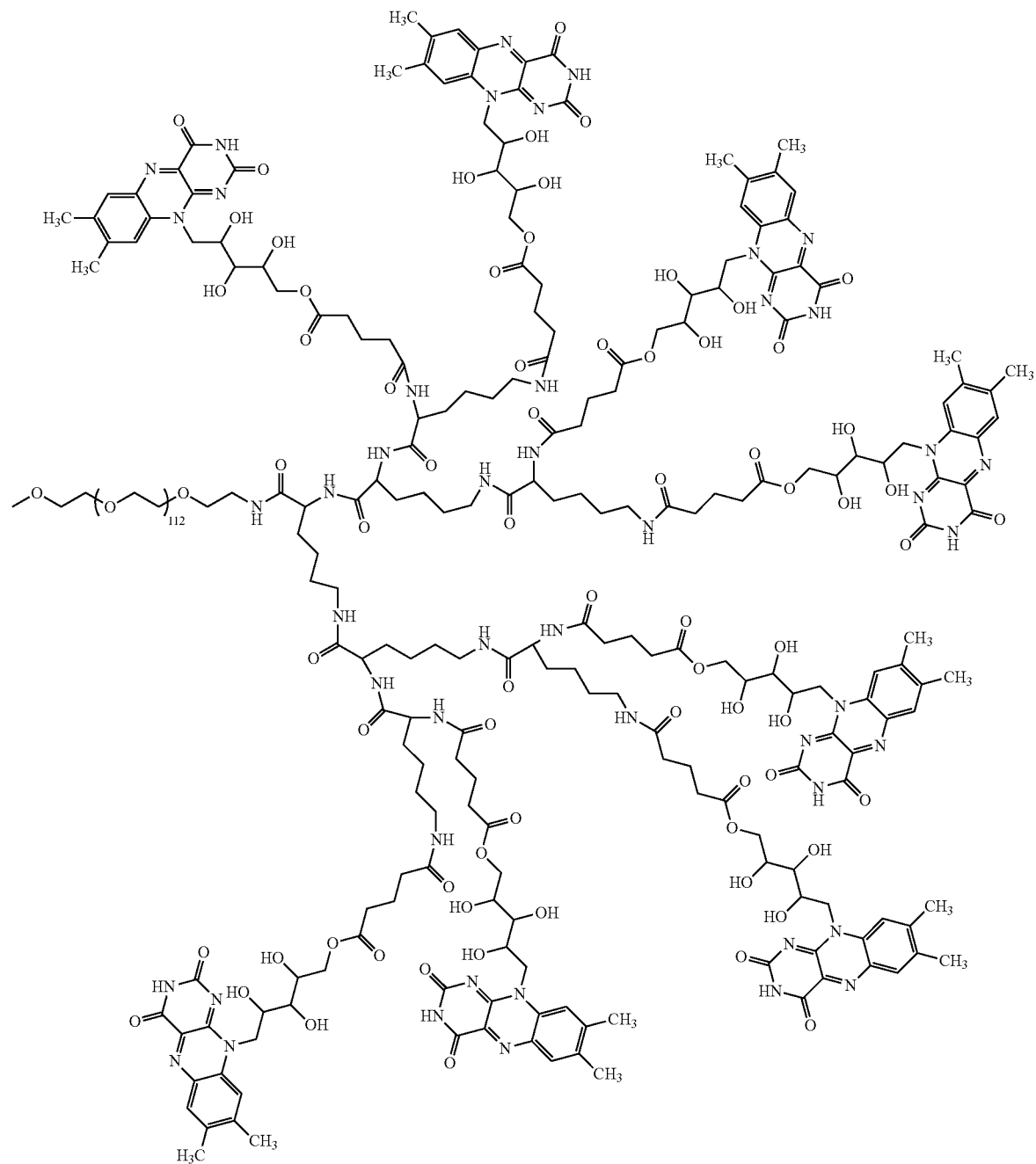

-continued
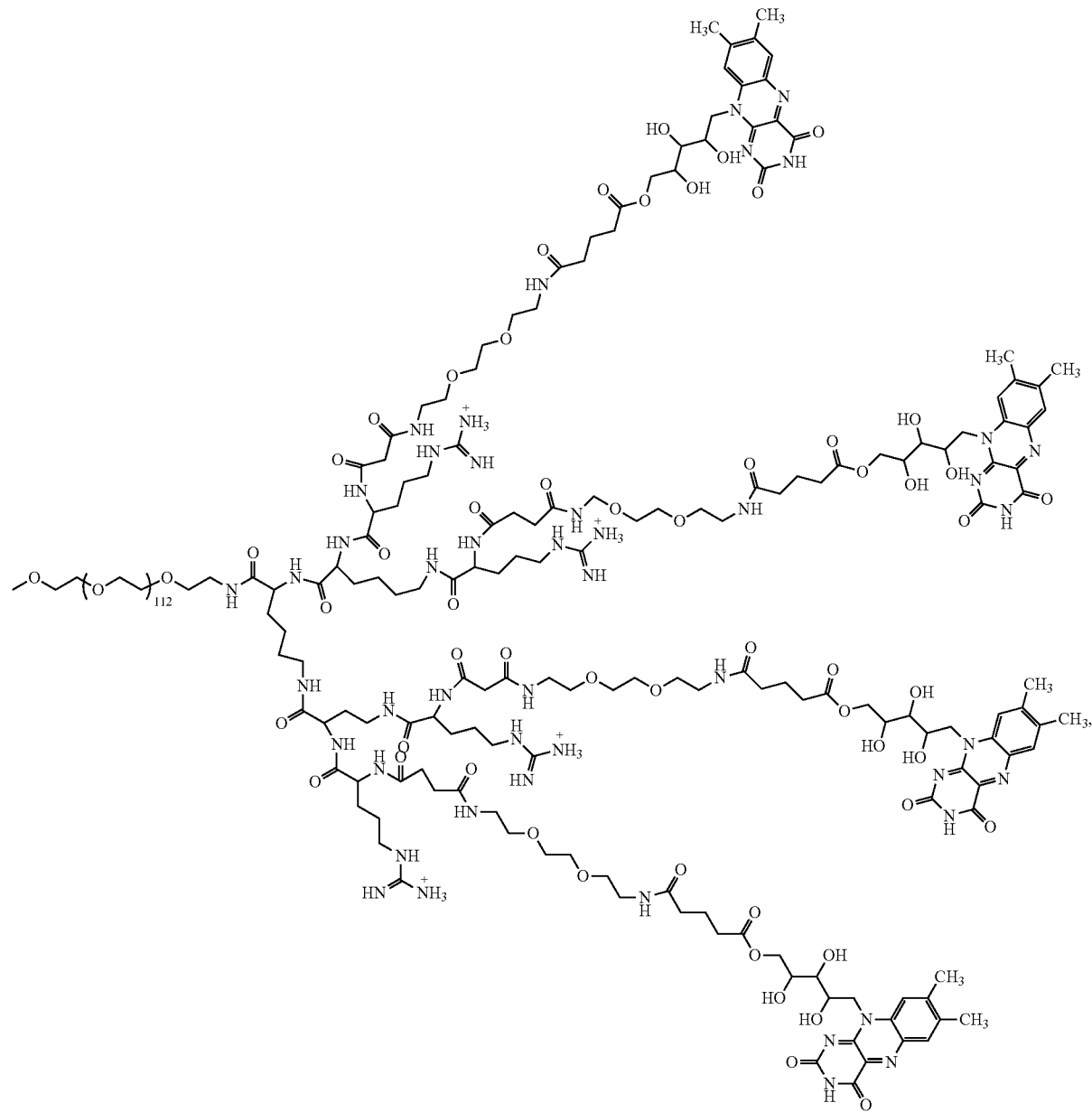

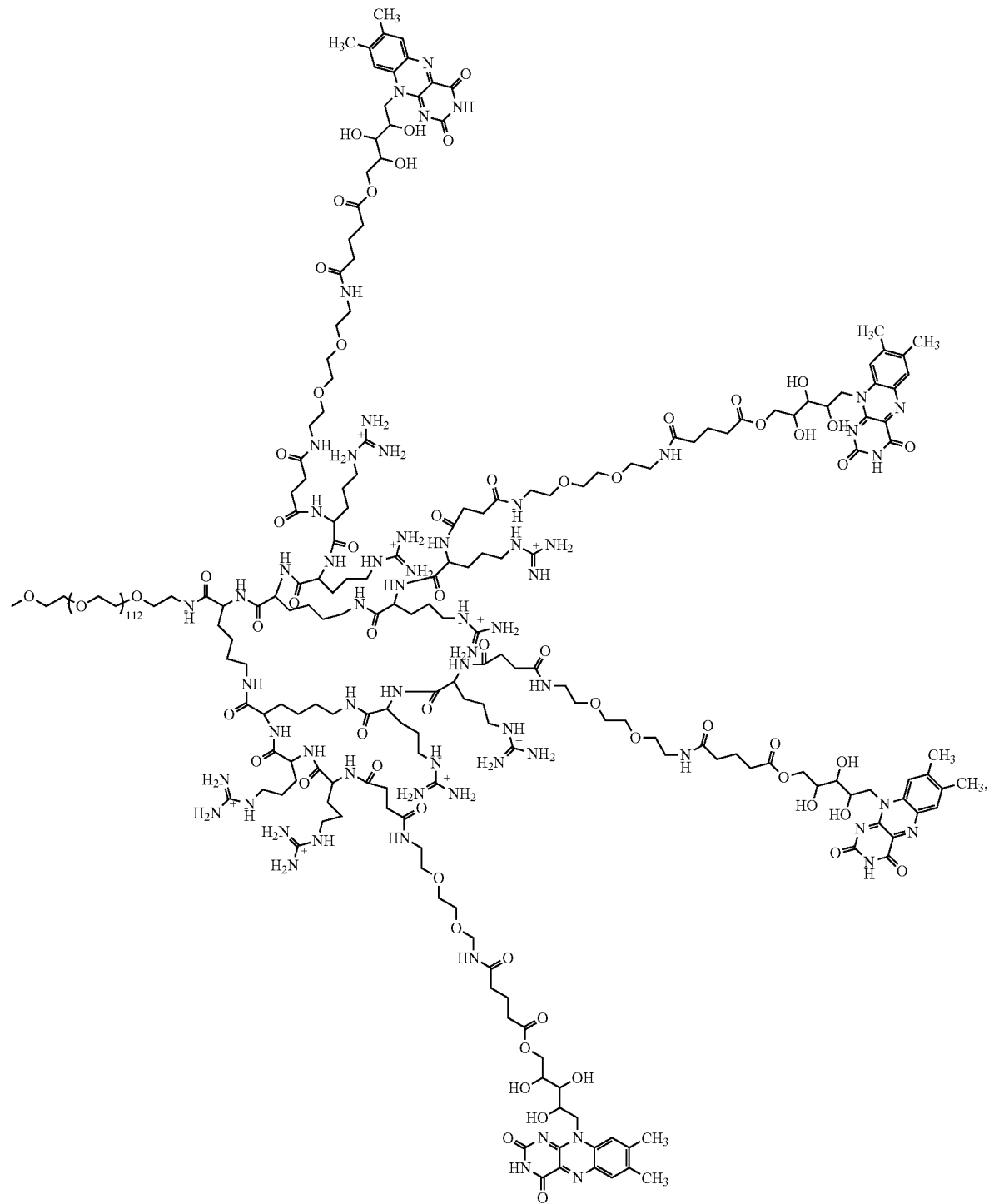

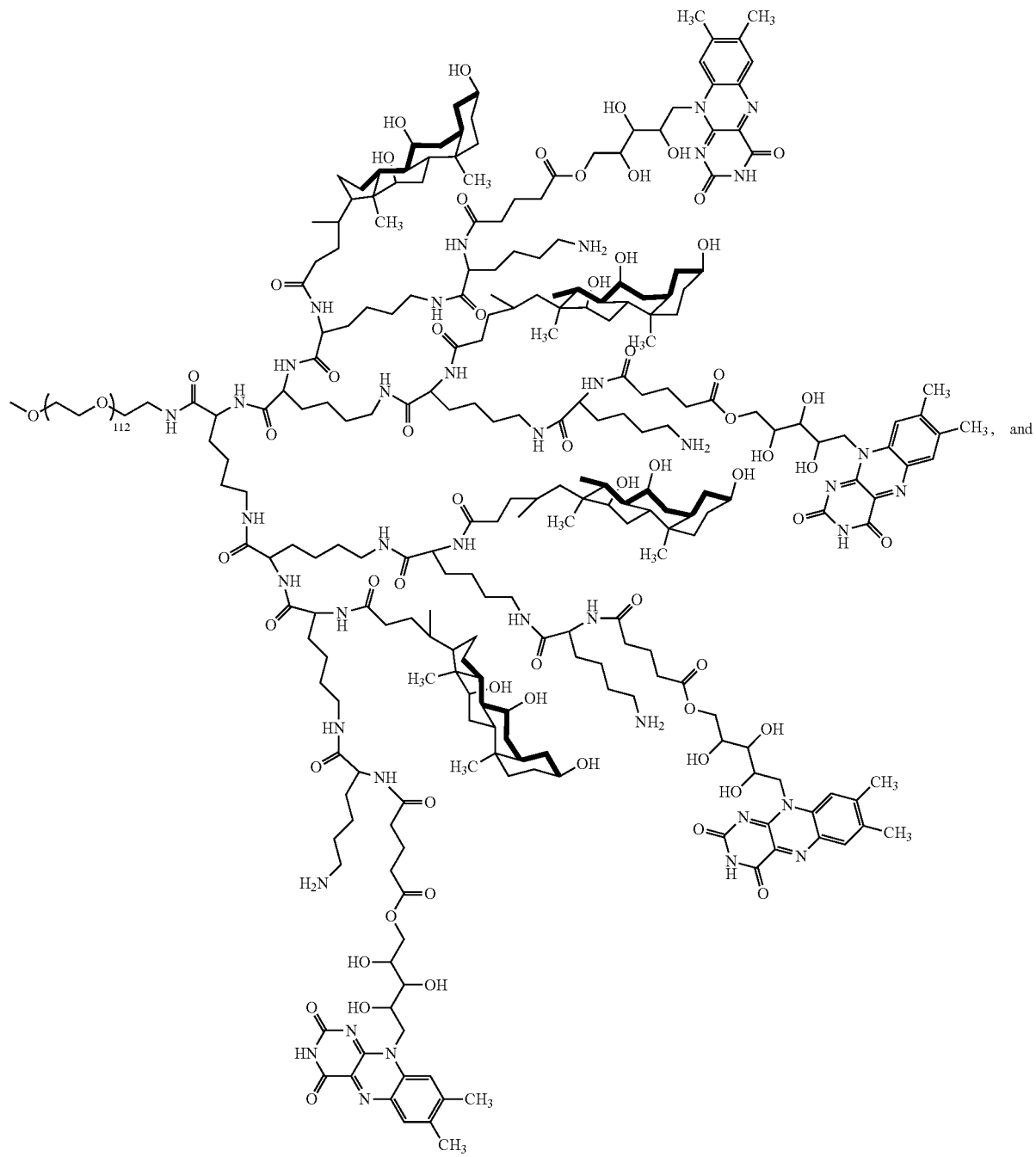

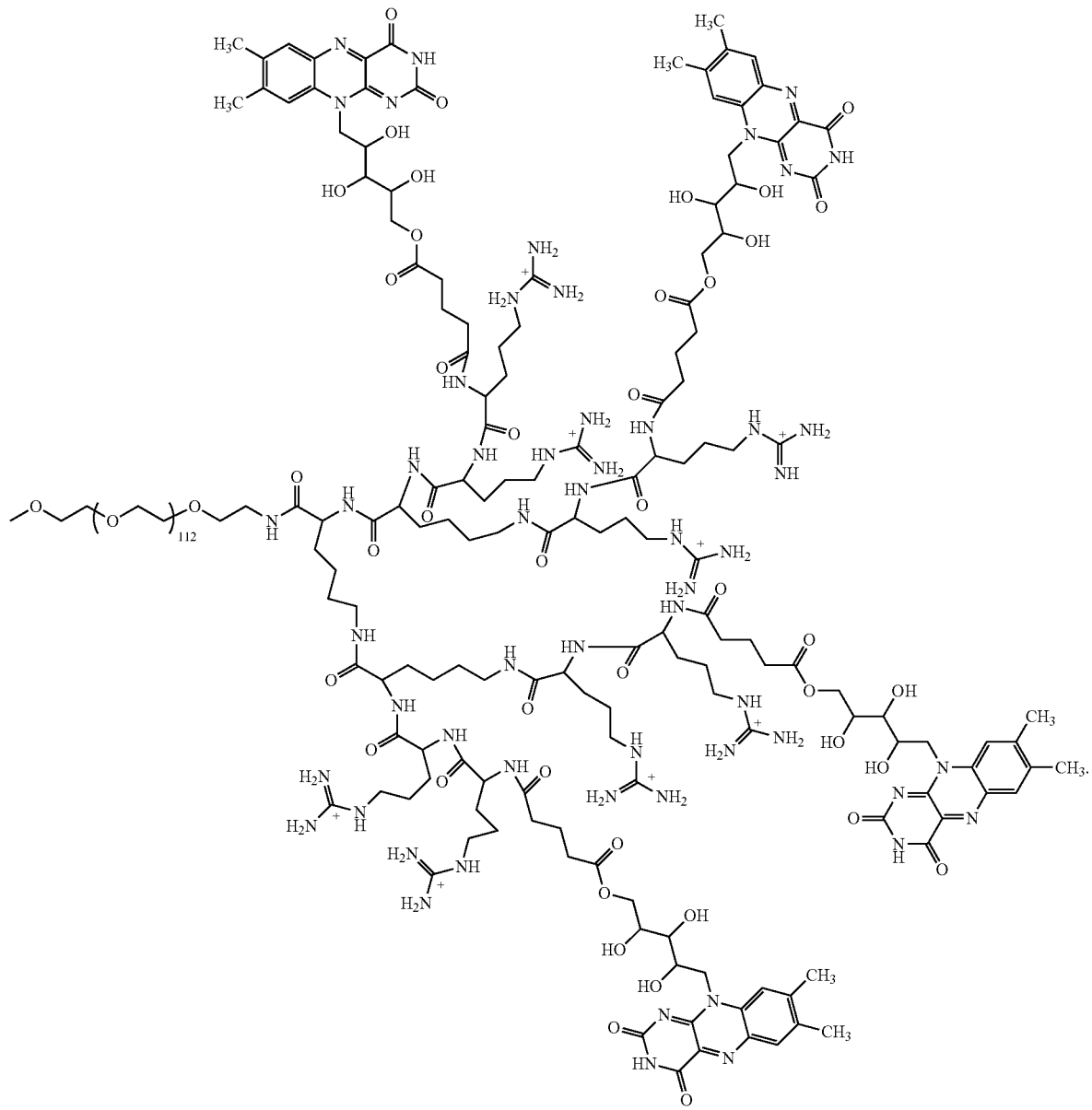

Statement 5. A composition comprising one or more compounds of any one of the preceding Statements and methotrexate or an anthracycline.

Statement 6. The composition of Statement 5, where the anthracycline is selected from the group consisting of daunorubicin, doxorubicin, epirubicin, idarubicin, and combinations thereof.

Statement 7. The composition of Statement 5 or 6, where the one or more compounds of any one of Statements 1-4 are present as a nanocarrier.

Statement 8. The composition of any one of Statements 5-7, where for each

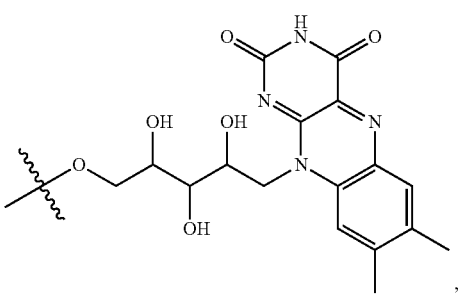 [SMILES: *OCC(O)C(O)C(O)Cn1c2nc(=O)[nH]c(=O)c-2nc2cc(C)c(C)cc21 ; ","]

there is one methotrexate or anthracycline present.

Statement 9. The composition of any one of Statements 5-8, wherein the composition has a nanocarrier:methotrexate/anthracycline mass ratio of 1:1 to 1:1.6.

Statement 10. A method of delivering a therapeutic agent to a subject in need of treatment comprising administering to the subject an effective amount of a composition of any one of Statements 5-9.

Statement 11. The method of Statement 10, wherein the subject in need of treatment is seeking treatment from the group consisting of inflammation, autoimmune disorders, organ transplants, solid tumors, bone cancer, breast cancer, leukemia, acute lymphocytic, breast cancer, head and neck cancer, leukemia, lung cancer, lymphoma, non-Hodgkin's lymphoma, hematological cancer, cervical cancer, bladder cancer, and ovarian cancer.

Statement 12. The method of any one of Statements 10-11, wherein for each

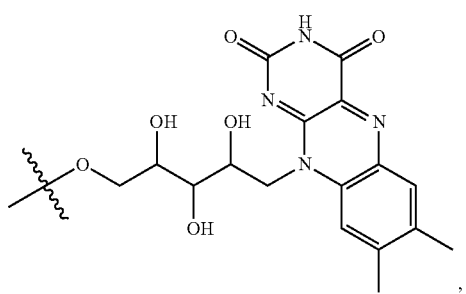 [SMILES: *OCC(O)C(O)C(O)Cn1c2nc(=O)[nH]c(=O)c-2nc2cc(C)c(C)cc21 ; ","]

there is one methotrexate or anthracycline present.

Statement 13. The method of any one of Statements 10-12, wherein the composition has a nanocarrier:methotrexate/anthracycline mass ratio of 1:1 to 1:1.6.

Statement 14. The method of any one of Statements 10-13, wherein the composition of any one of Statements 5-9 provides a dose of 1.5 to 3 times the recommended dose of doxorubicin or a liposomal doxorubicin formulation.

Statement 15. A kit comprising: i) at least one compound of any one of Statements 1-4 and methotrexate, an anthracycline, or a combination thereof; and ii) a set of instructions, wherein the instructions describe how to use the compound or composition.

The following examples are presented to illustrate the present disclosure. These examples are not intended to limiting in any manner.

Example 1

The following example provides a description of riboflavin-containing nanocarriers for drug delivery.

Doxorubicin (DOX) is a commonly used anticancer chemo drug, and its clinical use is associated with dose-limiting cardiotoxicity. Herein, we present an amphiphilic riboflavin-containing linear-dendritic telodendrimer, which self-assembles into well-defined nanocarriers for DOX delivery with reduced toxicity and improved activity. These nanocarriers are characterized by the ultra-high drug loading capacity (1:1 to 1:1.6, drug/nanocarrier, w/w), sustained drug release with reduced initial burst release and optimal particle sizes (20~40 nm) for passive tumor targeting, which benefit from the strong binding between DOX and riboflavin. We observed a 2~2.5-fold increase in maximum tolerated dose for these nanoformulations when compared to the clinically approved free DOX and PEGylated liposomal nanoformulation Doxil®. These nanoformulations significantly prolonged the drug blood circulation time over the free drug, which also improve the passive tumor targeting and drug accumulation in mice bearing tumor xenografts, e.g. Raji lymphoma, MDA-MB-231 breast cancer, and SKOV3 ovarian cancer. Significant tumor growth inhibition and prolonged survival were observed in mice bearing SKOV3 ovarian cancer xenograft treated with these nanoformulations. These promising preclinical results of the riboflavin-containing DOX nanoformulations presented in this study indicate their potential application for cancer therapy.

Examples of telodendrimers include those shown in FIGS. 24-29.

Material and Methods

Materials

Doxorubicin hydrochloride (DOX.HCl; AvaChem Scientific, San Antonio, Tex.) and Doxil® (Ben Venue Laboratories Inc., Bedford, Ohio) were obtained from the Regional Oncology Center Pharmacy, State University of New York (SUNY) Upstate Medical University. Monomethyl-terminated poly(ethylene glycol) monoamine hydrochloride (MeO-PEG-NH$_2$.HCl, Mw 5 kDa) were purchased from JenKem Technology USA Inc. (Fmoc)Lys(Boc)-OH, (Fmoc)Lys(Fmoc)-OH were purchased from AnaSpec Inc. (San Jose, Calif.). Tetrazolium compound [3-(4,5-dimethyl-thiazol-2-yl)-5-(3-carboxymethoxyphenyl)-2-(4-sulfophenyl)-2H-tetrazolium, MTS] and phenazine methosulfate were purchased from Promega (Madison, Wis.). Rf, CA, glutaric anhydride and all other chemicals were purchased from Sigma-Aldrich (St. Louis). The preparation of CA derivatives (CA NHS ester) was described in the previous publication.

The nomenclatures of the TDs are followed the system used in the previous publications. For example, TD named PEG$^{5k}$Rf$_8$ means that the molecular weight of PEG is 5 kDa with eight Rf molecules conjugated on the periphery amino groups of polylysine; PEG$^{5k}$CA$_4$Rf$_4$ indicates that four CA and four Rf molecules are conjugated on the α-amino and ε-amino groups, respectively.

7,8-dimethyl-10-((2R,3R,4S)-2,3,4-trihydroxypentyl-5-carboxybutyryl) benzo[g]pteridine-2,4 (3H, 10H)-dione (Rf—COOH) synthesis 0.5 g Rf was added into a 50-mL round bottom flask, then 10 mL of dimethyl sulfoxide (DMSO), and 6 mL pyridine were added and heat to nearly 90° C. until Rf dissolved. 0.5 g glutaric anhydride and 0.1 g 4-dimethylaminopyridine (DMAP) were dissolved in 1 mL DMSO and then added into the flask. The reaction was heated at 70° C. overnight. After the reaction completion confirmed by thin-layer chromatography (TLC), it was cooled down to room temperature. Reaction solution was transferred to a 500-mL flask, and 15 mL dichloromethane (DCM) and 200 mL ethyl acetate were added to the reaction solution to precipitate the product. Finally, the precipitates were washed twice with pure ethyl acetate.

Td Synthesis—

General procedure for TD synthesis has been reported in our previous publications and is described briefly as following: the TDs were synthesized by solution-phase peptide chemistry starting from MeO-PEG-NH$_2$.HCl. N-terminal-protected lysine was used to synthesize the branched scaffold of TD. Triethylamine (TEA, 1 equiv) was added to neutralize the hydrochloride on PEG. Diisopropyl carbodimide (DIC, 3 equiv) and N-hydroxybenzotriazole (HOBt, 3 equiv) were used as coupling reagents in dimethylformamide (DMF) to form amide bonds. The complete reaction was confirmed by the negative Kaiser test result. The ice-chilled ether was added to the reaction solution to precipitate PEGylated intermediates, and then washed by chilled ether twice. Fmoc-protection groups were removed by the treatment with 20% 4-methyl piperidine in DMF for 30 min. TD was precipitated and washed with chilled ether for three times. Homo TD PEG$^{5k}$Rf$_8$ (TD-1) synthesis: A dendritic polylysine was synthesized by three repeated (Fmoc)Lys(Fmoc)-OH coupling as mentioned above. At the end, the polylysine was capped with NHS ester of Rf carboxylic acid derivative using HOBt/DIC as coupling reagents. The hybrid TD PEG$^{5k}$CA$_4$Rf$_4$ (TD-2) synthesis: A dendritic polylysine with orthogonal protected α-(N-Fmoc) and ε-(N-Boc) amino groups was synthesized on MEO-PEG-NH$_2$ after two repeated (Fmoc)Lys(Fmoc)-OH couplings followed by a (Fomc)Lys(Boc)-OH coupling using HOBt/DIC chemistry. Then, the Fmoc group was removed by the treatment of 20% 4-methylpiperidine in DMF, followed by the coupling of CA NHS on the α-position of lysine. Then, Boc protecting groups were removed by treatment of 50% trifluoracetic acid (TFA) in DCM for 0.5 h. Rf carboxylic acid derivative reacted with the ε-amine of lysine to generate hybrid TD. TDs were precipitated twice and washed three times with cold ether, and then dialyzed for purification.

Drug Loading and Characterization—

DOX was encapsulated into TD micelles by a thin-film hydration method. DOX-HCl was dissolved in chloroform (CHCl$_3$)/methanol (MeOH) (10:1 v/v) and neutralized by the addition of triethylamine (TEA, 3 equiv.). The TD was also dissolved in CHCl$_3$/MeOH (10:1 v/v) and transferred into the drug solution at certain TD-drug ratios. Solvents were evaporated to dryness and a thin film of homogeneous drug-TD mixture was casted on the flask wall, which was further dried under the high vacuum for 1 h. Then the film was hydrated in phosphate buffered saline (PBS), followed by a 5-min sonication. The particle size distributions of the drug-loaded micelles were measured by dynamic light scattering (DLS) (Microtrac) and transmission electron microscopy (TEM) (a JEOL JEM-1400 instrument at 80 kV) with negative staining by 1% uranyl acetate. The particle stability of DOX-loaded micelles upon storage was monitored by DLS. Any unloaded drug precipitate will be removed by filtration through 0.22 m filter. Drug loading content (DL %) and loading efficiency (LE %) were analyzed by HPLC and calculated as the following equations: DL %=(mass of encapsulated DOX/mass of TD used for DOX encapsulation)×100%; LE %=(mass of encapsulated DOX/mass of DOX added)×100%.

Size Exclusive Chromatography (SEC)—

The encapsulated DOX and free DOX were separated by SEC using Sephadex G-25 (GE Healthcare Life Sciences). The column (8×40 mm) was equilibrated with PBS. A 40 μL sample solution of free DOX or DOX-loaded Rf-containing nanoformulations at DOX concentration of 1 mg/mL was applied to the column. The flow rate through the column was kept at 0.7 ml/min during the separation. 96-well plates were used to collect each droplet from the beginning. Then 10 μL solution was taken out from each well and transferred to another 96-well plate. 90 μL DMSO was added into each well and mixed gently to destroy micelle structure and release drug into solution. The fluorescence signals of DOX were measured at ex/em 520/600 nm by a microplate reader (Synergy H1).

Ultracentrifuge Filtration—

The Spin-X centrifuge tube filters (MWCO 5,000 Da, Corning) were used to separate free DOX from DOX-PEG$^{5k}$Rf$_8$ (DOX-TD-1) and DOX-PEG$^{5k}$CA$_4$Rf$_4$ (DOX-TD-2). 100 μL of DOX-loaded Rf-containing nanoformulations were added onto the filter. After centrifugation at 13,000 g for 10 min, the free DOX was collected through the filter. The UV absorbance of DOX at 550 nm (UV absorbance of Rf has overlapped with DOX at 450 and 500 nm) was detected by NanoDrop spectrophotometer (NanoDrop 2000c, Thermo Scientific) to determine drug loading efficiency.

Agarose Gel Electrophoresis—

Samples with loading buffer (30% glycerol aqueous solutions) were loaded into agarose gel (1.5% wt) in Tris-acetate-EDTA (TAE) buffer. The gel was running for 2 h at a constant current of 20 mA. The gel with the samples containing fetal bovine serum (FBS) was stained with 1% coomassie blue for 0.25 h followed by detaining overnight. Then, the gel was imaged by a Bio-Rad Universal Hood II Imager (Bio-Rad Laboratories, Inc.) using SYBR green (ex/em 497/520 nm) and coomassie blue modes. Finally, the imaging pictures were adjusted by the Image Lab 3.0 software.

In Vitro Drug Release—

The drug release profile of DOX formulations were measured by a dialysis method. 300 μL of free DOX, Doxil® or DOX-loaded nanoformulations were loaded into dialysis cartridges with 3.5 kDa MWCO dialysis membrane (Thermo Scientific, Rochford, Ill.). The cartridge was dialyzed against 50 mL PBS and gently shaken at 37° C. at 100 rpm. The PBS solutions were changed every 4 h. 1 μL of drug solution within dialysis cartridge will be withdrawn at different time points and diluted with 9 μL of DMSO. Then the concentration of DOX were measured using Synergy H1 microplate reader (BioTek, Winooski, Vt.) at excitation 520 nm/emission 590 nm. Data were reported as the average percentage of DOX accumulative release for each triplicate samples.

Cell Culture and Animals—

Ovarian cancer cell line SKOV3, breast cancer cell line MDA-MB-231, T-cell lymphoma cell line Jurkat, B-cell lymphoma cell line (Raji), myeloma cell line H929, myelogenous leukemia cell line K562 were purchased from American Type Culture Collection (Manassas, Va., USA). These cells were cultured in RPMI-1640 or DMEM medium supplemented with 10% fetal bovine serum, 100 U mL$^{-1}$ penicillin G and 100 μg/mL streptomycin at 37° C. using a humidified 5% CO$_2$ incubator. Specific-pathogen free female BALB/c mice aged 4-6 weeks were purchased from Charles river (Hollister, Calif.); female athymic nude mice (Nu/Nu strain), aged from 4-6 weeks were purchased from Jackson (Sacramento, Calif.). All the animals were kept under pathogen-free conditions according to the AAALAC (Association for Assessment and Accreditation of Laboratory Animal Care) guidelines and were allowed to acclimatize for at least 4 days before any experiments. All the animal experiments were performed in the compliance with the institutional guidelines and according to the protocol approved by the Committee for the Humane Use of Animals of State University of New York (SUNY) Upstate Medical University.

Cell Viability Study—

Raji, Jurkat, K562, and H929 cells were seeded in a 96-well plate with the cell density of 8×10$^3$ cells per well. MDA-MB-231, and SKOV3 cells were seeded in a 96-well plate with the cell density of 4×10$^3$ cells per well. After the overnight incubation, the cells were treated with different concentrations of DOX formulations, as well as the blank polymers. After 72 h incubation, Cell Titer 96 Aqueous Cell Proliferation Reagent, which is composed of MTS and an electron-coupling reagent phenazine methosulphate, was added to each well according to the manufacturer's instructions. The cell viability was determined by measuring the absorbance at 490 nm using a microplate reader (BioTek Synergy H1). Untreated cells served as a control. Results were shown as the average cell viability of triplicate wells via a formula: Cell viability %=[($OD_{treat}$-$OD_{blank}$)/($OD_{control}$-$OD_{blank}$)×100%].

Cellular Uptake Study
Confocal Fluorescence Microscopy—

MDA-MB-231 breast cancer cells were incubated with free DOX, Doxil®, and DOX-loaded Rf-containing nanoformulations at the final DOX concentration of 10 μM for free DOX and 30 μM for Doxil® and DOX-loaded Rf-containing nanoformulations for 30 min and 2 h at 37° C. on 8-well chamber slide, respectively. The cells were washed three times with cold PBS, and fixed by 4% paraformaldehyde for 10 min. The nuclei were counterstained by 4',6-diamidino-2-phenylindole (DAPI). The slides were mounted with cover slips and cells were imaged with a Nikon FV1000 laser scanning confocal scanning microscope.

Cell Lysis and Drug Extraction—

1×105 MDA-MB-231 cells were incubated with free DOX, and DOX-loaded nanofromulations with different DOX concentrations at 1, 3, and 9 μM for 0.5 h and 2 h at 37° C., respectively. The cells were washed with PBS for three times. 100 μL extraction buffer containing 10% Triton X-100, deionized water and acidified isopropanol with 0.75 N HCl with a 1:2:15 volume ratio, were added to the cells, and DOX were extracted overnight at 4° C. The fluorescence of each cell lysate supernatant was measured at excitation of 520 nm and emission of 600 nm using microplate reader (BioTek Synergy H1).

Hemolytic Toxicity—

1 mL of fresh blood from a healthy human volunteer was collected into 5 mL PBS solutions with 20 mM EDTA. Red blood cells (RBCs) were separated by centrifugation at 1000 rpm for 10 min. Then the RBCs were washed by PBS for three times and were suspended in 20 mL PBS. Blank polymers were added into 200 μL RBC solutions with the concentration range from 10 to 1000 μg/mL followed by gentle vortex and incubation at 37° C. for 0.5 h, 4 h, and 24 h, respectively. The samples were centrifuged at 1000 rpm for 5 min. The hemoglobin in supernatant was measured by the UV absorbance at 540 nm using a NanoDrop spectrophotometer (NanoDrop $2000^C$, Thermo Scientific). PBS and Triton-100 (2%) were also incubated with RBCs for a negative and positive control, respectively. The hemolytic toxicity was calculated by the following formula: Hemolysis %=[($OD_{sample}$-$OD_{PBS}$)/($OD_{triton}$-$OD_{PBS}$)]×100%.

Maximum Tolerated Dose (MTD) Studies—

Healthy specific pathogen-free female BALB/c mice aged 4-6 weeks were administrated intravenously with DOX-HCl, Doxil®, DOX-TD-1, DOX-TD-2 at the dose of 10, 20, and 25 mg/kg for either single or three treatments, respectively (n=4-5). We monitored the mice survival and body weight change daily for 2 weeks. On day 7 after the last dose, we collected the blood from each mouse by tail vein bleeding for blood count analysis by an Hemavet instrument (Hemavet 950FS, Mascot). The MTD was defined as the allowance of 15% loss of median body weight and cause neither death due to toxic effects nor significant changes in the general signs within two weeks after the last dose.

Pharmacokinetic Studies—

Healthy specific pathogen-free female BALB/c mice aged 4-6 weeks were administrated intravenously with DOX-HCl, Doxil®, DOX-TD-1, DOX-TD-2 at a single dose of 10 mg/kg, respectively (n=4-5). Blood was collected from mice tail vein at different time points. Plasma of each sample was collected, diluted by 10-fold with DMSO. The fluorescence of DOX was measured by a microplate reader (Synergy H1, BioTek) at excitation of 520 nm and emission of 600 nm. The pharmacokinetic parameters were calculated by an add-in program PKsolver in Microsoft Excel. AUC (area under the curve), $C_{max}$ (maximum drug concentration), $t_{1/2}$ (terminal half-life), and Cl (total body clearance) were determined.

Fluorescence Small Animal Imaging—

Raji lymphoma, MDA-MB-231, and SKOV3 xenograft tumor bearing mice model were established by subcutaneous injection of $1\times10^7$ cells in 100 μL of Matrigel and PBS (1:1 v/v) at the right or left flank of female nude mice aged 4-6 weeks. The fluorescent nanoformulations for injection are prepared by a hydrophobic near-infrared dye DiD and DOX co-loaded in TD-1 and TD-2, respectively, at a ratio of 0.2:1:5 (w/w/w, DiD/DOX/TD). Then the DiD-DOX co-loaded Rf-containing nanoformulations were filtered with 0.22 am sterile filter. Free DiD in PBS was used as the control group. All the formulations were intravenously injected through tail vein. The mice were anaesthetized and imaged by IVIS® (In vivo Imaging System) 200 (perkinElmer) at 0.5, 1, 2, 4, 8, 24, 48, 72 h different time points with the ex/em 625/700 nm. Finally, the mice were euthanized, tumor and all the major organs were taken out for ex vivo imaging. Living Image software (Caliper Life Sciences) were used to define and measure the fluorescence intensity in the place of interest.

Tumor and Tissue Microscopic Imaging—

Healthy Balb/c mice were treated with free DOX, Doxil, DOX-TD-1D, and DOX-TD-2D at MTD dose. Mice were euthanized in the following day. Major organs including heart, liver, and kidney were harvest and buried in OCT (cryo-embedding medium) and frozen, stored at −80° C. Tissue slides were prepared on a Minotome Cryostat, dried for 0.5 h and fix with 4% paraformaldehyde for 10-15 min, and subjected to pathological analysis by haemotoxylin and eosin (H&E) staining. In addition, the tumors were obtained from the in vivo fluorescence imaging mice. The slides were prepared according to the same processes. The nuclei were stained by DAPI. Cover slips were mounted with the slides and imaged by Nikon FV1000 laser scanning confocal scanning microscope.

In Vivo Efficacy for Tumor Treatment—

SKOV3 xenograft tumor bearing mice model was established by subcutaneous injection of $1\times10^7$ cells in 100 μL of Matrigel and PBS (1:1 v/v) at the right or left flank in female nude mice aged 4-6 weeks. After tumor volume reached 150-200 $mm^3$, mice were treated with PBS, DOX-HCl (q4d×3, 8 mg/kg), Doxil® (q4d×3, 10 mg/kg), dialyzed DOX-TD-1 (q4d×3, 20 mg/kg), and dialyzed DOX-TD-2 (q4d×3, 20 mg/kg), respectively (n=4-5). Bodyweight changes were monitored and tumor sizes were measured by a digital caliper once a day in the first 3 weeks, then once every other day. The tumor volume was calculated by the equation: Tumor volume=(L×$W^2$)/2, in which L and W are the longest and shortest in tumor diameters (mm), respectively. When the tumor volume reached to 2,000 $mm^3$, the mice were euthanized. To compare each group, the relative tumor volume was calculated at each time point (Relative tumor volume=absolute tumor volume/initial tumor volume). On day 7 of the last dose, blood samples were collected from each mouse for blood cell counting by a Hemavet instrument (Hemavet 950FS, Mascot).

Statistical Analysis—

Data are presented as means±SD. Linear regression model was fitted by ordinary least square in the correlation studies. Cell viability curves were fitted by top, bottom and $IC_{50}$ three-parameter model. The significance in all the statistical analysis was at a probability of P<0.05. Statistical analysis will be performed by Students t-test for comparison of two groups, and one-way analysis of variance for multiple groups, followed by Newman-Keuls test if overall P<0.05.

Results and Discussion
DOX-Loading in Rf-Containing Nanoformulations—

Figure 2:
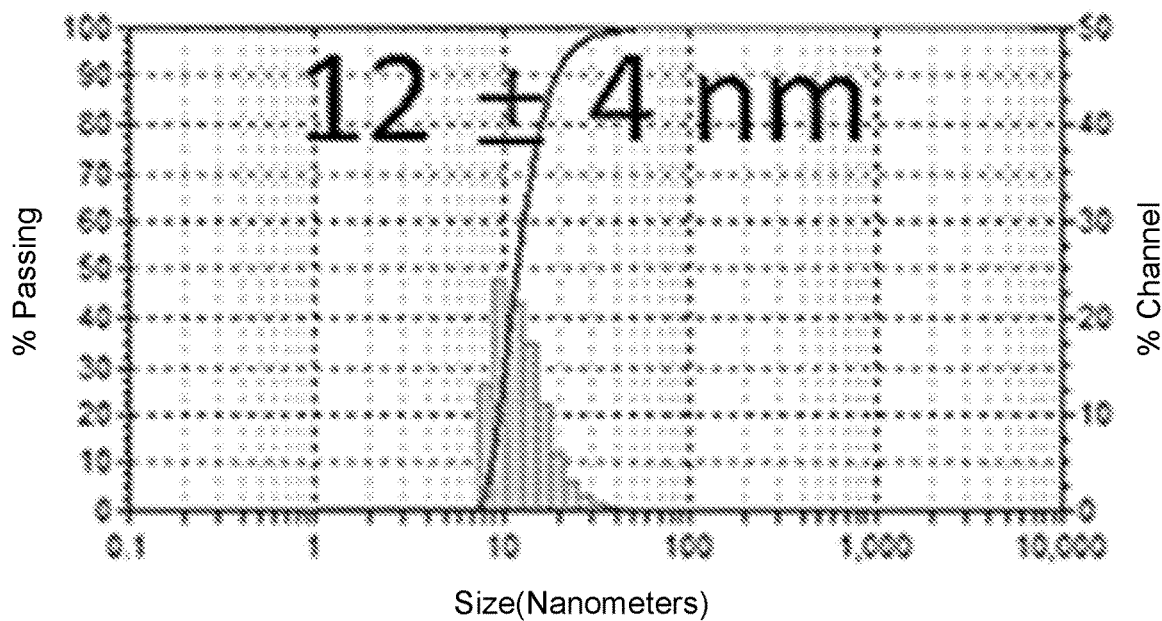
FIG. 2 shows (A, B) particle size of blank TD-1 (A) and TD-2 (B) nanocarriers at a concentration of 1 mg/mL. (C, D) DOX-TD-1 (1:1 w/w) (C) and DOX-TD-2 (1:1 w/w) (D) nanocarriers at a concentration of 1 mg/mL obtained by DLS. (E-H) TEM image of blank TD-1 (E) and TD-2 (F) micelles, 1:1 (w/w) DOX-TD-1 (G) and DOX-TD-2 (H) micelles.
Figure 2:
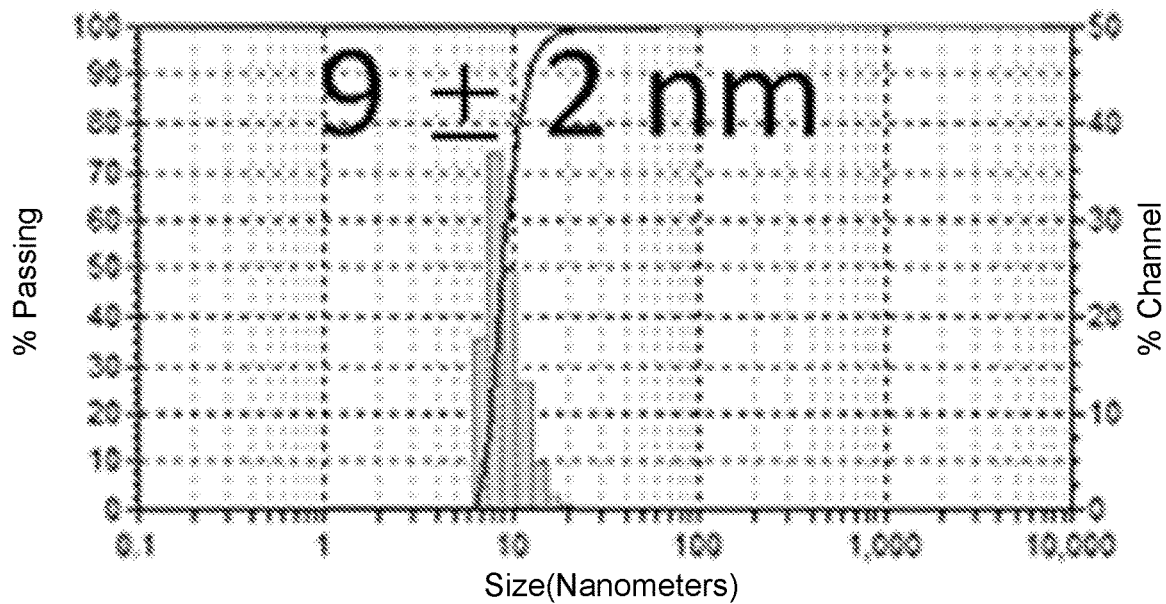
Figure 2:
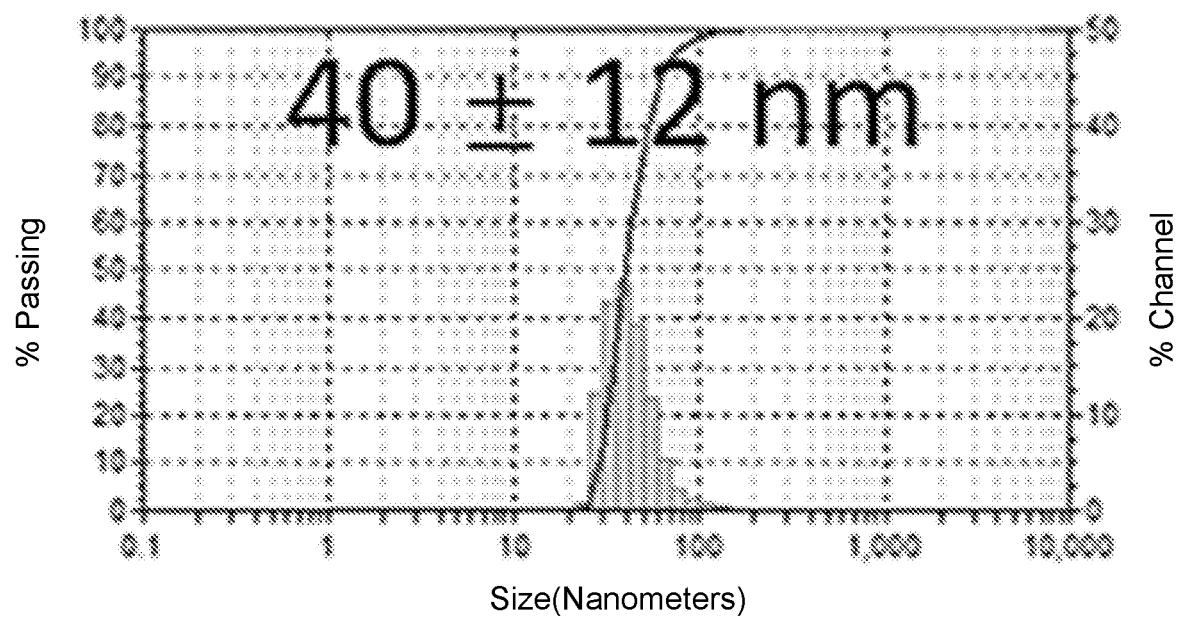
Figure 2:
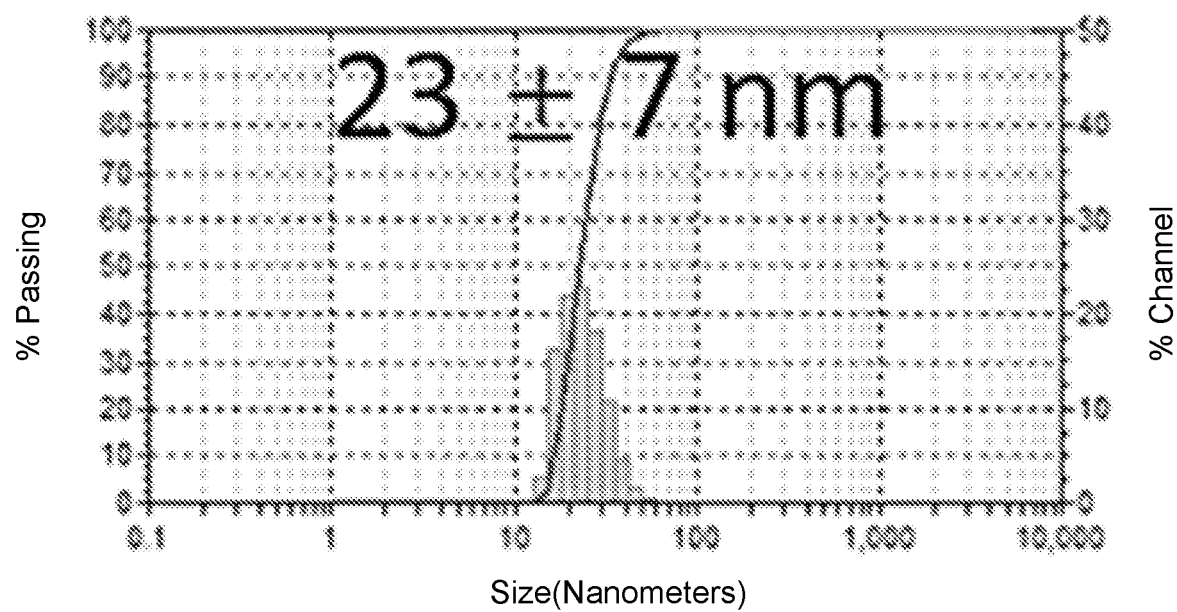
Figure 2:
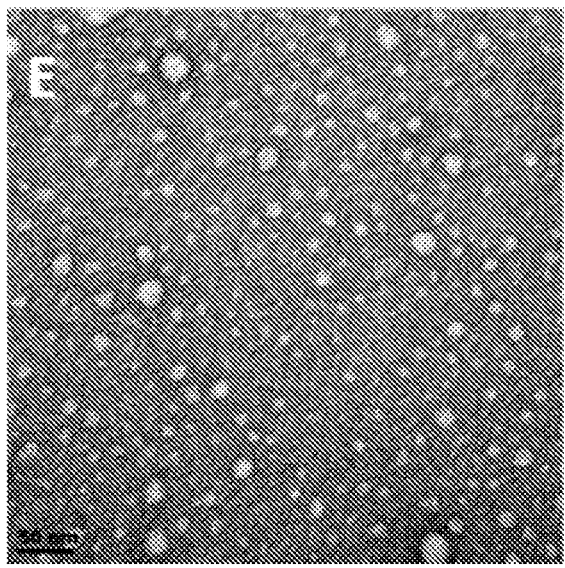
Figure 2:
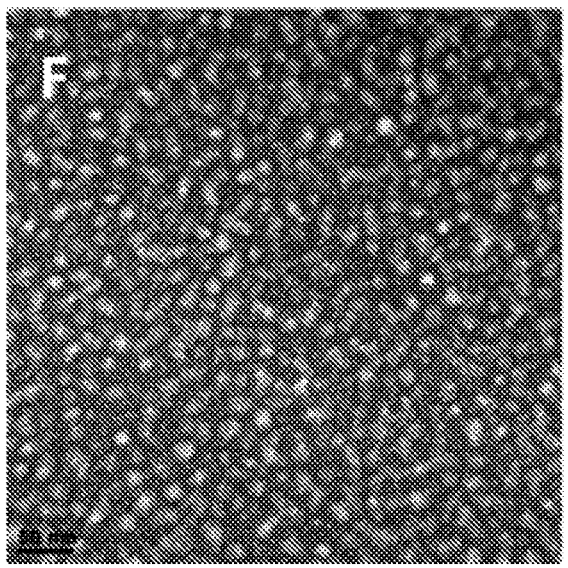
Figure 2:
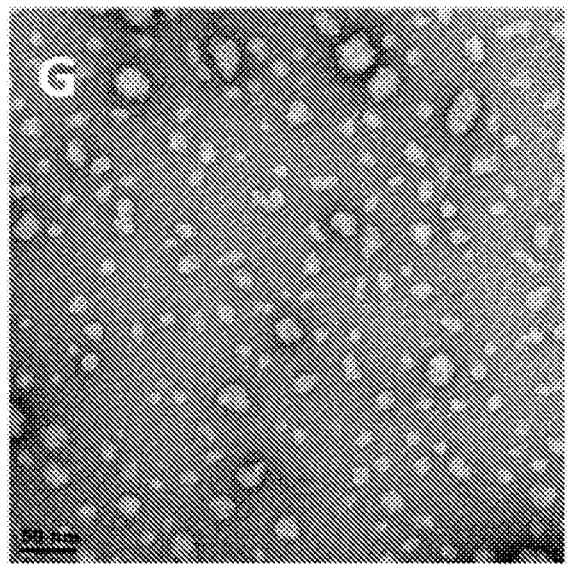
Figure 2:
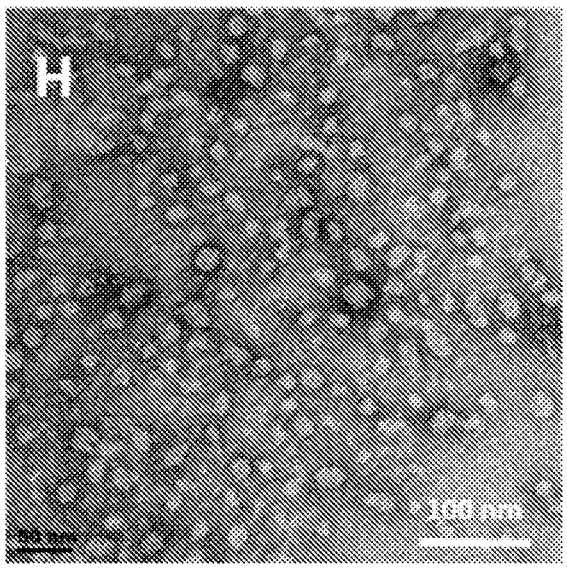
Figure 13:
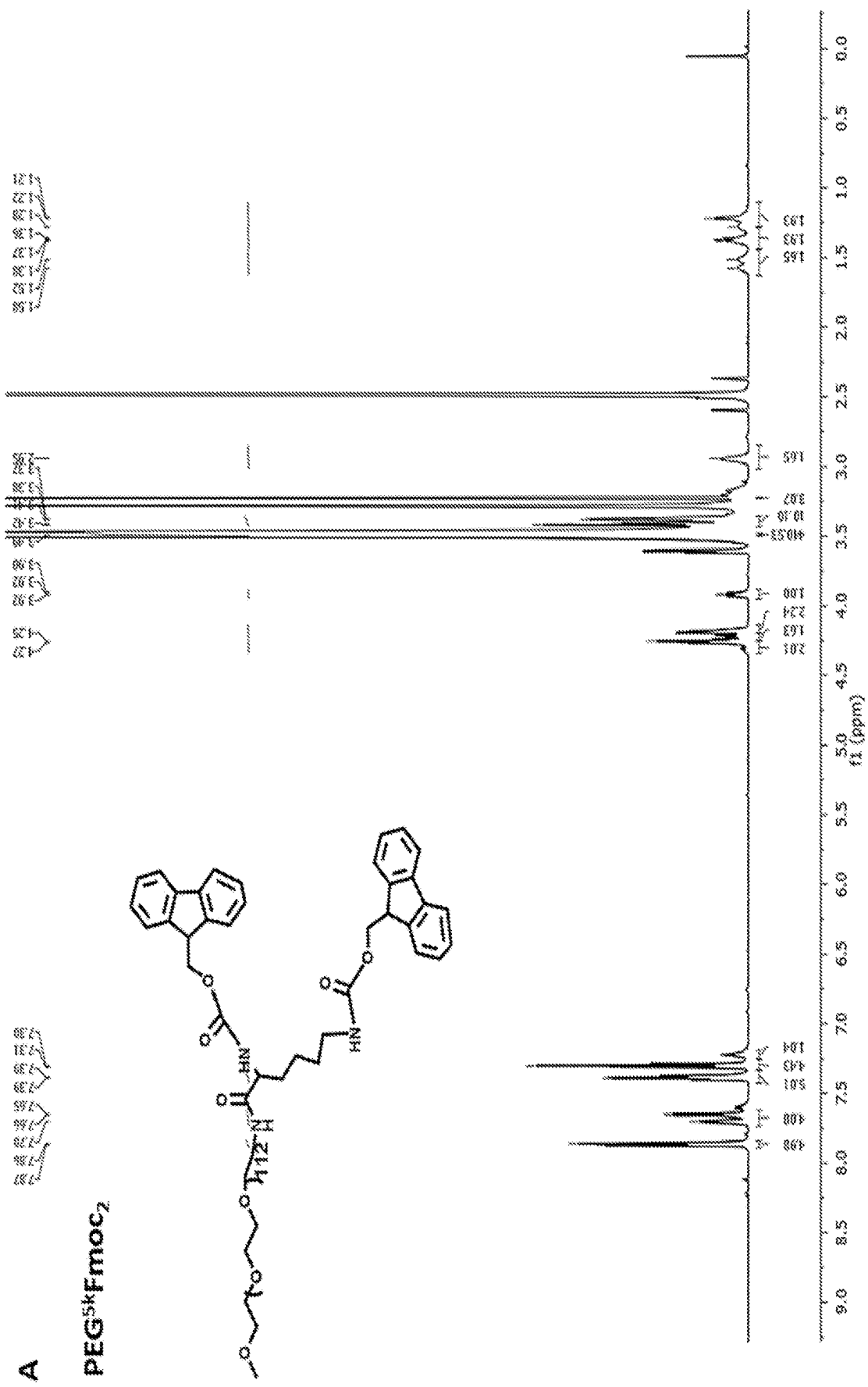
FIG. 13 shows (A-H) $^1$H NMR spectra of PEG$^{5k}$Fmoc$_2$ (A), PEG$^{5k}$fmoc$_4$ (B), PEG$^{5k}$Fmoc$_8$ (C), PEG$^{5k}$Fmoc$_4$Boc$_4$ (D), PEG$^{5k}$CA$_4$Boc$_4$ (E), TD-1(F), TD-2 (G), and Rf—COOH (H). (I) MALDI-TOF MS of Rf, Rf—COOH, and the intermediate telodendrimers for synthesis of TD-1 and TD-2.
Figure 13:
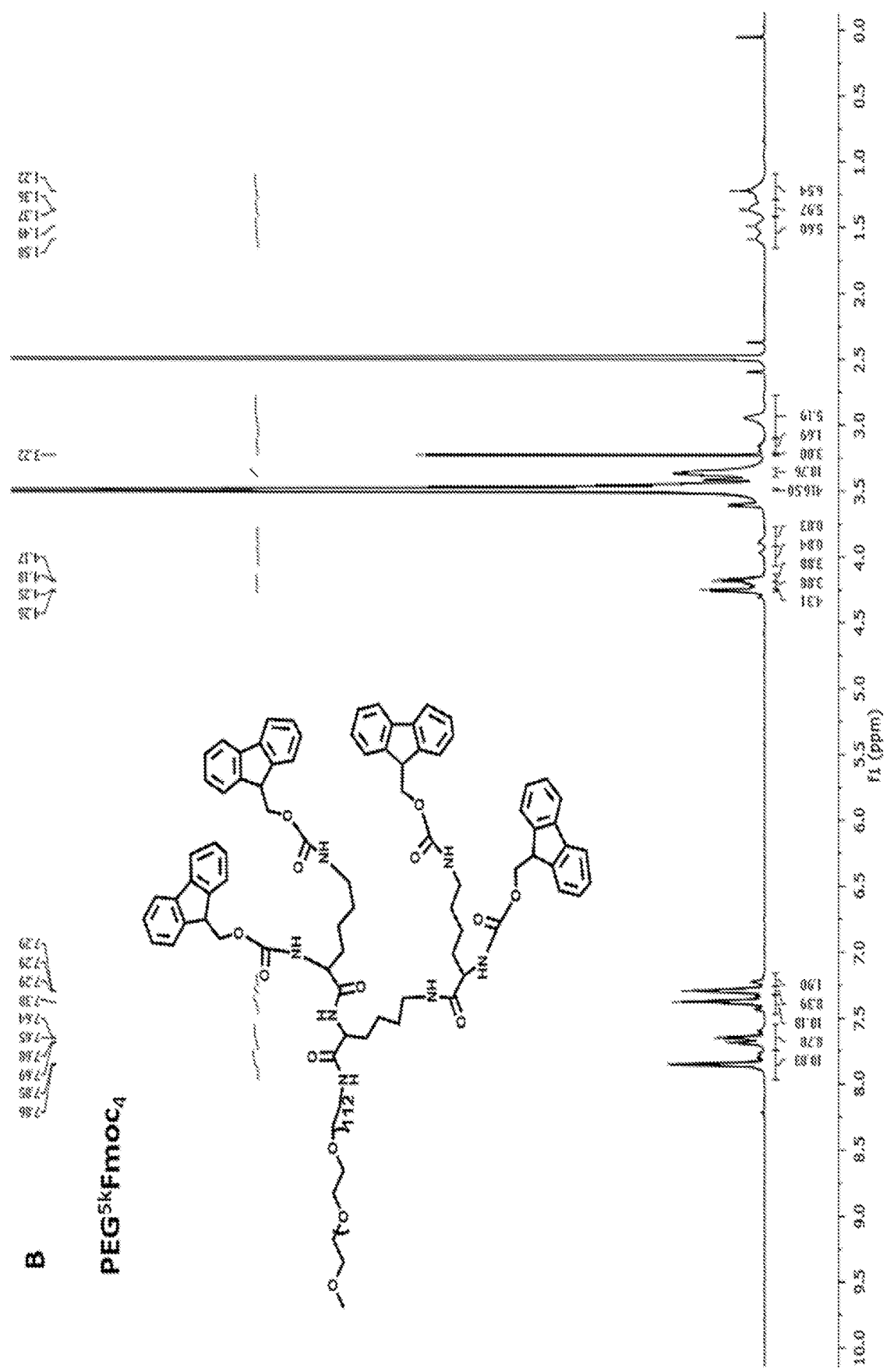
Figure 13:
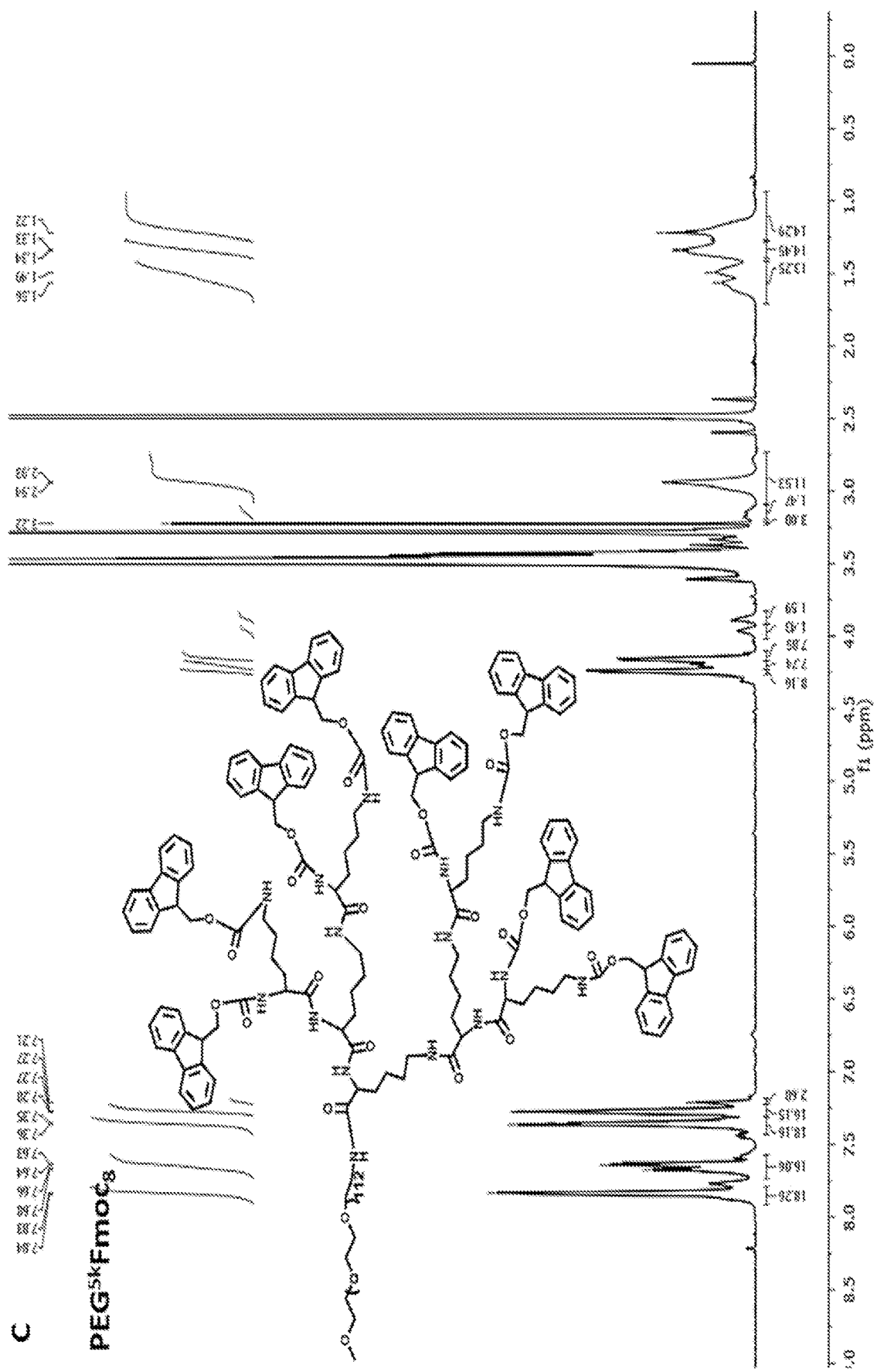
Figure 13:
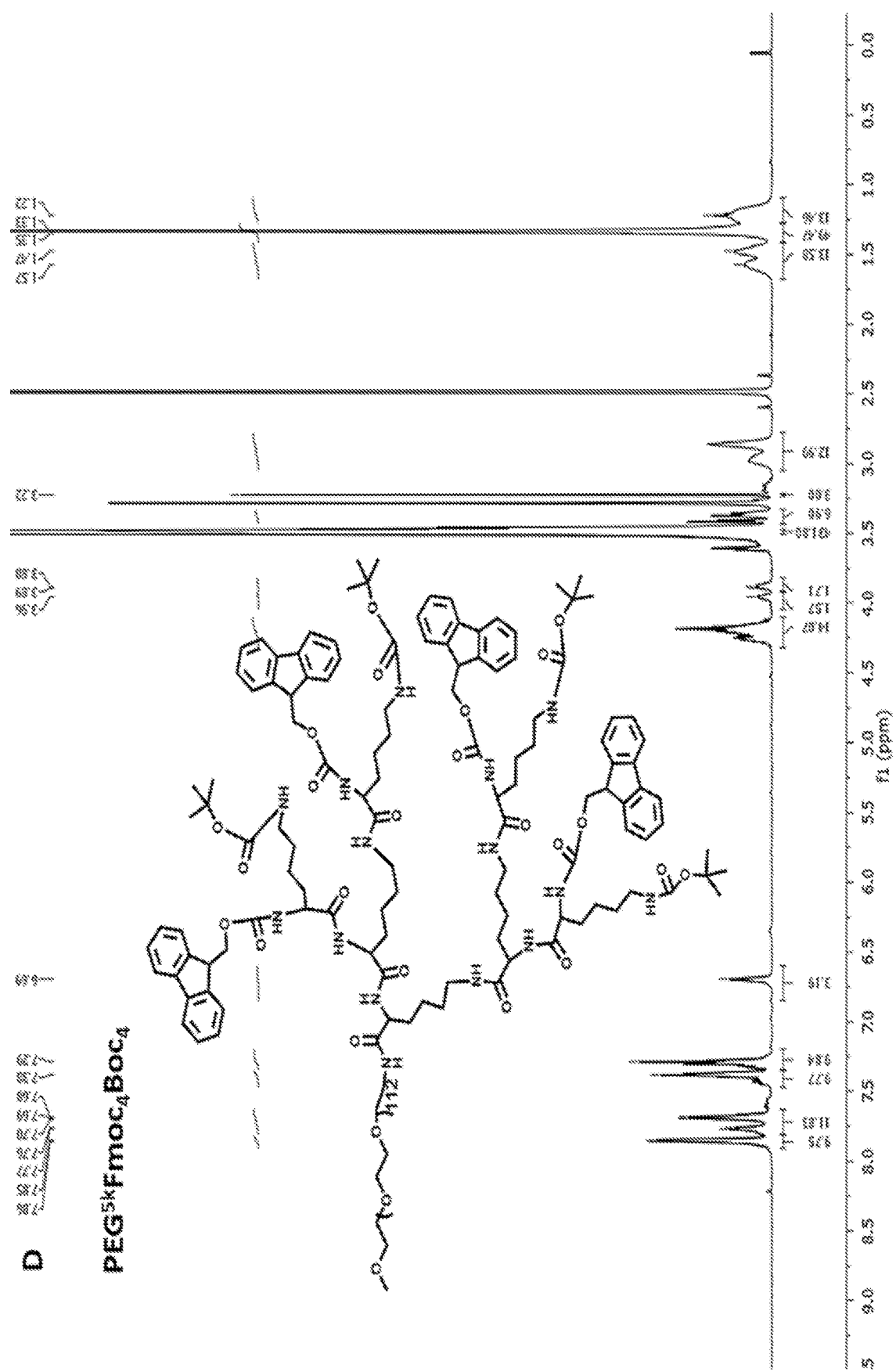
Figure 13:
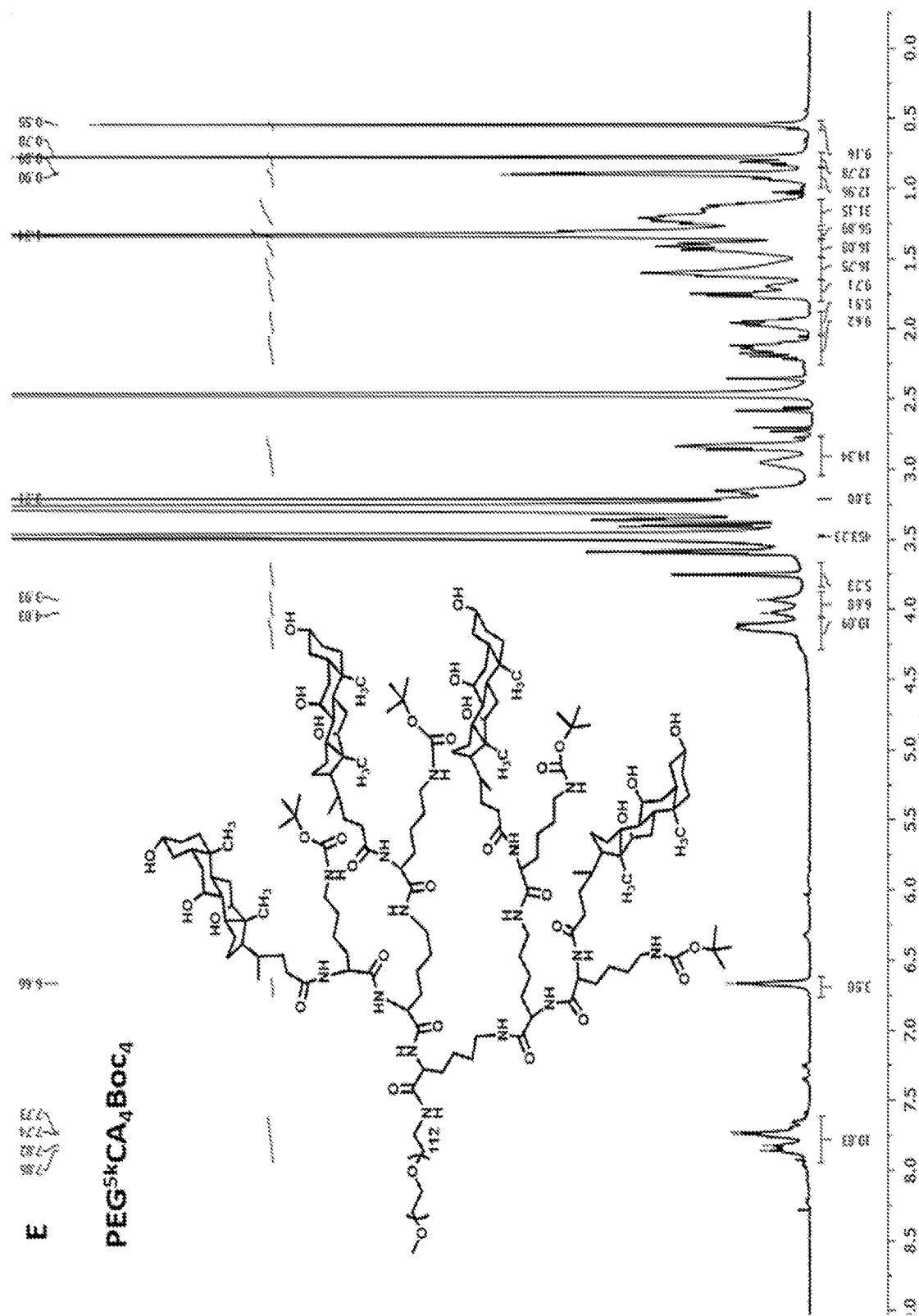
Figure 13:
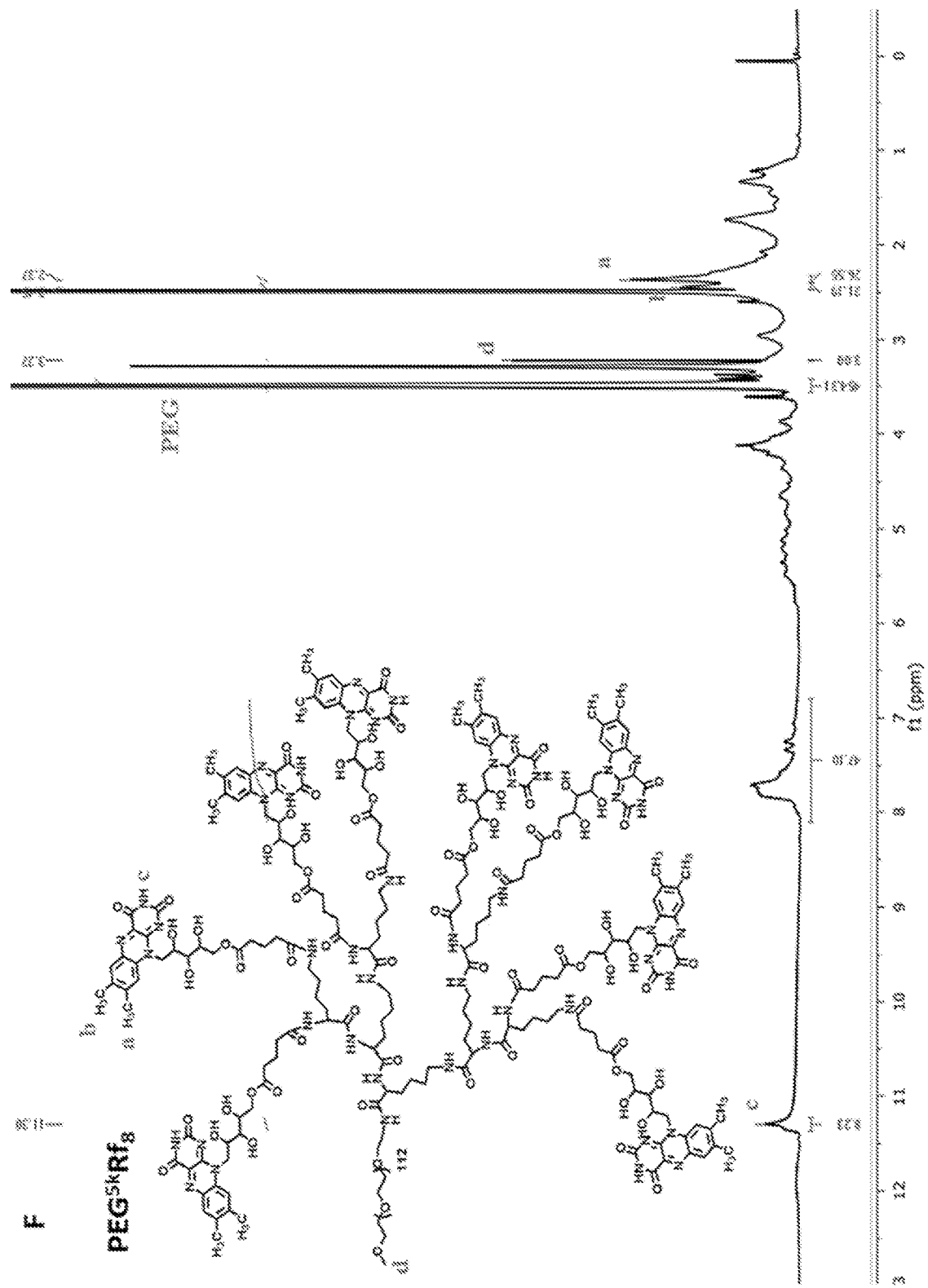
Figure 13:
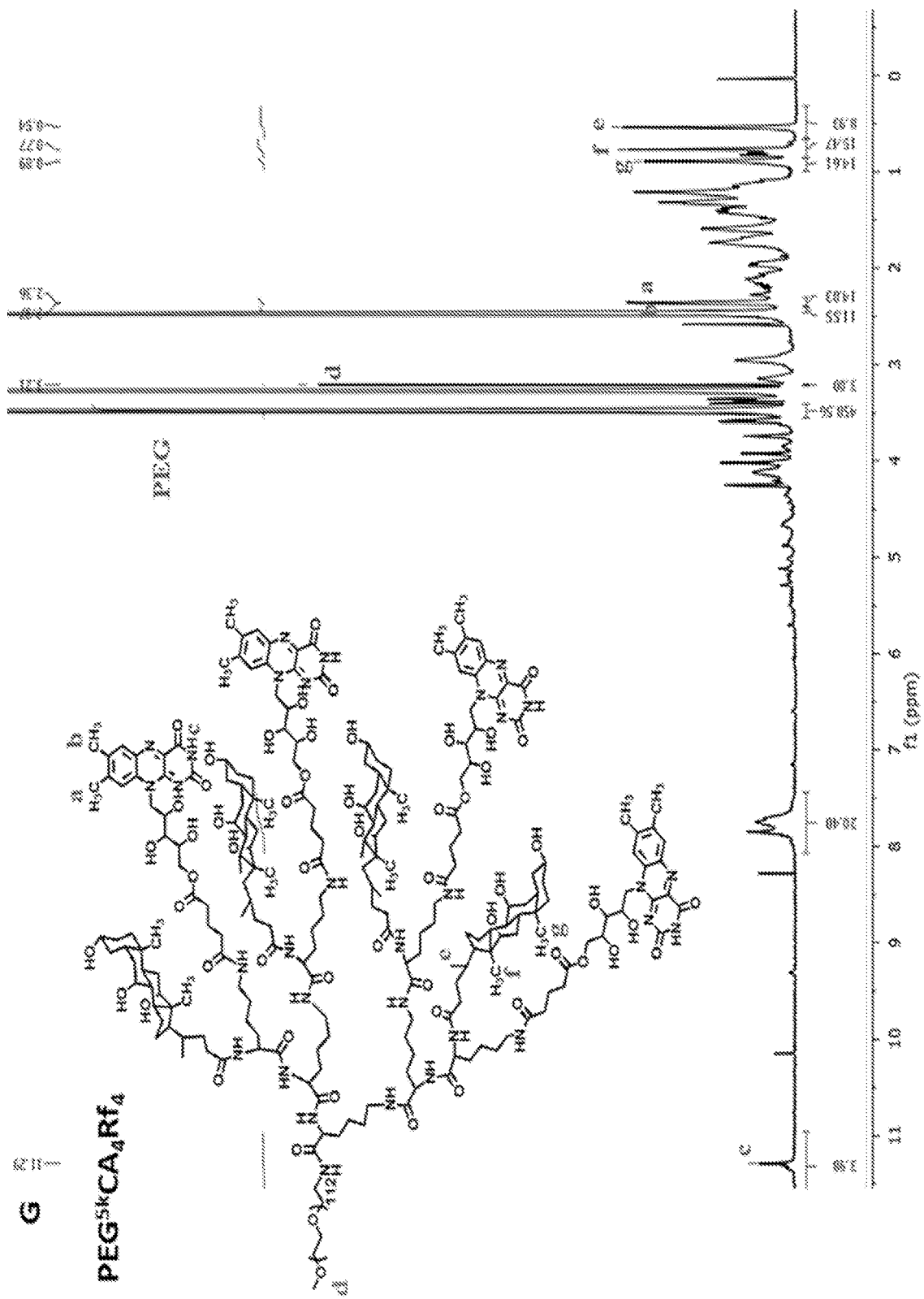
Figure 13:
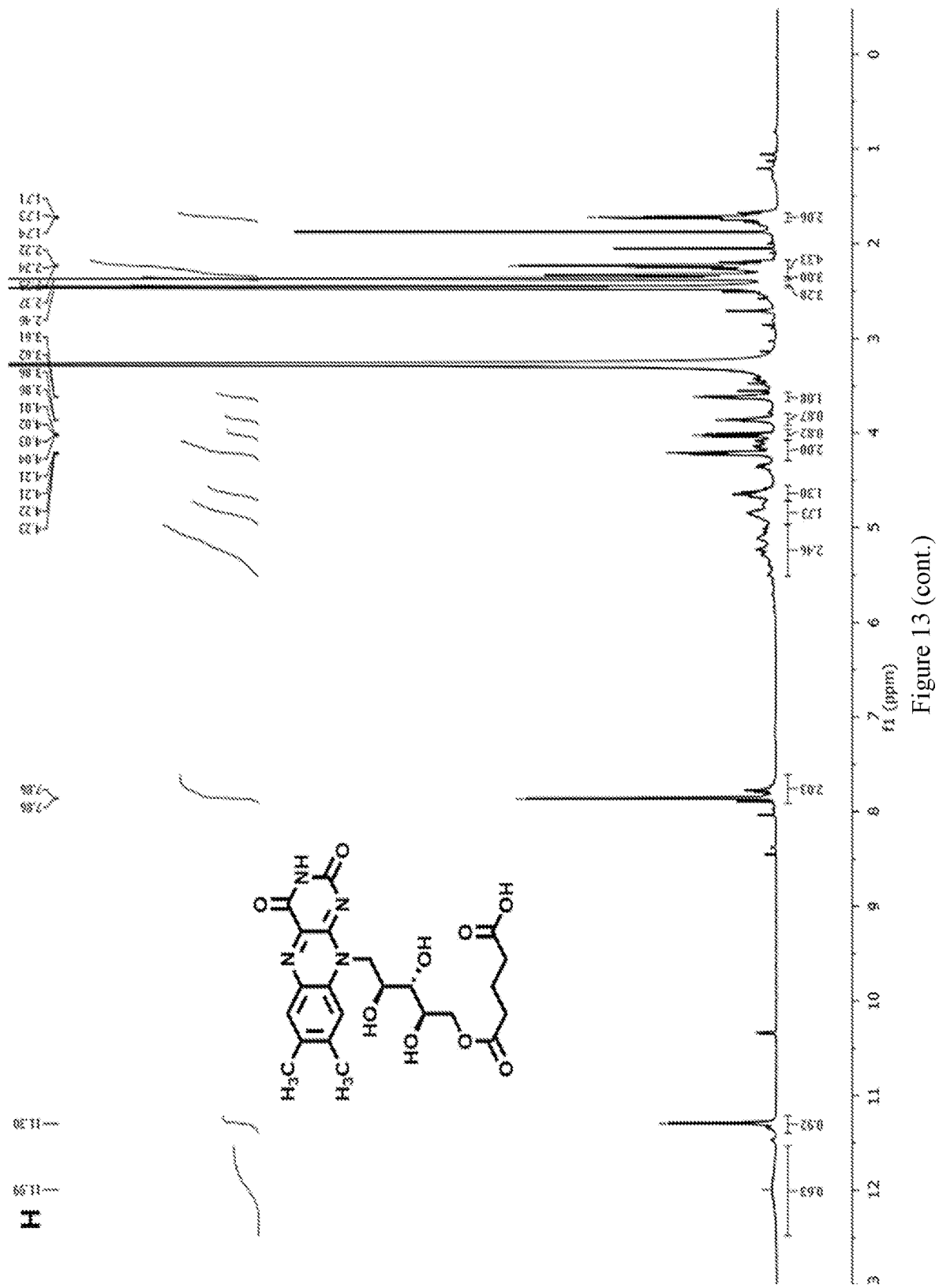
Figure 13:
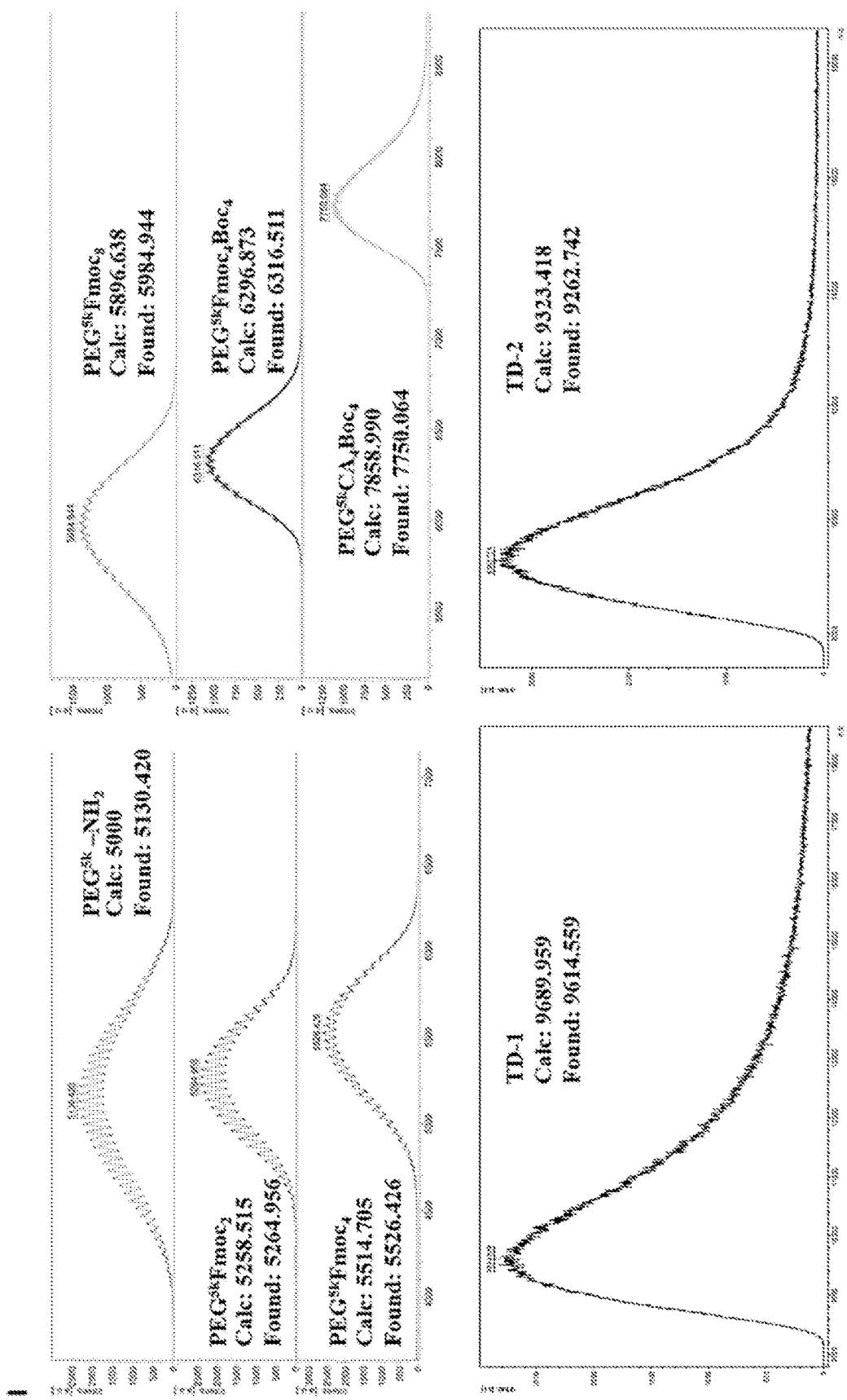
Figure 13:
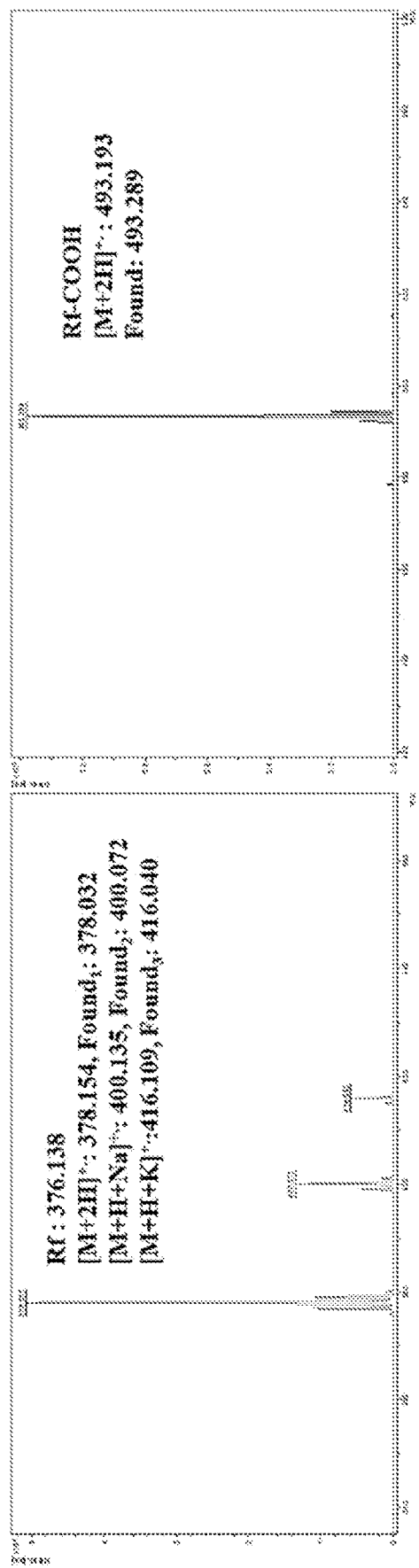
Figure 14:
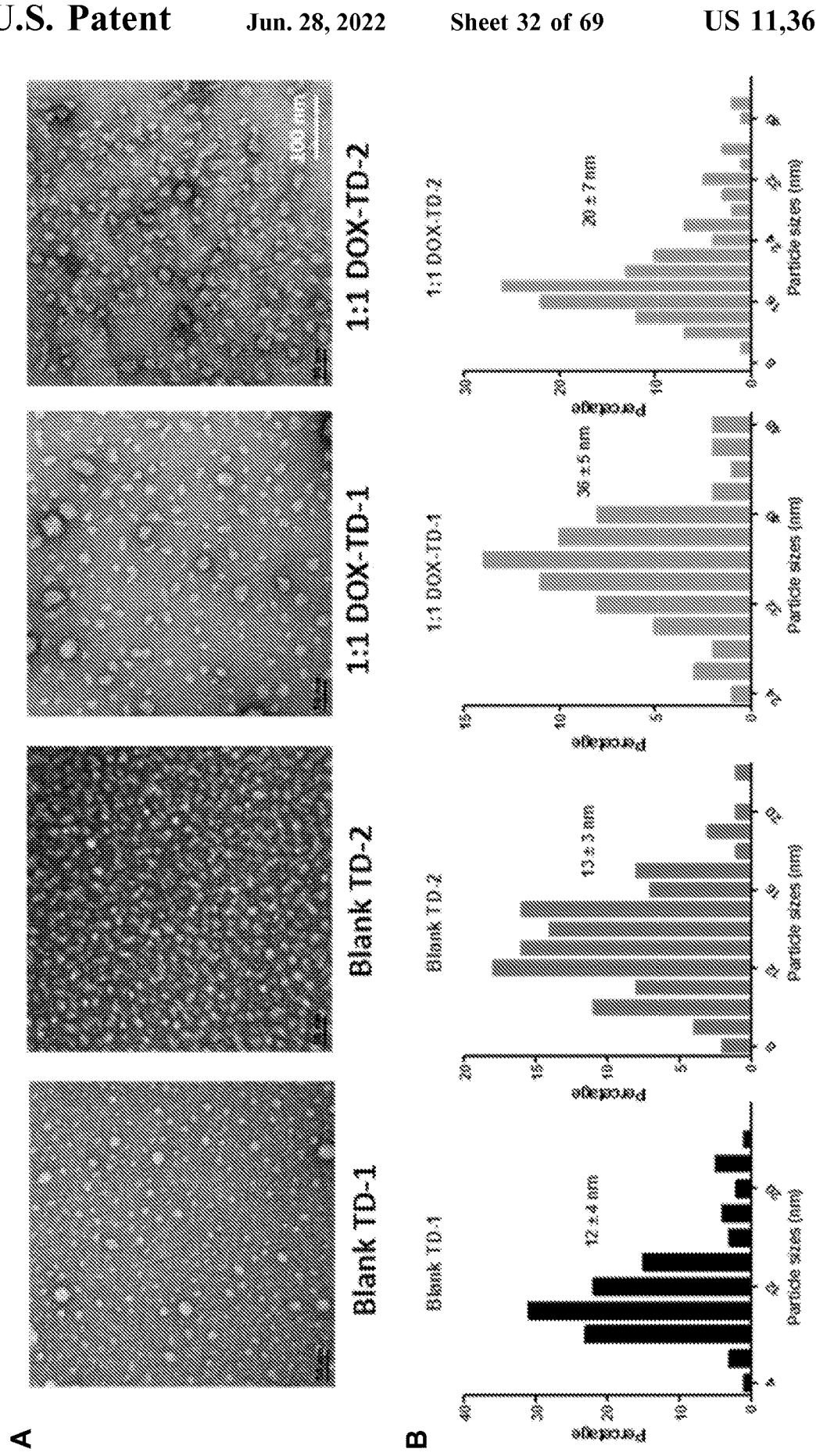
FIG. 14 shows (A) TEM images of blank TD-1, TD-2, 1:1 mass ratio of DOX-TD-1, and DOX-TD-2. (B) Particle size statistics from TEM images of blank TD-1, TD-2, 1:1 mass ratio of DOX-TD-1, and DOX-TD-2 by Nano Measurer 1.2 (B).

The DBM for DOX is Rf, which imposes amphiphilic and structural properties to provide an ideal environment for stabilizing unprecedentedly high amount of DOX with outstanding formulation stability. To conjugate Rf onto the TD backbone, a carboxylic acid derivative of Rf was synthesized and conjugated on the peripheral of $PEG^{5k}Rf_8$ (TD-1) (FIG. 1A) after three steps of lysine coupling. In parallel, a hybrid TD $PEG^{5k}CA_4Rf_4$ (TD-2) was also synthesized as a comparison through orthogonal protecting peptide chemistry as reported in our previous study (FIG. 1B). These TDs were characterized by proton nuclear magnetic resonance ($^1$H NMR) and matrix-assisted laser desorption ionization time of flight mass (MALDI-TOF MS), which revealed precise structures as designed (FIG. 13). As expected, both TD-1 and TD-2 formed well-dispersed spherical micelles with particle sizes of 12 and 9 nm (FIGS. 2A, B, E & F), respectively. DOX was loaded in Rf-containing TD micelles by a thin film hydration method. Remarkably, DOX-TD-1 and DOX-TD-2 nanoformulations exhibited ultra-high DOX loading capacity up to 1/1 ratio in mass and nearly 100% drug loading efficiency. The DOX-TD-1 and DOX-TD-2 nanoparticles are clearly soluble in PBS with particle sizes of 40 and 23 nm (FIGS. 2C & D), respectively, detected by DLS. TEM studies revealed the pseudospherical and narrowly dispersed micelles with the mean diameters consistent with DLS analysis, i.e. 36±5 and 20±7 nm for DOX-TD-1 and DOX-TD-2, respectively (FIGS. 2G & H, FIG. 14).

Figure 3:
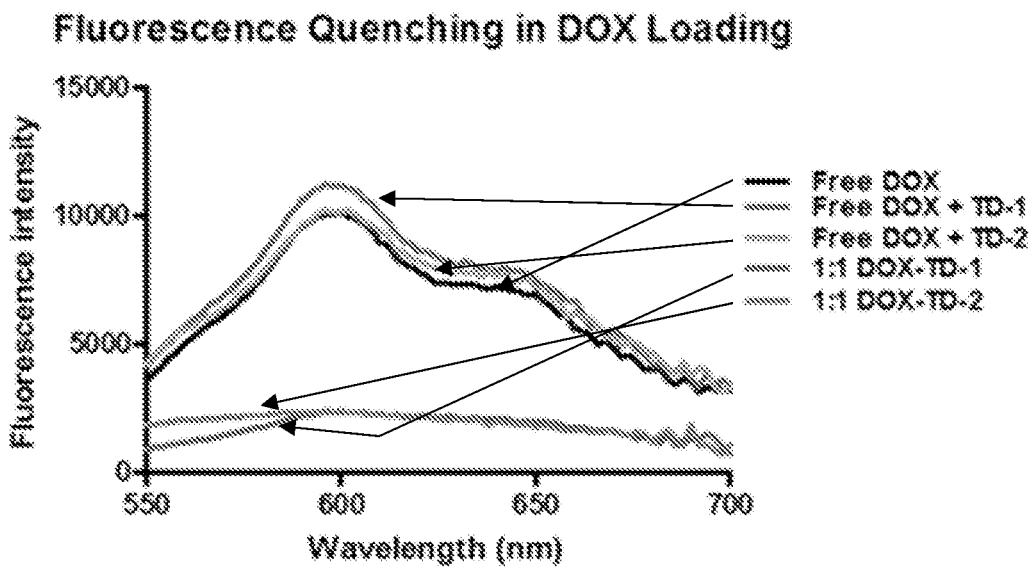
FIG. 3 shows DOX loading efficiency. (A) Fluorescence spectra of free DOX, mixture of free DOX and TD-1, mixture of free DOX and TD-2, DOX-TD-1, and DOX-TD-2 at a concentration of 1 mg/mL. (B) SEC retention time of free DOX, DOX-TD-1, and DOX-TD-2. (C) $^1$H NMR of free DOX, blank TD-1, and DOX-TD-1 (1:10, 1:2, and 1:1 w/w ratio) at a DOX concentration of 0.8 mg/mL. The drug loading efficiency (LE) was calculated based on the DOX integrations between 7.25-7.75 ppm relative to PEG integrations in TDs.
Figure 3:
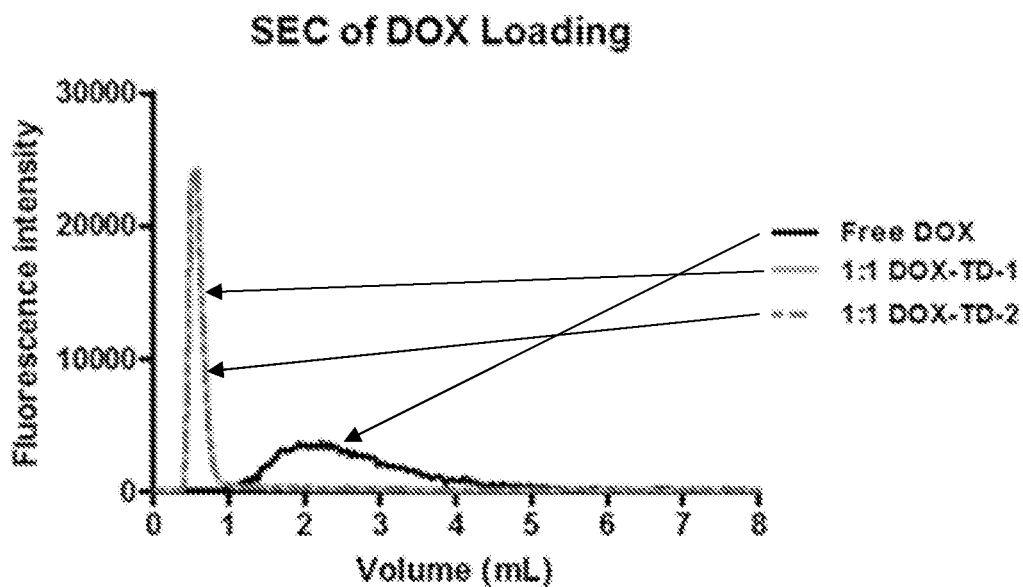
Figure 3:
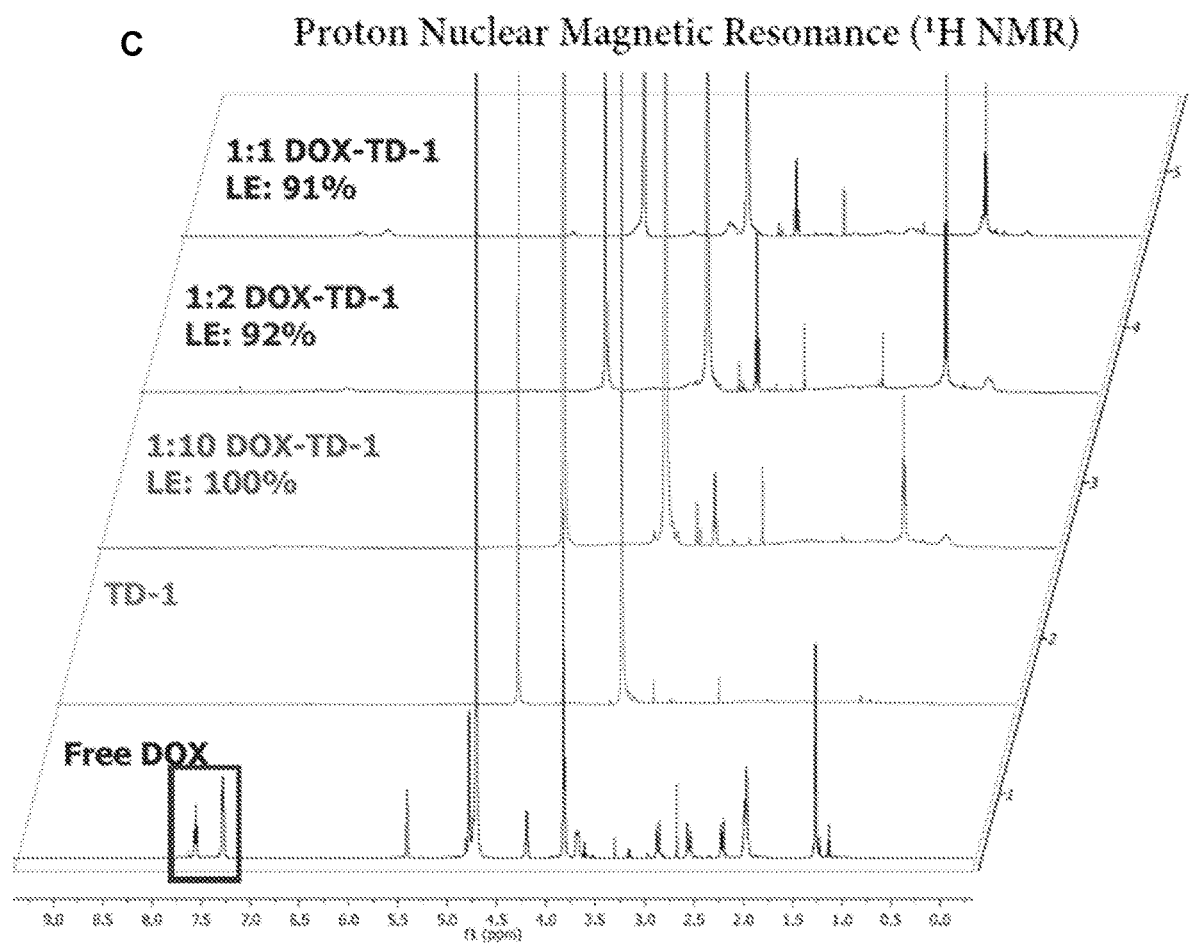
Figure 15:
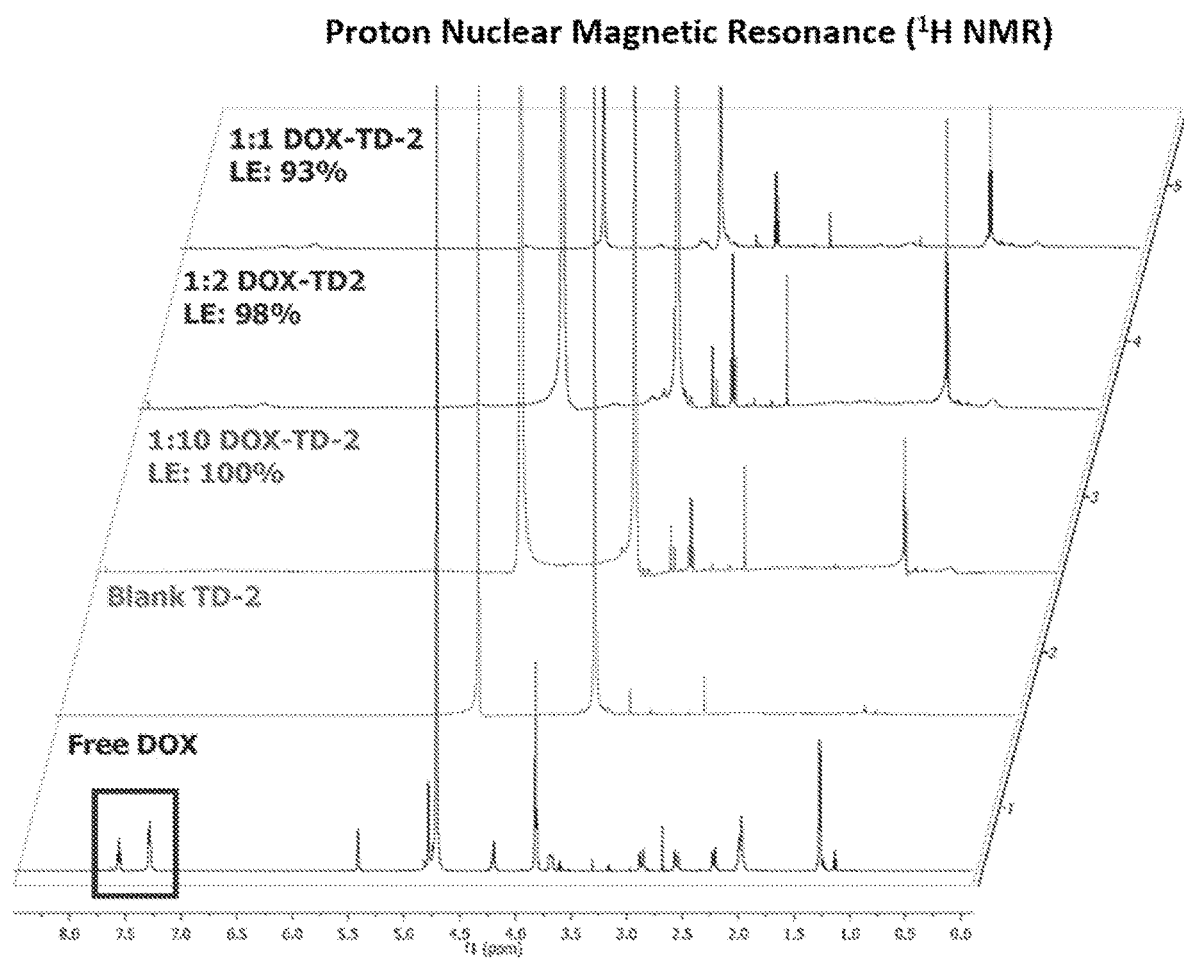
FIG. 15 shows $^1$H NMR of free DOX, blank TD-2, and DOX-TD-2 (1:10, 1:2, and 1:1 w/w ratio) at a DOX concentration of 0.8 mg/mL.

To confirm that the ultra-high loading capacity for DOX in both TD-1 and TD-2 are indeed encapsulated in the nanocarriers other than free DOX in solution, we took several different methods to quantitatively and qualitatively analyze the DOX encapsulation efficiency: i.e. fluorescence quenching, size exclusive chromatography (SEC), $^1$H NMR, and ultracentrifuge filtration. DOX has strong intrinsic fluorescence signal when it dissolved molecularly in aqueous solutions or organic solvents. The fluorescent signal of DOX is usually quenched when molecular stacking and aggregation occurs, especially for π-π stacking, after encapsulated into a nanocarrier. As shown in FIG. 3A, the fluorescent signal of DOX was quenched significantly after loaded in Rf-containing TDs at 1:1 mass ratio, in comparison with that of the free DOX. In contrast, the DOX fluorescence signal maintained after physically mixed with these TDs in aqueous solution other than through a thin-film loading process. No free DOX was detected in the DOX nanoformulations after SEC analysis, indicating almost 100% DOX loading efficiency (FIG. 3B). From $^1$H NMR spectra, the proton signal of free DOX dissolved in $D_2O$ was clearly detected, while the proton signal of the encapsulated DOX in the nanocarriers were significantly decreased by the reduced molecular motion by physical entanglement in nanocarriers. Based on the integration of protons signals on the aromatic rings of DOX, the LE of both Rf-containing nanoformulations were over 90% (FIG. 3C, FIG. 15). The relatively low LE detected by NMR is due to the detection of the loosely bounded DOX in nanocarriers, which is not necessary to be free DOX in solution. The ultracentrifuge filtration was used to separate free DOX and encapsulated DOX. By detection of DOX UV-absorbance, free DOX amount was calculated in each nanoformulation. The LEs for DOX-TD-1 and DOX-TD-2 are 97% and 100%, respectively (Table 1). These results indicated both Rf-containing TDs indeed have ultra-high DOX loading capacity at 1:1 mass ratio with almost 100% loading efficiency within relatively small particle sizes of 20-40 nm. In this environment, even at an ultra-high loading ratio, the DOX remains molecularly dispersed well in the micelle having a spherical shape. Due to their low viscosity, they can be readily injected as prepared at high concentration. This formulation property compares very favorably to other DOX formulations in clinics and in the late stage clinical trials.

TABLE 1

Particle sizes of fresh and 1 month-stored DOX-TD-1 and DOX-TD-2 at 1:1 mass loading ratio.

| Nanoformulations | DOX-TD-1 | DOX-TD-2 |
|---|---|---|
| UV abs. before Cent. | 1.328 | 1.347 |
| UV abs. after Cent. | 0.038 | 0.003 |
| LE % | 97% | 100% |

Stability of DOX-Loaded Rf-Containing Nanoformulations—

Figure 4:
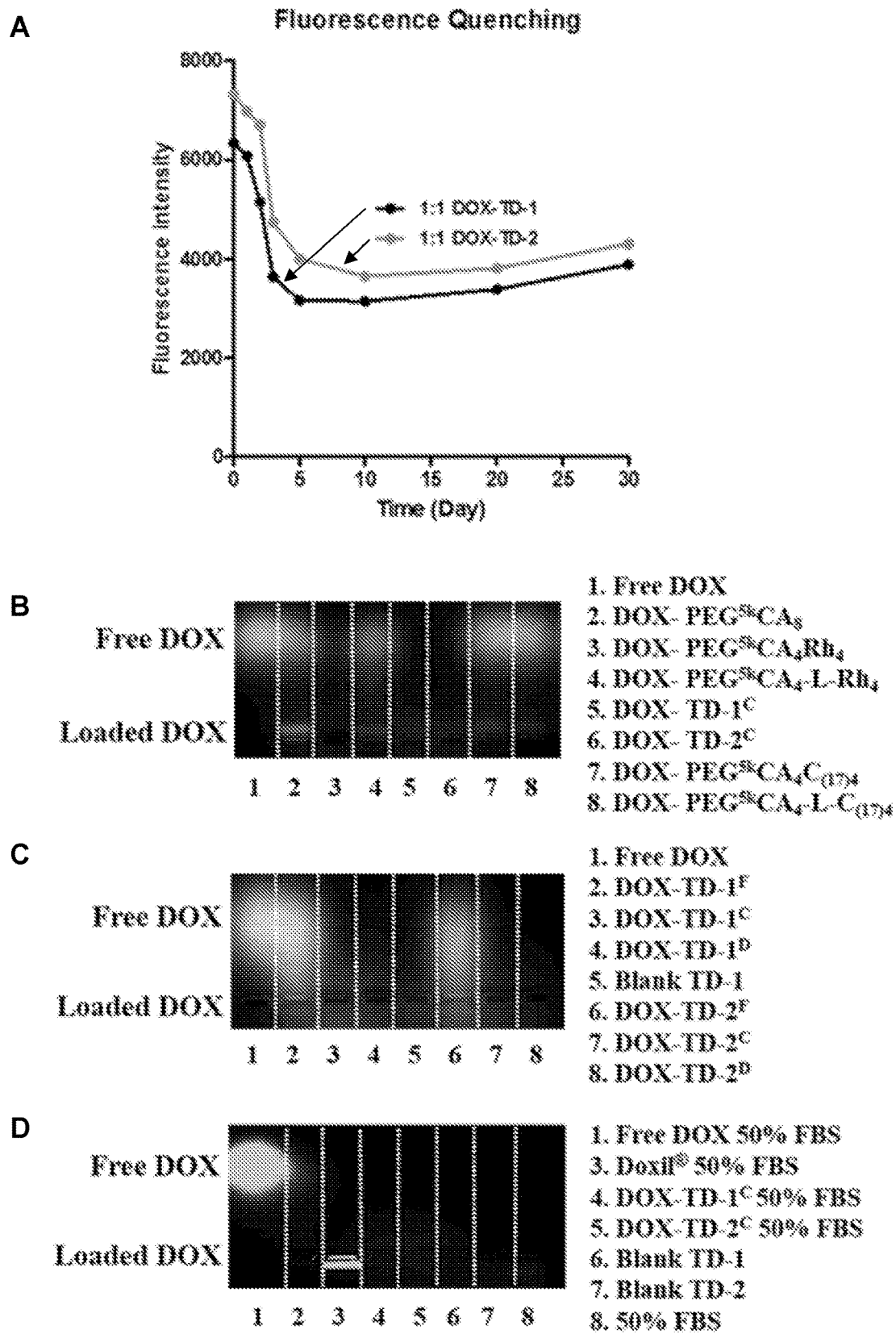
FIG. 4 shows DOX loading stability. (A) Fluorescence quenching of DOX-TD-1 and DOX-TD-2 at a concentration of 1 mg/mL monitored for 1-month. (B-D) Agarose gel electrophoresis of free DOX, DOX-TD-1, DOX-TD-2, and other our previously reported TD-based DOX nanoformulations (B), fresh, cured, and dialyzed DOX-TD-1 (C), and 50% FBS with free DOX, Doxil®, cured DOX-TD-1 and DOX-TD-2 (D). $^F$ means fresh, $^C$ means cured, $^D$ means dialyzed.
Figure 16:
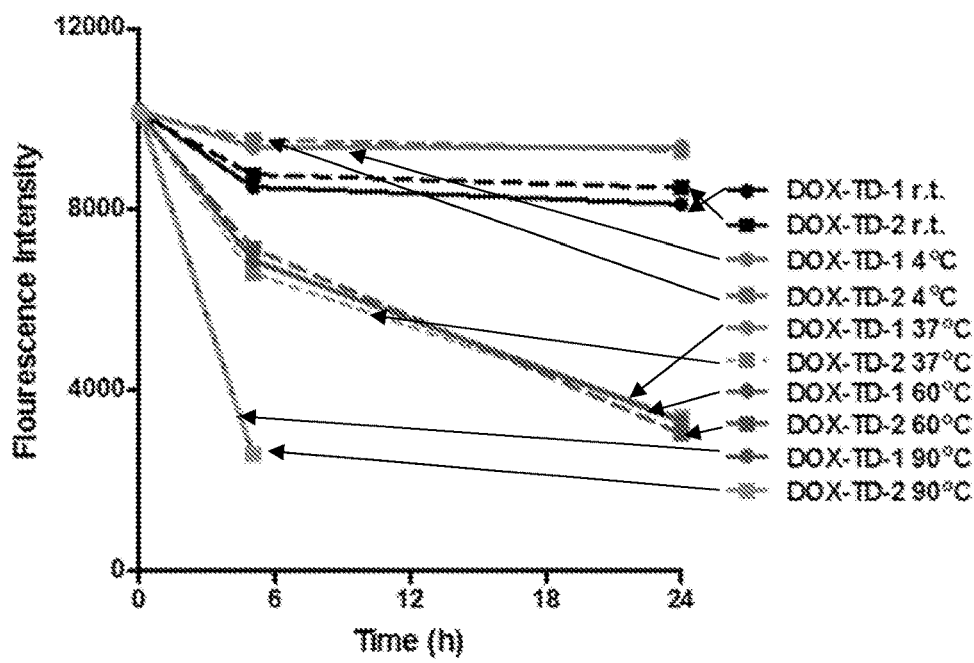
FIG. 16 shows (A) DOX loading stability of fluorescence quenching of DOX-TD-1 and DOX-TD-2 at concentration of 1 mg/mL monitored for 24 h at 4° C., room temperature, 37° C., 60° C., and 90° C. (B-D) DOX fluorescence intensity of free DOX (B), DOX-TD-1c (C), and DOX-TD-2c (D) in 0%, 5%, 10%, 30%, and 50% FBS.
Figure 16:
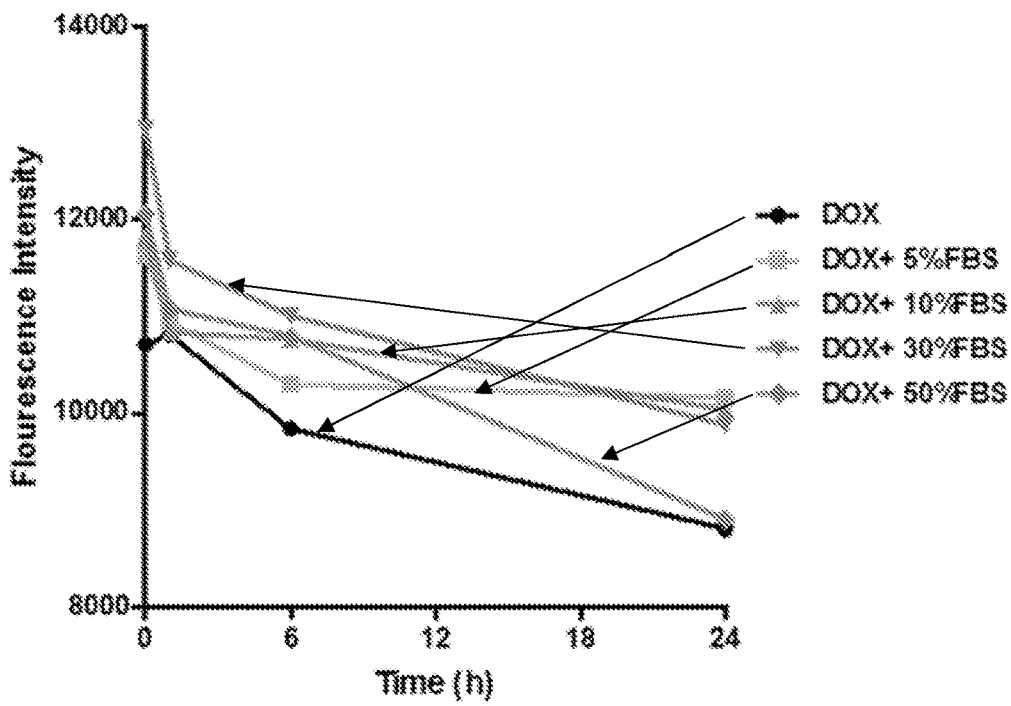
Figure 16:
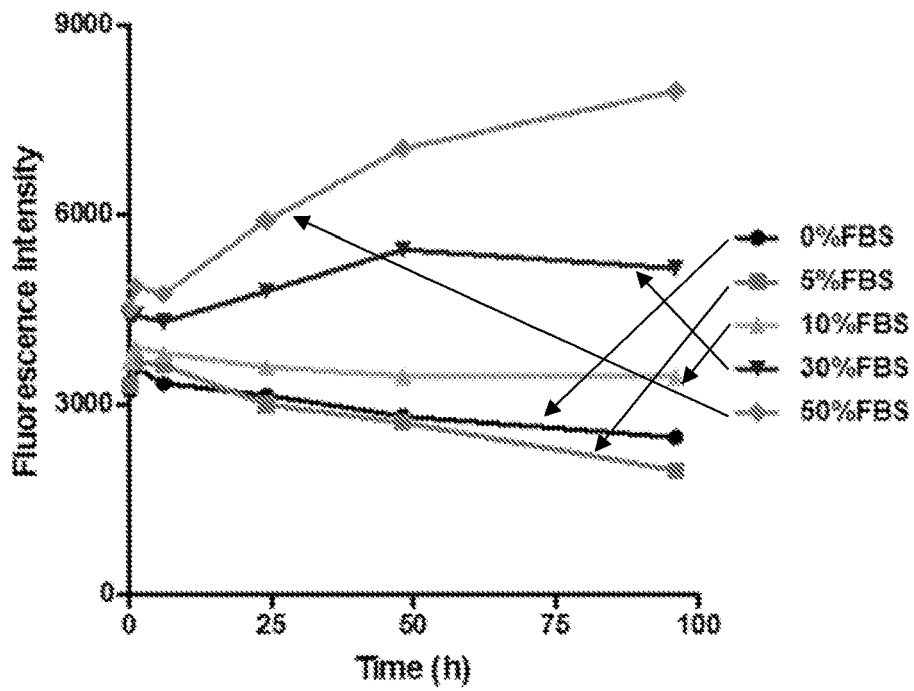
Figure 16:
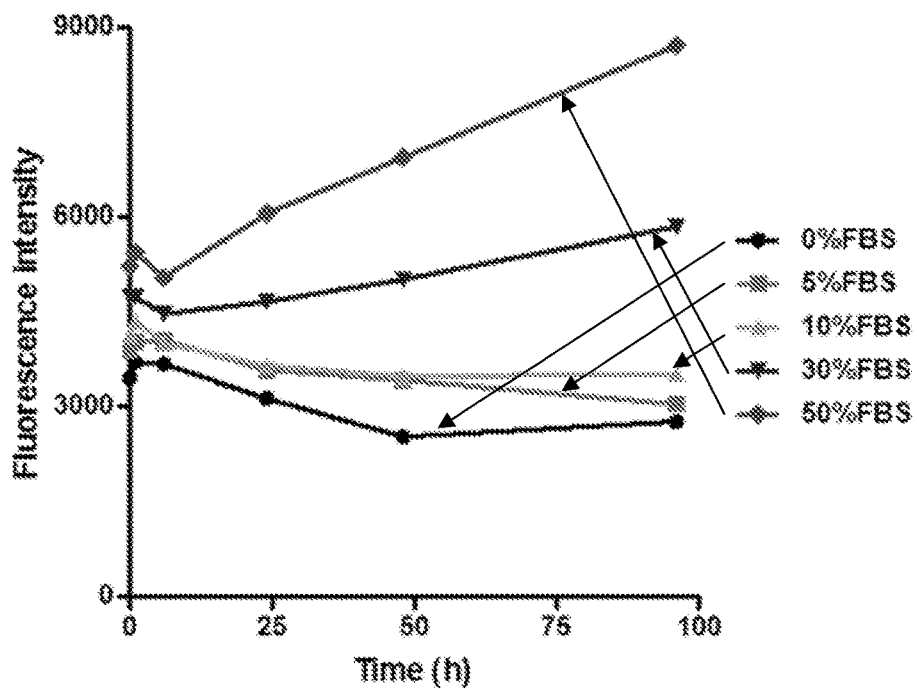

We have continuously monitored these two nanoformulations for months and found no changes at ambient conditions. DOX-loaded Rf-containing nanoformulations were stored at room temperature for a month. The particle sizes and fluorescence signal of these samples were monitored without further ultra-sonication. After a month-long storage, the particle sizes of DOX-TD-1 and DOX-TD-2 remain around 37 and 24 nm (Table 2), respectively, without significant difference when compared to the fresh samples. The fluorescence signal of encapsulated DOX was further quenched gradually upon storage during 5 days at room temperature in comparison to the freshly loaded samples (FIG. 4A). We named these samples with a 5-day annealing process as 'cured' samples. This annealing process can be accelerated by the increased temperature, e.g. 37° C. (FIG. 16A). This phenomenon indicates a dynamic molecular rearrangement within the core of the nanocarriers, where the loosely bounded and randomly dispersed DOX molecules (highly fluorescent) start to anneal to form stacking with Rf and DOX (quenched) within the core of a micelle (FIG. 5). It is also correlated with the size and morphology changes from 12 to 40 nm, 9 to 23 nm, and from spherical to the nano-constructs under TEM after DOX loading (FIGS. 2E, F, G & H), which indicate the aligned molecular stacking. It is surprising to us that the number of DOX molecules is about two and four times more than Rf in TD-1 and TD-2, respectively, at an efficient loading ratio of 1:1 (drug/nanocarrier). It indicates that Rf serves as an efficient anchor or seed, other than a physical barrier, for DOX and DOX oligomers to stably reside in the core of TD nanocarriers. Therefore, majority of the loosely bounded DOX in the freshly prepared nanoformulations can be dynamically rearranged into the core of Rf-containing nanocarriers efficiently by a simply 5-day storage at room temperature or one day at 37° C. The rest small amount loosely bounded DOX from cured nanoformulations can be easily removed by a dialysis for 10 h, which remains 70% of DOX still encapsulated with the fluorescence efficiently quenched.

TABLE 2

DOX loading efficiency from ultracentrifugation filtration of DOX-TD-1 and DOX-TD-2 at 1:1 mass loading ratio.

| Samples | Size (nm) (Fresh) | Size (nm) (1 month) |
|---|---|---|
| 1:1 DOX-TD-1 | 40 ± 12 | 45 ± 16 |
| 1:1 DOX-TD-2 | 23 ± 7 | 21 ± 5 |

Electrophoresis has been applied to characterize the efficiency for nanocarriers in complexing with gene and protein molecules. As the DOX molecule has a positively charged amine, which can migrate in the agarose gel along an electric field. In contrast, if DOX is stably loaded in a nanocarrier, it will be trapped in the loading well due to the size and charge effects. This is the first time to apply agarose gel electrophoresis to characterize DOX loading efficiency and stability in various nanocarriers. As expected, free DOX migrate efficiently to the cathode across the agarose gel under an electric field (FIG. 4B). The cured 1:1 (DOX:TD) mass loading ratio DOX-TD-1 and DOX-TD-2 (DOX-TD-$1^C$ & DOX-TD-$2^C$) nanoformulations were characterized in comparison with our previously reported sub-optimal and optimized TD nanoformulations at a 1:10 (DOX:TD) mass loading ratio, including DOX-PEG$^{5k}$CA$_8$, DOX-PEG$^{5k}$CA$_4$Rh$_4$, DOX-PEG$^{5k}$CA$_4$-L-Rh$_4$, DOX-PEG$^{5k}$CA$_4$C17$_4$, and DOX-PEG$^{5k}$CA$_4$-L-C17$_4$. FIG. 4B showed that DOX loaded in TD-1, TD-2, and PEG$^{5k}$CA$_4$Rh$_4$ were completely trapped in the loading well with the fluorescence still efficiently quenched; while DOX leaks out from the nanocarriers formed by TD with weaker DBMs, e.g. PEG$^{5k}$CA$_8$, PEG$^{5k}$CA$_4$C17$_4$, and PEG$^{5k}$CA$_4$-L-C17$_4$. Surprisingly, DOX partially leaks out from a three-layered TD PEG$^{5k}$CA$_4$-L-Rh$_4$ with a very strong DBM, rhein (Rh). In contrast to the two-layered hybrid PEG$^{5k}$CA$_4$Rh$_4$ that can trap DOX stably in the core of the nanocarriers, partial DOX was trapped in the CA-containing intermediate layer loosely in the three-layered PEG$^{5k}$CA$_4$-L-Rh$_4$ micelles, which leaks out of the nanocarrier driven by electric force. All above results indicate that our newly developed DOX-TD-1 and DOX-TD-2 nanoformulations has superior DOX loading capacity and stability than our previously reported nanoformulations. Further, we apply this method to evaluate DOX encapsulation stability in freshly prepared, cured over time, and dialyzed DOX-TD-1 and DOX-TD-2 (DOX-TD-$1^D$ & DOX-TD-$2^D$) nanoformulations. As shown in FIG. 4C, DOX leaked out partially from the freshly prepared DOX-TD-1 and DOX-TD-2 (DOX-TD-$1^F$ & DOX-TD-$2^F$) nanoformulations and migrated as a tailed band, indicating the leaked DOX are loosely bounded other than free DOX. While DOX loaded in the cured and dialyzed samples were still trapped in the loading wells and the fluorescence signals were significantly quenched. This observation is consistent with the previous fluorescence quenching study.

Although the nanoformulations are stable for month in PBS solution, we still cannot assume that they will also stable in the blood, which contains high protein concentrations. Micelle is a dynamic nano-construct that can exchange both payload drugs and surfactant/polymer matrices with surroundings, especially in the blood circulation in the presence of serum proteins. Therefore, we investigated DOX encapsulation stability in DOX-TD-1 and DOX-TD-2 nanoparticles in the presence of fetal bovine serum (FBS) by fluorescent measurements and agarose gel electrophoresis. Doxil® is known to be the most stable DOX nanoformulation, which was therefore used as a positive control to be compared with our DOX-loaded Rf-containing nanoformulations. Once the FBS was added into DOX-TD-1 and DOX-TD-2 formulations, the 30% and 50% FBS samples showed DOX fluorescence slightly increased immediately and then became stable (FIGS. 16B, C & D), indicating there was a small amount of DOX that exchanged between micelles and FBS. However, majority of the DOX was still stably loaded in our micelles when compared to the free DOX mixed with FBS (FIG. 16B). After 24 h incubation with FBS, the fluorescence intensity increased slightly in 30% and 50% FBS samples (FIGS. 16C & D). As shown in FIG. 4D, no significant DOX leaked out from the DOX-TD-1 and DOX-TD-2 formulations or associated with FBS when compared to the free drug, implying high stability of our DOX-encapsulated Rf-containing nanoformulations in vivo. DOX interact with serum proteins. Therefore, the polymer micelles are competing with the serum protein for DOX binding, suggesting that serum albumin represents a sink for DOX from Rf-containing nanoformulations, and there should be a rapid exchange between this two DOX locations. For the in vivo situation, we think DOX can be released from micelles to the serum albumin to reach a dynamic equilibrium as the polymer are excreted by kidney. However, it should be noted that our nanoformulations are still stable in the presence of serum as shown in the agarose gel electrophoresis. Thus, in the initial moment when the concentration of DOX in the blood is high, a significant portion of DOX molecules remain in the micelles. This may help us to explain that the MTD of our nanoformulations is much higher than free DOX. All these results suggest that compared to the TDs we designed previously, these Rf-containing nanoformulations have significantly enhanced DOX loading capacity and stability due to the strong interactions between Rf and DOX.

In Vitro Drug Release Profiles—

Figure 6:
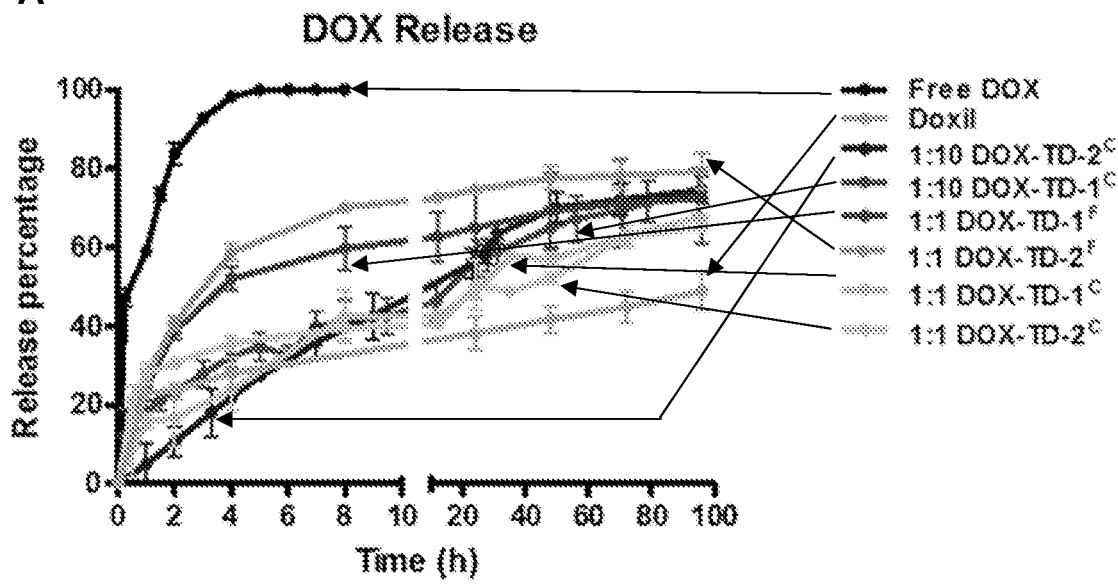
FIG. 6 shows (A) in vitro cumulative DOX release profiles of free DOX, Doxil®, fresh and cured 1:1 and 1:10 DOX-TD-1 and DOX-TD-2 nanoformulations in PBS at 37° C. (B) In vitro cumulative DOX release profile of dialyzed 1:1 and 1:10 DOX-TD-1 and DOX-TD-2 nanoformulations at pH 7.4 and 5.5 at 37° C. The fluorescence of DOX remained in the dialysis bag at different time points were measured. Data are represented as a mean±SD of triplicate samples.
Figure 6:
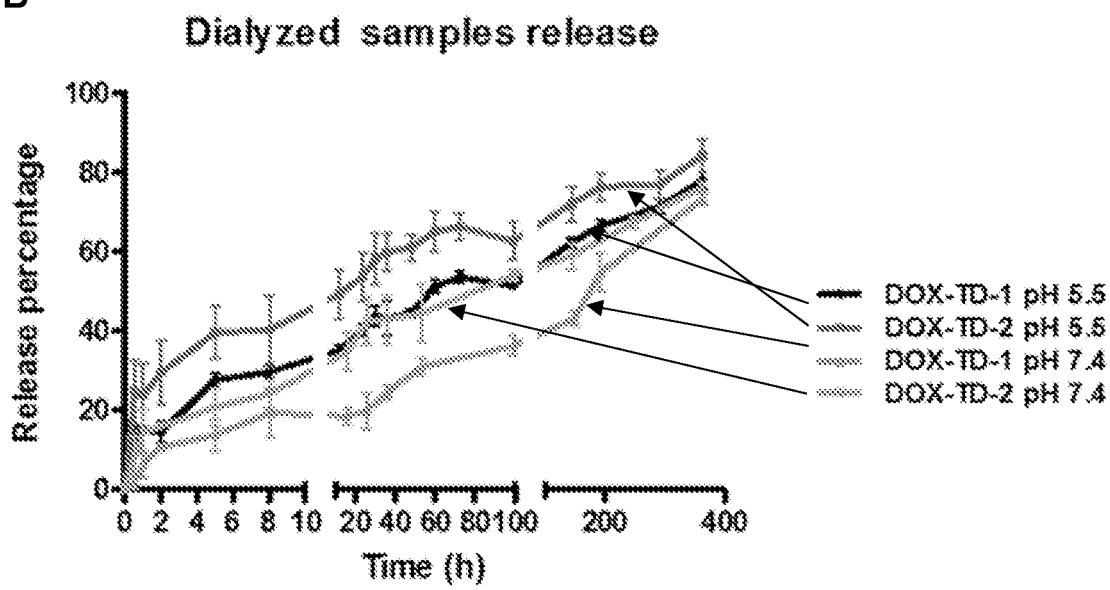

The in vitro drug release behaviors of the fresh, cured and dialyzed DOX-TD-1 and DOX-TD-2 were evaluated in PBS at 37° C. under a sink condition, i.e. frequently refreshed PBS buffers. Free DOX diffused very fast through the dialysis membrane with a complete drug release within 8 h (FIG. 6A). The freshly loaded DOX-TD-1 and DOX-TD-2 with high drug loading content at 1:1 mass ratio exhibited a two-phase drug-release profile with an initial burst release of 50% of drug, followed by a slow linear release profile. In contrast, the cured nanoformulations significantly reduced the initial burst release to ~20% drug released within the first hour and followed by a zero-ordered linear release profile with 50% of drug released at about 24 h only by a simply longer time storage of the samples. DOX-TD-1 exhibited slightly slower release profile in both cases than DOX-TD-2, due to the higher density of Rf as the drug binding moieties. Compared to the nanoformulations with a lower drug loading content, i.e. 1:10 (DOX:TD) mass ratio, the cured ultra-high DOX-loaded nanoformulations exhibited similar sustained drug release profile with reduced initial burst release. Doxil® exhibited the lowest DOX release profile, which may reduce the drug bioavailability and decrease the activity in cancer treatment. In addition, the dialyzed samples also exhibited slower DOX release profiles. As shown in FIG. 6B, at neutral pH condition, both of our DOX nanoformulations with dialysis showed slow drug release without obvious initial burst release. With the decrease of pH to 5.5, DOX release was accelerated due to the increased solubility of DOX in acidic condition, implying an effective DOX release in lysosome or endosome with lower pH environments.

In Vitro Cytotoxicity Assay—

Figure 7:
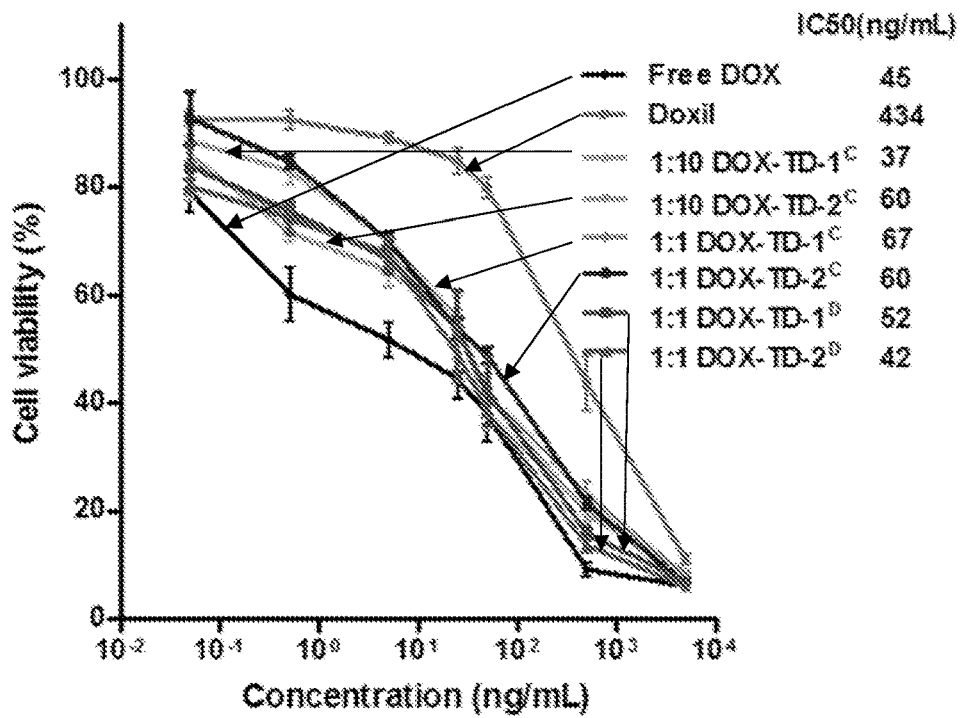
FIG. 7 shows (A, B) cell viability of MDA-MB-231 (A) and SKOV3 (B) incubation for 72 h with free DOX, Doxil®, DOX-loaded Rf-containing nanoformulations. (C) Cell viability of SKOV3 treated for 2 h with free DOX, Doxil®, DOX-loaded Rf-containing nanoformulations incubation for 72 h. Left to right in each group is Free DOX, DOXIL, 1:10 DOX-TD-1$^C$, 1:10 DOX-TD-2$^C$, 1:1 DOX-TD-1$^C$, 1:1 DOX-TD-2$^C$, 1:1 DOX-TD-1$^D$, and 1:1 DOX-TD-2$^D$ (D) Hemolytic properties of Rf-containing TDs after incubation with red blood cells at 37° C. for 24 h. Left to right in each group is Free DOX, DOXIL, 1:10 DOX-TD-1$^C$, 1:10 DOX-TD-2$^C$, 1:1 DOX-TD-1$^C$, 1:1 DOX-TD-2$^C$, 1:1 DOX-TD-1$^D$, and 1:1 DOX-TD-2$^D$.
Figure 7:
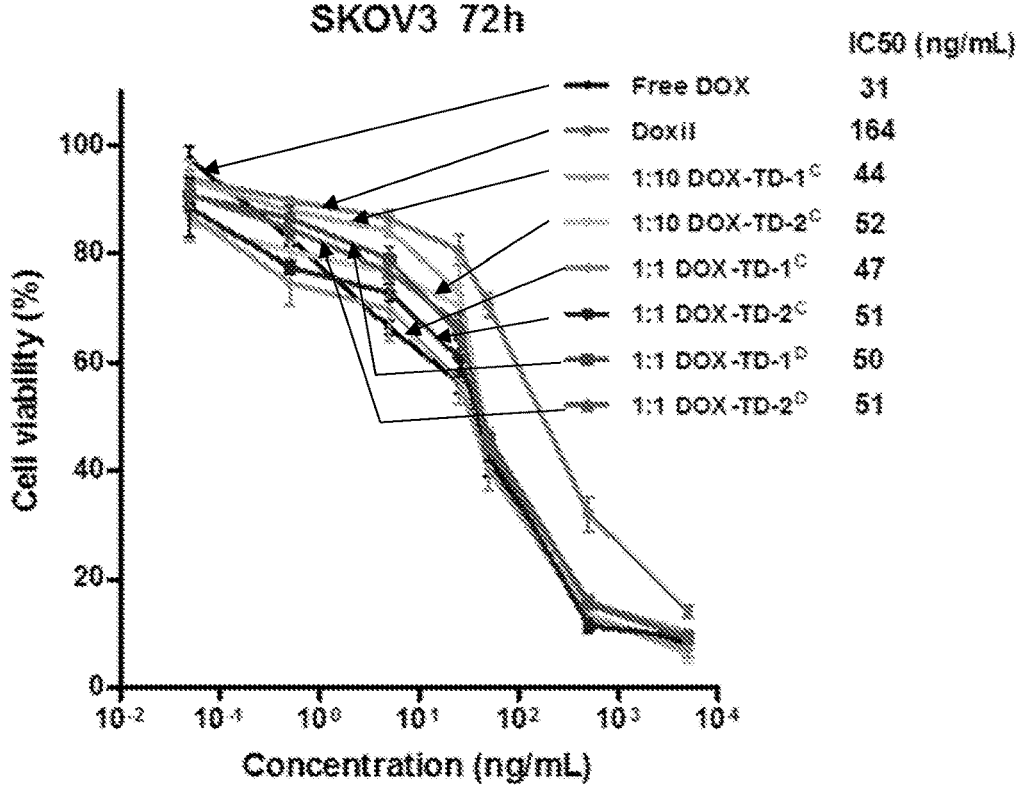
Figure 7:
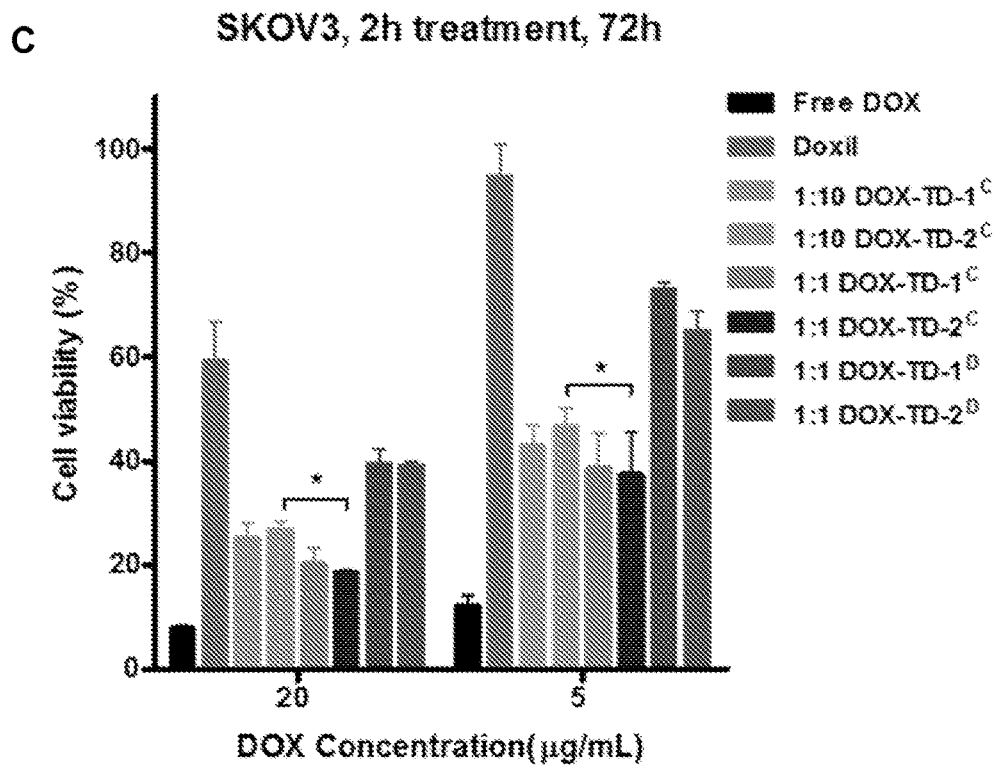
Figure 7:
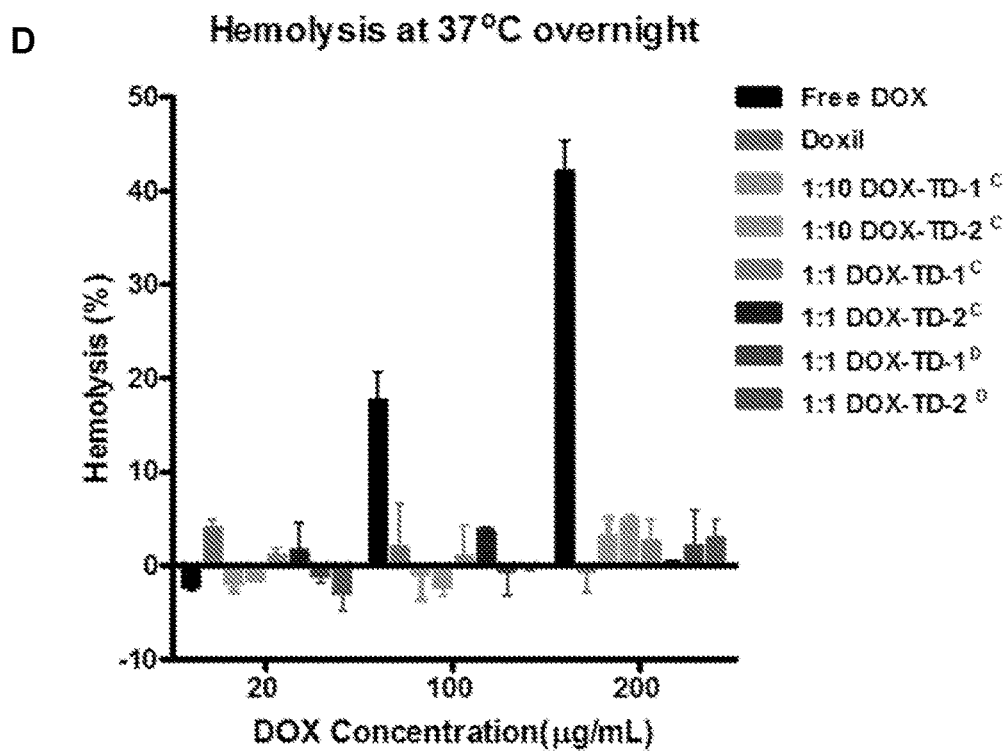
Figure 17:
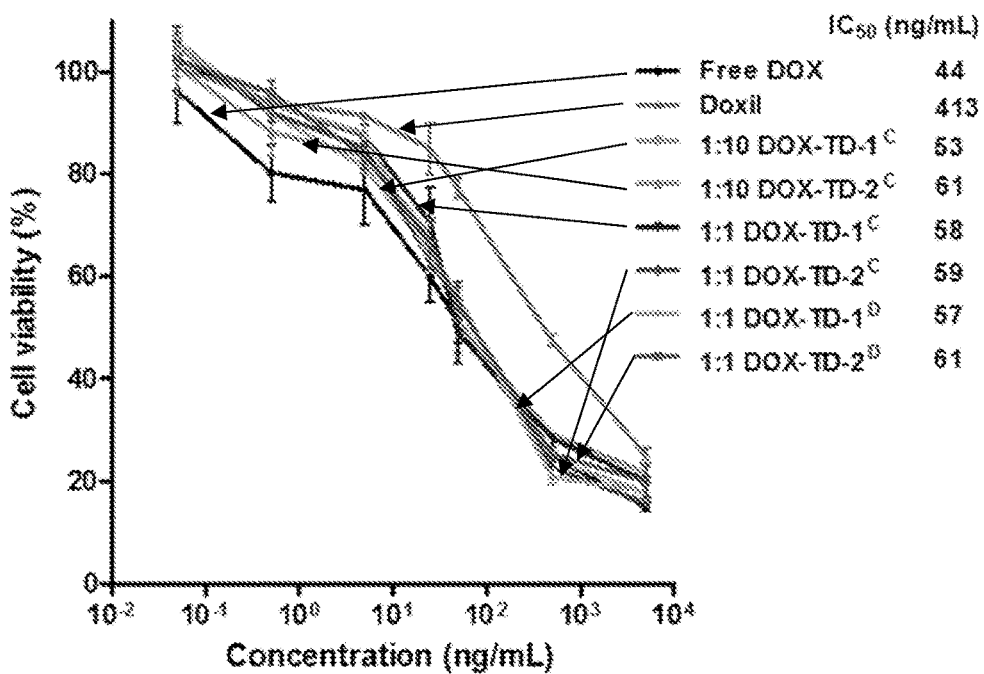
FIG. 17 shows cell viability of Raji (A), Jurkat (B), K562 (C), and H929 (D) cells after 72 h incubation with free DOX, Doxil, and DOX-loaded Rf-containing nanoformulations.
Figure 17:
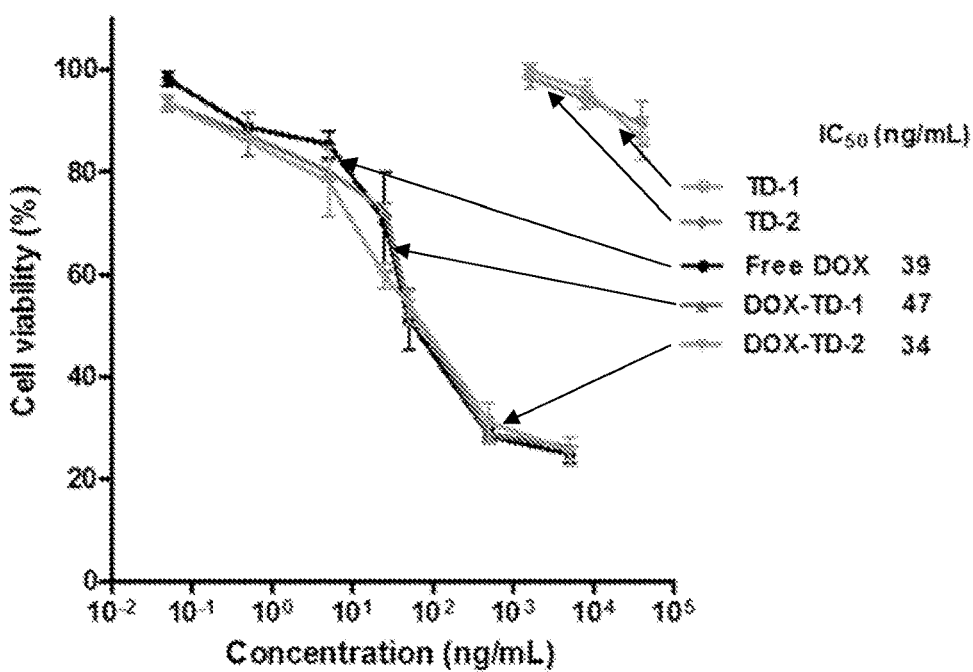
Figure 17:
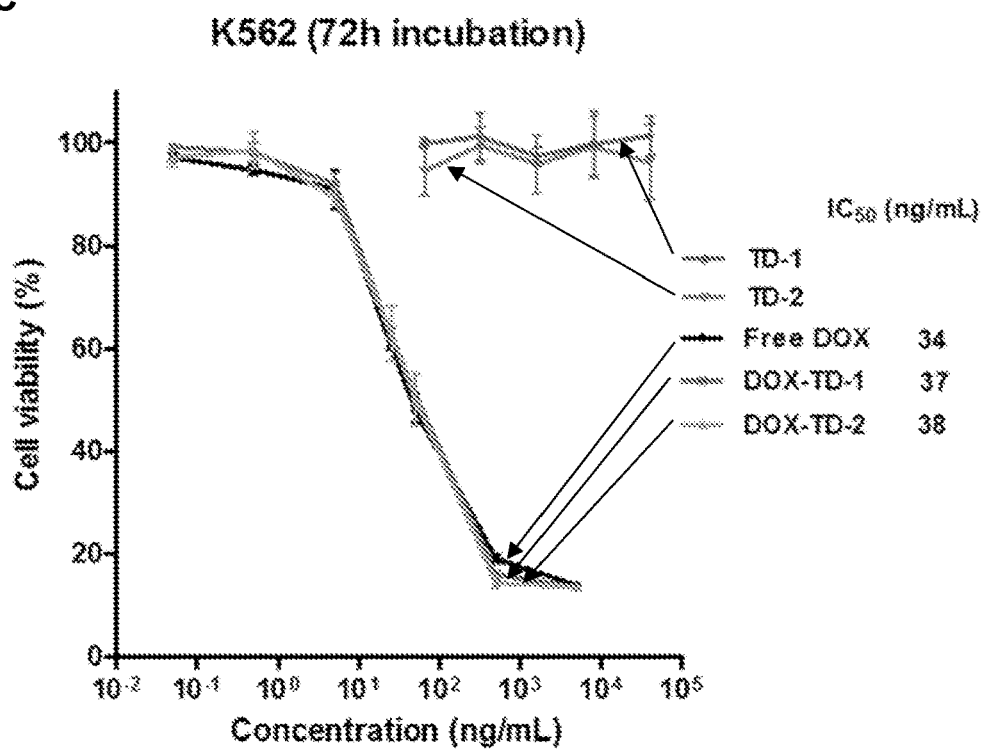
Figure 17:
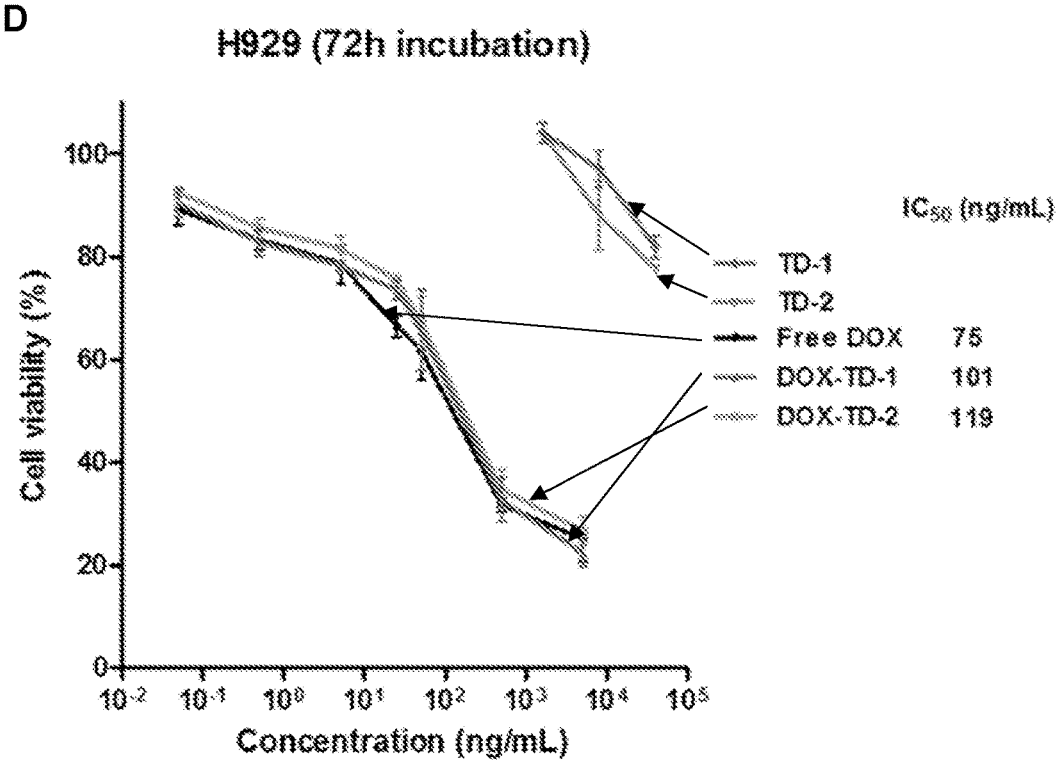

DOX has been applied to treat various cancers in clinic. Therefore, we chose an array of cancer cell lines to evaluate the efficacy of our DOX nanoformulations, e.g. Jurkat and Raji lymphoma, H929 multiple myeloma, K562 leukemia, MDA-MB-231 breast cancer, and SKOV-3 ovarian cancer cells. Cell viability after incubation with various DOX formulations with concentrations ranging from 0.05 to 5000 ng/mL were measured by MTS assays. After 72 h incubation with the DOX formulations, there was no significant difference in $IC_{50}$ between free DOX and our DOX nanoformulations in both suspension cell lines, such as Raji, K562, H929 and Jurkat cells (FIG. 17) and adherent cancer cell lines, such as MDA-MB-231 and SKOV3 (FIGS. 7A & B). However, Doxil exhibited 5-10 times higher $IC_{50}$ than free DOX, indicating less potent than free DOX and our DOX nanoformulations in these cancer cell lines, due to its highly DOX loading stability and inefficient drug release (FIGS. 7A & B). As we expected, the blank TD-1 and TD-2 had no significant cytotoxicity against all these cells tested at concentrations of 8-625 µg/mL with cell viability inhibition less than 10% (FIG. 17).

In addition, we compared the antitumor efficacy between the cured, dialyzed nanoformulations with an ultra-high DOX loading ratio (1:1, DOX/TD, w/w) or a lower DOX loading ratio (1:10, DOX/TD, w/w) to answer the question of that whether less DOX-loading amount will improve our DOX nanoformulations stability or not. SKOV3 cells were exposed to DOX formulations for 2 h, then changed to fresh medium without DOX formulations for 72 h incubation. As shown in FIG. 7C, all the nanoformulation-treated groups (Doxil®, DOX-TD-1, and DOX-TD-2) displayed significantly higher cell viability at both concentrations of 5 and 20 µM when compared to the free DOX-treated group, indicating reduced systemic toxicity of all the nanoformulations. In comparison with Doxil, the DOX-TD-1, and DOX-TD-2 formulations exhibited improved cytotoxicity in only 2 h exposure, due to their optimized drug loading stability and release. Significant differences were found between the cured DOX-TD-2 groups with ultra-high and lower loading ratios at both concentrations of 5 and 20 M, other than the DOX-TD-1, although the cell viabilities of DOX-TD-1 and DOX-TD-2 at the same loading ratio were similar, and the difference between the samples with ultra-high and lower loading ratios was only less than 10%. Dialyzed nanoformulations groups (DOX-TD-$1^D$ & DOX-TD-$2^D$) showed nearly 70% and 40% cells survived at 5 and 20 µM, respectively, which is nearly 1.5 times higher than those treated with the cured nanoformulations with 1:1 and 1:10 loading ratios. These results indicated that the decreased DOX loading amount could slightly enhance drug loading stability. However, in comparison with the dialysis method with over 70% (w/w) DOX still encapsulated, sacrifice of DOX loading capacity to 10% (w/w) is inefficient to improve DOX loading stability. The dialyzed samples, in which most of the loosely bonded DOX were removed, exhibited the highest stability and could minimize the systemic toxicity during the blood circulation. The bioactivity of the DOX loaded in the dialyzed nanoformulations was also confirmed by MTS assay with a 72 h DOX-formulation incubation (FIGS. 7A & B), and the result indicated that the loaded DOX molecules were still active and potent enough to kill tumor cells. The high stability and sustained drug release profile could enable these Rf-containing nanoformulations circulate for a much longer time and accumulate much more DOX in tumor sites by EPR effect in vivo when compared to the random diffusion of free DOX. Thus, compared to free DOX, the dialyzed DOX nanoformulations may perform less systemic toxicity and superior cancer treatment efficacy in vivo.

Figure 18:
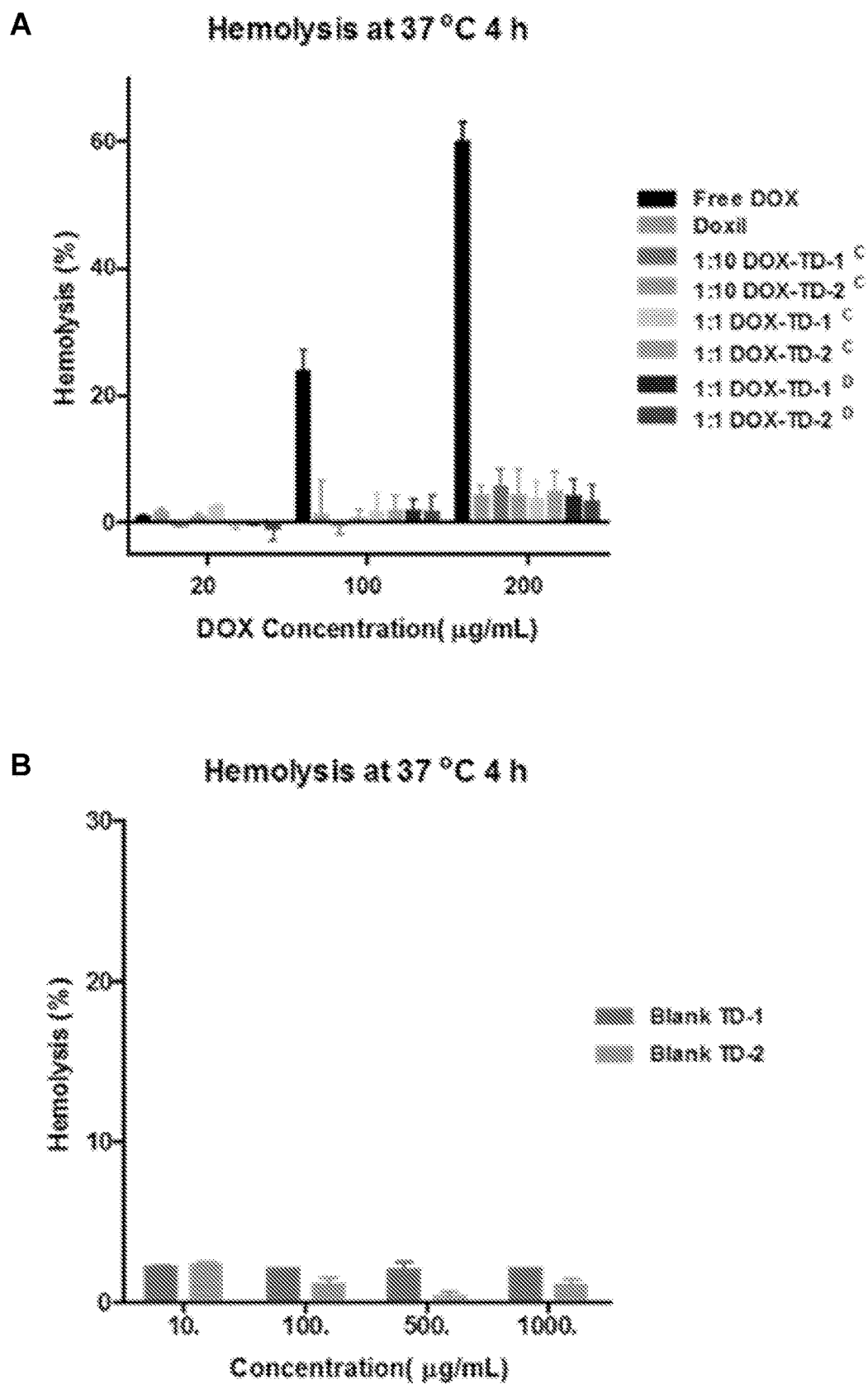
FIG. 18 shows (A) hemolytic properties of Rf-containing nanoformulations after incubation with red blood cells at 37° C. for 4 h. Left to right in each group is Free DOX, DOXIL, 1:10 DOX-TD-1, 1:10 DOX-TD-$2^C$, 1:1 DOX-TD-1, 1:1 DOX-TD-$2^C$, 1:1 DOX-TD-$1^D$, and 1:1 DOX-TD-$2^D$. (B, C) Hemolytic properties of blank TDs after incubation with red blood cells at 37° C. for 4 h (B). Left to right in each group is Blank TD-1 and Blank TD-2 for both (B) and (C).
Figure 18:
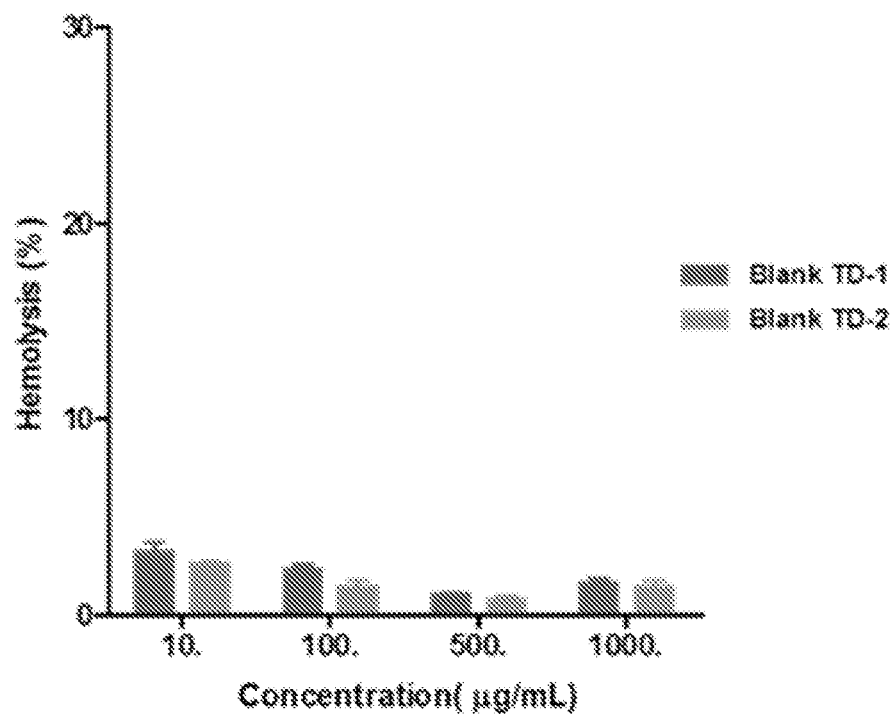

The hemolytic activities of blank TD-1 and TD-2 on human RBCs were studied to examine the hemocompatibility for systemic administration. After incubated with the RBC suspension at 37° C. for 0.5 h, 4 h and overnight, the hemolysis rates of nanoparticles were below 4% at concentrations ranging from 10 to 1000 µg/mL (FIG. 7D, FIG. 18), suggesting potential safety to use through intravenous (i.v.) injection.

Cellular Uptake—

Figure 8:
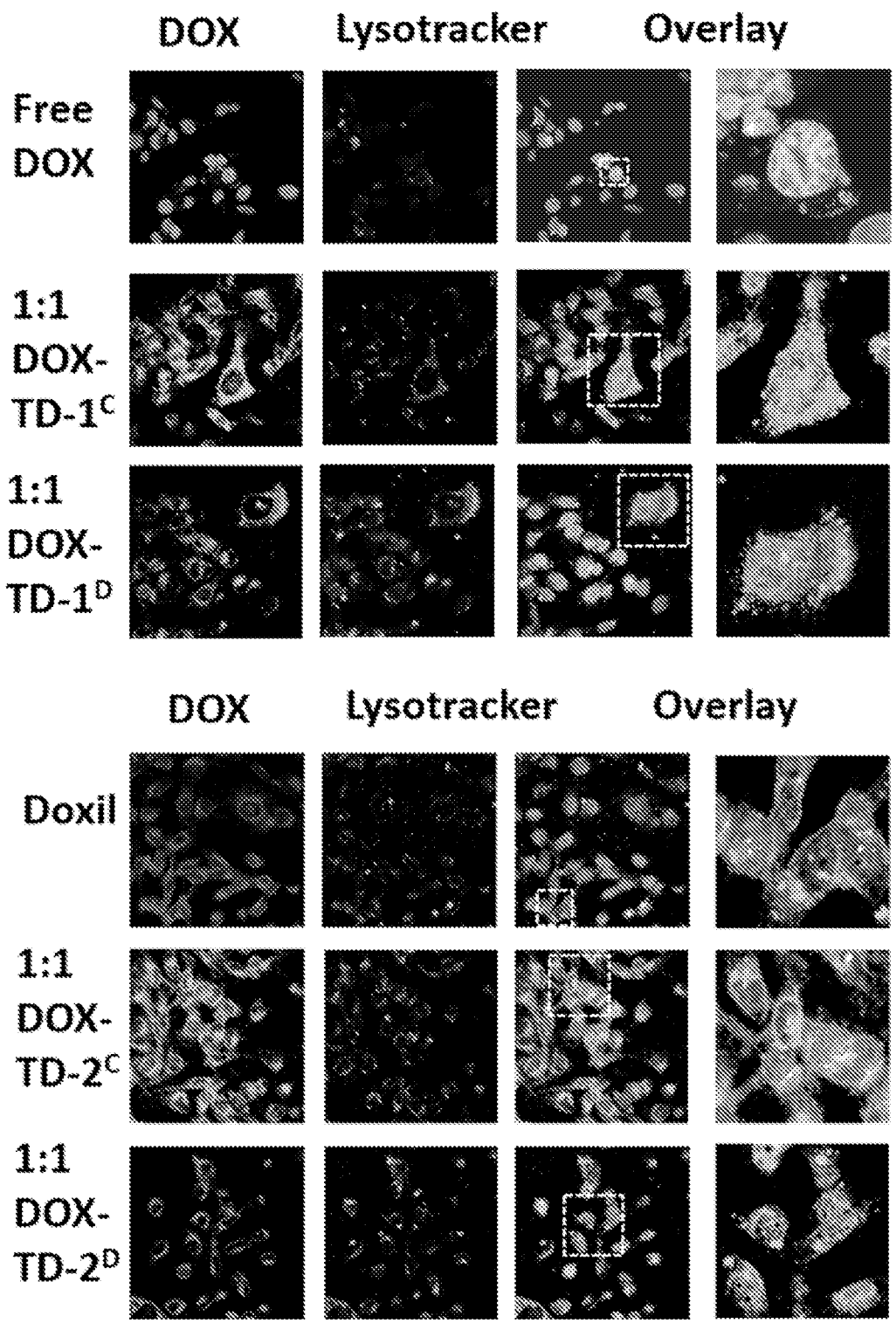
FIG. 8 shows confocal fluorescence microscopy images of MDA-MB-231 cells incubated with free DOX (10 μM), Doxil®, DOX-loaded Rf-containing nanoformulations at a DOX concentration of 30 μM for 2 h.
Figure 19:
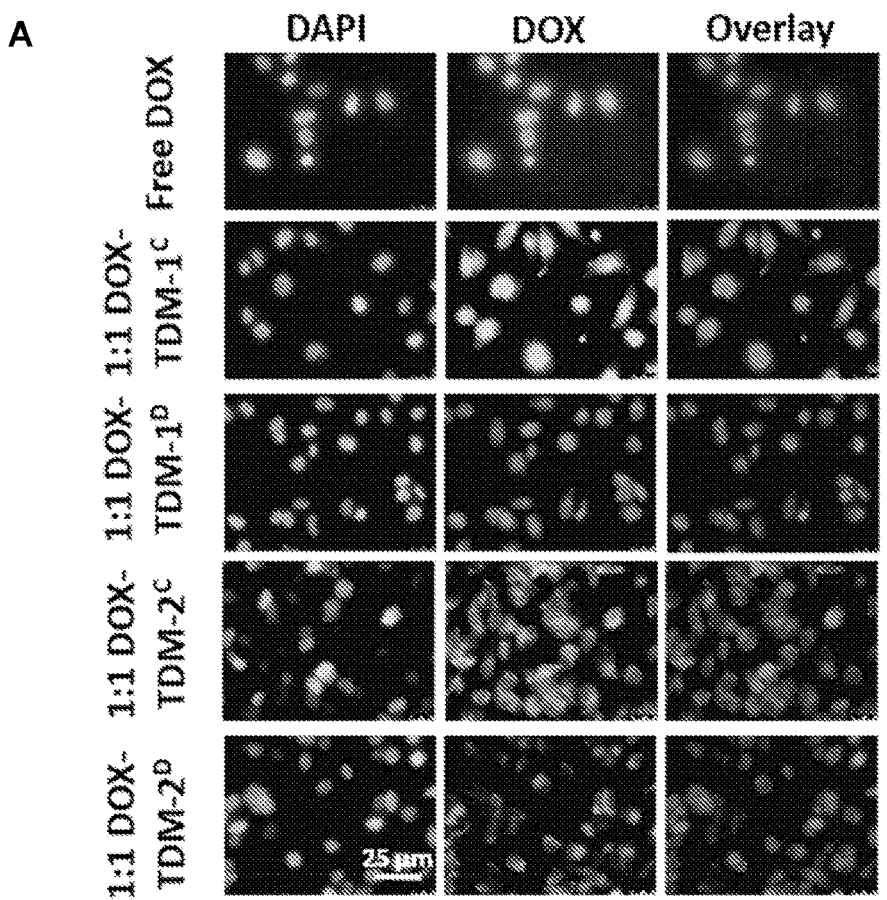
FIG. 19 shows (A) Confocal fluorescence microscopy images of MDA-MB-231 cells incubated with free DOX (10 μM), DOX-loaded Rf-containing nanoformulations at a DOX concentration of 30 M for 5 h. The scale bar is 25 m. (B) Quantitatively cellular uptake of DOX formulations at concentration of 3 and 9 μM by MDA-MB-231 cells via cell lysis and extraction. Free DOX, 1:1 DOX-TD-$1^C$, 1:1 DOX-TD-$2^C$, 1:1 DOX-TD-$1^D$, and 1:1 DOX-TD-$2^D$.
Figure 19:
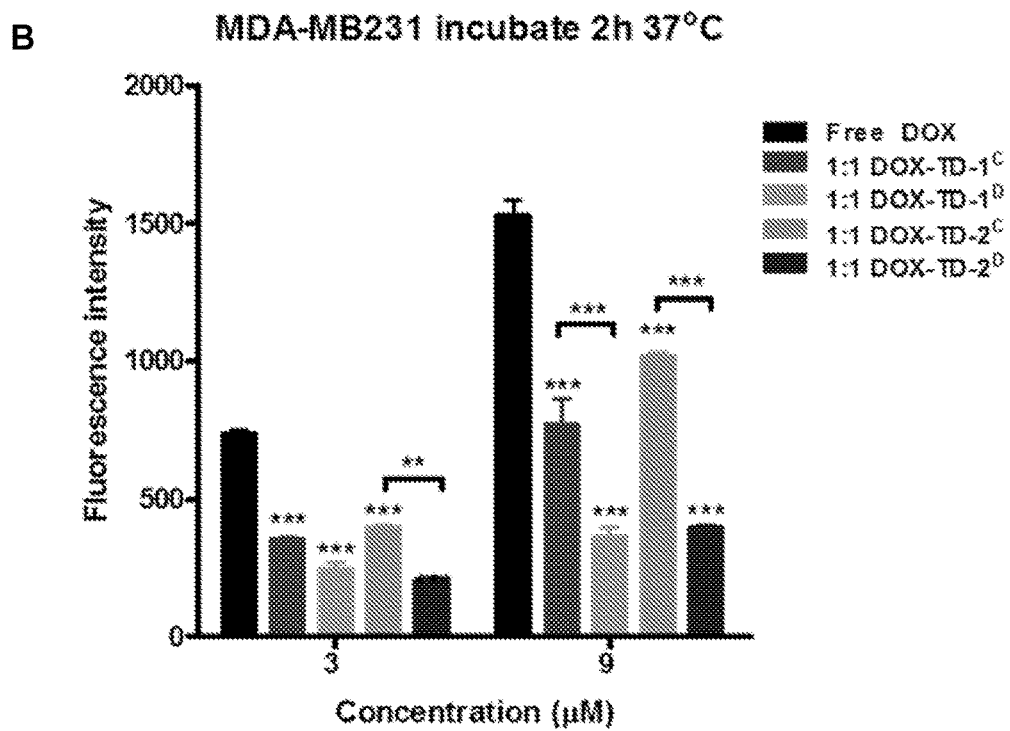

Cellular uptake behaviors of our DOX nanoformulations, Doxil® and free DOX were investigated in an MDA-MB-231 cell line using confocal microscopy. As shown in FIG. 8, free DOX efficiently translocated into the cell nuclear after 2 h incubation at 37° C. In contrast, our DOX nanoformulations mainly located in the cytosol and were co-localized with lysotracker, like Doxil®. It suggests that free DOX diffuses into cancer cells automatically, while the nanoformulations were taken up by an endocytosis pathway and further merged into lysosomes. Among the nanoformulations, Doxil® exhibited the lowest fluorescent signal, indicating inefficient cellular uptake due to its "hyper"-stealth properties and slower drug release, which may reduce drug availability in cancer treatment. Dialyzed samples showed lower fluorescent intensity in the cellular uptake study than the cured nanoformulations, which is correlated with the less burst release and the significant fluorescence quenching for the dialyzed samples. After 5 h, the encapsulated DOX released out from nanoparticles and located in the cell nuclear (FIG. 19A). Considering the fluorescent quenching effects in the nanoformulations, we further extracted DOX from cell lysis after drug incubation for 2 h to quantitatively compare DOX cellular uptake for each formulation (FIG. 19B). Compared to free DOX, the nanoformulations showed less cellular uptake at both high and low drug concentrations. The fluorescence intensities of DOX from our cured nanoformulations were almost half of that for free DOX. Dialyzed nanoformulations exhibited nearly 50% less fluorescence of DOX than that of the cured nanoformulations, which was consistent with fluorescent imaging studies. It suggested that the dialyzed nanoformulations would further minimize off-targeting toxicity of payload DOX during blood circulation.

Pharmacokinetic (PK) Studies in Healthy BALB/c Mice—

Figure 9:
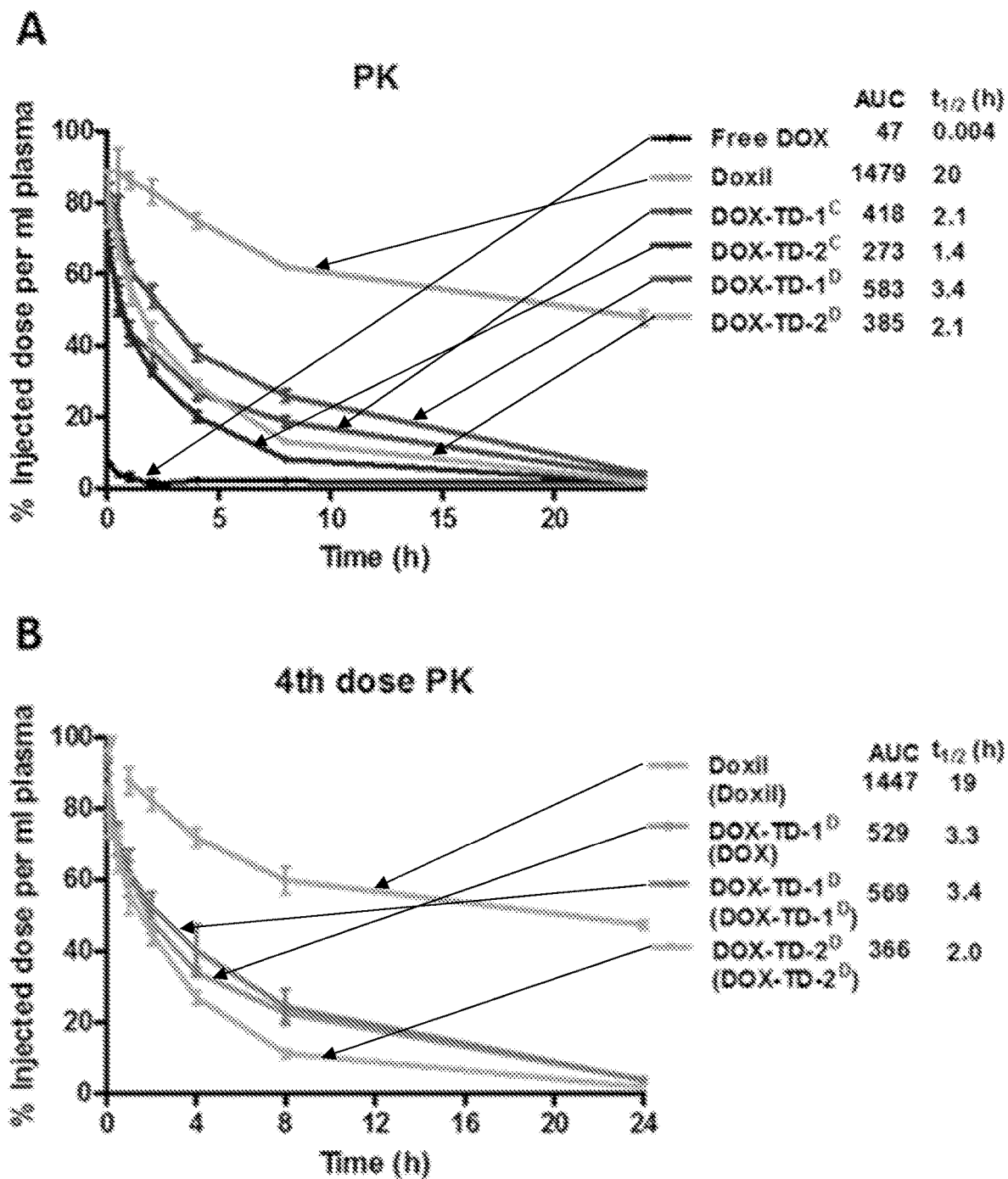
FIG. 9 shows pharmacokinetics of free DOX, Doxil®, and DOX-loaded nanoformulations at a dose of 10 mg/kg by intravenous injection in BALB/c mice (A), and the BALB/c mice with 1 or 3 doses of DOX formulations pre-treatment before the PK study (B). The pre-treatment formulations show in the brackets.

The PK profiles of DOX-loaded Rf-containing nanoformulations were investigated in BALB/c mice through intravenous administration in comparison with free DOX and Doxil®. As shown in FIG. 9A, free DOX administration resulted in rapid clearance from blood circulating with a $t_{1/2}$ of 0.004 h analyzed by fluorescent measurements of plasma at different time points. As expected, Doxil® had a very long blood circulation time ($t_{1/2}$=20 h), which contributed to a 32-fold increase in area under the curve (AUC) when compared to free DOX. Similarly, our DOX nanoformulations also presented significantly improved PK profiles with about 500 times prolonged $t_{1/2}$ than free DOX. The dialyzed nanoformulations exhibited prolonged circulation than the cured nanoformulations and the DOX-TD-1 nanoformulations had longer $t_{1/2}$ than DOX-TD-2 due to stronger drug binding and none initial burst drug release as demonstrated in FIG. 6A. More than 10-fold increase in plasma AUC for dialyzed DOX-TD-1 nanoformulations was observed in comparison with free DOX. It is highly suspected that Doxil® is too stable to be available for efficient cancer treatment. Such improved PK profiles right between free DOX and Doxil® via the optimized drug encapsulation has been revealed in our previous study to be essential for efficient tumor targeted drug delivery by EPR effects. In addition, the efficient interstitial diffusion of small sized nanoparticles and readily local drug release are promising to further improve anticancer effects in comparison to both DOX and Doxil®.

Some studies reported that anti-PEG IgM might be induced after repeated administration of PEGylated nanoparticles, yielding fast clearance of nanoformulations in vivo. To address this concern, we continuously treated wild type BALB/c mice with different DOX nanoformulations for total four times in every four days at a dose level 10 mg/kg. Right after the fourth treatment, blood samples were collected for PK analysis. As shown in FIG. 9B, DOX-TD-$1^D$, DOX-TD-$2^D$ and Doxil® exhibited similar PK profiles with almost identical AUCs when compared to the first dose PK studies (FIG. 9A). It indicates no fast clearance of nanoformulations after repeated administration, which may be due to the suppression of the contacted immune cells by the payload DOX within nanocarriers preventing anti-PEG IgM production.

Maximum Tolerance Dose (MTD) and Toxicology Studies in Healthy Mice—

Figure 10:
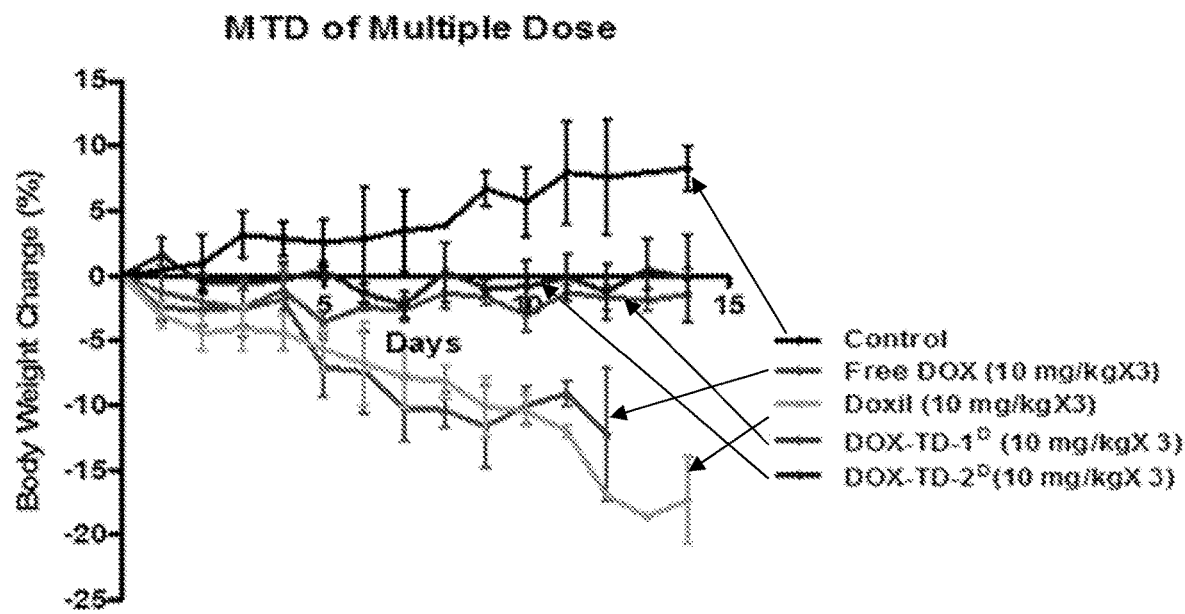
FIG. 10 shows (A, B) bodyweight change of healthy BALB/c mice administrated intravenously with q4d×3 10 mg/kg of free DOX, Doxil®, and dialyzed DOX-TD-1$^D$, DOX-TD-2$^D$ (A), and BALB/c mice administrated intravenously with q4d×3 at dose ranging from 15 mg/kg to 25 mg/kg of dialyzed DOX-TD-1$^D$ and DOX-TD-2$^D$ (B). (C) Blood cell counts on day 7 after the last dose in multiple dose MTD studies. Left to right in each group is PBS control, Free DOX 10X3, DOXIL 10X3, DOX-TD-1$^D$ 10X3, and DOX-TD-2$^D$ 10X3. (D) CK, LDH levels on day 7 after the last dose. Dose were given at days 0, 4, and 8. Left to right in each group is PBS control, Free DOX 10X3, DOXIL 10X3, DOX-TD-1$^D$ 10X3, DOX-TD-2$^D$ 10X3, DOX-TD-1$^D$ 25X3, and DOX-TD-2$^D$ 25X3. (E) Histological examination of heart tissue by H&E staining from animals treated with free DOX, Doxil (10 mg/kg×3), DOX-TD-1, and DOX-TD-2 (10 mg/kg×3, 25 mg/kg×3) or PBS. Tissues were obtained 7 days after the last dose of q4d×3 regimen.
Figure 10:
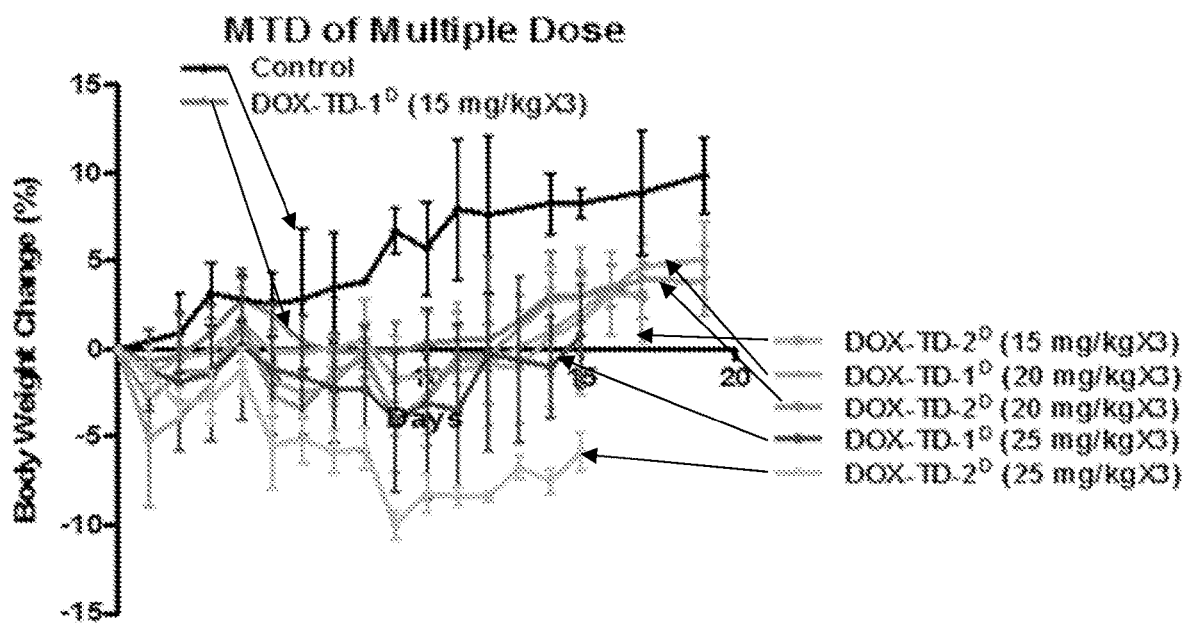
Figure 10:
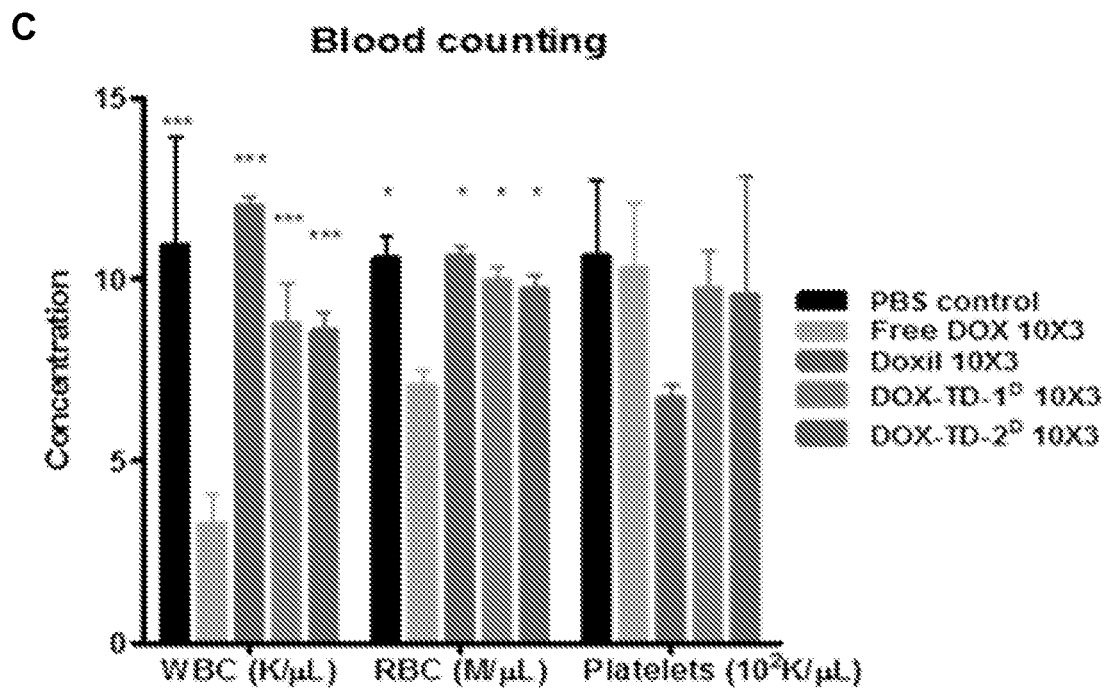
Figure 10:
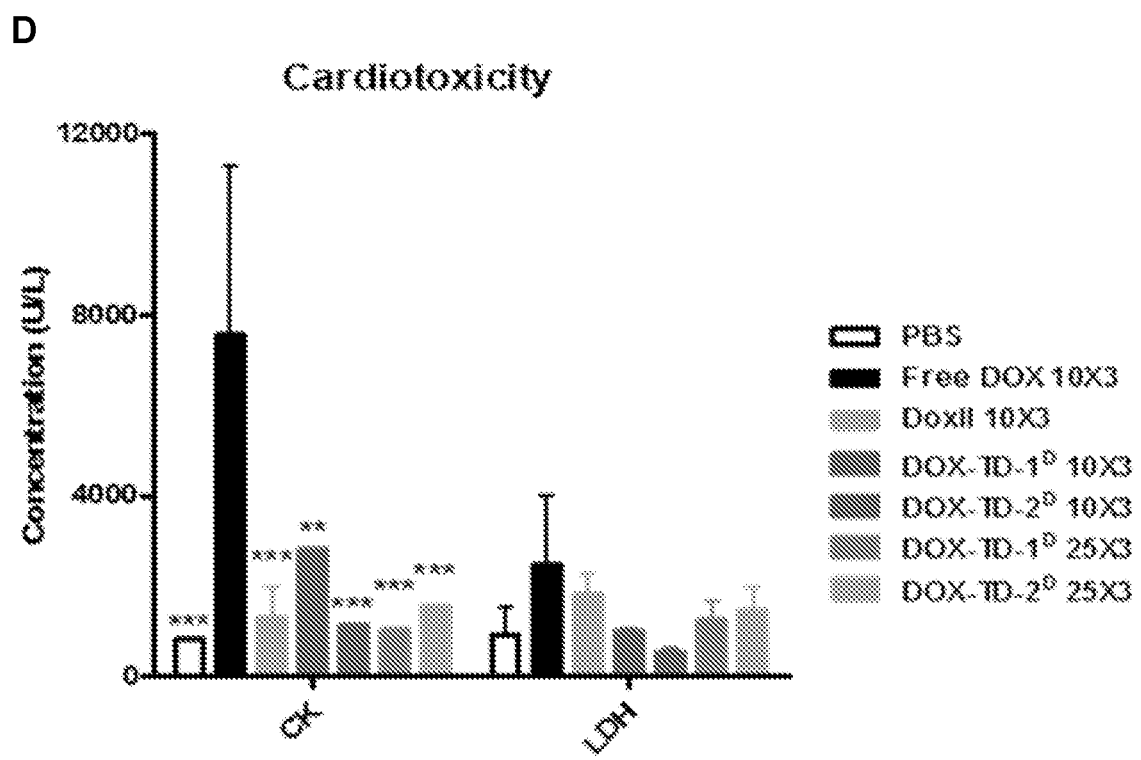
Figure 10:
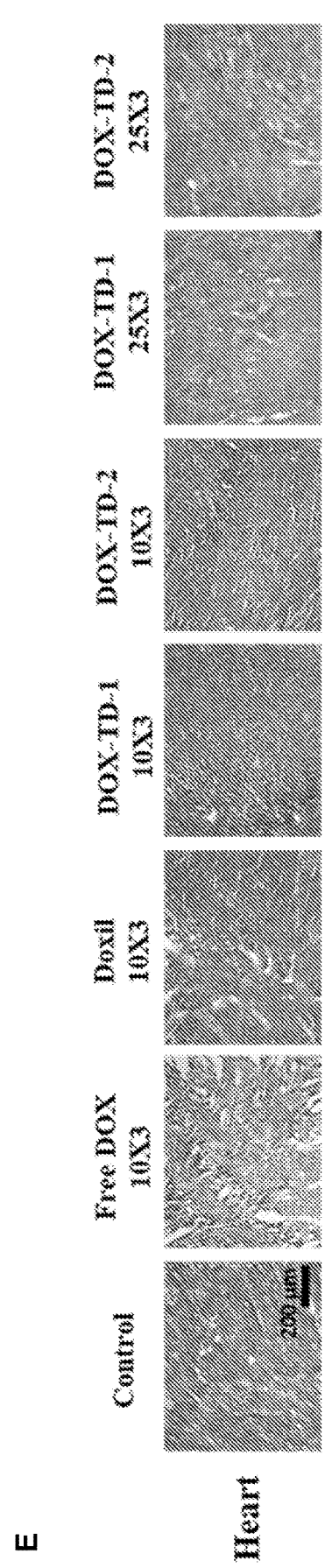
Figure 20:
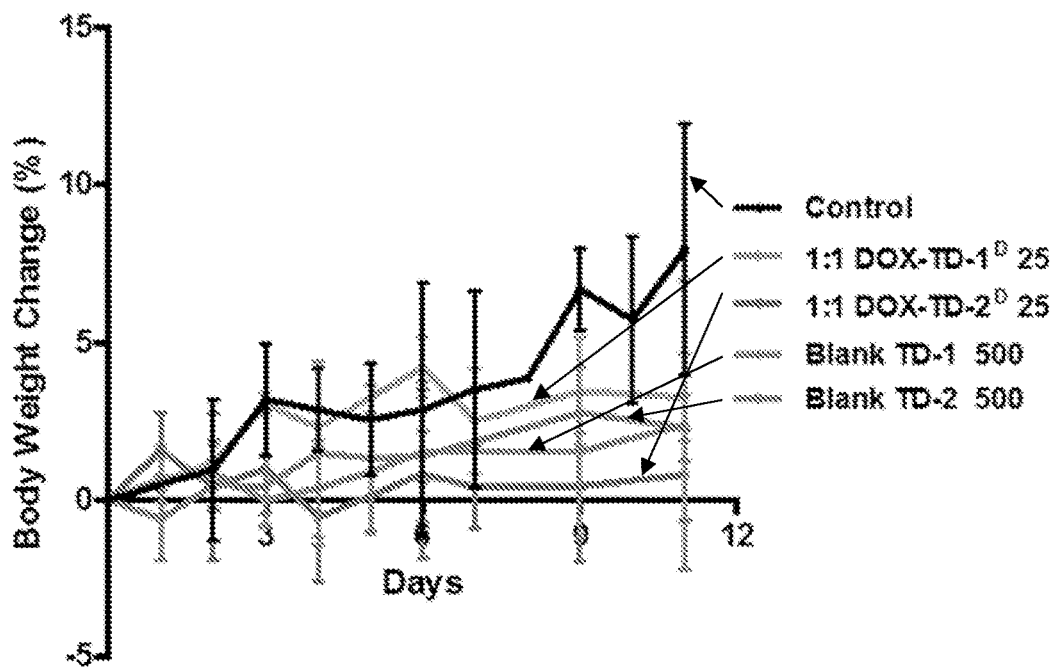
FIG. 20 shows (A) bodyweight change of healthy BALB/c mice administrated intravenously with single 25 mg/kg of DOX-TD-$1^D$, DOX-TD-$2^D$, 500 mg/kg of blank TD-1, and TD-2. (B, C) Blood cell counts on day 7 after the single (B, from left to right in each group is Control, 1:1 DOX-TD-$1^D$ 25, 1:1 DOX-TD-$2^D$ 25, Blank TD-1 500, and Blank TD-2 500), and overnight (C, left to right in each group is Control, 1:1 DOX-TD-$1^D$ 15X3, 1:1 DOX-TD-$2^D$ 15X3, 1:1 DOX-TD-$1^D$ 20X3, 1:1 DOX-TD-$2^D$ 20X3, 1:1 DOX-TD-$1^D$ 25X3, and 1:1 DOX-TD-$2^D$ 25X3) and the last of multiple dose in multiple dose MTD studies (C). (D) BUN, ALT, and AST levels on day 7 after the last dose. Dose were given at days 0, 4, and 8. Left to right in each group is PBS, Free DOX 10X3, DOXIL 10X3, 1:1 DOX-TD-$1^D$ 10X3, 1:1 DOX-TD-$2^D$ 10X3, 1:1 DOX-TD-$1^D$ 25X3, and 1:1 DOX-TD-$2^D$25X3
Figure 20:
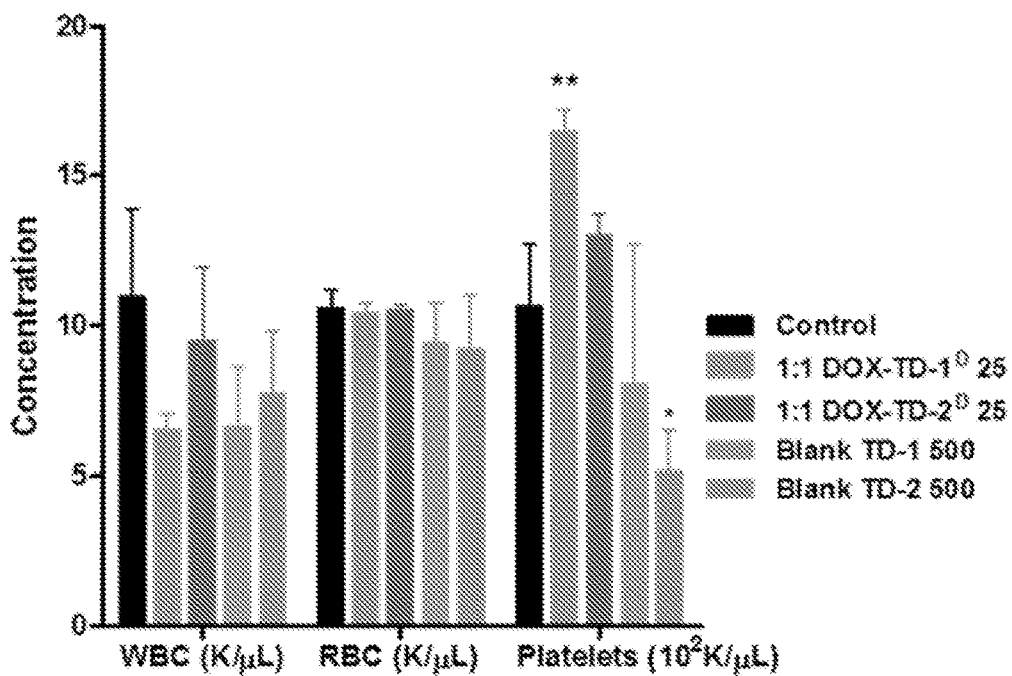
Figure 20:
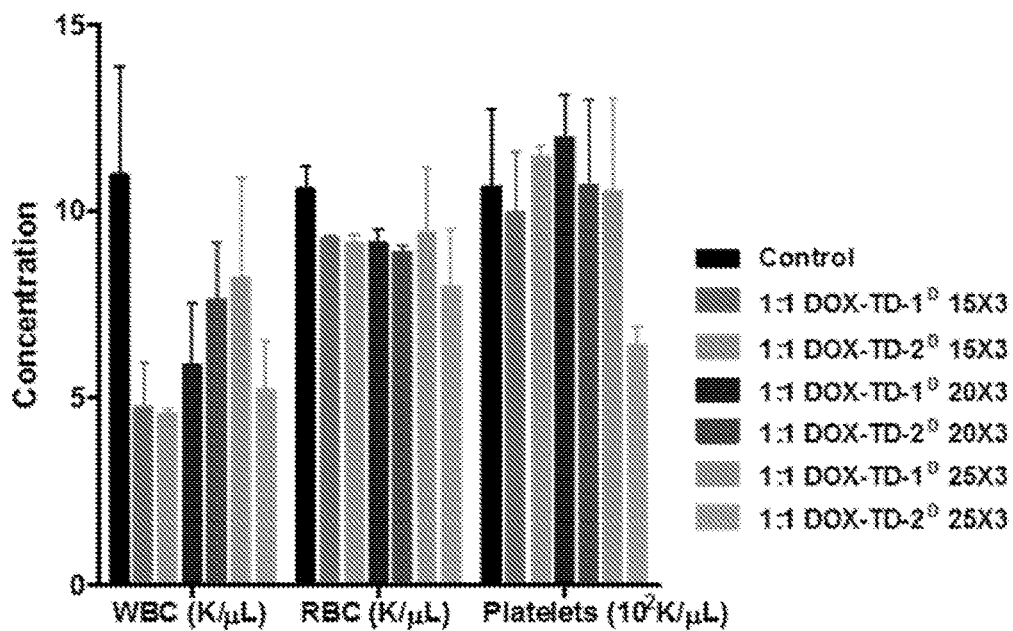
Figure 20:
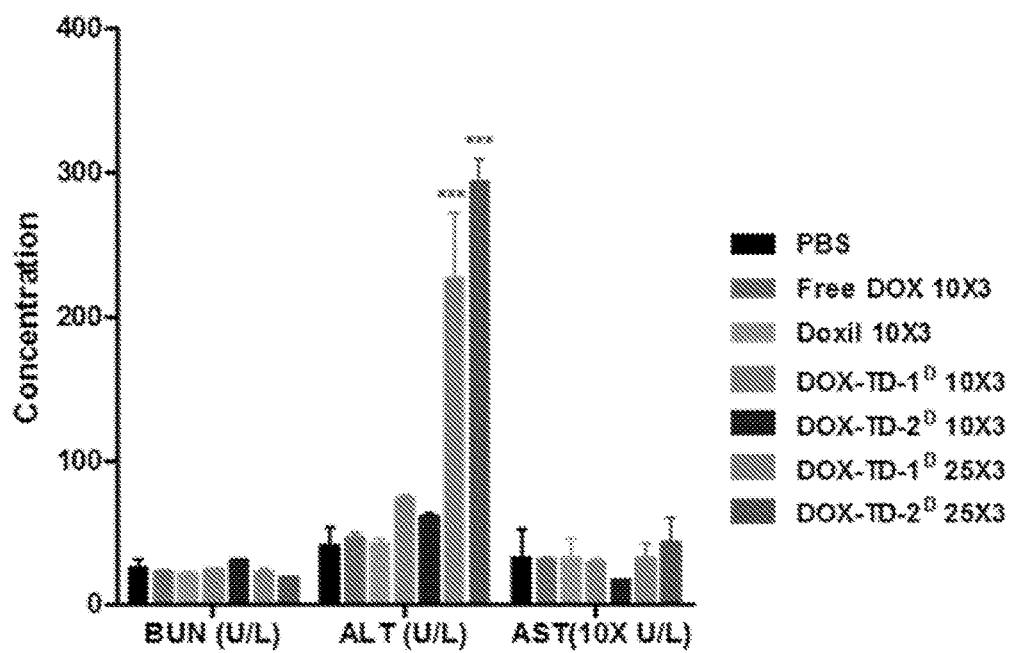

We estimated MTD by dose escalation in BALB/c mice by a single dose injection or a regimen of every fourth day for a total 3 injections, which will be used in subsequent cancer treatment studies. In single dose injection groups, mice treated with the dialyzed DOX-TD-1 and DOX-TD-2 maintained normal body weight, and no noticeable changes in behavior were observed up to 25 mg/kg dose (FIGS. 10A & B). Moreover, single dose i.v. injections of 500 mg/kg of blank TD-1 and TD-2 micelles were well tolerated without noticeable changes in general activity and body weight (FIG. 20A). This dose is over 8-fold higher than that needed in the treatment studies. Meanwhile, the blood samples were collected on Day 7 after the treatment for blood cell counting, i.e. red blood cells (RBC), white blood cells (WBC), hemoglobin (Hb), and platelets. Normal WBC, RBC and Hb counts were observed (FIG. 10C, FIG. 20B). The platelets decreased in the mice treated with blank TD-2 at 500 mg/kg when compared to the PBS control group, which however still fell in the normal range.

In the triple-dose treatment groups (FIGS. 10A & B), dialyzed DOX-TD-1 and TD-2 treated mice barely slowed weight loss and noticeable changes in behavior up to 25 mg/kg dose. We found that mice administrated with 10 mg/kg of free DOX and Doxil® lost nearly approx. 15% body weight. All the mice in free DOX treatment group were found to have abdominal dropsy on Day 4 after the last injection. Dry eye syndrome was found in the mice treated with Doxil®. In clinic, myelosuppression is a common side effect for chemotherapy. Therefore, the blood samples were also collected on Day 7 after the last dose (FIG. 10C, FIG. 20C). Consistently, the WBC and RBC number of free DOX treated group were significantly decreased, while dialyzed nanoformulations, Doxil® resulted in normal blood counts similar to PBS group.

In clinic, of the accumulative cardiomyopathy is a dose-limiting side effect for DOX. Therefore, blood enzyme levels of mice in the above triple-dose treatment studies were analyzed to uncover any possible organ dysfunctions. As shown in FIG. 10D, creatine kinase (CK) in free DOX treated group was found nearly 6-fold higher than that of the PBS control group, indicating severe cardiotoxicity caused by free DOX. As expected, no significant changes in CK and lactate dehydrogenase (LDH) levels was observed in mice treated with all nanoformulations at 10 mg/kg and even 25 mg/kg. No alteration in BUN, ALT and AST was observed in mice treated with all the DOX formulations at 10 mg/kg, indicating normal function of kidney and liver. However, we noticed that a significant increase in ALT, but not AST, in mice treated with high dose of our nanoformulations, i.e. DOX-TD-1 and DOX-TD-2 at 25 mg/kg (FIG. 20D). It may indicate potential liver damage, which needs further examination.

To further confirm the organ functions in animals after MTD studies, we harvested heart, liver and kidney on day 7 after blood collection for histology analysis. As shown in FIG. 10E, heart tissue in mice treated with free DOX at 10 mg/kg was significantly damaged in comparison with that in PBS control group, which is correlated with the increased CK level and further confirm the cardiotoxicity of free DOX. In contrast, all the nanoformulation treatment groups maintained the intact structure of heart tissue the same as the normal hearts in PBS groups. In addition, kidney physiological structures were also ruined by the treatment of free DOX at 10 mg/kg, which was evidenced by the white-off kidney at harvest. In addition, such kidney dysfunction may explain the accumulation of abdomen fluid accumulation observed in these mice. On the contrary, kidney structures remained normal in mice treated with all nanoformulations. Liver structures are normal in mice treated with free DOX and Doxil® and our nanoformulations at low dose of 10 mg/kg. We carefully examined the liver structures in the mice treated with our nanoformulations at high dose 25 mg/kg. It revealed no significant structural alteration in these liver slides. Although, the increased ALT levels in mice treated with 25 mg/kg of our nanoformulation might be a transient change, we determined the MTD for DOX-TD-$1^D$ and DOX-TD-$2^D$ nanoformulations to be 20 mg/kg as a q4d×3 regimen, which will be applied in the following treatment studies. Free DOX at 10 mg/kg has shown significant body weight lost and organ toxicity in mice, therefore, we chose 8 mg/kg as MTD dose for free DOX according to the literature. The MTD level of Doxil® was determined to be 10 mg/kg, according to 15-20% body weight lost. As results, our nanoformulation doubles the MTD level of Doxil® and even reaches to 2.5-fold of MTD of free DOX. The ultra-high DOX loading ability of the Rf-containing nanoformulations enables a largely decrease of excipient dose. This may be one of the factors for the high MTD when compared to free DOX and Doxil®. Due to relatively high safety profile, we hypothesized that our DOX nanoformulations may obtain certain relevant advantages in clinic by allowing a high dose of DOX.

In Vivo and Ex Vivo Tumor Targeting—

Figure 11:
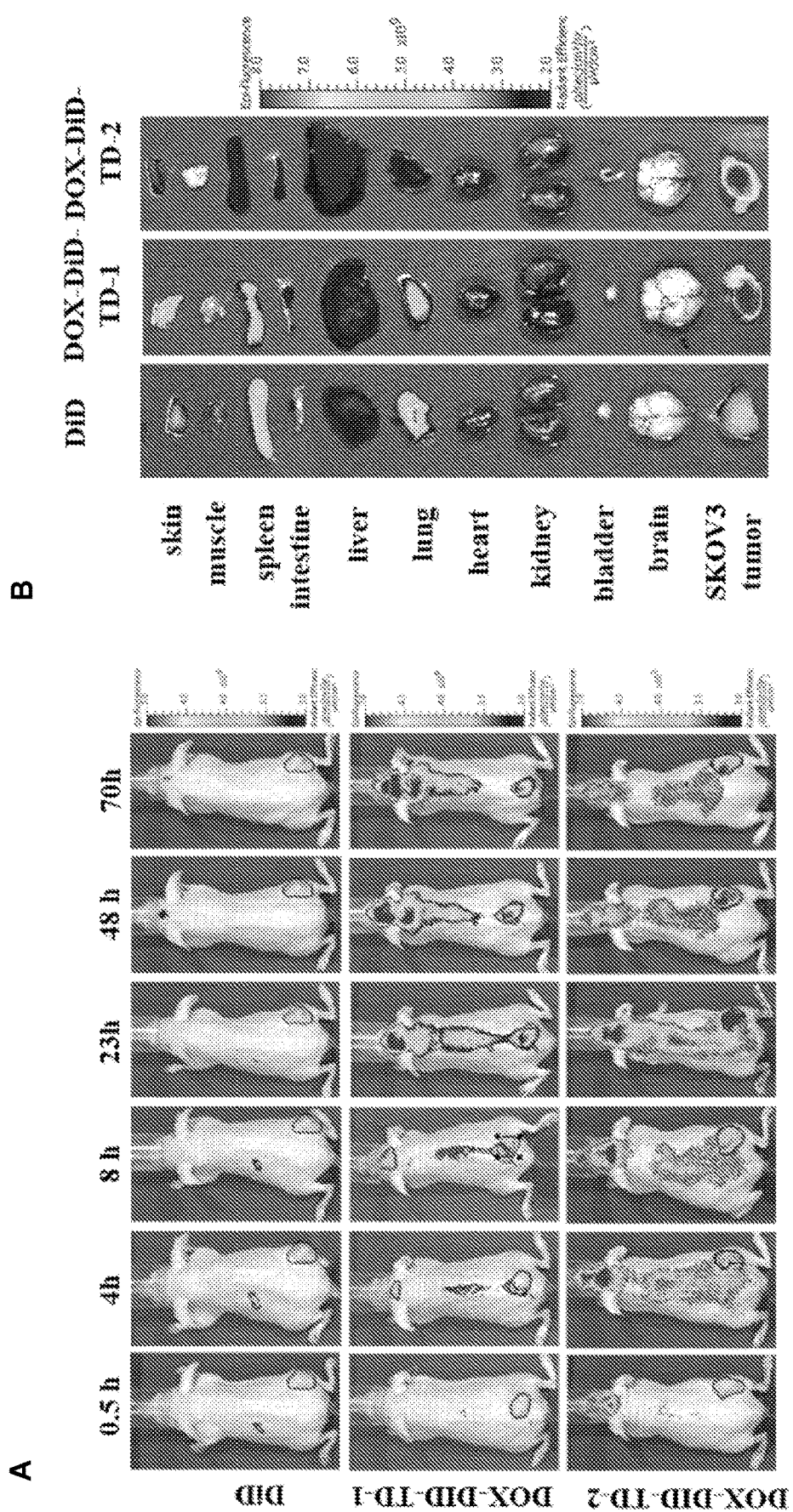
FIG. 11 shows (A) in vivo real-time imaging of free DiD and DiD-DOX-co-loaded Rf-containing nanoformulations i.v. injection in SKOV3 xenograft tumor bearing nude mice by IVIS. (B) Representative ex vivo optical images of tumors and major organs taken out at 70 h after i.v. injection of free DiD and DiD-DOX-co-loaded Rf-containing nanoformulations. (C) Quantitative fluorescent intensity of the tumors in SKOV3 xenograft tumor bearing nude mice for in vivo imaging. (D) Quantitative fluorescent intensity of the tumor and major organs in SKOV3 xenograft tumor bearing nude mice for ex vivo imaging. Left to right in each group is DiD, DiD-DOX-TD-1, and DiD-DOX-TD-2. (E) Fluorescence microscopy images of SKOV3 tumors obtained from mice treated with free DiD, DiD-DOX-TD-1, and DiD-DOX-TD-2.
Figure 11:
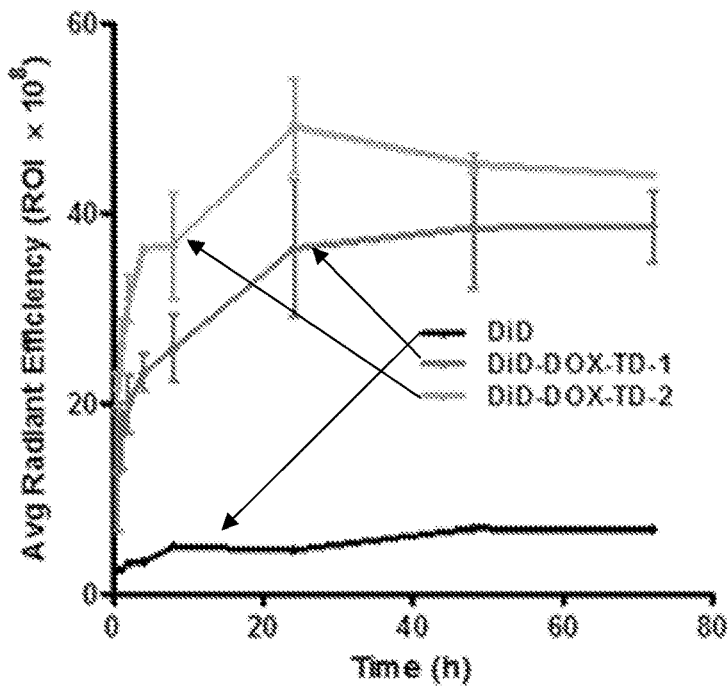
Figure 11:
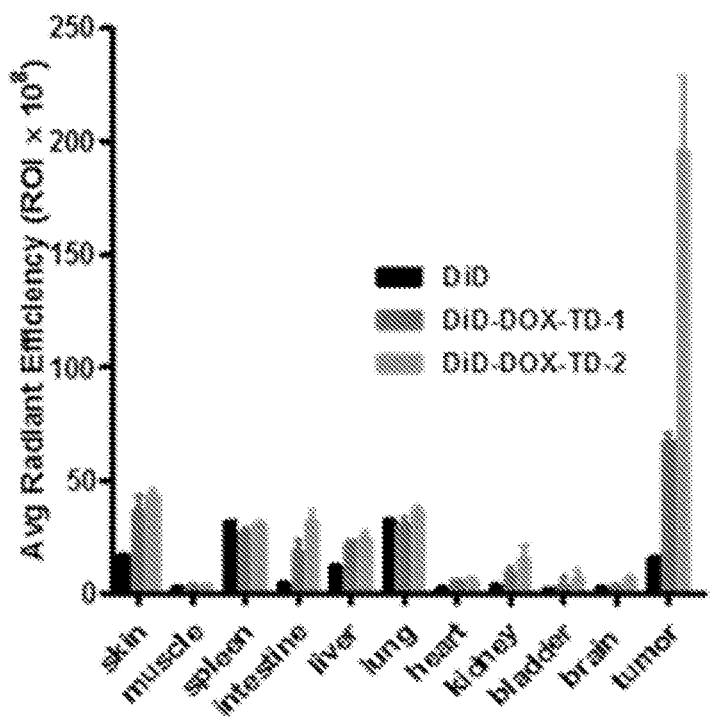
Figure 11:
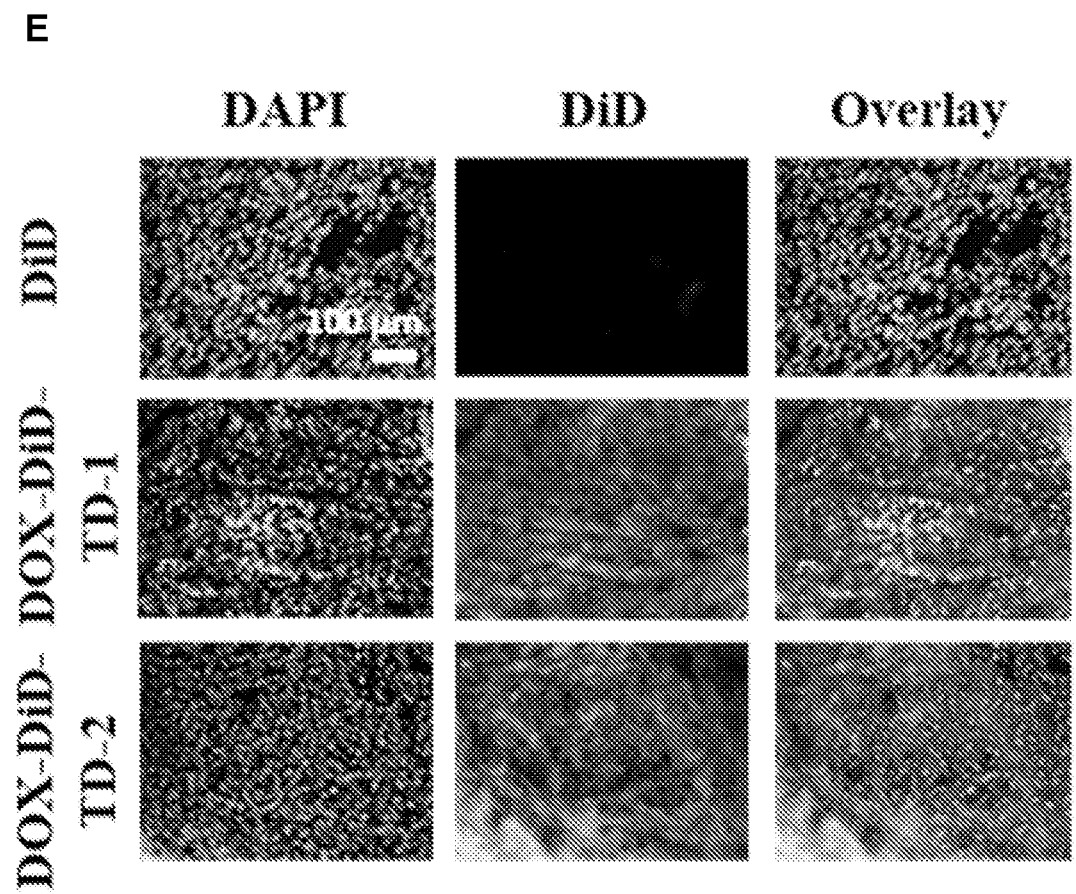
Figure 21:
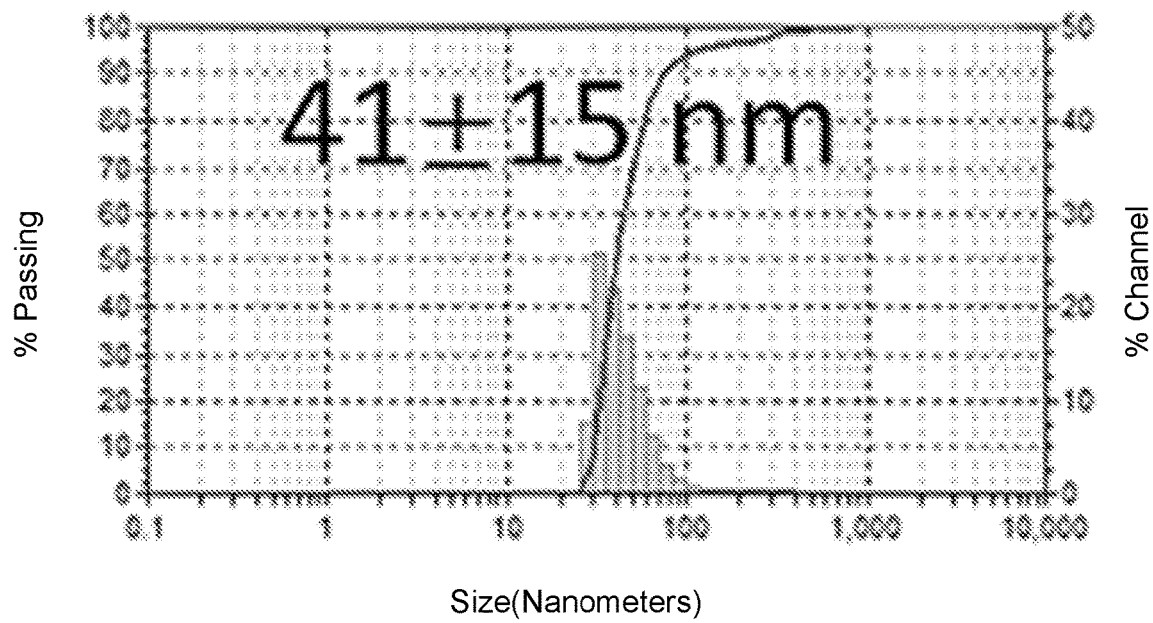
FIG. 21 shows (A, B) particle size of DiD-DOX-TD-1 (0.2:2:10 w/w/w) (A) and DOX-TD-2 (0.2:2:10 w/w/w) (B) nanocarriers at concentration of 10 mg/mL obtained by DLS. (C) Fluorescence quenching of DiD-DOX-TD-1. (D) Release profiles of DOX and DiD from DiD-DOX-co-loading TD-1 nanoparticles. Left to right in each group is DiD, DOX-DiD-TD-1, and DOX-DiD-TD-2.
Figure 21:
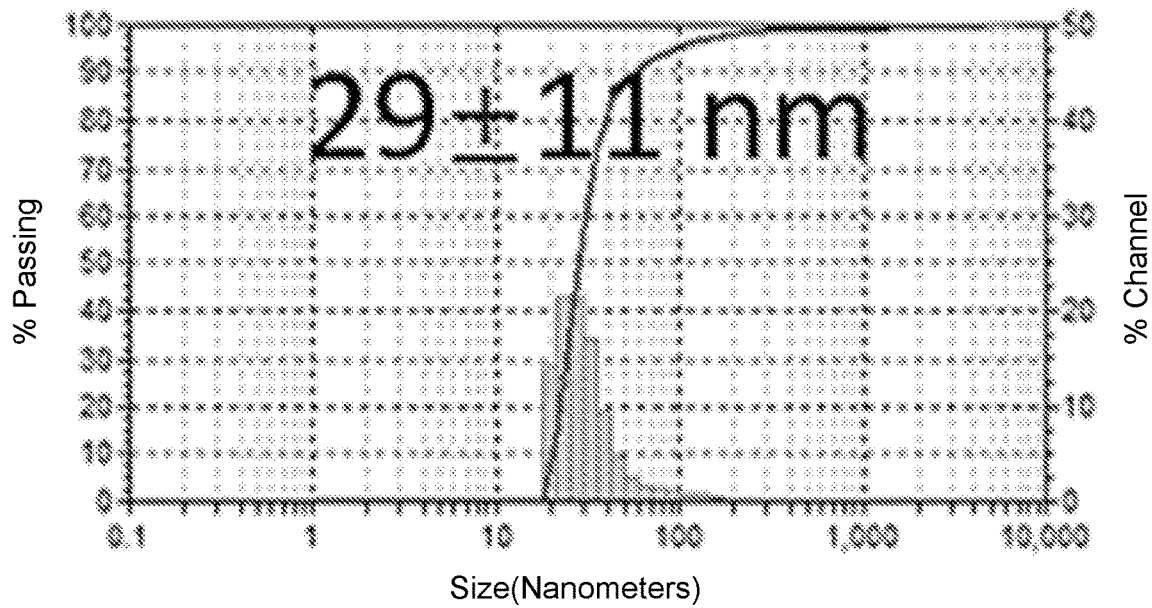
Figure 21:
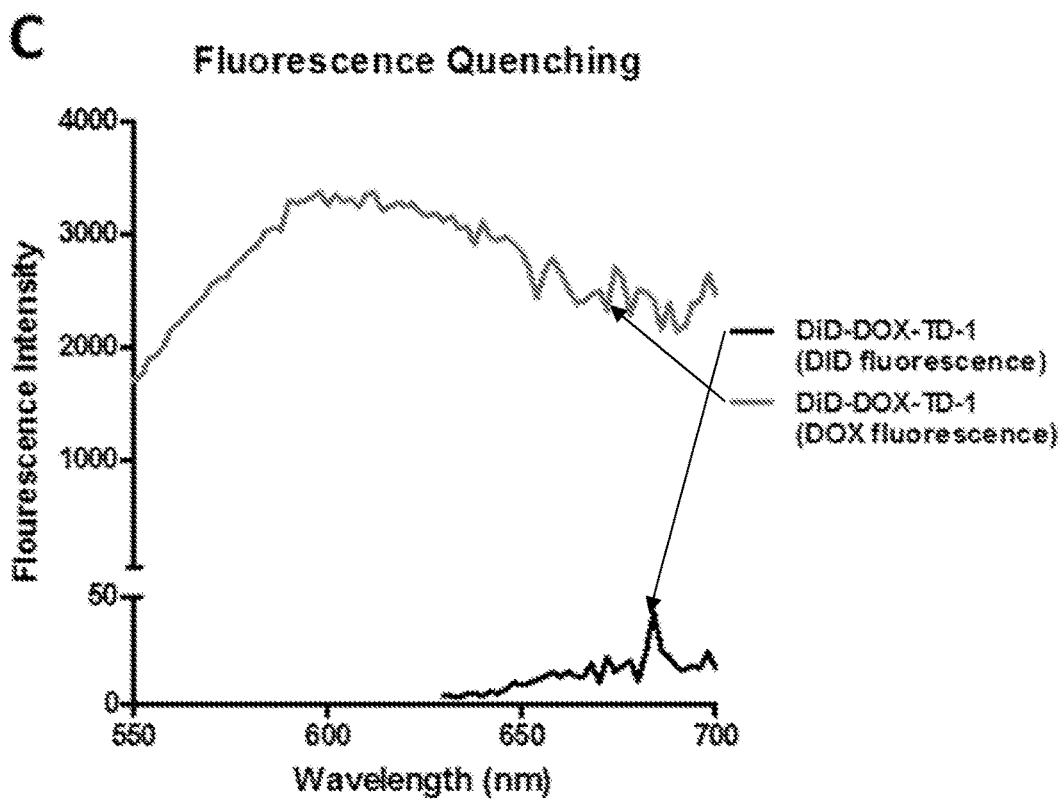
Figure 21:
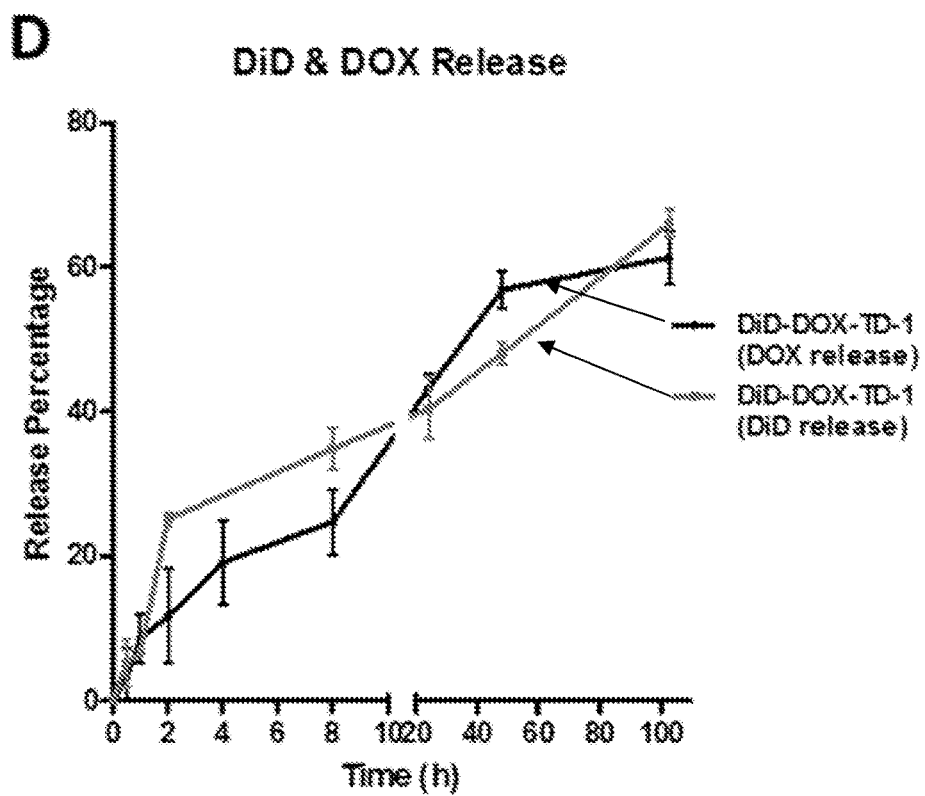
Figure 22:
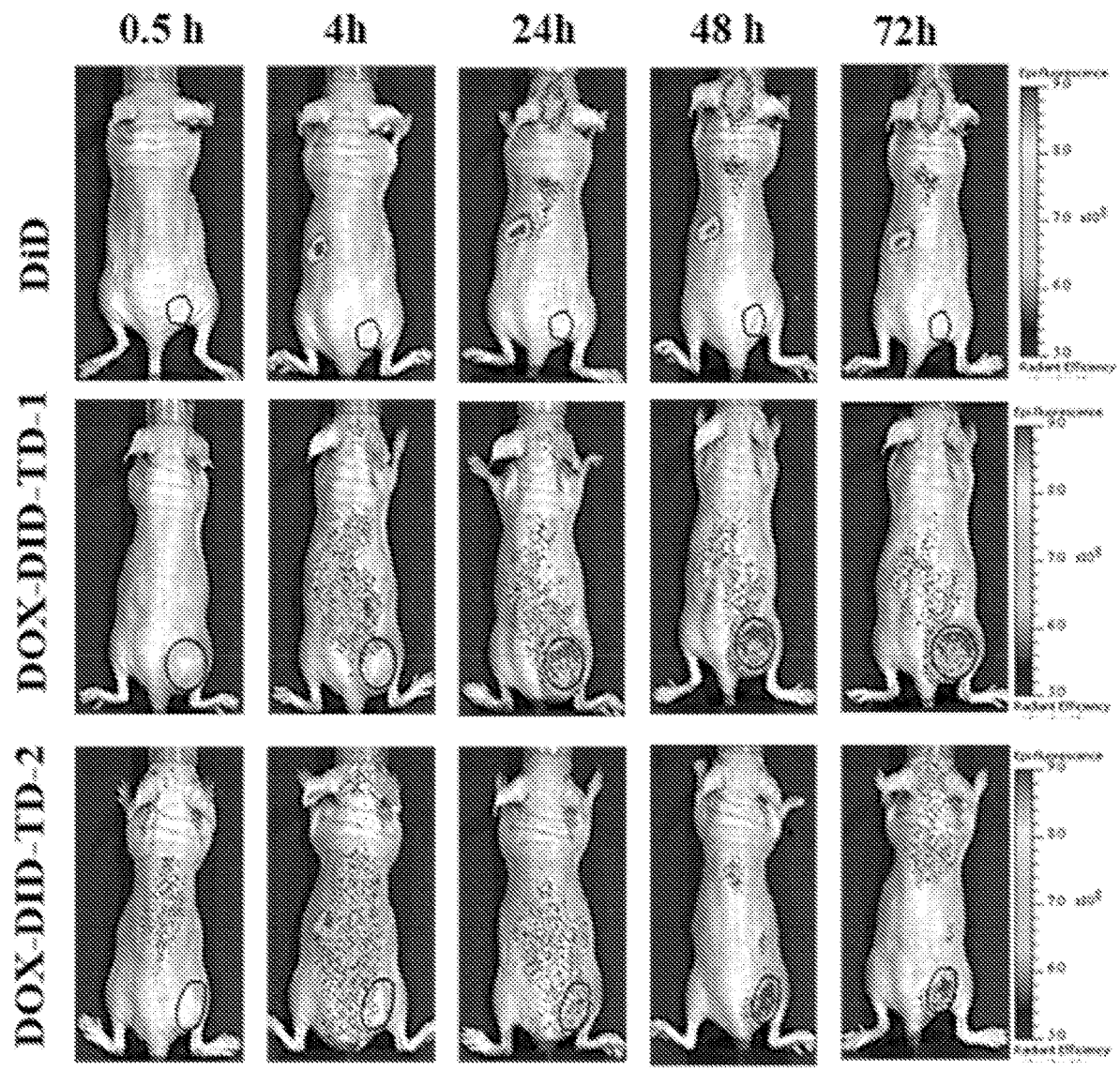
FIG. 22 shows (A) in vivo real-time imaging of free DiD and DiD-DOX-loaded Rf-containing nanoformulations i.v. injection in Raji xenograft tumor bearing nude mice by IVIS. (B) Representative ex vivo optical images of tumors and major organs taken out at 70 h after i.v. injection of free DiD and DiD-DOX-loaded Rf-containing nanoformulations. (C) Quantitative fluorescent intensity of the tumor in Raji xenograft tumor bearing nude mice in vivo imaging. (D) Quantitative fluorescent intensity of the tumor and major organs in Raji xenograft tumor bearing nude mice ex vivo imaging.
Figure 22:
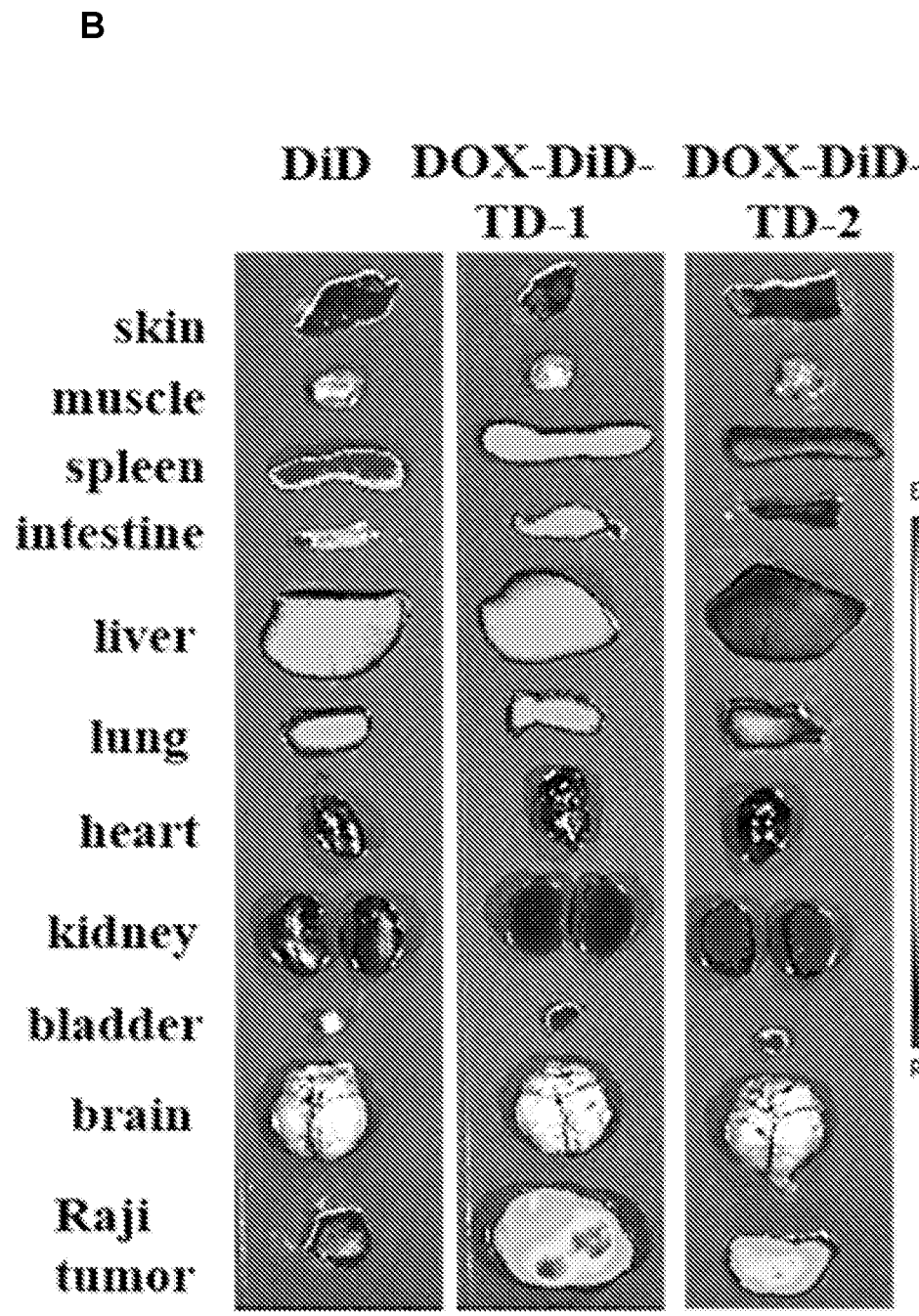
Figure 22:
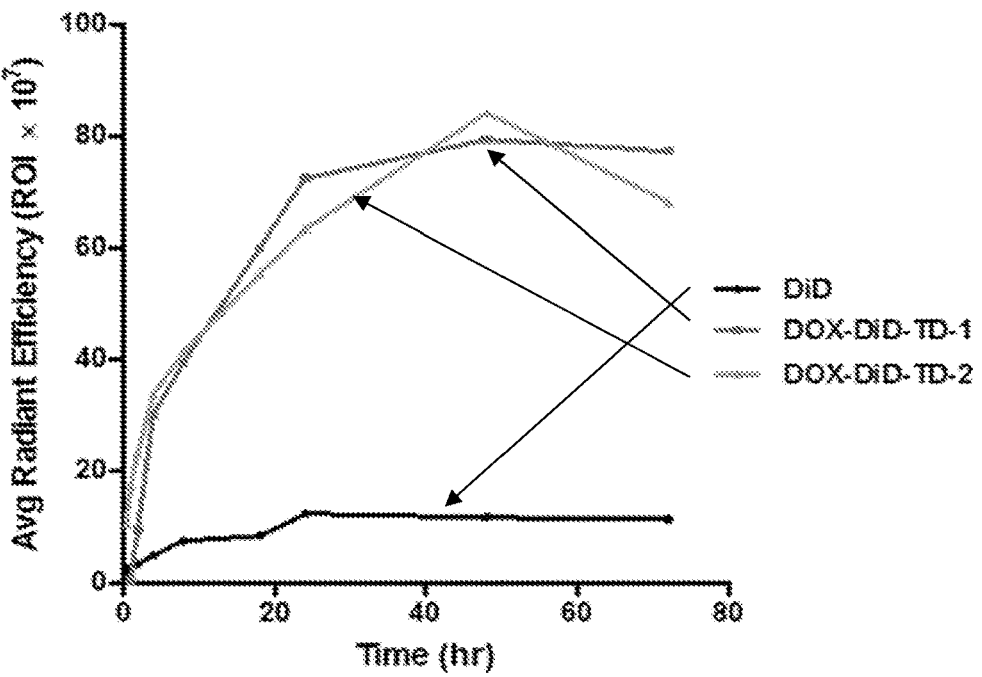
Figure 22:
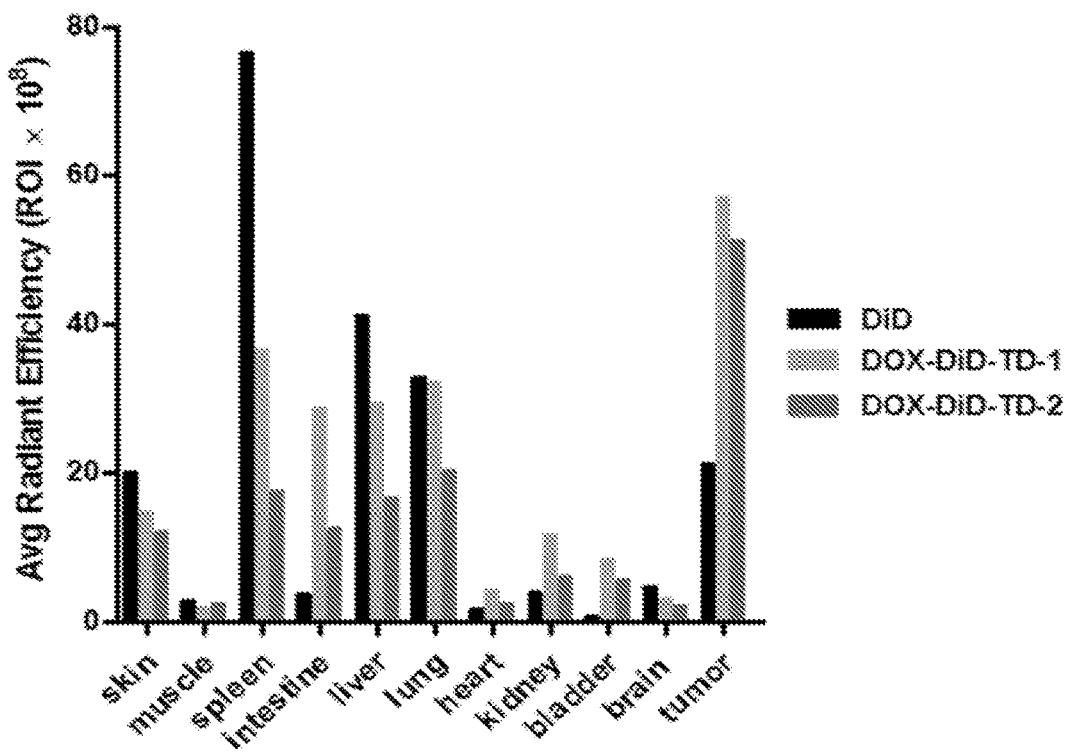
Figure 23:
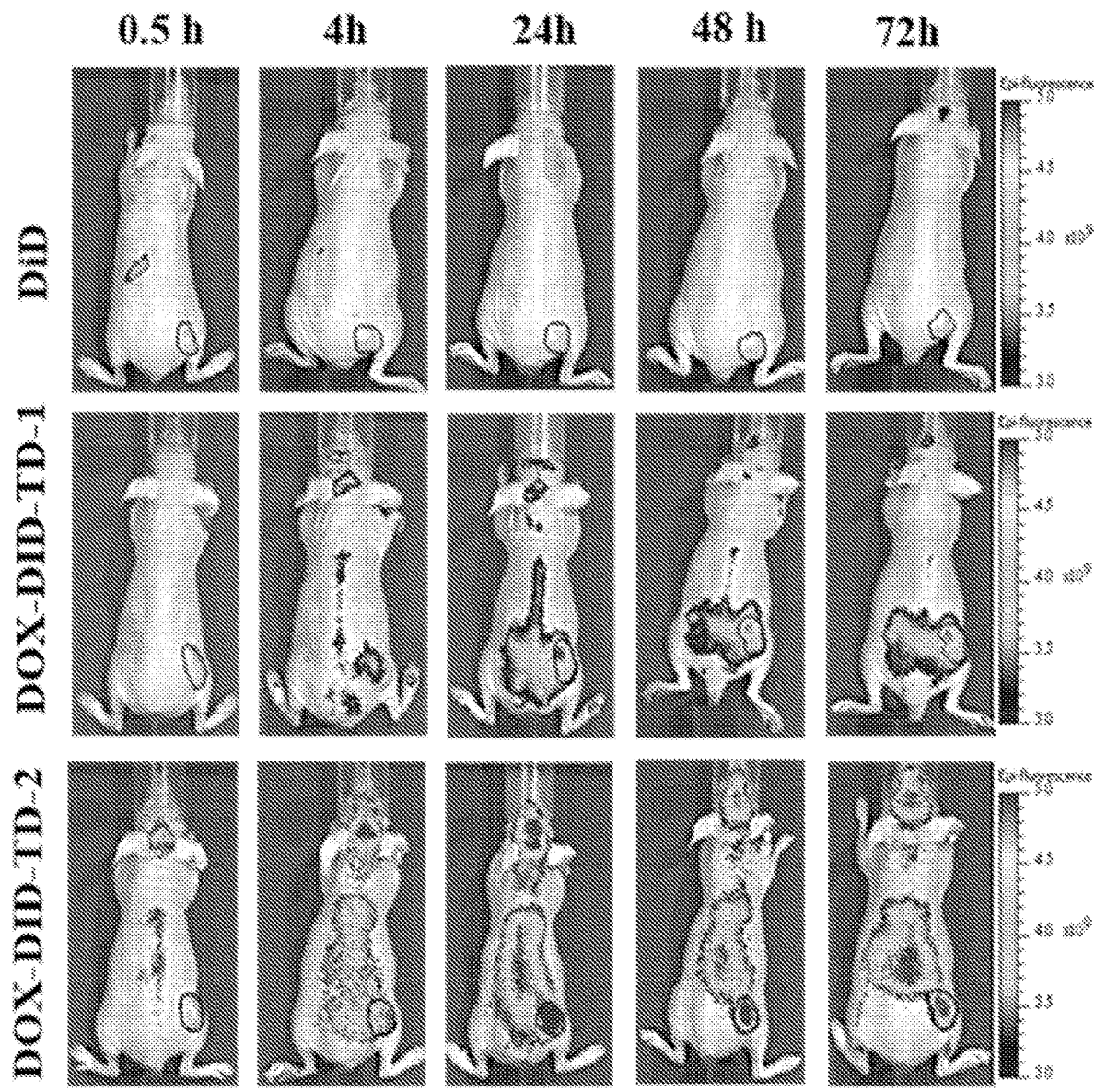
FIG. 23 shows (A) in vivo real-time imaging of free DiD and DiD-DOX-loaded Rf-containing nanoformulations i.v. injection in MDA-MB-231 xenograft tumor bearing nude mice by IVIS. (B) Representative ex vivo optical images of tumors and major organs taken out at 70 h after i.v. injection of free DiD and DiD-DOX-loaded Rf-containing nanoformulations. (C) Quantitative fluorescent intensity of the tumor in Raji xenograft tumor bearing nude mice in vivo imaging. (D) Quantitative fluorescent intensity of the tumor and major organs in MDA-MB-231 xenograft tumor bearing nude mice ex vivo imaging. Left to right in each group is DiD, DiD-DOX-TD-1, and DiD-DOX-TD-2. (E) Fluorescence microscopy images of MDA-MB-231 breast cancer tumor obtained from mice treated with free DiD, DiD-DOX-TD-1, and DiD-DOX-TD-2.
Figure 23:
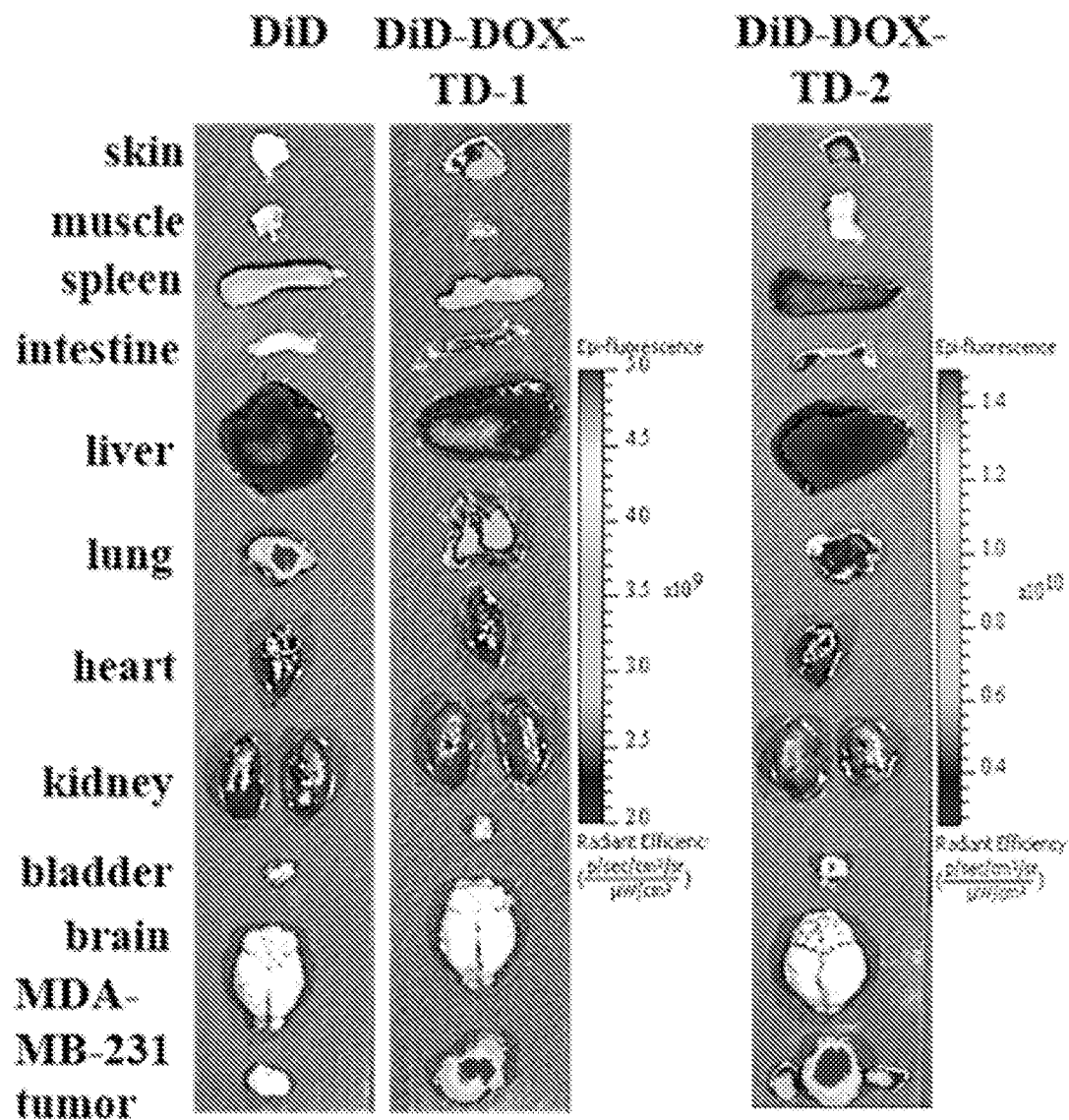
Figure 23:
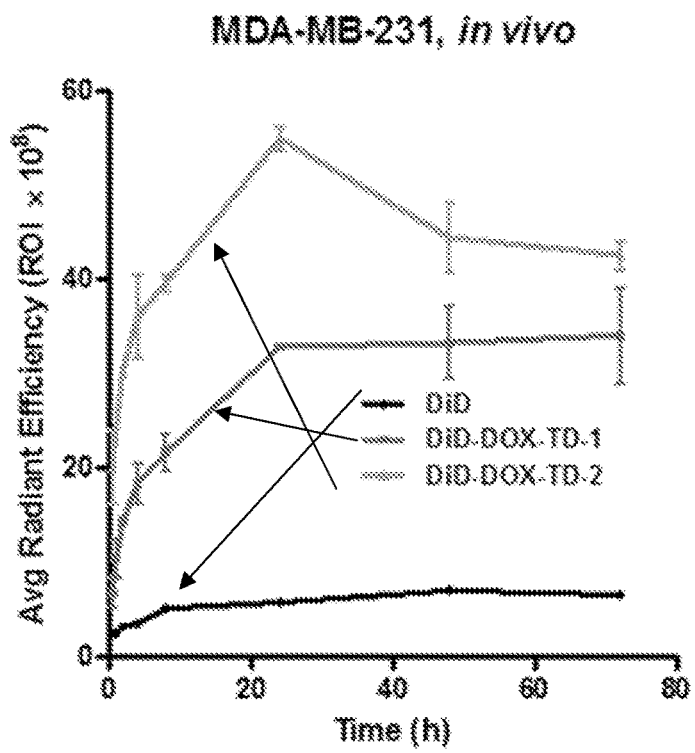
Figure 23:
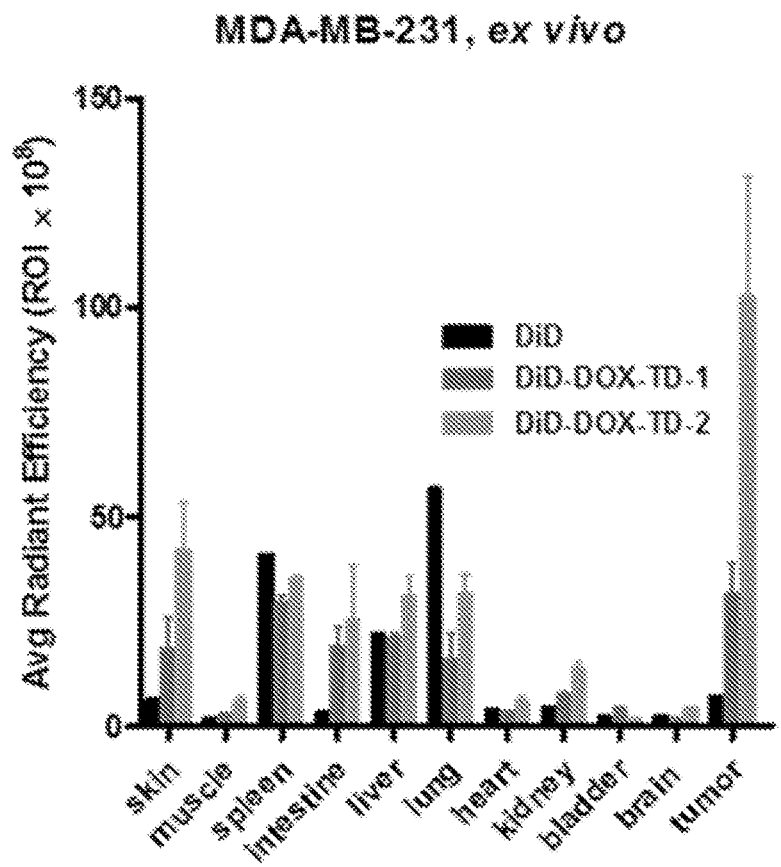
Figure 23:
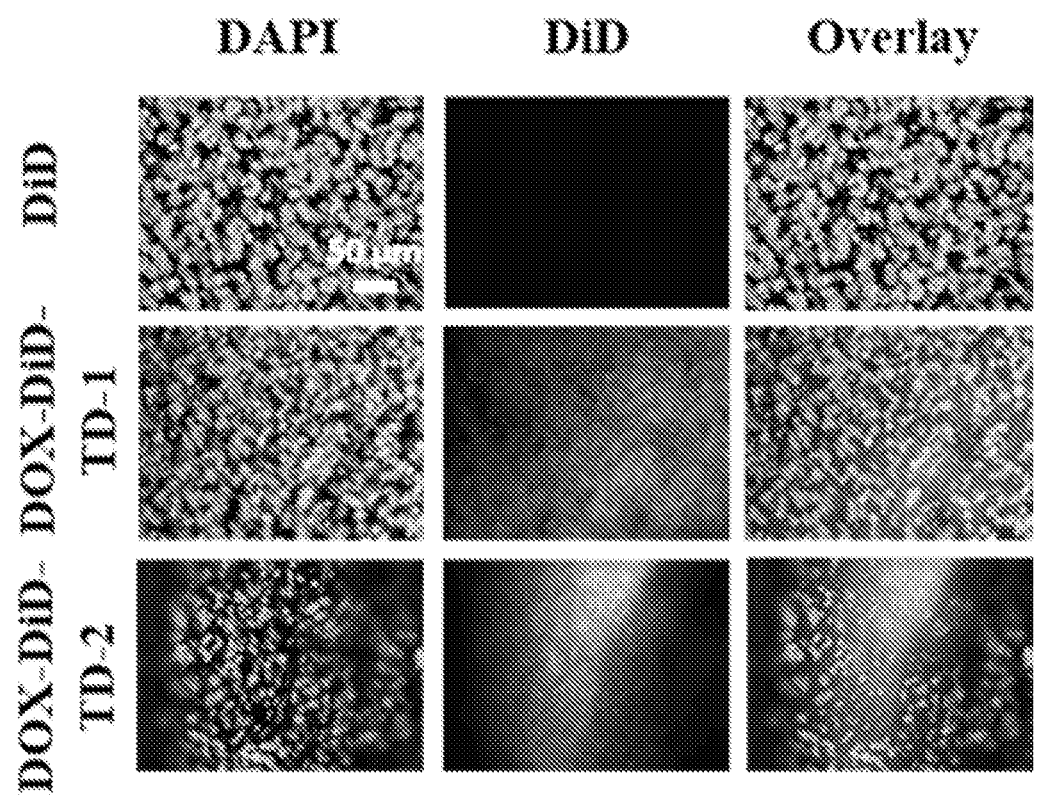
Figure 24:
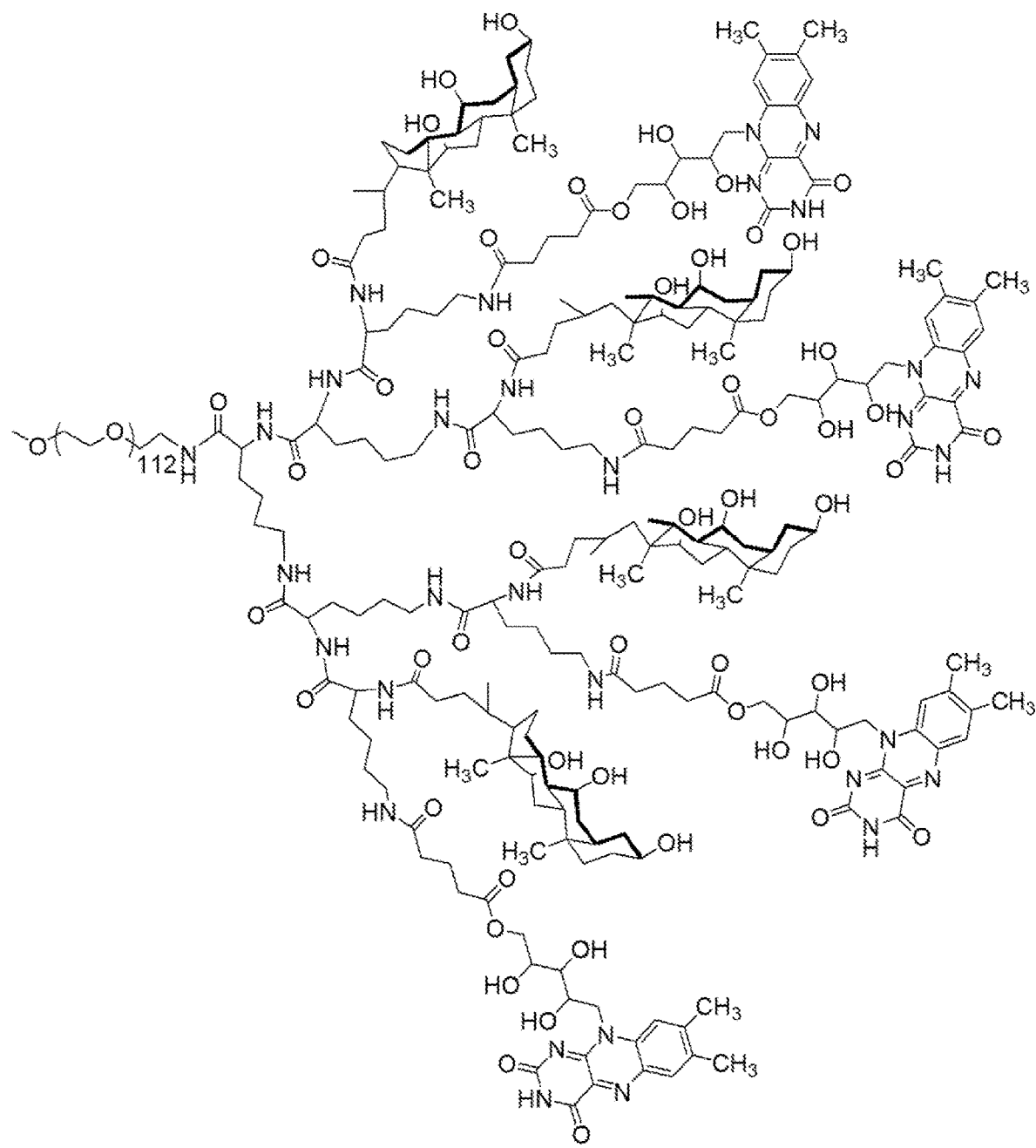
FIG. 24 shows the chemical structure for PEG$^{5K}$CA$_4$Rf$_4$.
Figure 25:
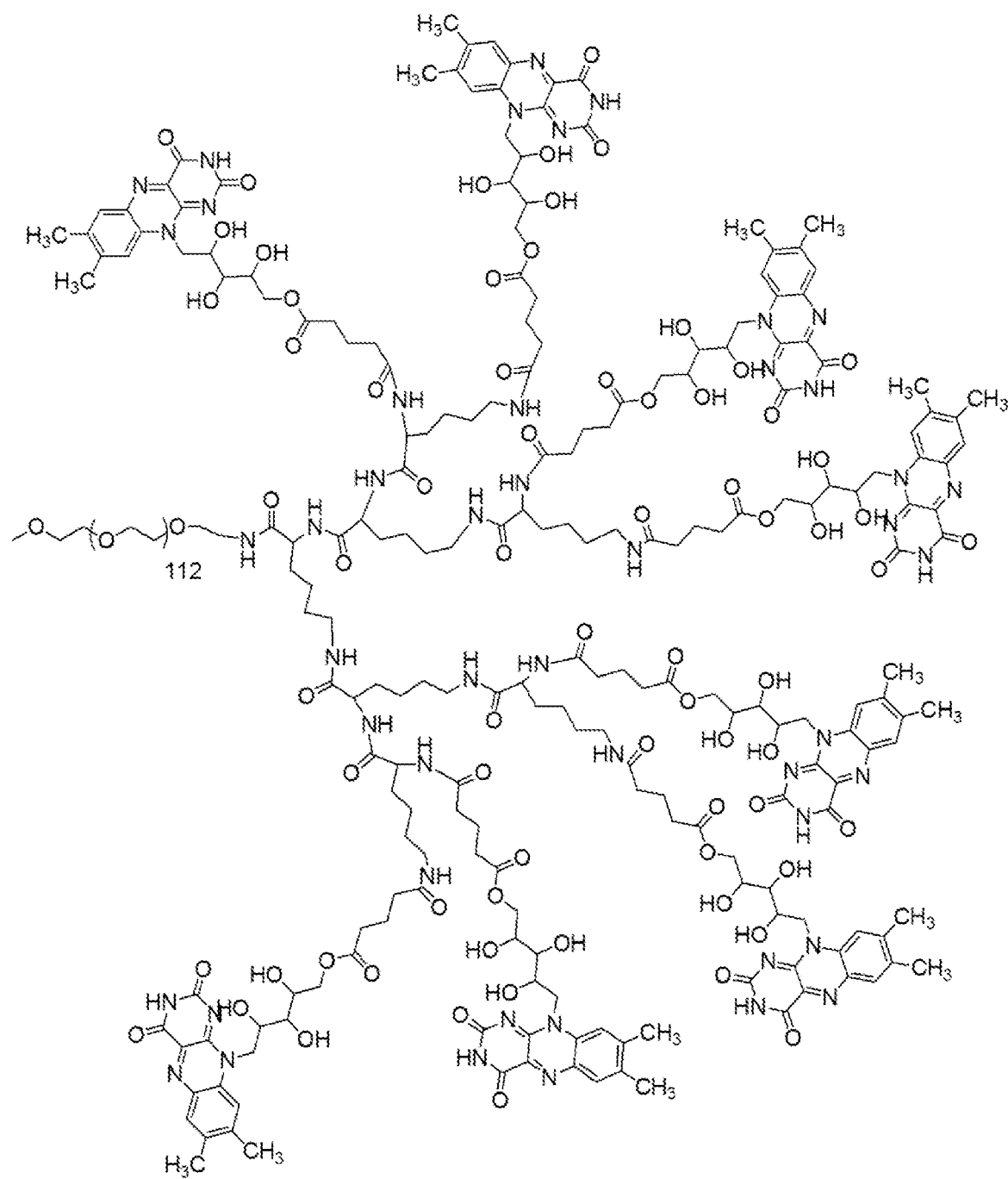
FIG. 25 shows the chemical structure for PEG$^{5K}$Rf$_8$.
Figure 26:
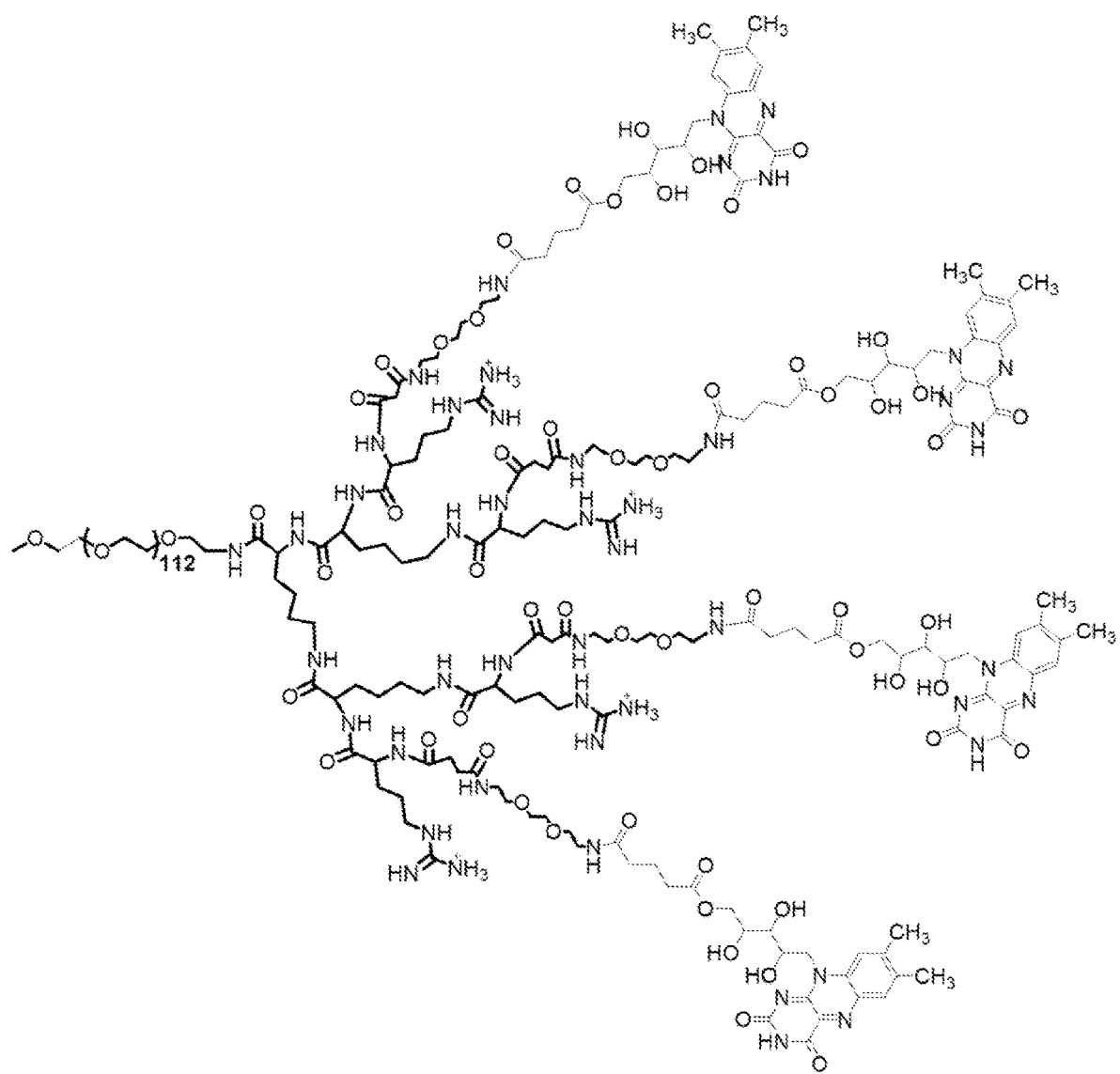
FIG. 26 shows the chemical structure for PEG$^{5k}$(Arg-Rf)$_4$.
Figure 27:
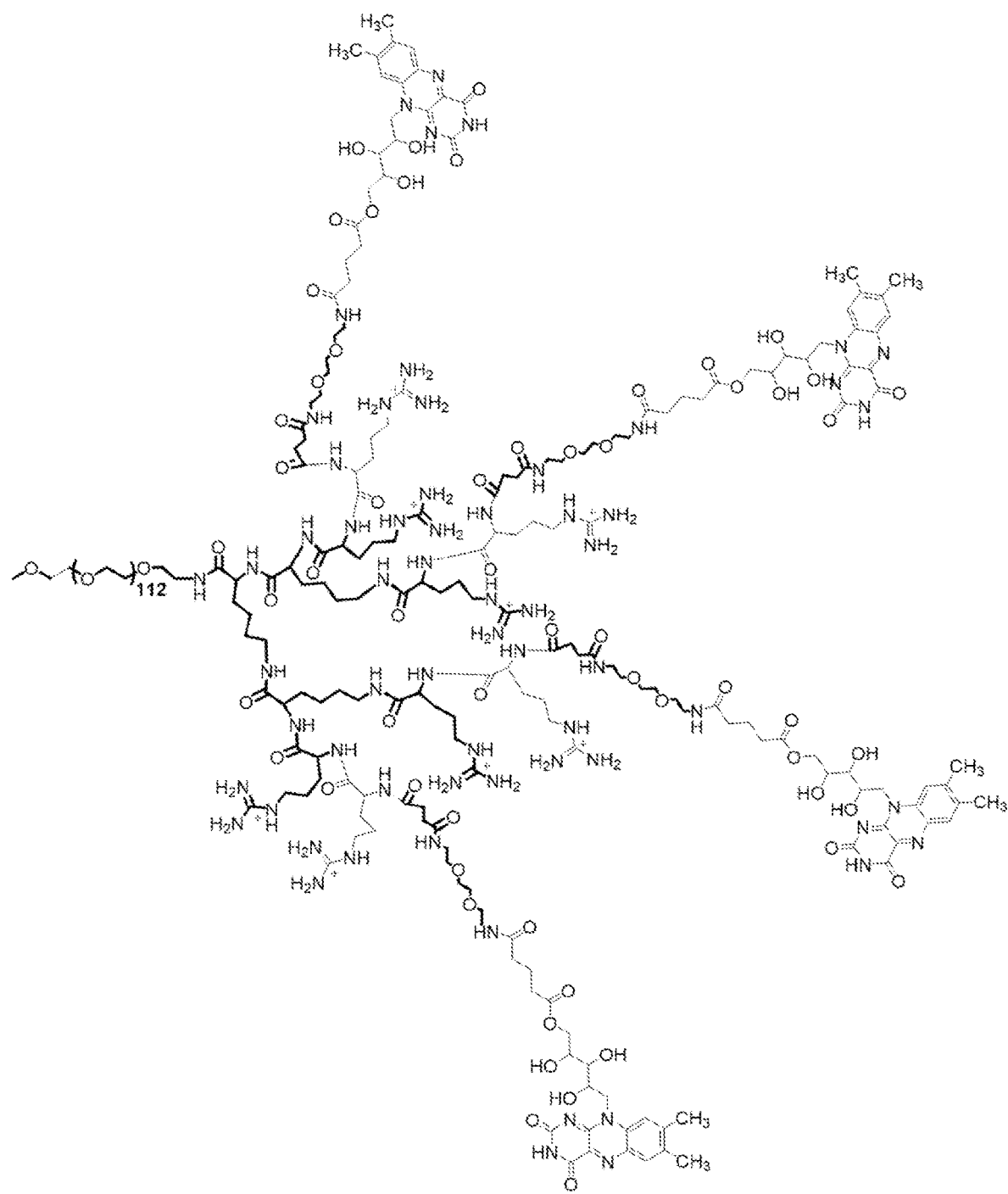
FIG. 27 shows the chemical structure for PEG$^{5k}$(Arg-Arg-L-Rf)$_4$.
Figure 28:
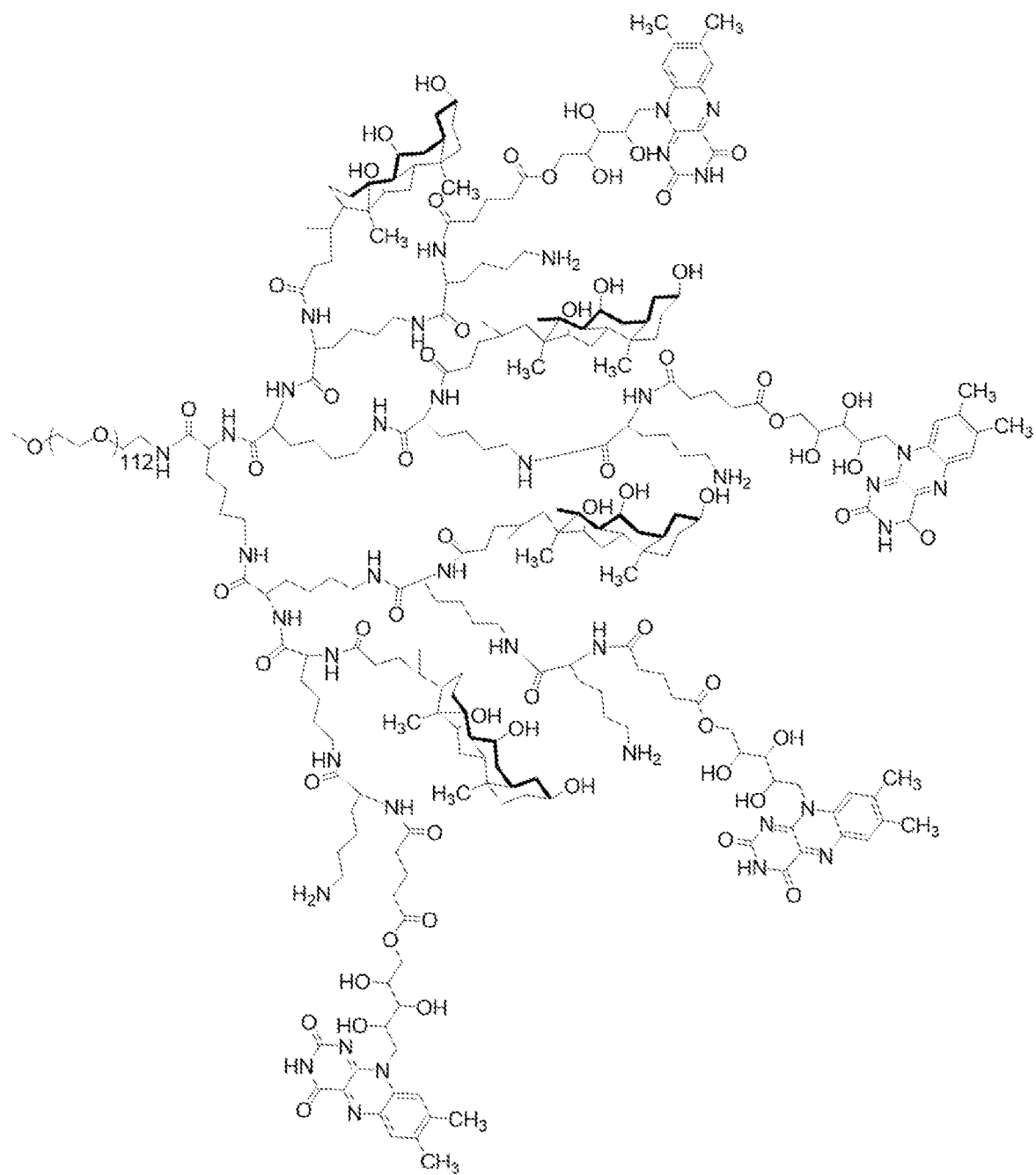
FIG. 28 shows the chemical structure for PEG$^{5k}$CA$_4$Rf$_4$(NH$_2$)$_4$.
Figure 29:
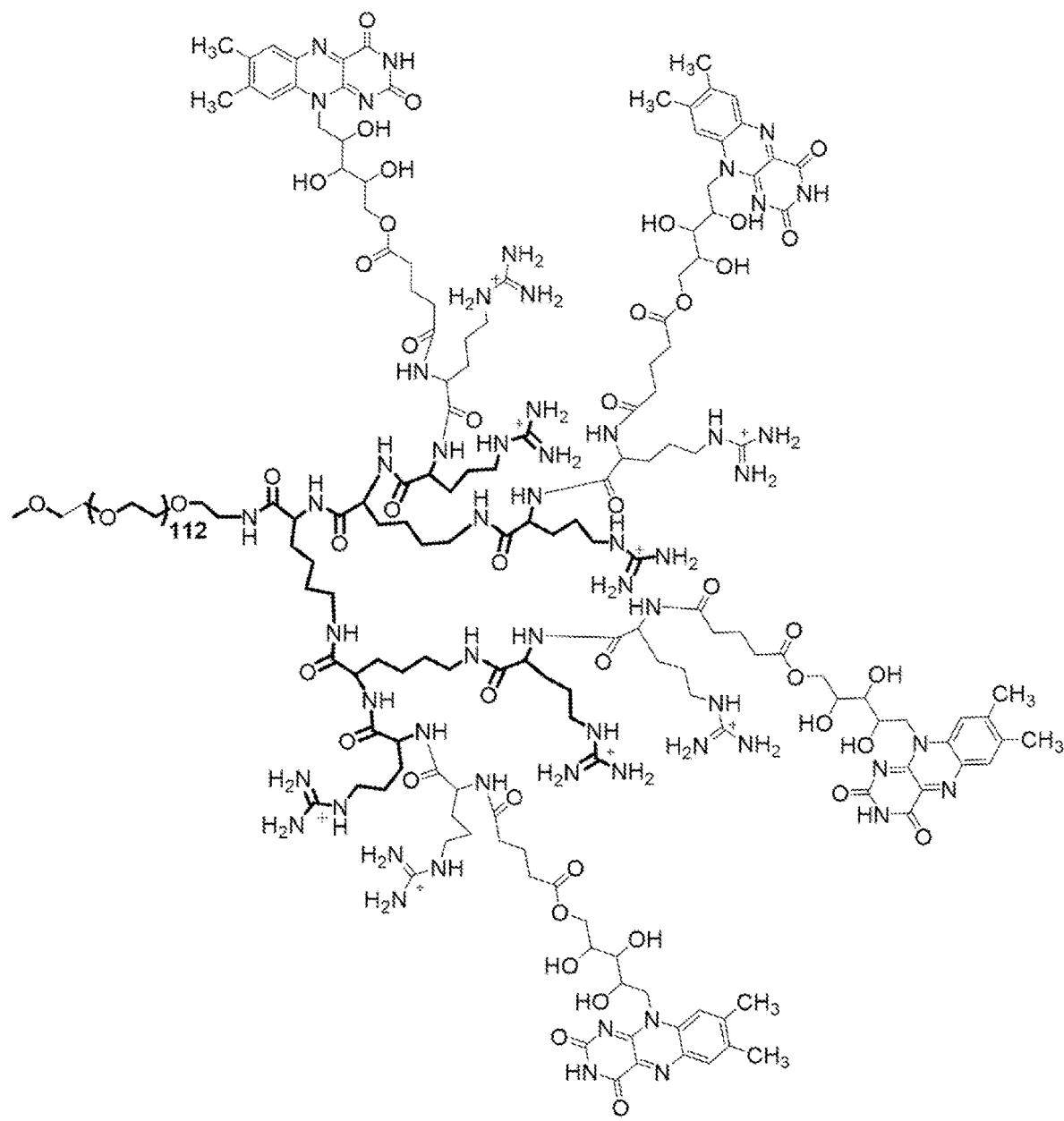
FIG. 29 shows the chemical structure for PEG$^{5k}$(Arg-Arg-Rf)$_4$.
Figure 30:
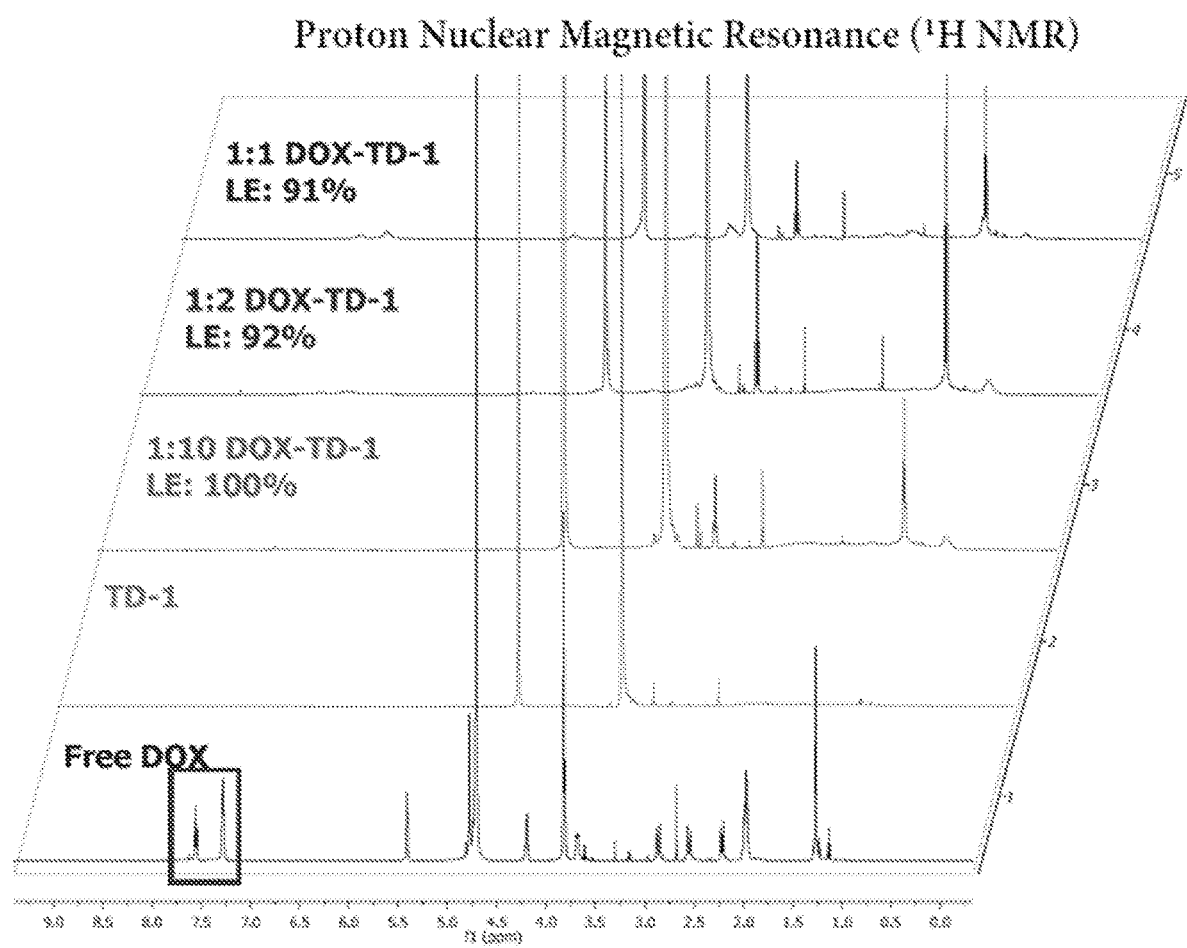
FIG. 30 shows ultra-high loading capacity of a composition of the instant disclosure. The nuclear magnetic resonance spectra show the loading of various compositions.
Figure 32:
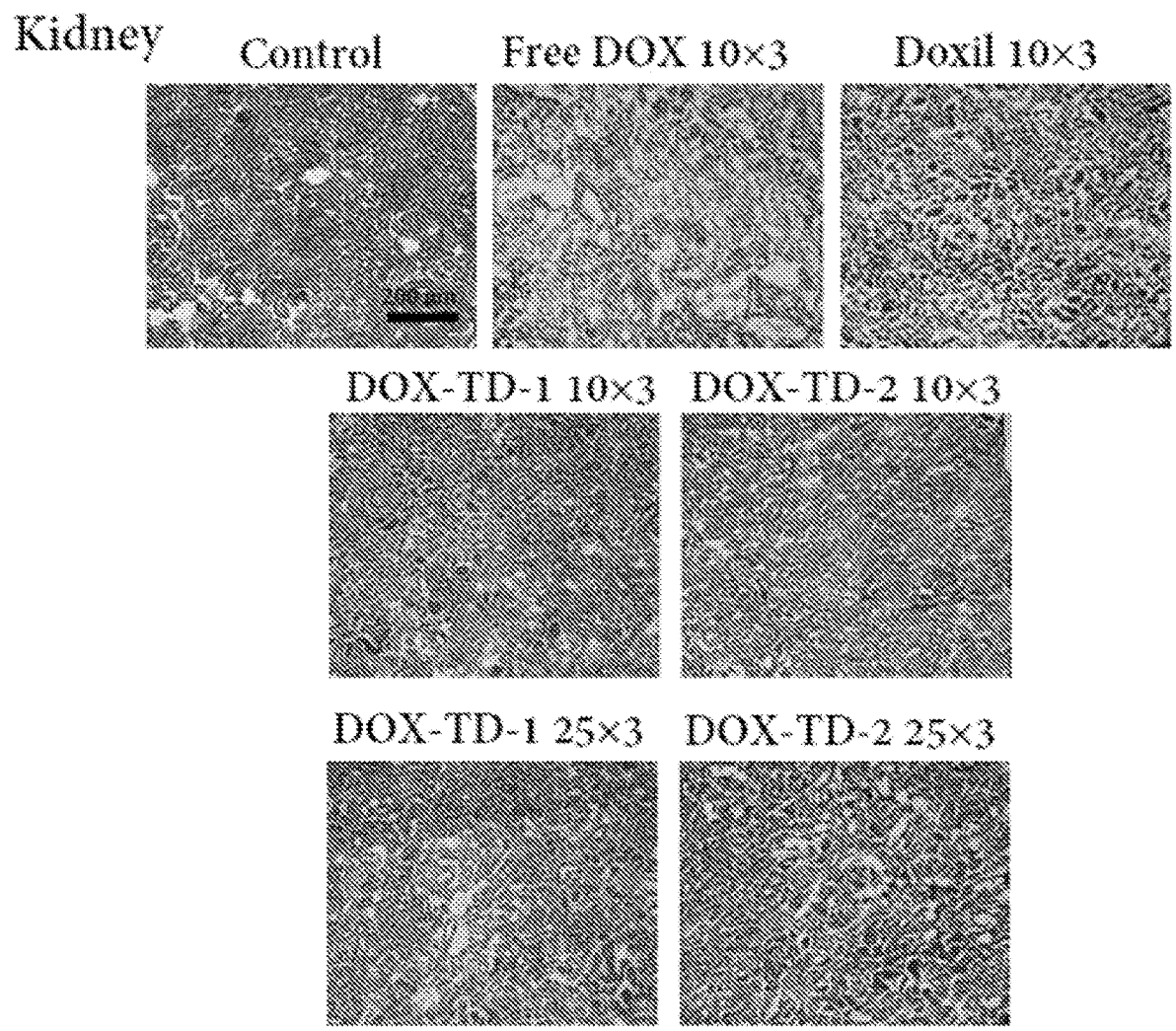
FIG. 32 shows pathological images of kidneys from the mice treated with different DOX formulations at different doses. Significant kidney tissue damage was observed in the mice treated with free DOX and all other groups showed no significant difference in comparison to the control group.
Figure 33:
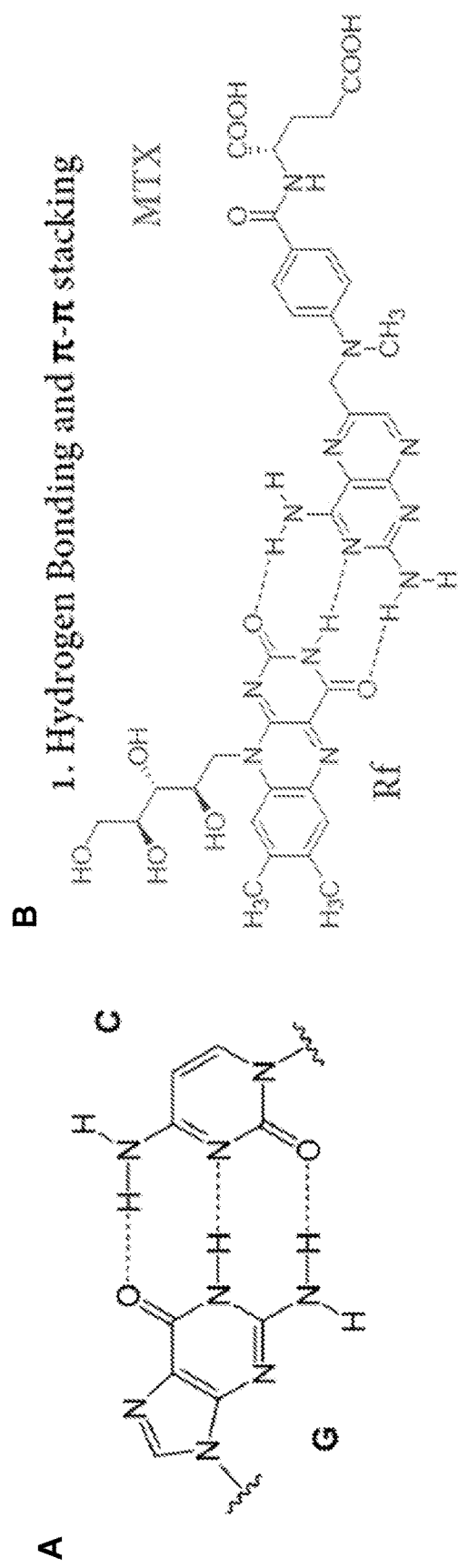
FIG. 33 shows DOX loading strategies. (A) Hydrogen bonding between Guanine and cytosine; (B) similar hydrogen bonding formed between riboflavin and methotrexate; (C) DLS particle sizes of MTX loaded PEG$^{5k}$Rf$_8$ micelles at drug loading ratio of 0.9:8.4 mass ratio (D) Size exclusive chromatography of free MTX and MTX loaded in micelles.
Figure 33:
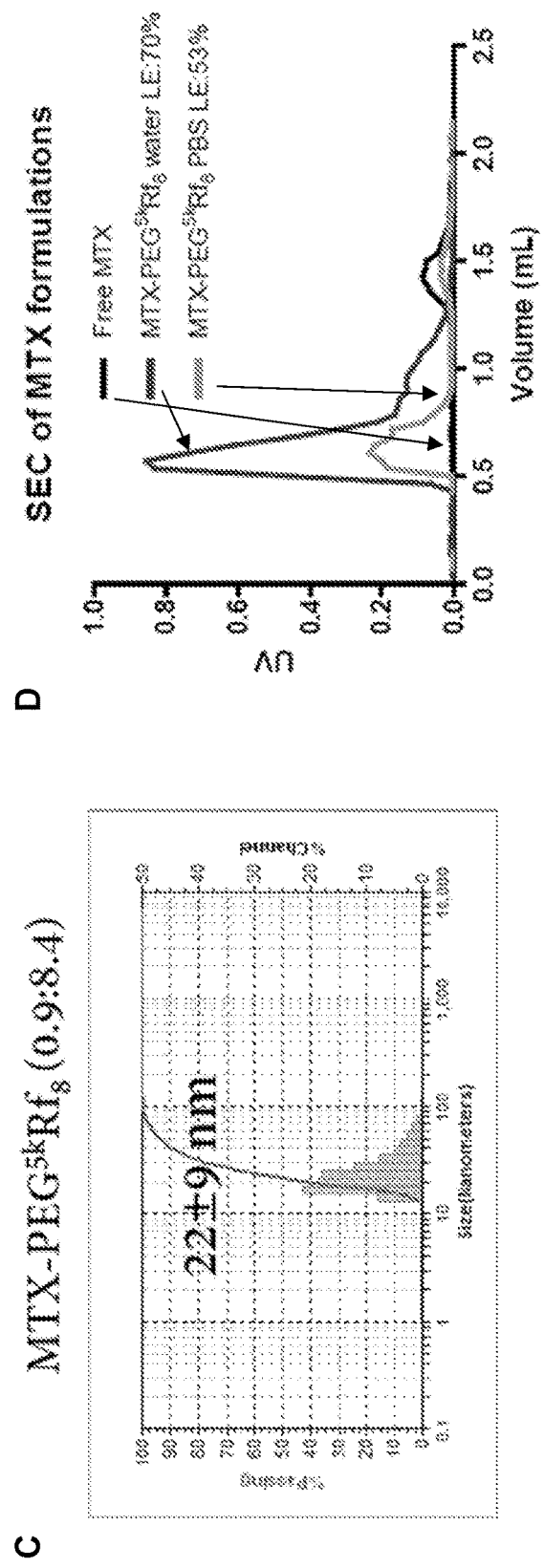
Figure 34:
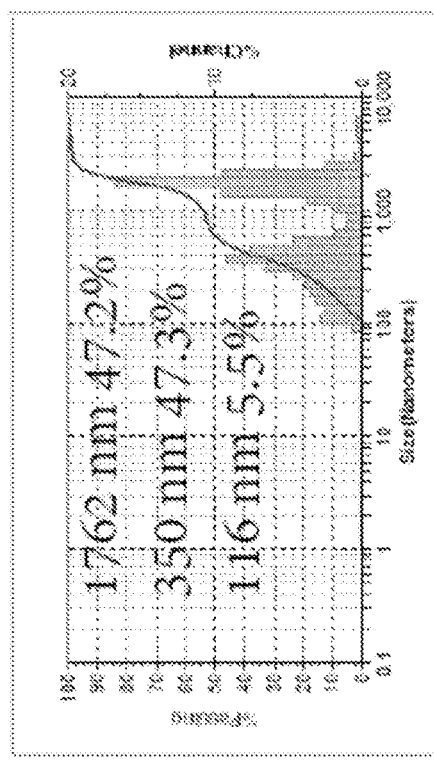
FIG. 34 shows methotrexate loading. DLS particle sizes of MTX loaded in PEG$^{5k}$Rf$_8$ micelles measured right after loading (A) or 1 h later (B); the loading efficiency is summarized in the table.
Figure 34:
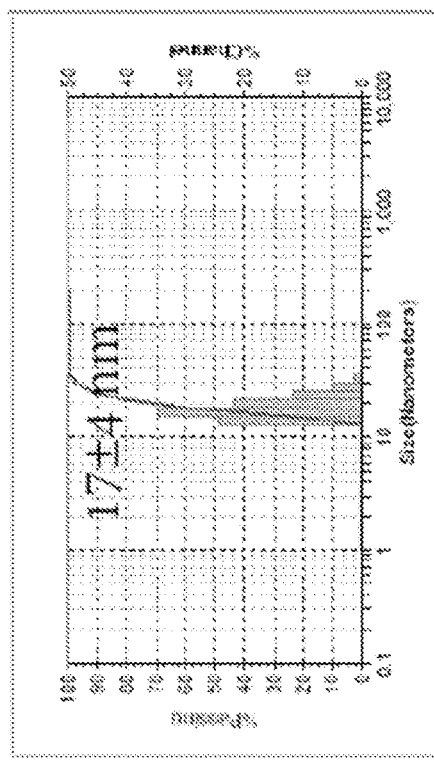
Figure 35:
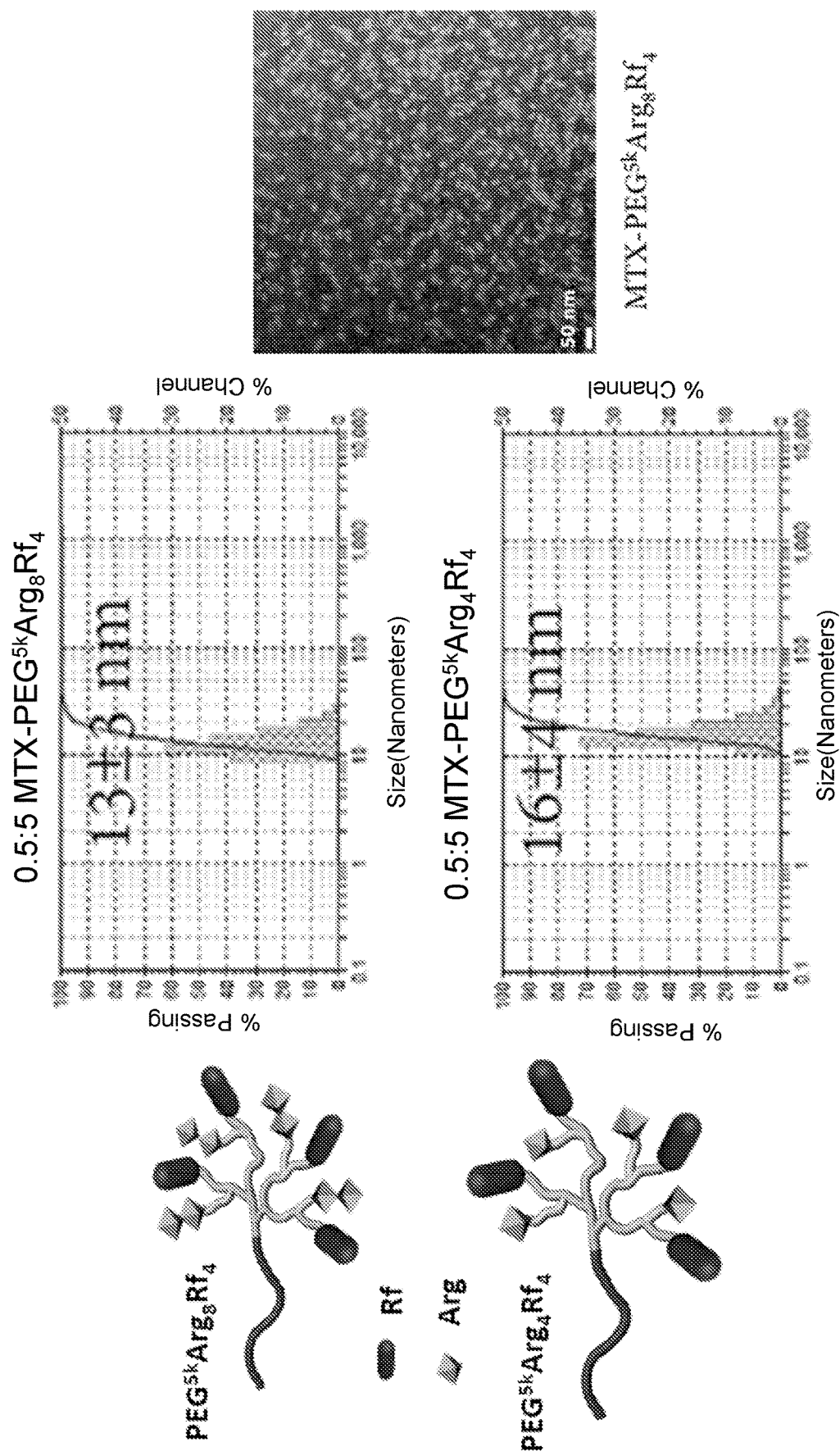
FIG. 35 shows the structural illustration of charged Rf-containing telodendrimers PEG$^{5k}$Arg$_8$Rf$_4$ and PEG$^{5k}$Arg$_4$Rf$_4$ micelles, and the DLS particle sizes and TEM images of MTX loaded micelles.
Figure 36:
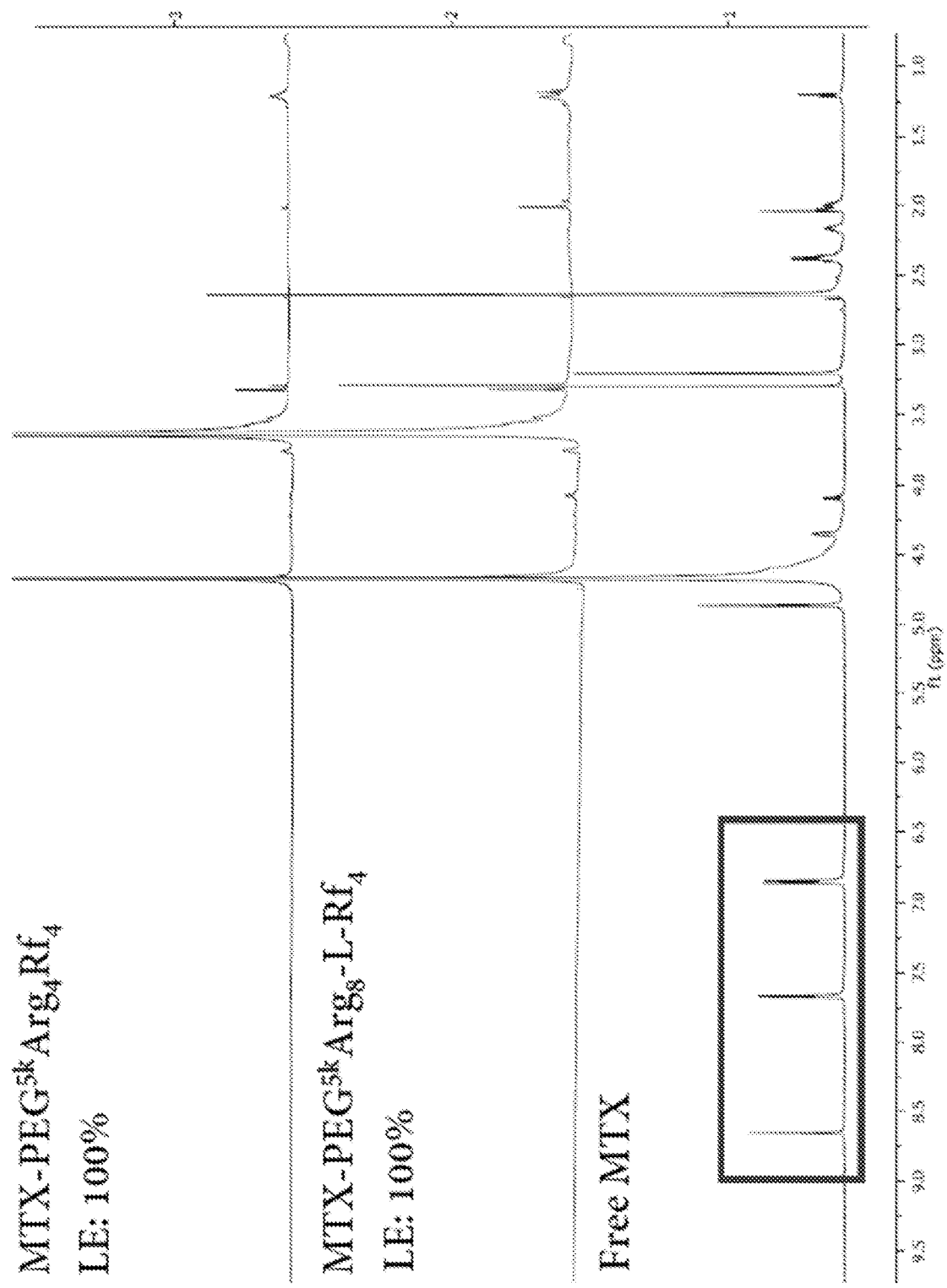
FIG. 36 shows proton nuclear magnetic resonance data showing methotrexate loading efficiency in water with almost 100% loading efficiency.
Figure 37:
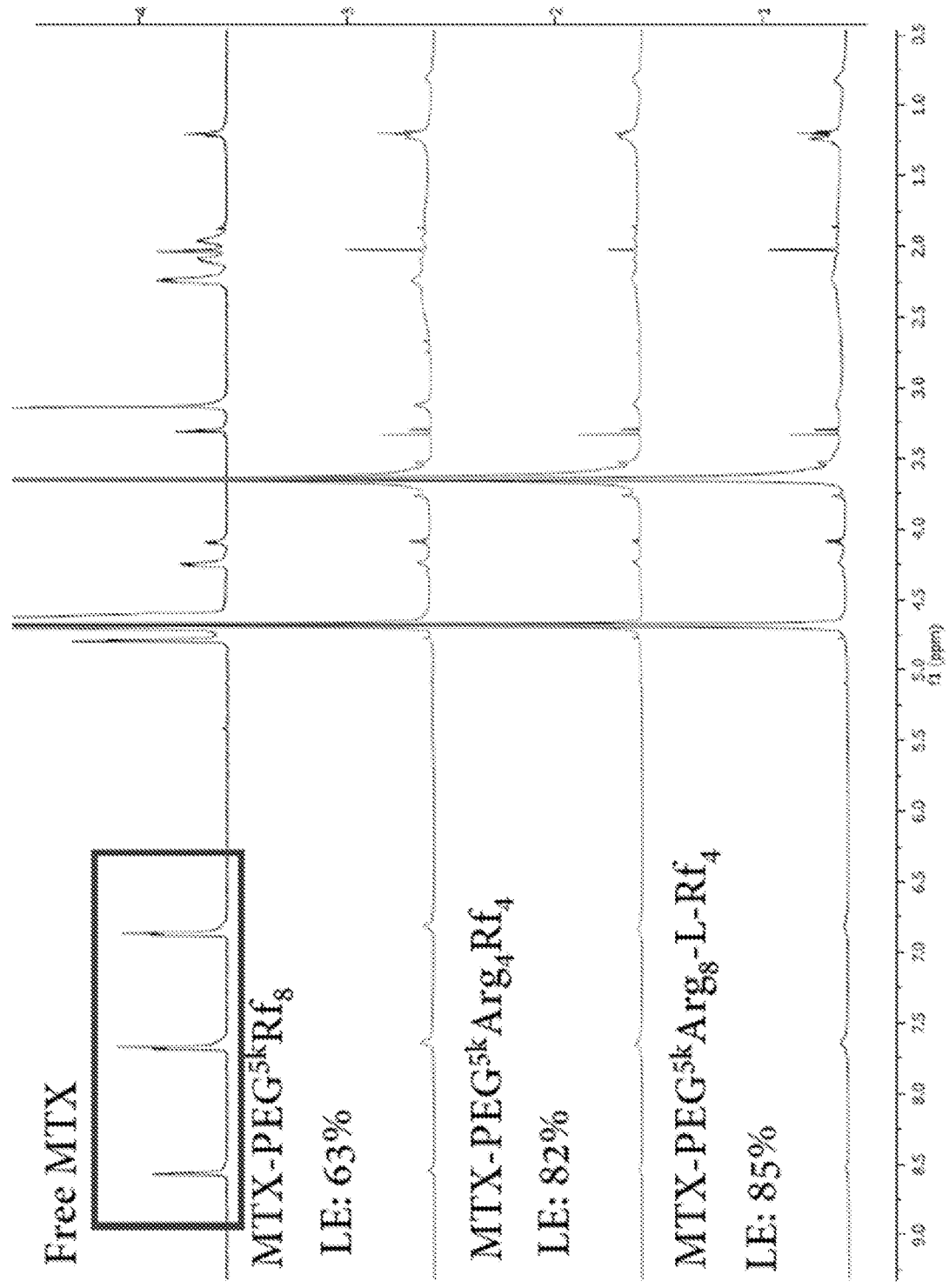
FIG. 37 shows proton nuclear magnetic resonance data show methotrexate loading efficiency in PBS were significantly improved by the charged riboflavin containing telodendrimers, in comparison to non-charged riboflavin telodendrimer.
Figure 38:
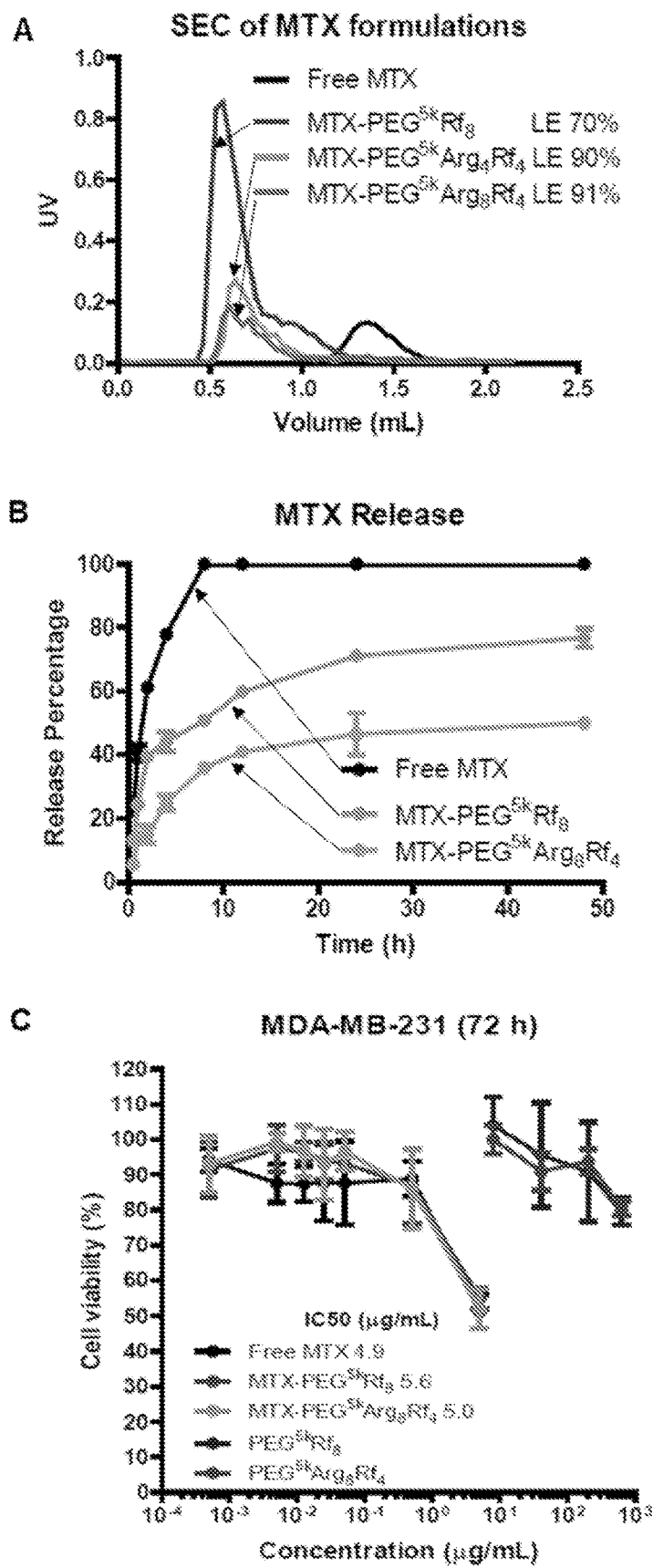
FIG. 38 shows in vitro characterization. (A) Size exclusion chromatography of MTX formulations. Drug loading efficiency was significantly enhanced by positive charged Rf-telodendrimers. (B) MTX release profile. Nanoformulations significantly prolong the drug release profile. (C) Cell viability assays indicate that nanoformulations of MTX kept the same potency with free MTX and the empty micelles are non-cytotoxic.
Figure 39:
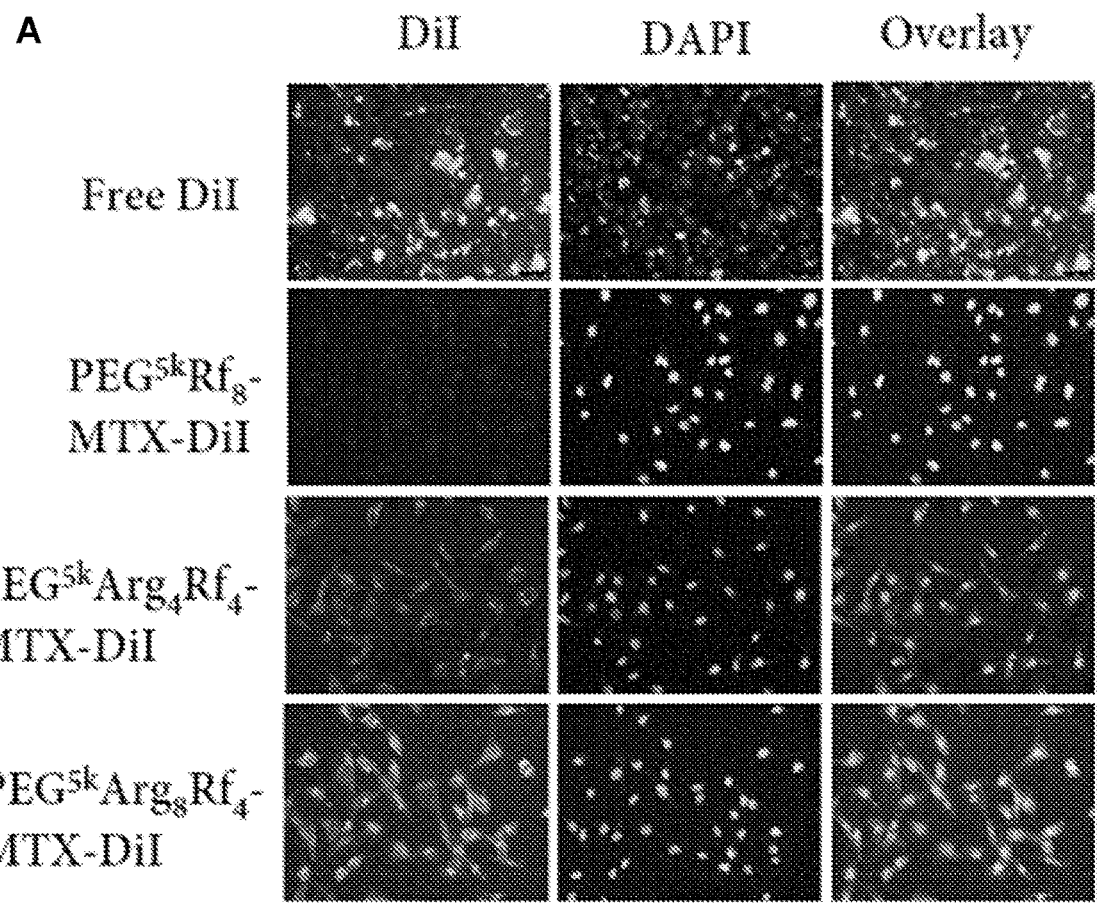
FIG. 39 shows cellular uptake data. (A) Confocal microscopic studies reveal that the positive charge enhanced cellular uptake of MTX and DiD co-loaded nanoparticles. (B) No hemolytic toxicity was found for riboflavin containing micelles, potential safety to use through i.v. injection. Left to right in each group is PEG$^{5k}$Rf$_8$, PEG$^{5k}$Arg$_4$Rf$_4$, and PEG$^{5k}$Arg$_8$Rf$_4$.
Figure 39:
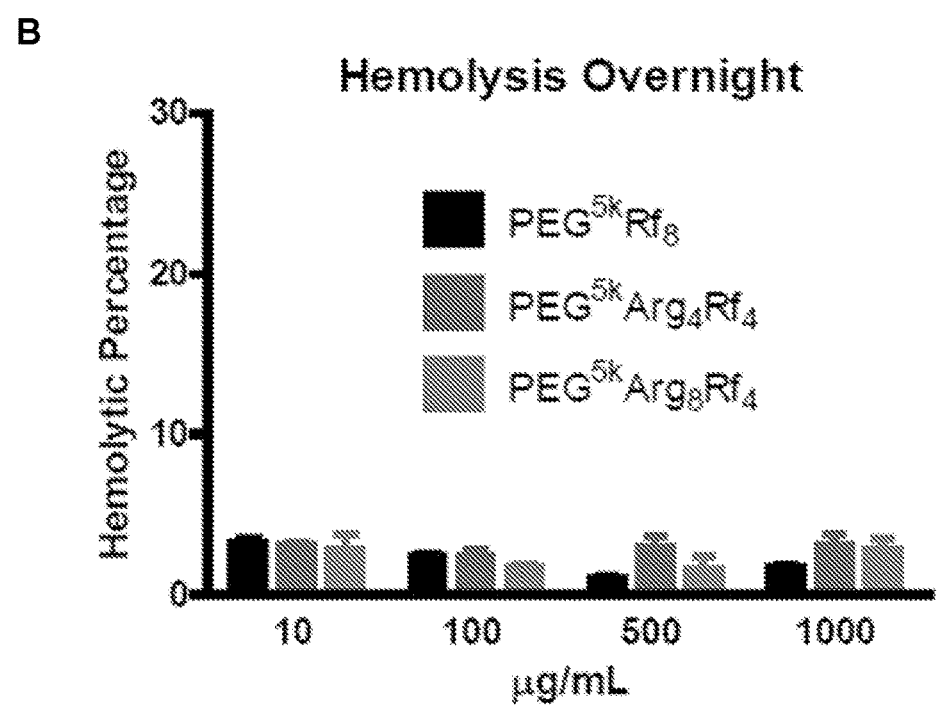
Figure 40:
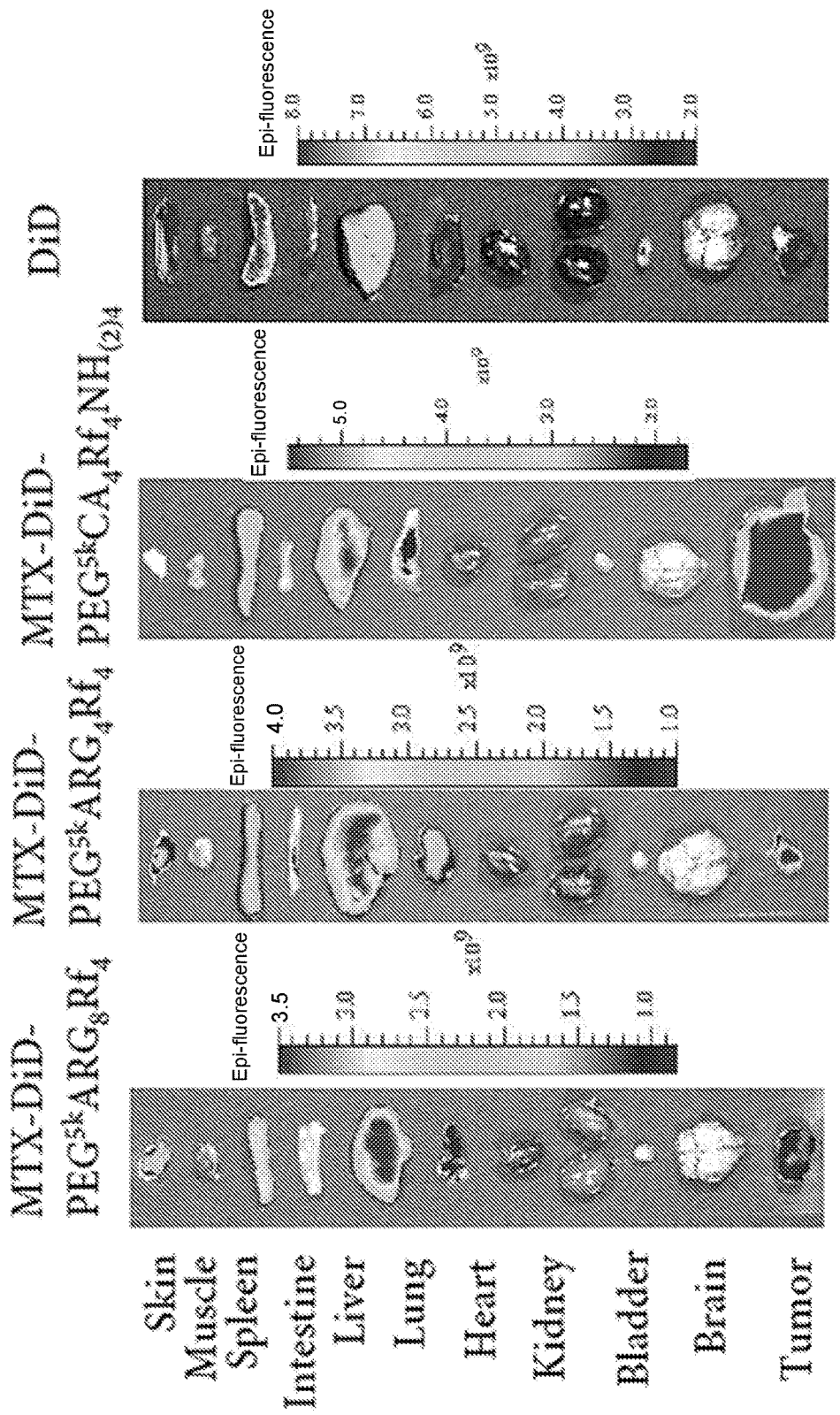
FIG. 40 shows IVIS imaging ex vivo. (A) The ex vivo imaging of major organs and tumor distributions of DiD and MTX co-loaded arginine containing micelles. (B) Quantitative analysis confirms that telodendrimers with four arginine or lysine reduces tumor uptake in comparison to telodendrimers with eight positive arginine. Left to right in each group is DiD, DiD-MTX-PEG$^{5k}$Arg$_4$Rf$_4$, DiD-MTX-PEG$^{5k}$Arg$_8$Rf$_4$, and DiD-MTX-PEG$^{5k}$CA$_4$Rf$_4$NH$_{(2)4}$.
Figure 40:
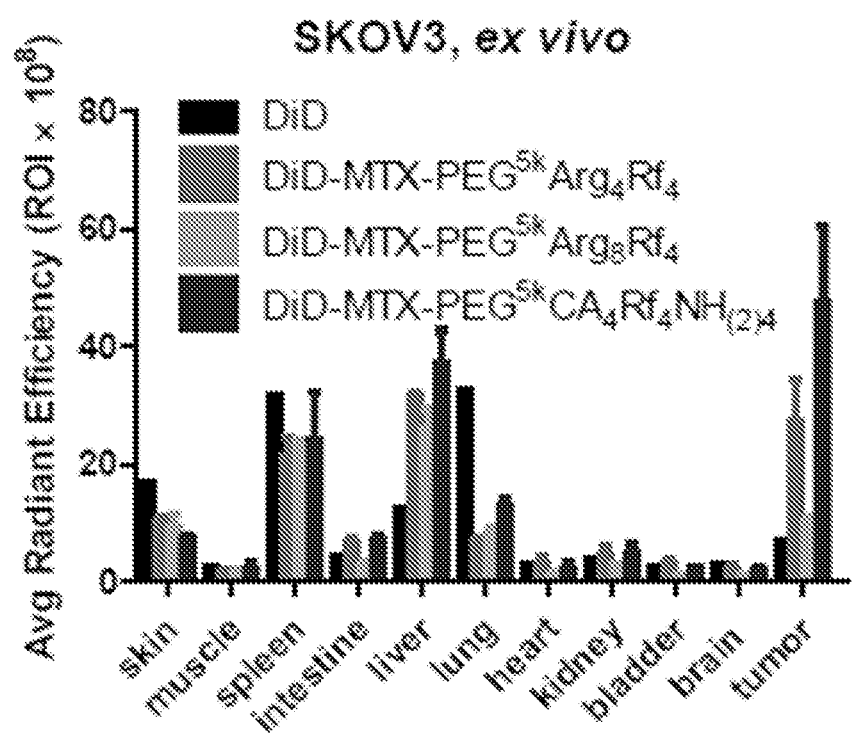

Our DOX nanoformulations with small particle sizes of 40 and 23 nm, respectively, were expected to cross tumor blood vessel easily and accumulate in the tumor site by EPR effects. Nude mice bearing xenograft tumors, e.g. Raji lymphoma, SKOV-3 ovarian cancer, and MDA-MB-231 breast cancer, were treated with DOX nanoformulations co-loaded with a near-infrared (NIR) dye DiD and monitored by small animal fluorescence imager. Only trace amount of DiD (2% in mass) was co-encapsulated in micelles, which did not affect the physical properties of the DOX nanoformulations, for example, particle sizes remained the same about 41 and 28 nm for DiD-DOX-TD-1 and DiD-DOX-TD-2, respectively (FIGS. 21A & B). The significant fluorescence quenching of DOX and DiD, and release of DiD from co-loading nanoparticles synchronized with DOX release profile were also observed in vitro (FIGS. 21C & D). Therefore, the NIR fluorescent signal of DiD can be used to trace the in vivo biodistribution of the payload DOX. The in vivo NIR fluorescent signal is sensing the in-situ accumulation and release of DiD and DOX, which is active for cancer treatment. It is important because significant tumor accumulation doesn't necessarily mean improved antitumor effects, for example Doxil®, due to limited drug release. The in vivo biodistribution of DiD-DOX nanoformulations in tumor bearing mice were monitored at different time after tail vein injections as shown in FIG. 11A (FIGS. 22 & 23). For free DiD injection, accumulation in spleen was observed in vivo as early as 1 hour after injection due to macrophage clearance of the hydrophobic DiD aggregates, which was metabolized and cleared after 24 to 48 hours. No specific tumor accumulation was visualized for the free DiD group. In contrast, mice treated with nanoformulations were detected to have gradually tumor uptake over 24 to 48 hours, which indicates the active drug accumulation specifically at tumor sites. In addition, TD-1 lights up in vivo slower and slightly weaker than TD-2 (FIGS. 11A & B), which may be correlated with relatively slower drug release. The ex vivo imaging of tumor and major organs at 70 h post-injection in (FIG. 11C) revealed the similar tumor specific accumulation for both nanoformulations, where weak tumor uptake and relatively high lung and spleen uptake were observed for free DiD injection. As a comparison, both nanoformulations significant increase tumor uptakes to over 4-fold higher than free DiD injection. (FIG. 11D). In fluorescence microscope imaging, compared to the DiD fluorescence of tumor in free DiD treated group, strong fluorescence signals were found in the tumors treated by DOX-DiD-TD-1 and DOX-DiD-TD-2 (FIG. 11E). These results are in good agreement with the previous reports that relatively small sized nanoparticles with optimized stability could target a tumor preferentially via EPR effect.

Antitumor Efficacy—

Figure 12:
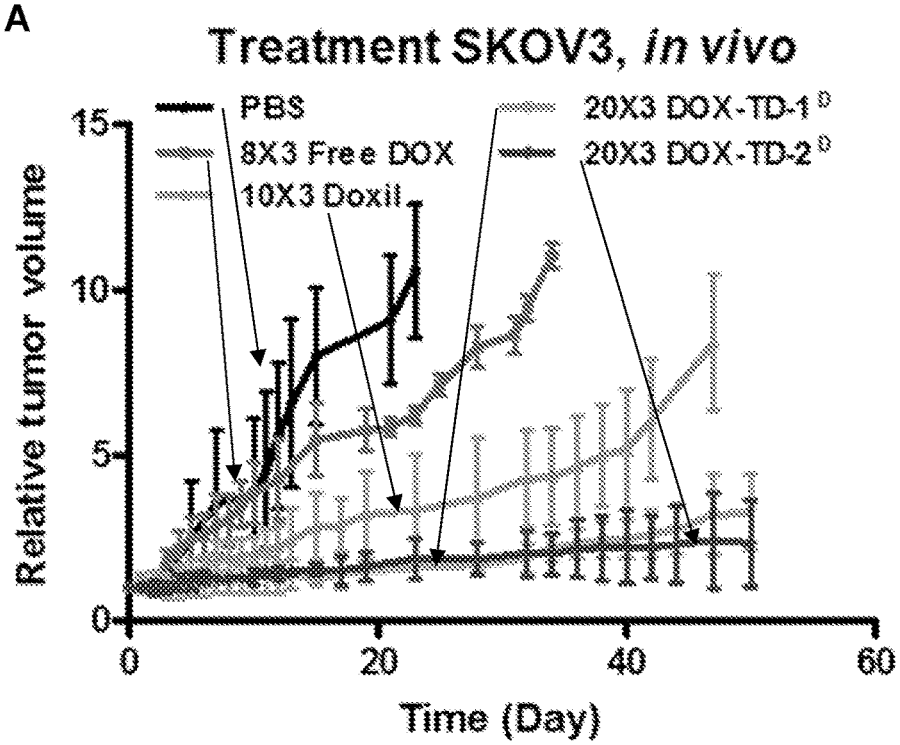
FIG. 12 shows in vivo anti-tumor efficacy (A), body weight changes (B) and survival curve (C) after i.v. injection of PBS, free DOX, Doxil®, dialyzed DOX-TD-$1^D$ and DOX-TD-$2^D$ in SKOV3 xenograft bearing nude mice. Three doses were given at days 0, 4, 8.
Figure 12:
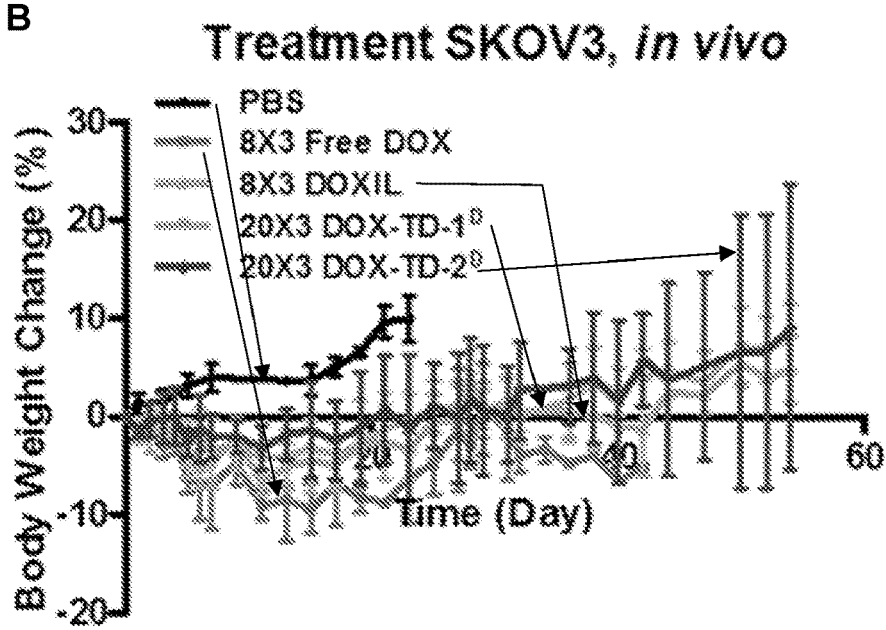
Figure 12:
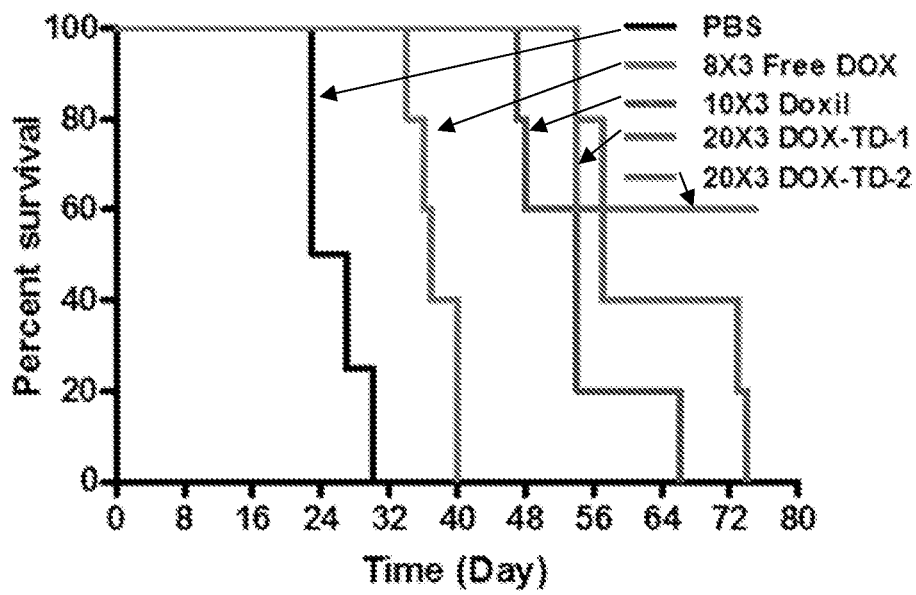

After demonstrating the in vivo tumor targeting properties of DOX-loaded nanoformulations, we evaluated their antitumor effects to nude mice bearing SKOV-3 ovarian xenograft tumors. Animals were treated with various DOX formulations on days 0, 4 and 8 for three consecutive dosage at their MTD levels in comparison with PBS control, i.e. DOX-TD-$1^D$, DOX-TD-$2^D$, DOX, Doxil® and PBS. The treatment started at tumor sizes of 150-200 mm³. Compared with PBS control group, free DOX at 8 mg/kg delayed tumor growth and prolonged animal survival from 27 to 37 days for the half-survival time. With increased dose and tumor targeted drug delivery, Doxil® further improved tumor inhibition when compared to the free DOX with a further increased half-survival time of 54 days. In contrast, our nanoformulations significantly inhibited tumor growth for more than 50 days (FIG. 12A). The growth of tumors was completely inhibited and even shrunk during the treatments and till day 30, while tumors were continuously progressing in DOX and Doxil® treatment groups. In the following days, 3 out of 5 mice in DOX-TD-$1^D$, and 2 out of 5 mice in DOX-TD-$2^D$ groups experienced tumor necrosis and were euthanized although with small tumor sizes. The tumor necrosis in these mice may be caused by the DOX treatment, which destroyed the nutrient and oxygen supply into the interior of tumor. There was no bodyweight lost over 15% in all the DOX formulations treated groups and PBS control group (FIG. 12B). Thus, all the groups treated with nanoformulations showed apparent therapeutic effects and extended survival time. No mice in the free DOX group survived longer than 40 days and last mice in Doxil® group was euthanized on day 66 due to oversized tumor (FIG. 12C). The last two of the mice (40%) treated by DOX-TD-$1^D$ survived longer than 73 days and three mice (60%) in DOX-TD-$2^D$ group survived without tumor progression even over 100 days. It clearly demonstrated that these Rf-containing nanoformulations of DOX significantly improved anticancer effects with the reduced toxicity and increased tolerated doses in comparison with both clinical formulations, e.g. DOX and Doxil®. We believe that the stable and efficient drug encapsulation in the small-sized nanoparticles is critical for tumor-targeted drug delivery and the improved in vivo anticancer effects. Although, DOX-TD-$2^D$ exhibits better anticancer effects in vivo than DOX-TD-$1^D$, both nanoformulations exhibited remarkable benefit of survival in SKOV3 models over both free DOX and Doxil®, and deserve further studies in the larger cohort studies for ovarian cancer and other cancer treatments.

CONCLUSION

Disclosed herein are Rf-containing telodendrimer nanoformulations with an ultra-high DOX loading capacity were investigated. The results revealed that the DOX-TD-1 and DOX-TD-2 micelles were 40 and 23 nm in diameter, respectively, with 100% (w/w) DOX loading content, provided advantage for systemic drug delivery. The initial burst release was significantly reduced by a simply 5-day storage at room temperature. Sustained release of DOX from the micelles was observed, which effectively inhibited the growth of several types of cancer cells in vitro. In the SKOV3 ovarian cancer, MDA-MB-231 breast cancer, and Raji lymphoma tumor bearing nude mice models, the drug-loaded micelles exhibited prolonged blood circulation time, much stronger accumulation in tumor, reduced distribution in other healthy organs, and significantly superior antitumor efficacy than free DOX and Doxil. These 2 Rf-containing nanoformulations with promising preclinical data that improved the bioavailability and reduced the toxic side effects of DOX would provide promising DOX nanocarrier platforms for clinical cancer treatment.

Example 2

The following example provides the loading of compositions and nanocarriers of the present disclosure, cell viability and toxicological data of compositions and nanocarriers of the present disclosure, in vivo imaging of subjects treated with compositions and nanocarriers of the present disclosure, and structural data of compositions and nanocarriers of the present disclosure.

FIGS. 30-40 disclose the loading of compositions and nanocarriers of the present disclosure, cell viability and toxicological data of compositions and nanocarriers of the present disclosure, in vivo imaging of subjects treated with compositions and nanocarriers of the present disclosure, and structural data of compositions and nanocarriers of the present disclosure.

Data in these figures show that Rf-telodendrimer nanocarriers for DOX delivery exhibited ultra-high drug loading capacity (e.g., 1:1 w/w), optimal stability, and small particle sizes (20-40 nm), and sustained DOX release with reduced initial burst release. The data also indicate prolonged PK profiles compared to free DOX. The data also indicate a 2~2.50-fold increase in MTD compared to clinically approved free DOX and DOXIL®. Further, both DOX RF-nanoformulations exhibited remarkable benefit of survival in SKOV3 models over both free DOX and DOXIL®.

Although the present disclosure has been described with respect to one or more particular embodiments and/or examples, it will be understood that other embodiments and/or examples of the present disclosure may be made without departing from the scope of the present disclosure.

The invention claimed is:

1. A compound, comprising: a structure selected from the group consisting of:

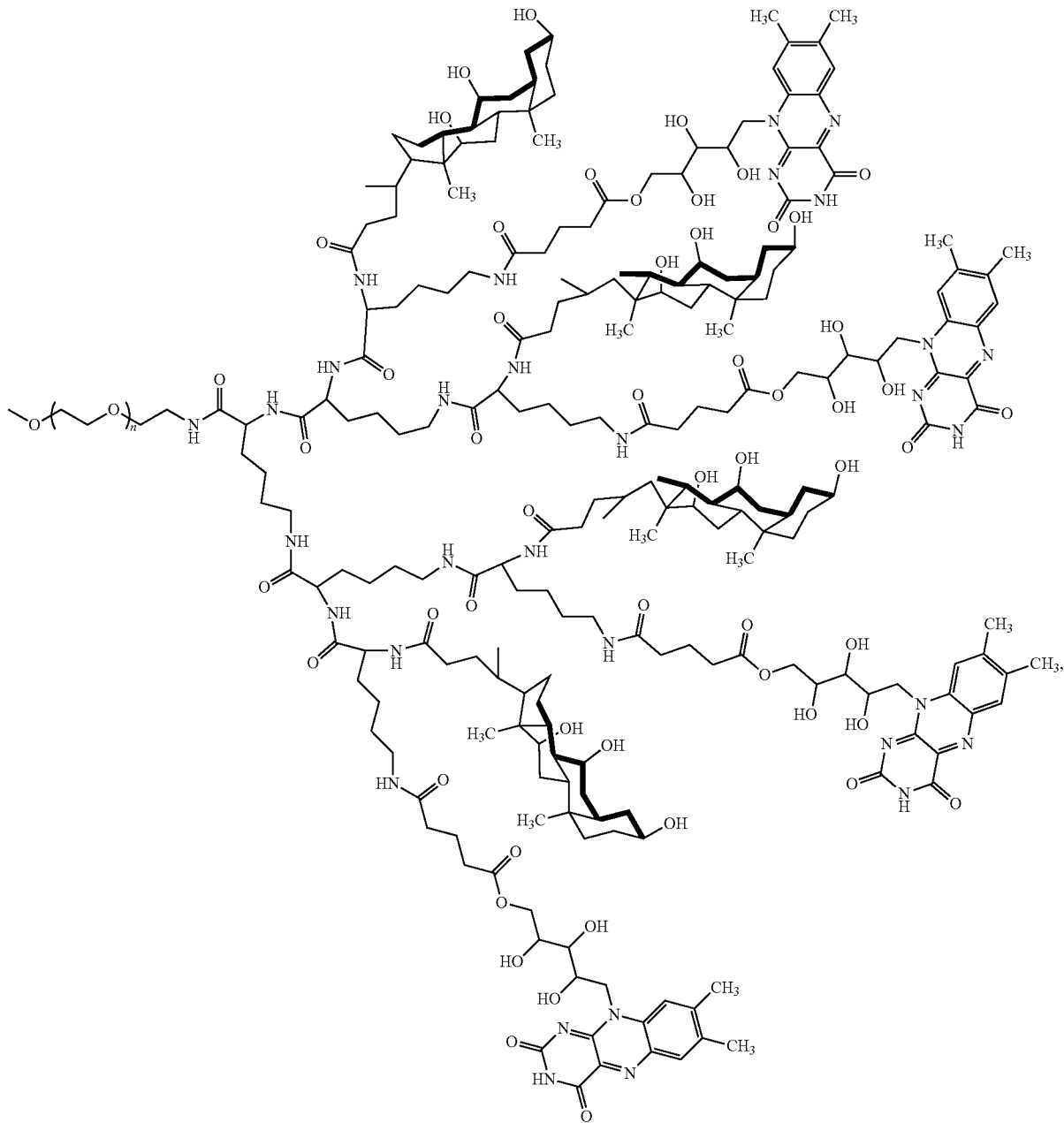

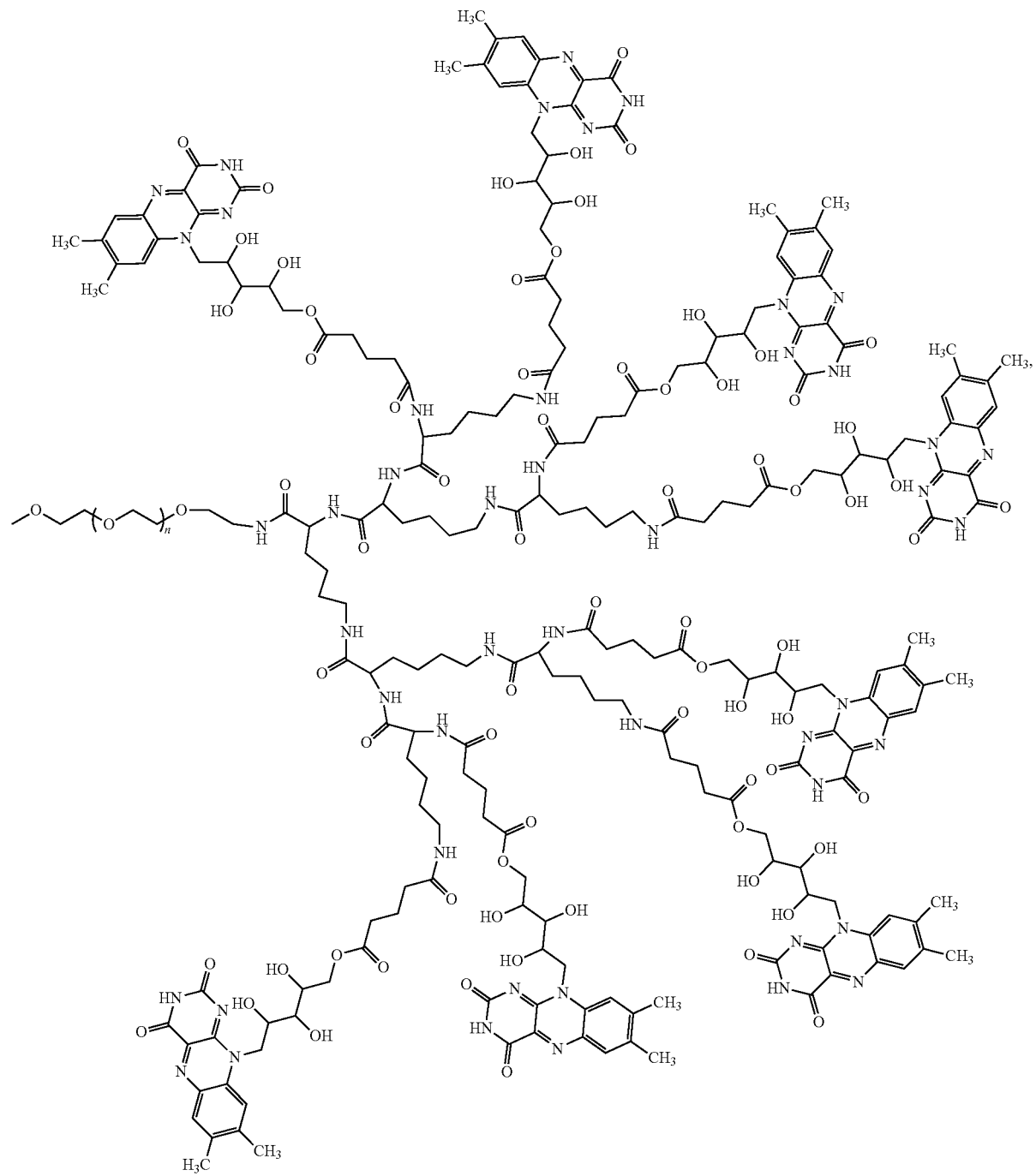

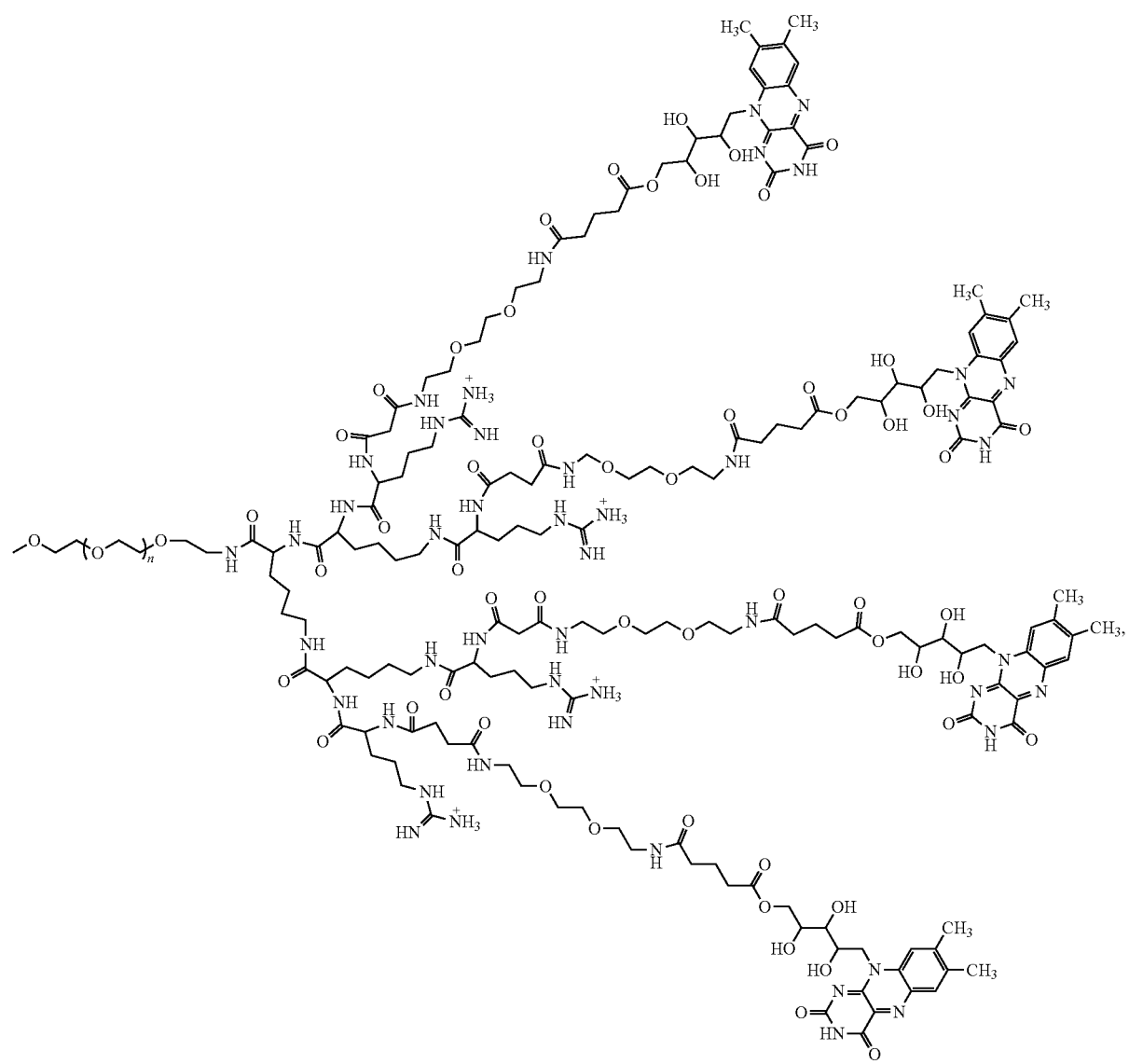

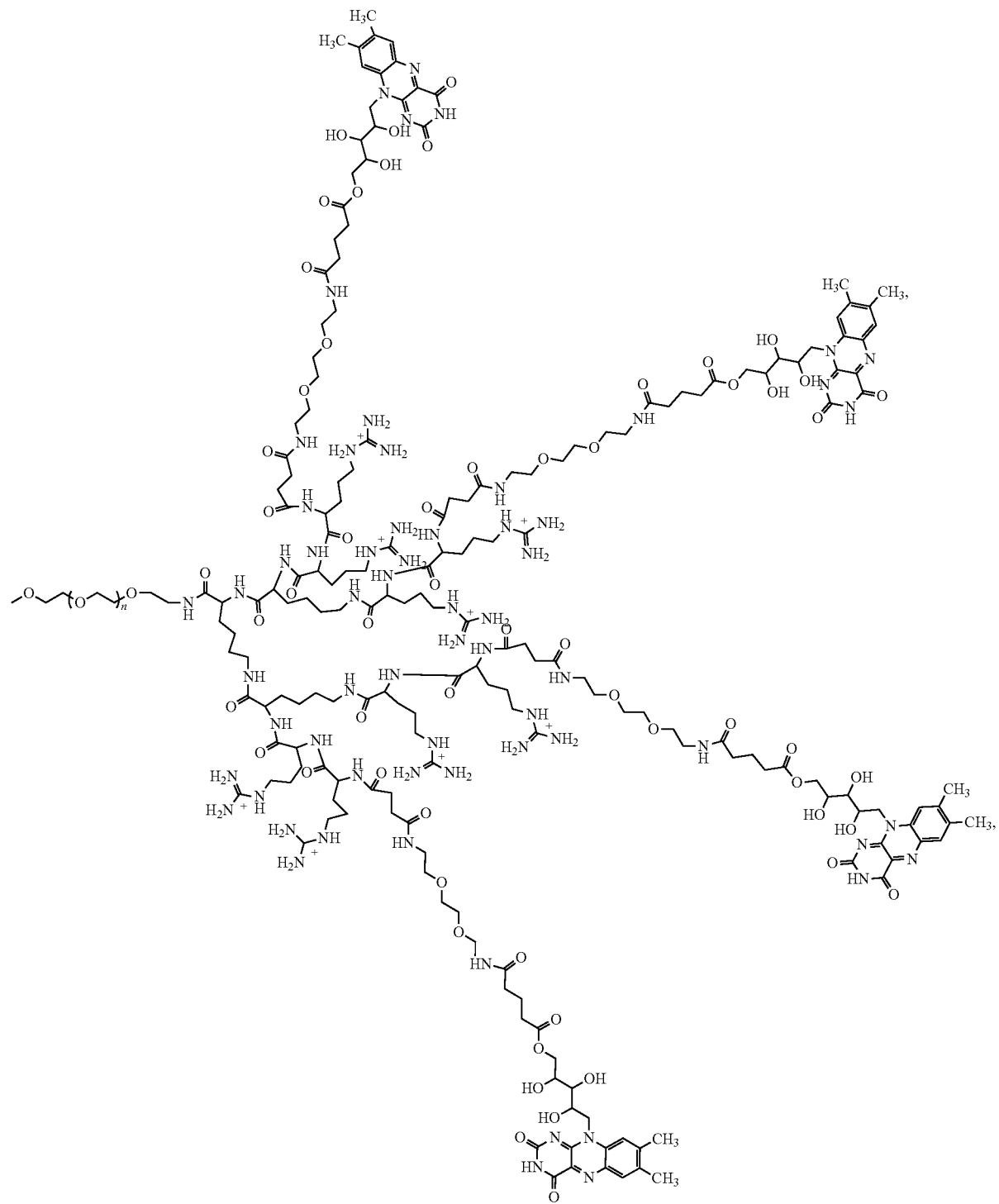

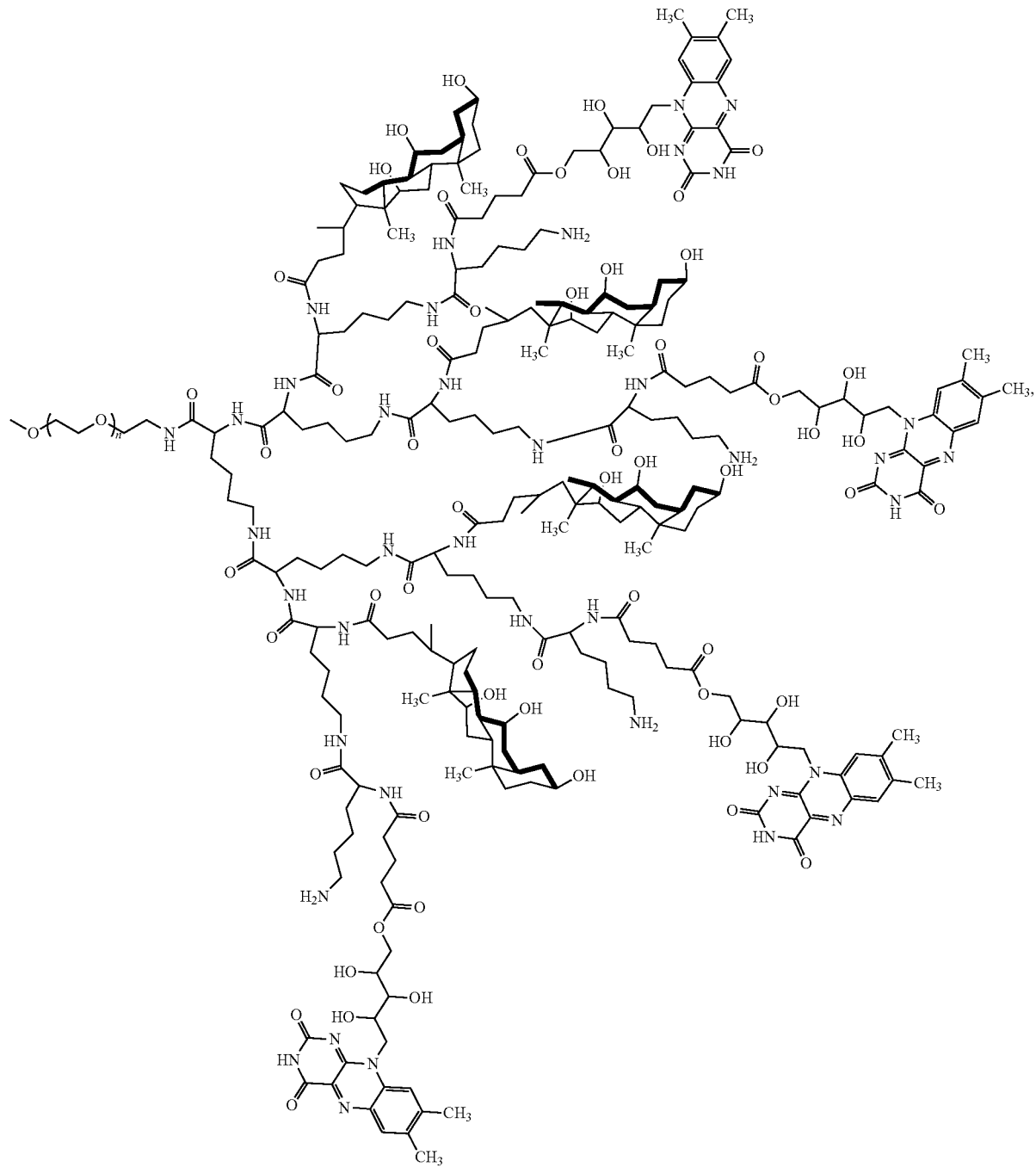

-continued
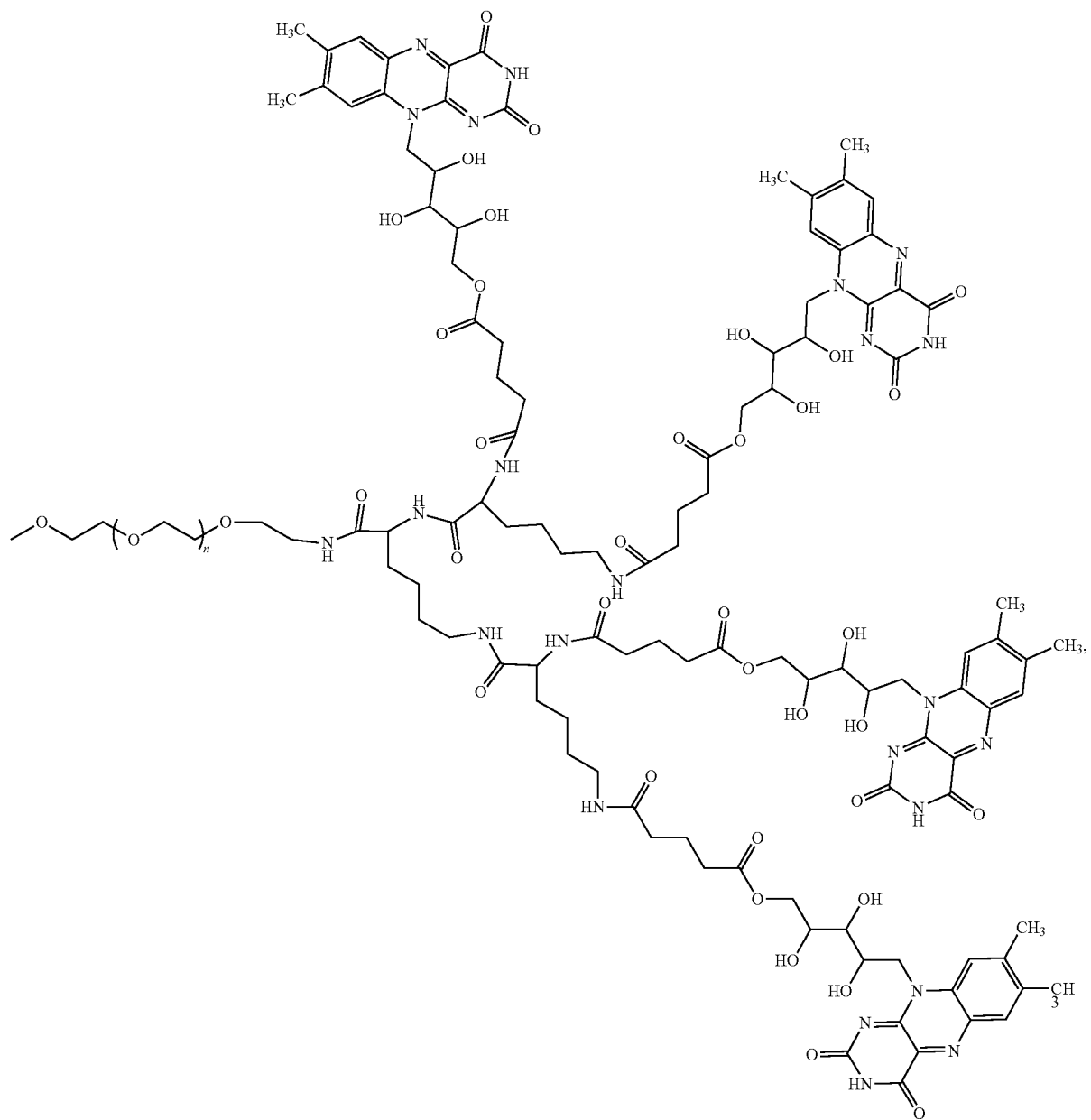

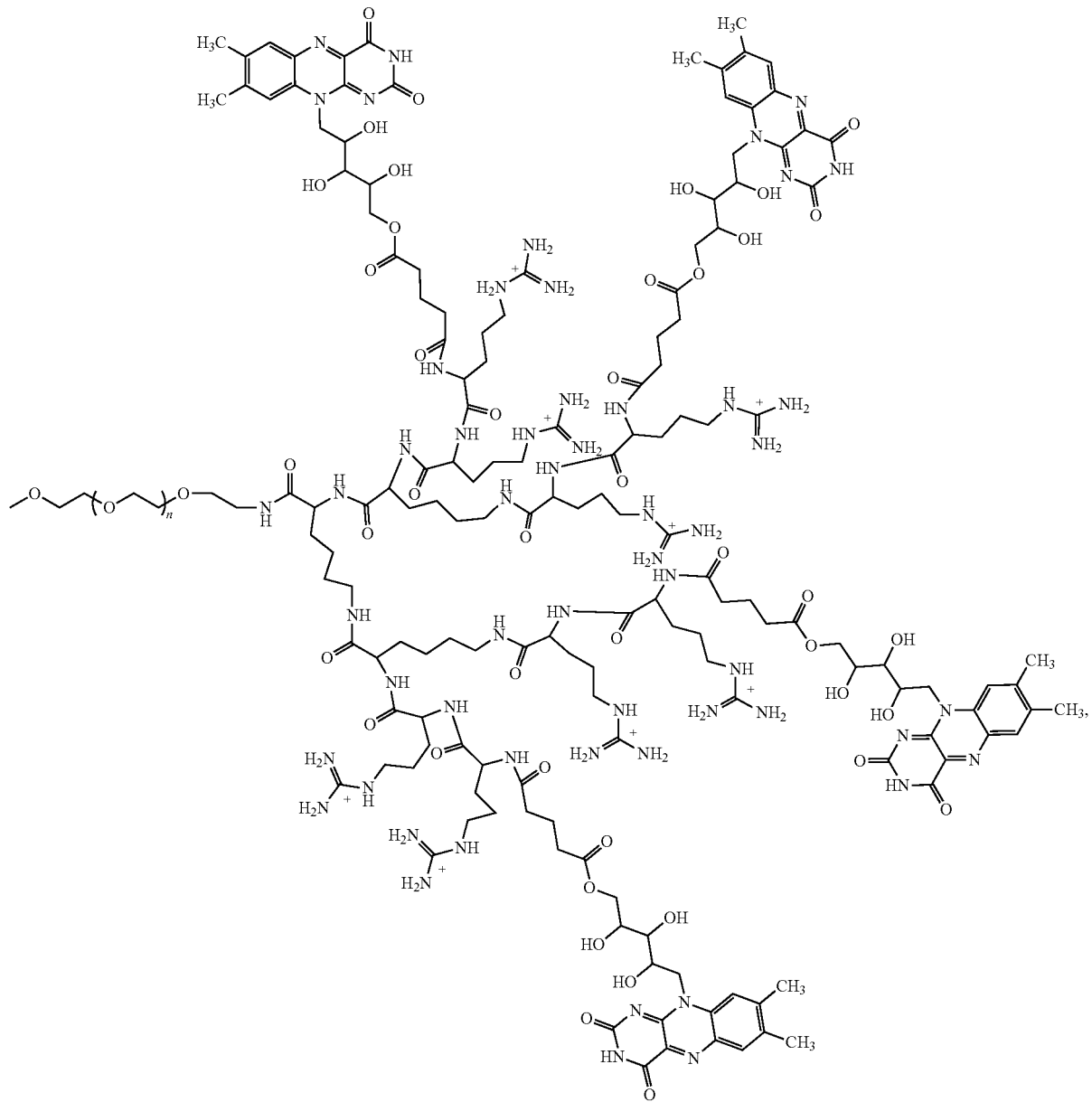

and
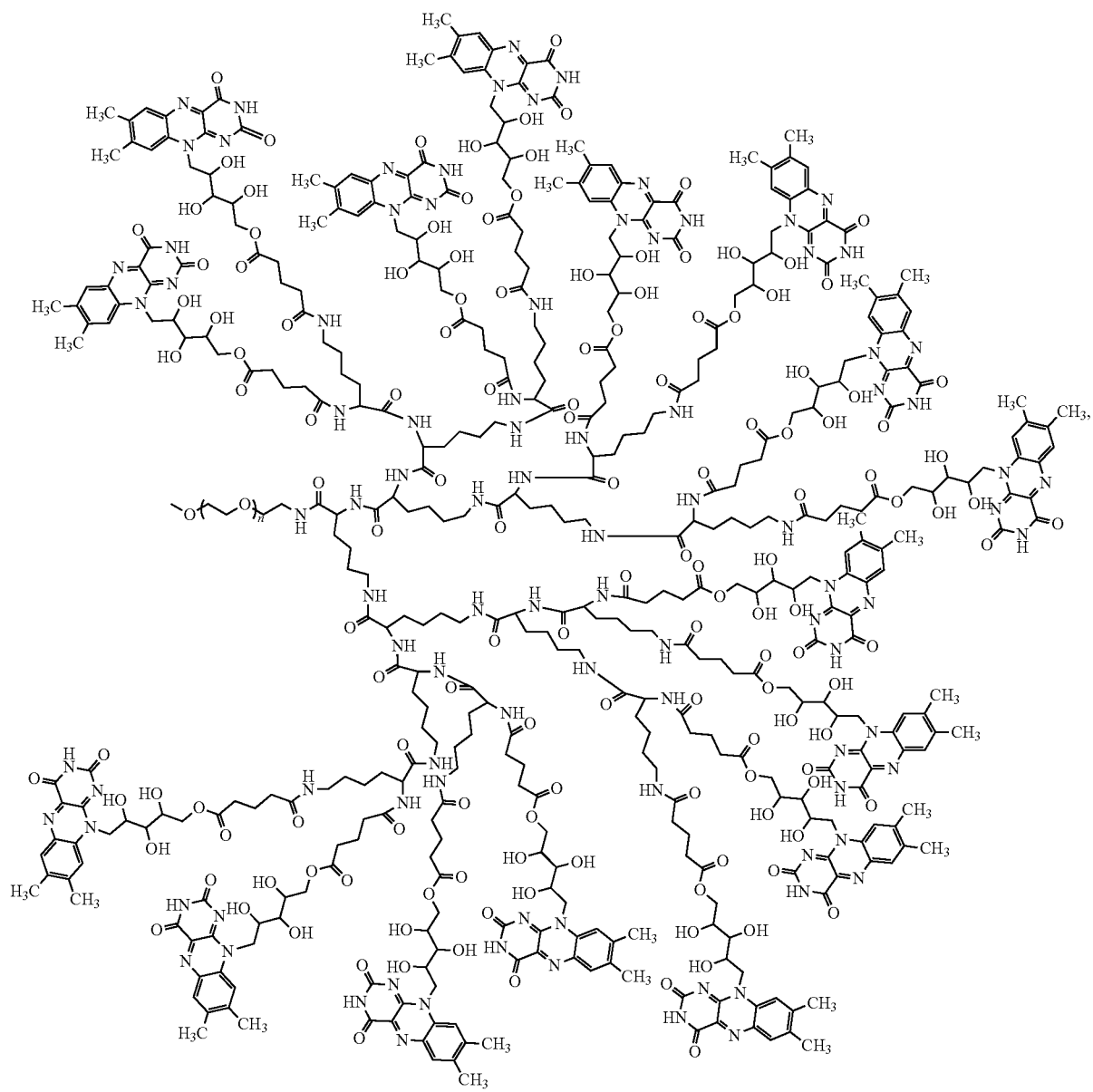
wherein n=10-500.

2. The compound of claim 1, wherein the compound is selected from the group consisting of
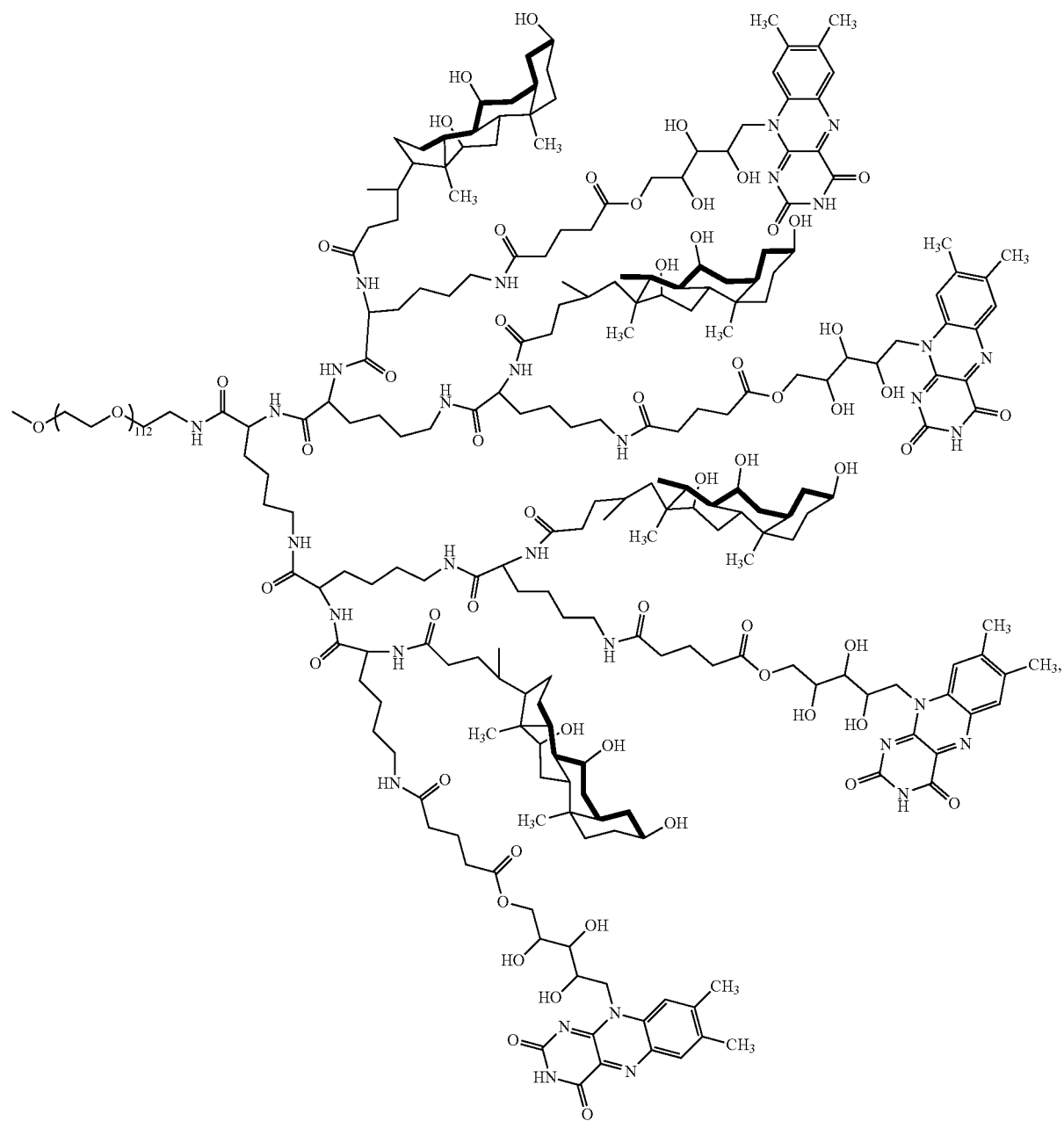

-continued
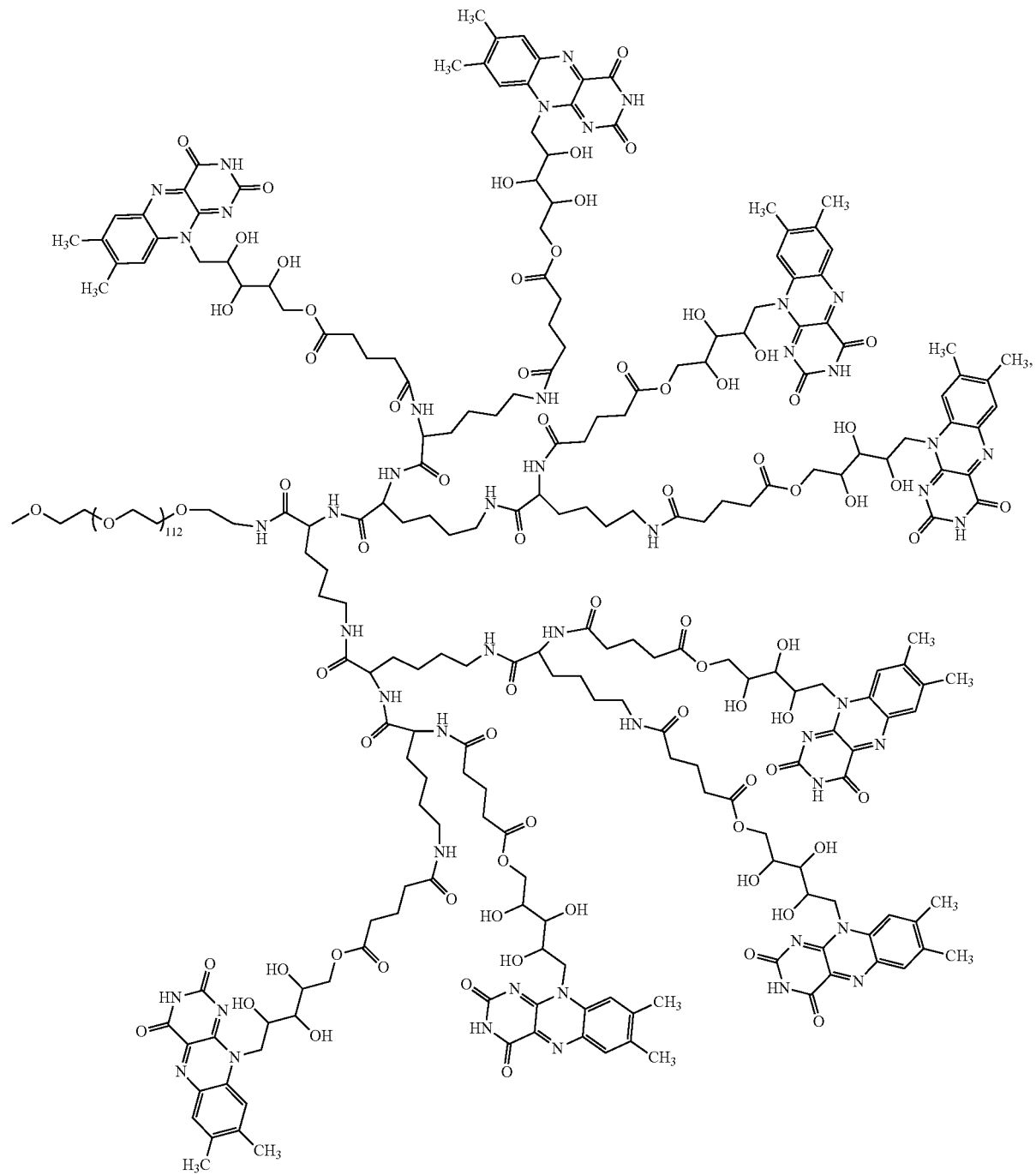

-continued
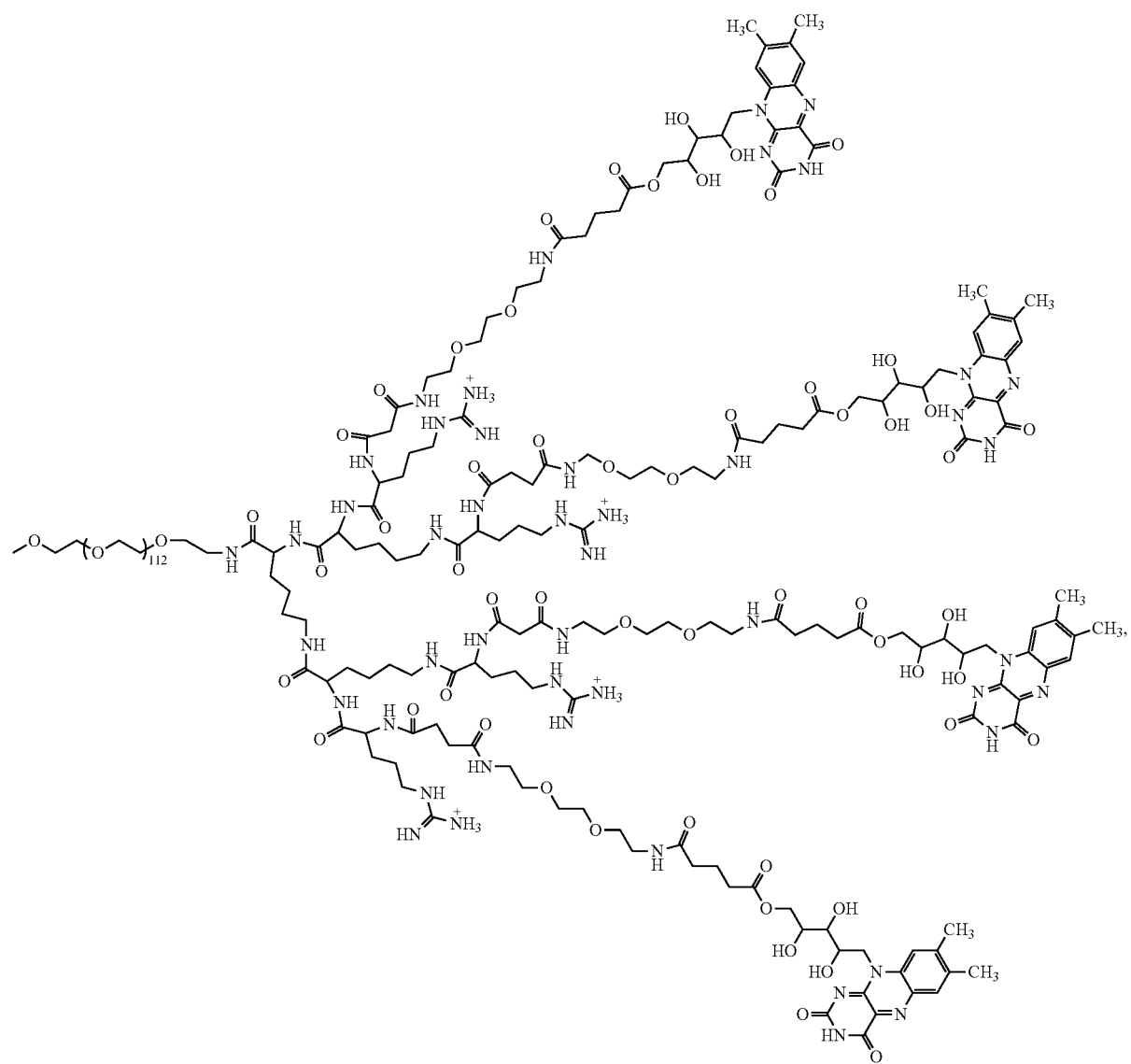

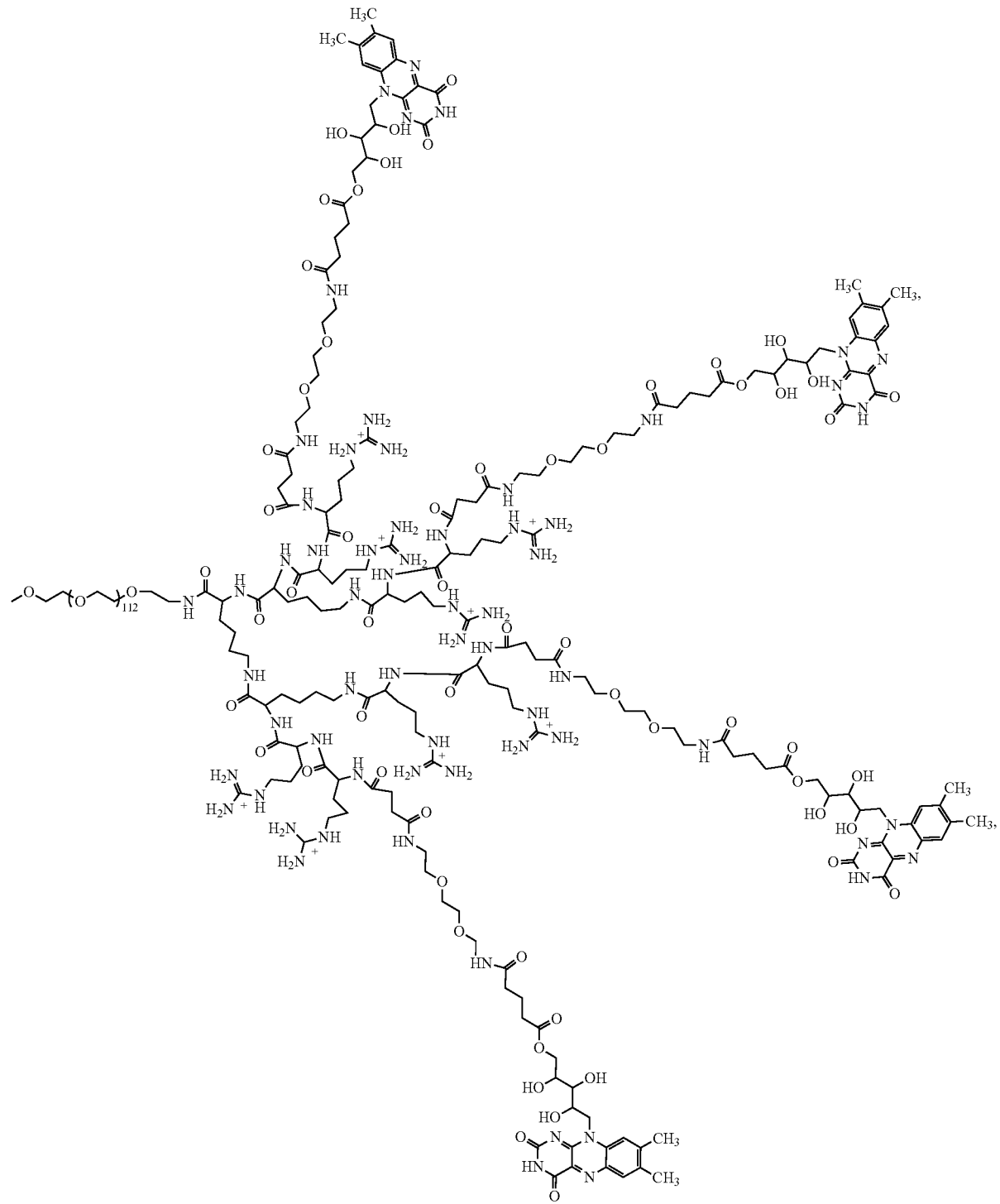

-continued
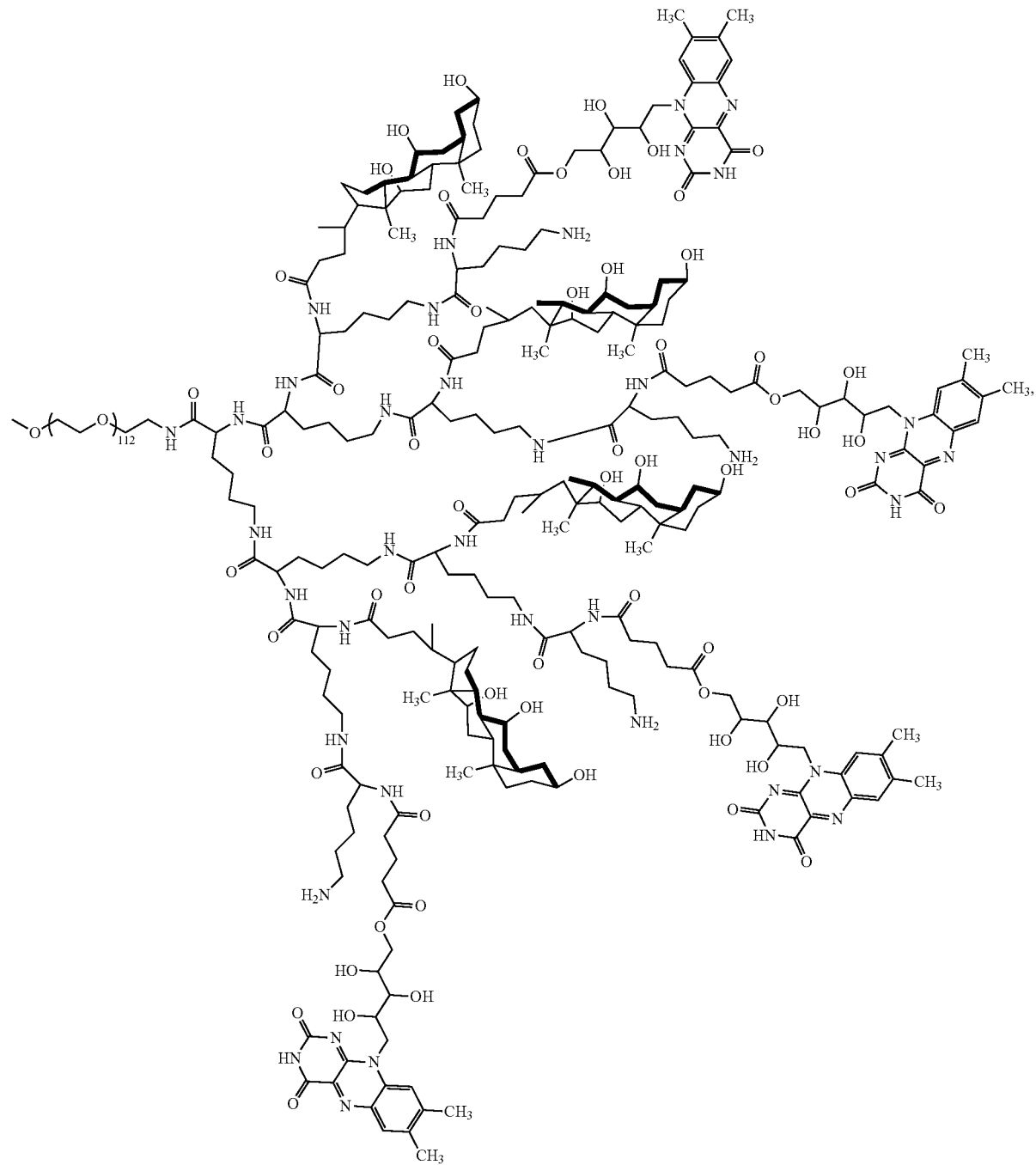

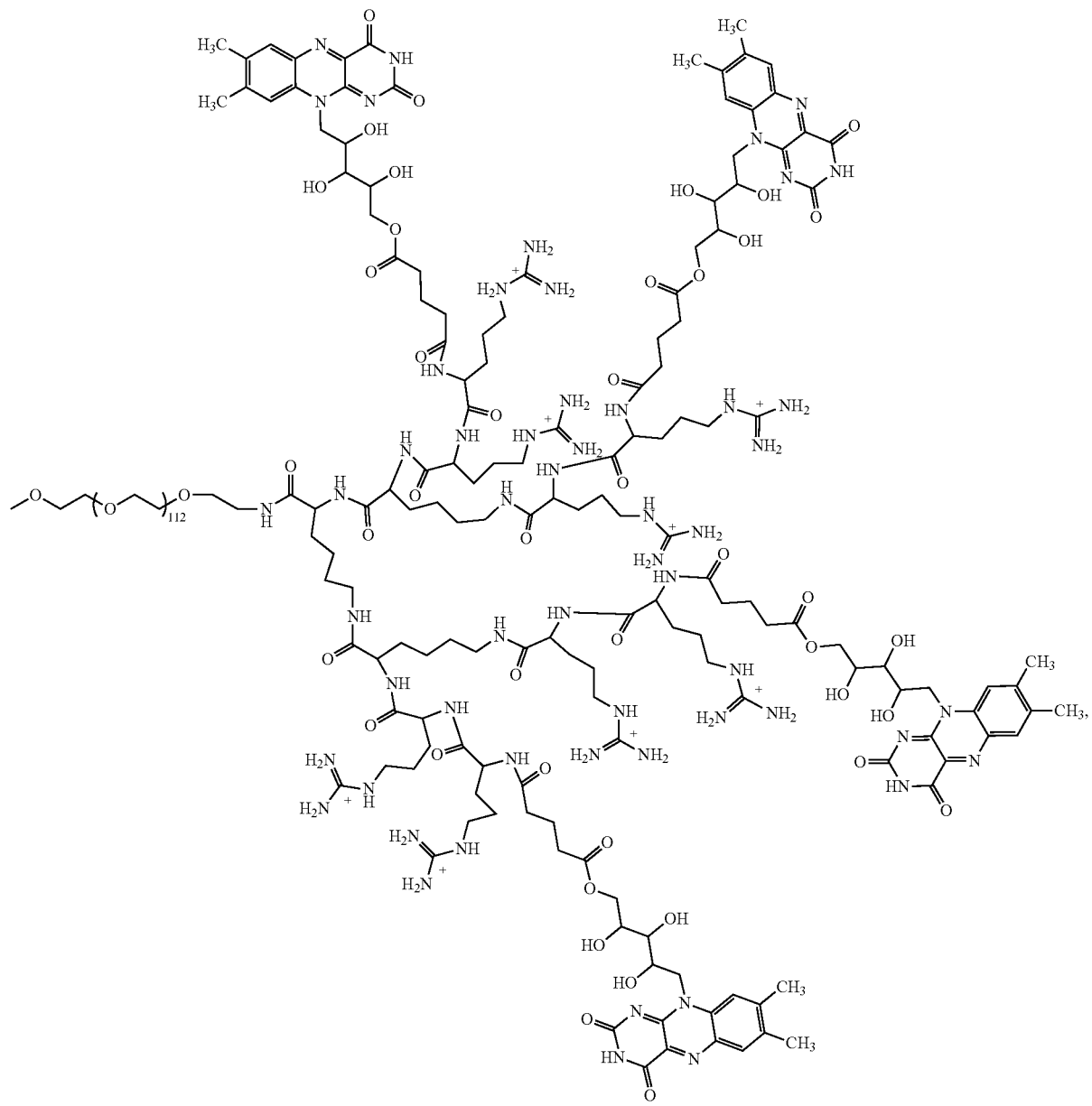

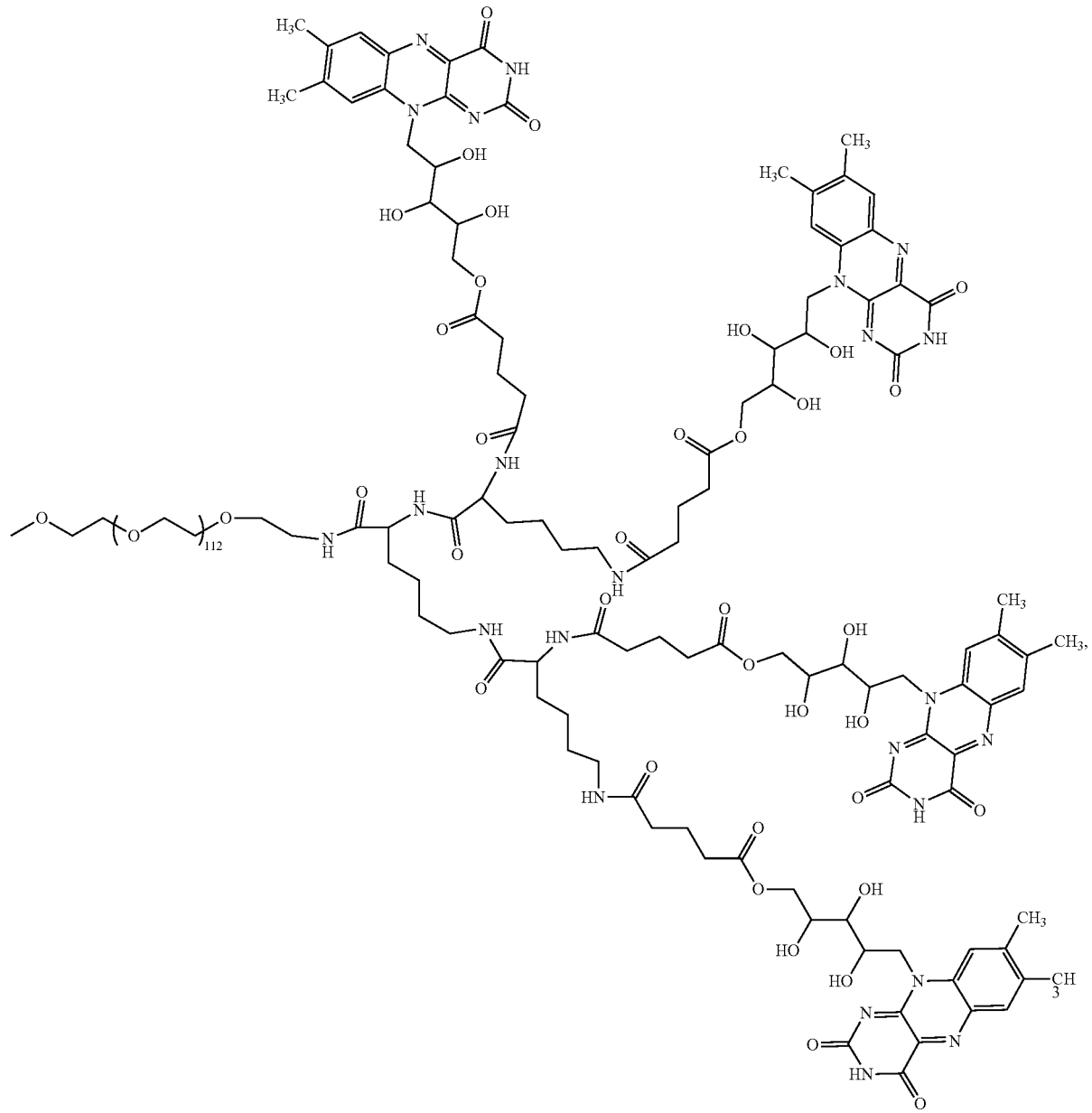

and
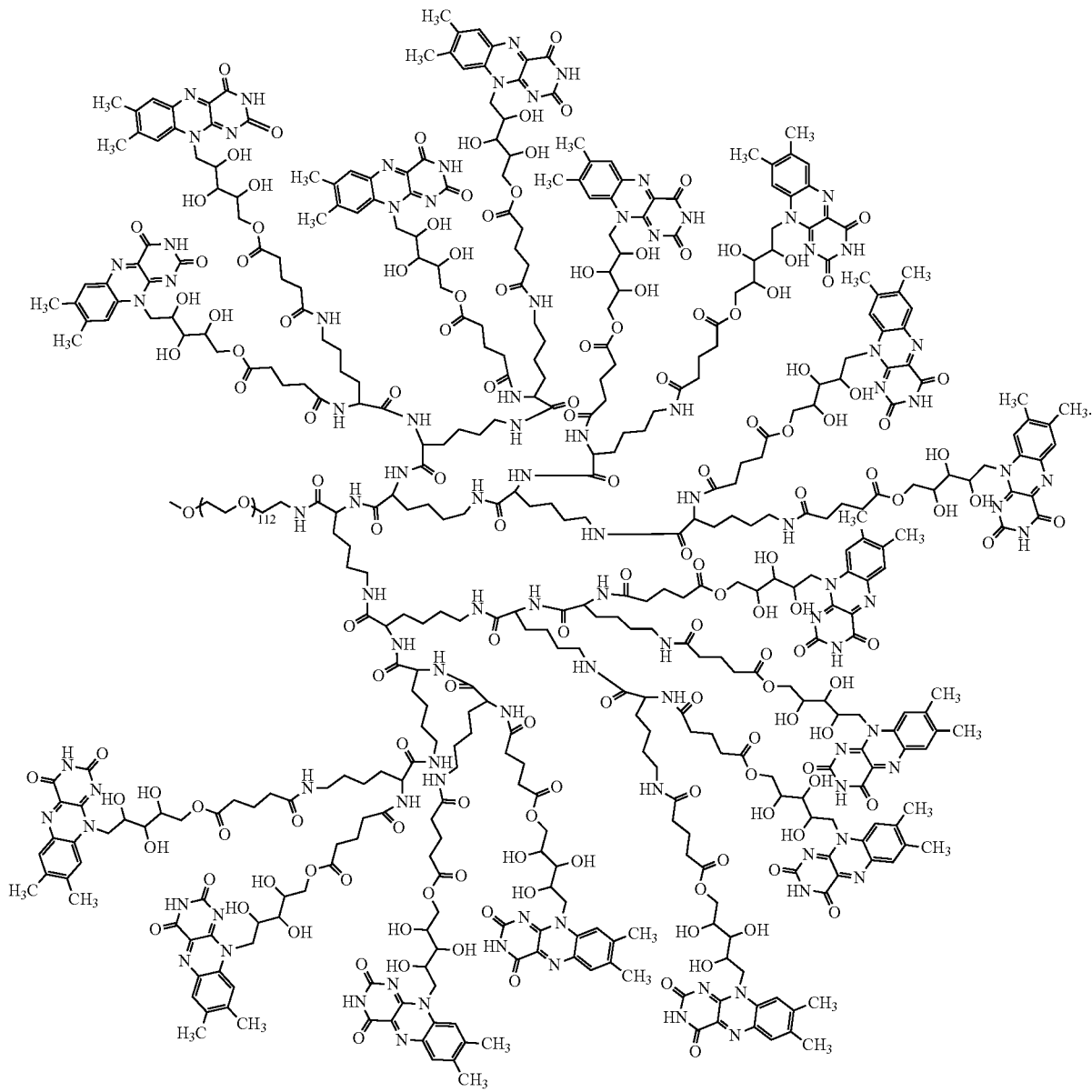
3. A composition comprising one or more compounds of claim 1 and a drug selected from the group consisting of methotrexate, anthracycline, and combinations thereof.
4. The composition of claim 3, wherein the anthracycline is selected from the group consisting of daunorubicin, doxorubicin, epirubicin, idarubicin, and combinations thereof.

5. The composition of claim 3, wherein the one or more compounds are present as a nanocarrier.

6. The composition of claim 3, wherein for each

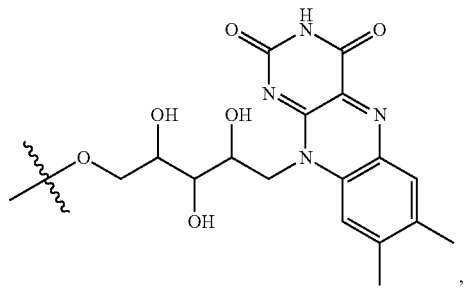 [SMILES: *OCC(O)C(O)C(O)Cn1c2nc(=O)[nH]c(=O)c-2nc2cc(C)c(C)cc21 ; ","]

there is one methotrexate or anthracycline present.

7. The composition of claim 3, wherein the composition has a nanocarrier:methotrexate/anthracycline mass ratio of 1:1 to 1:1.6.

8. A kit comprising:

i) at least one compound of claim 1 and a drug selected from the group consisting of methotrexate, anthracycline, and combinations thereof; and ii) a set of instructions, wherein the instructions describe how to use the compound or composition.

9. A compound, comprising: a structure selected from the group consisting of

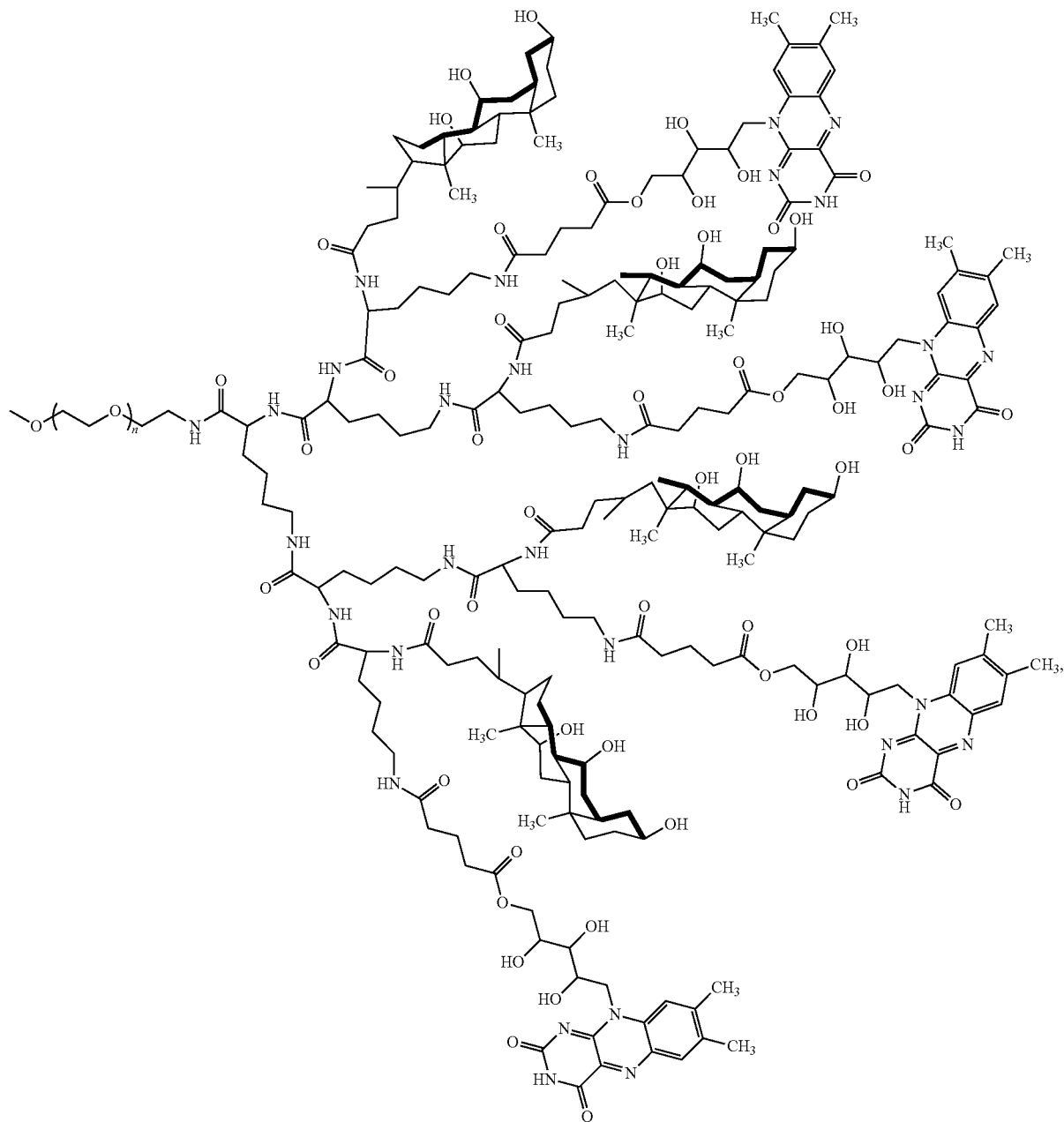

-continued
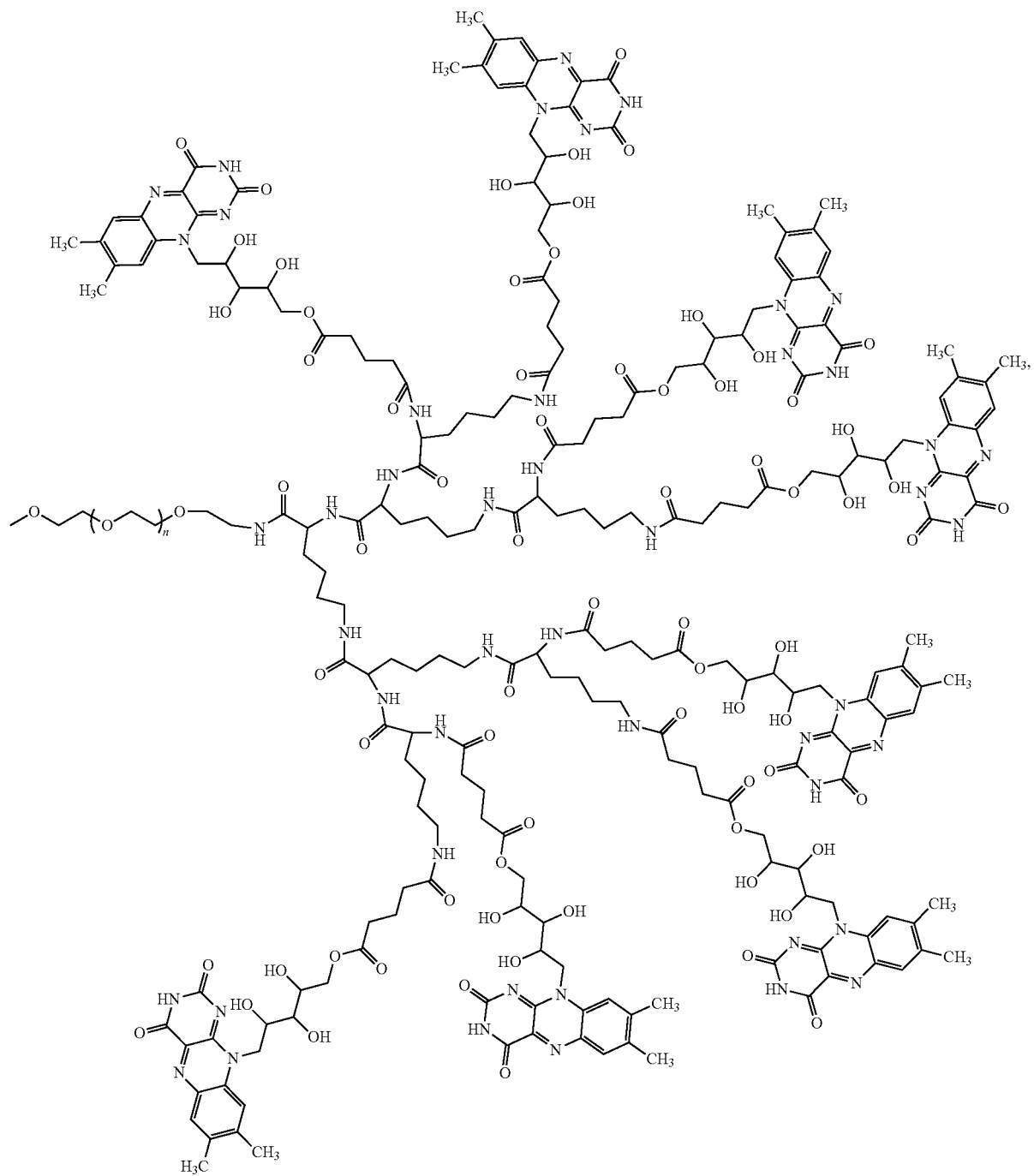

-continued
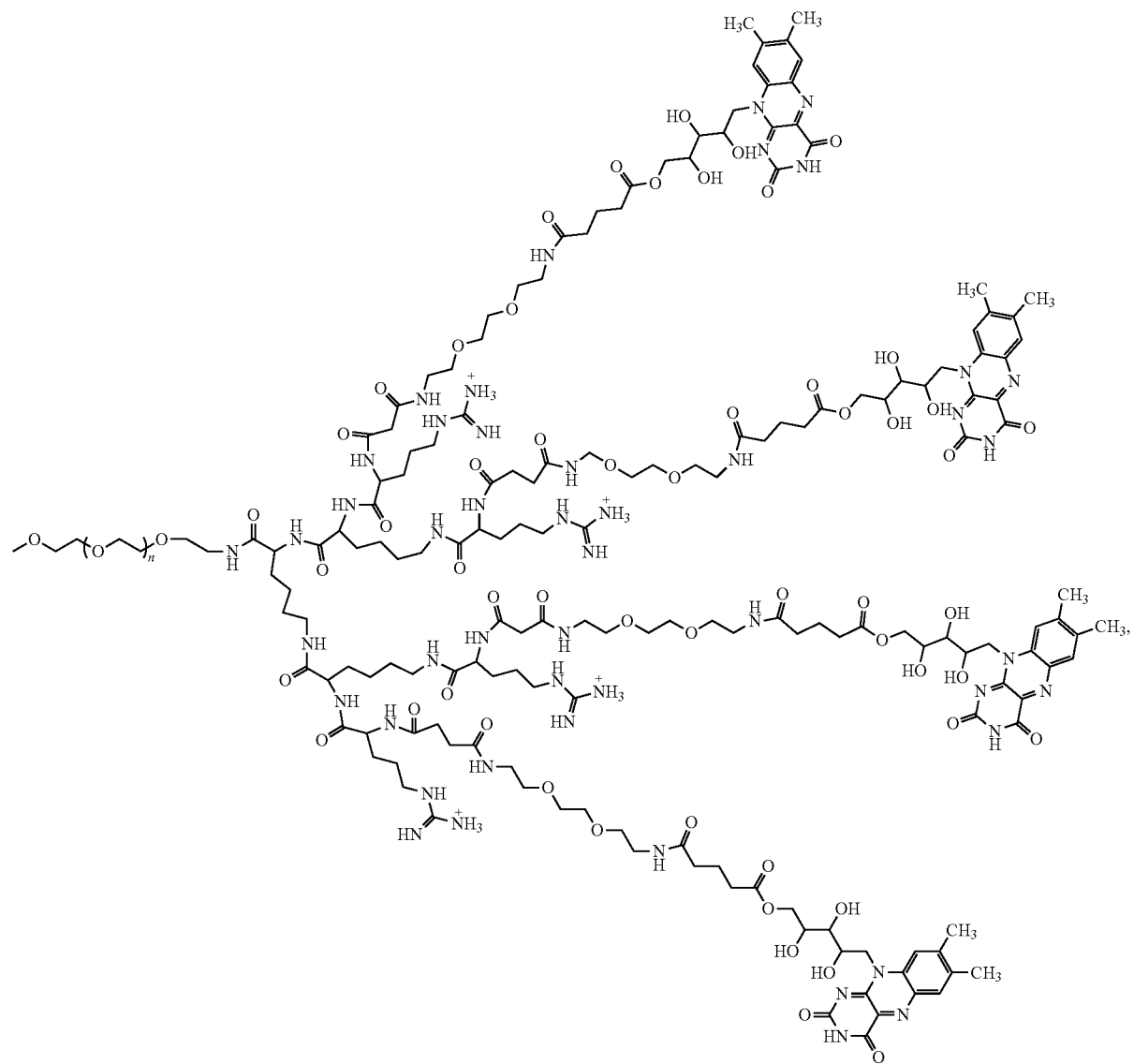

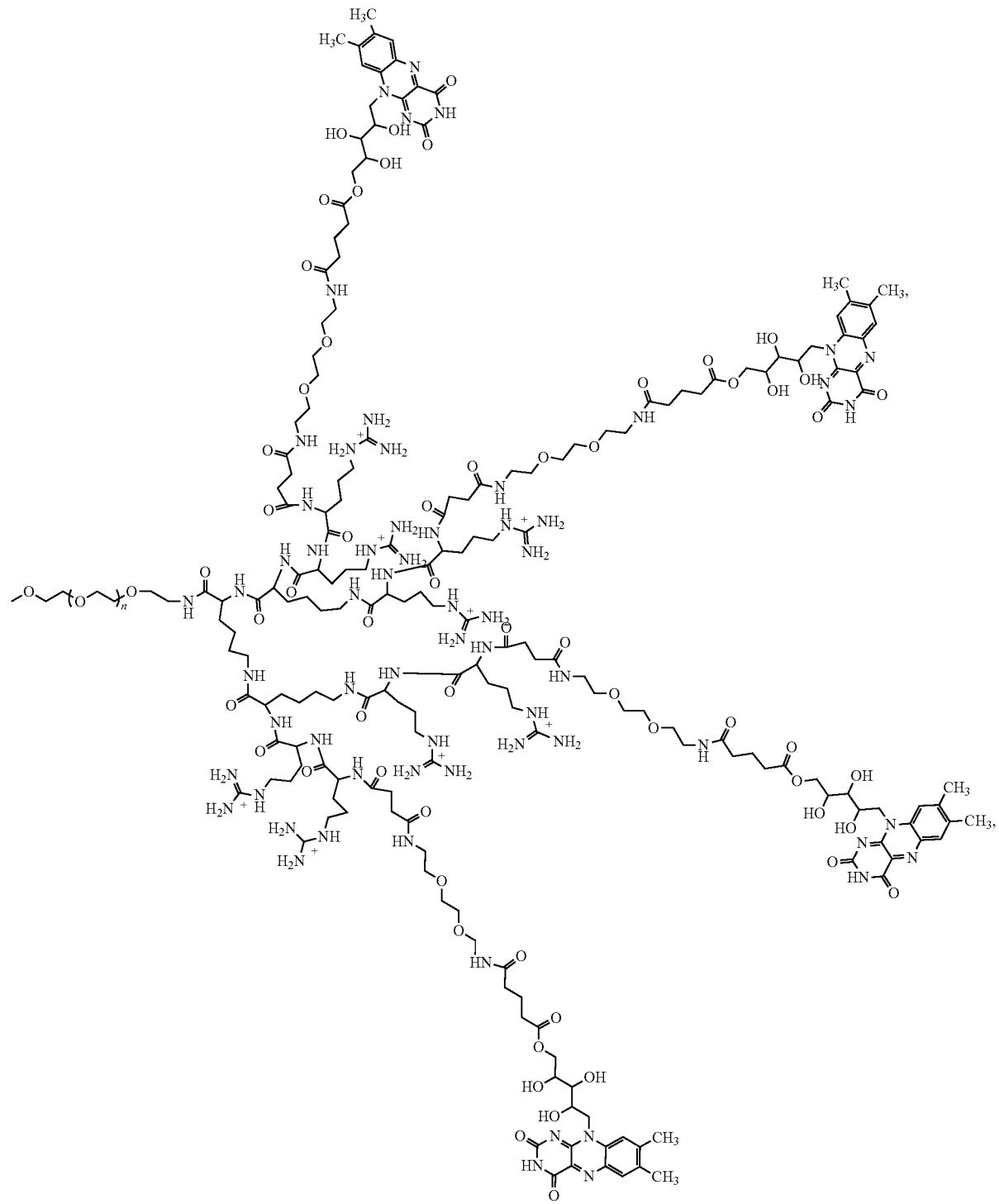

-continued
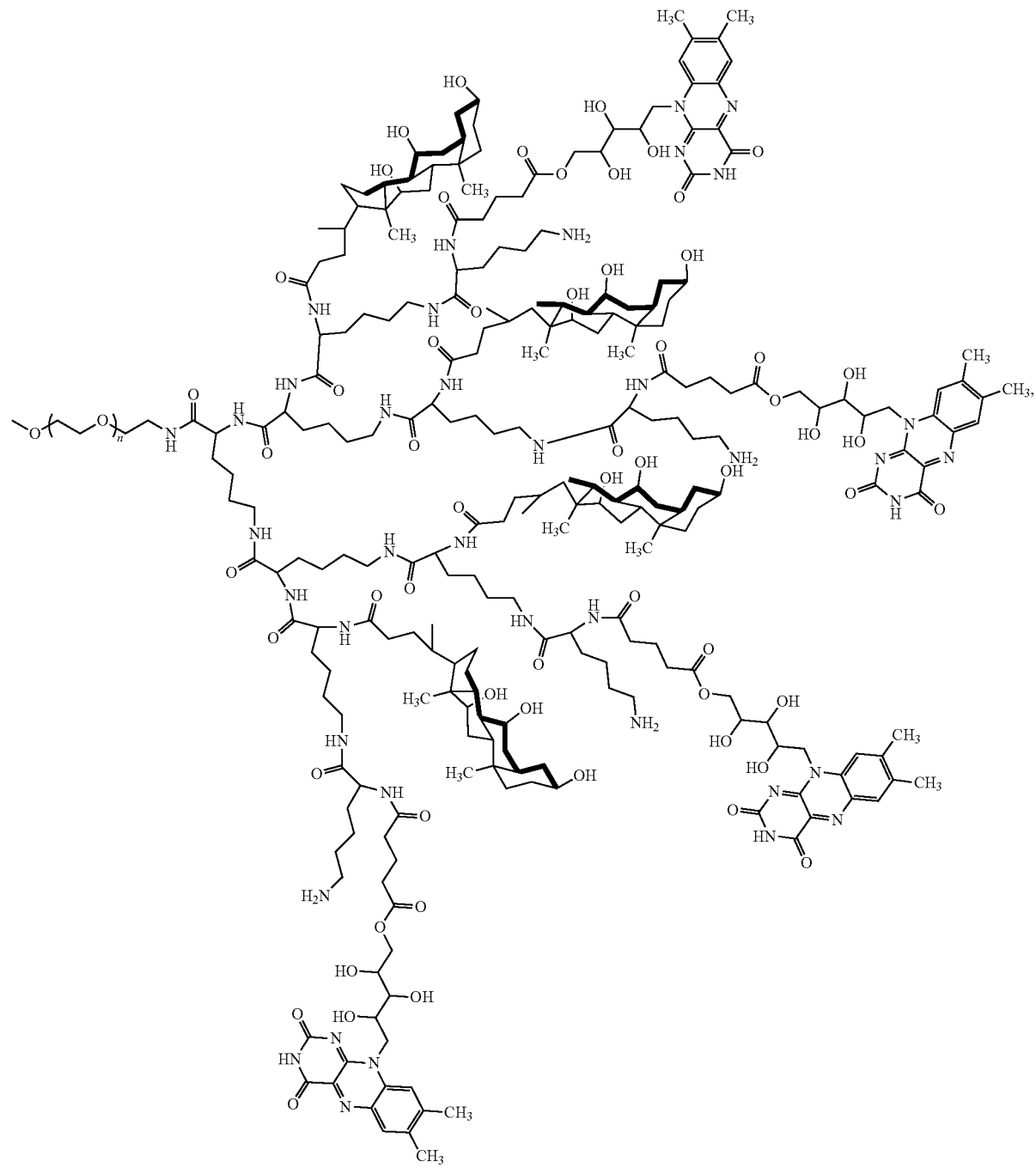

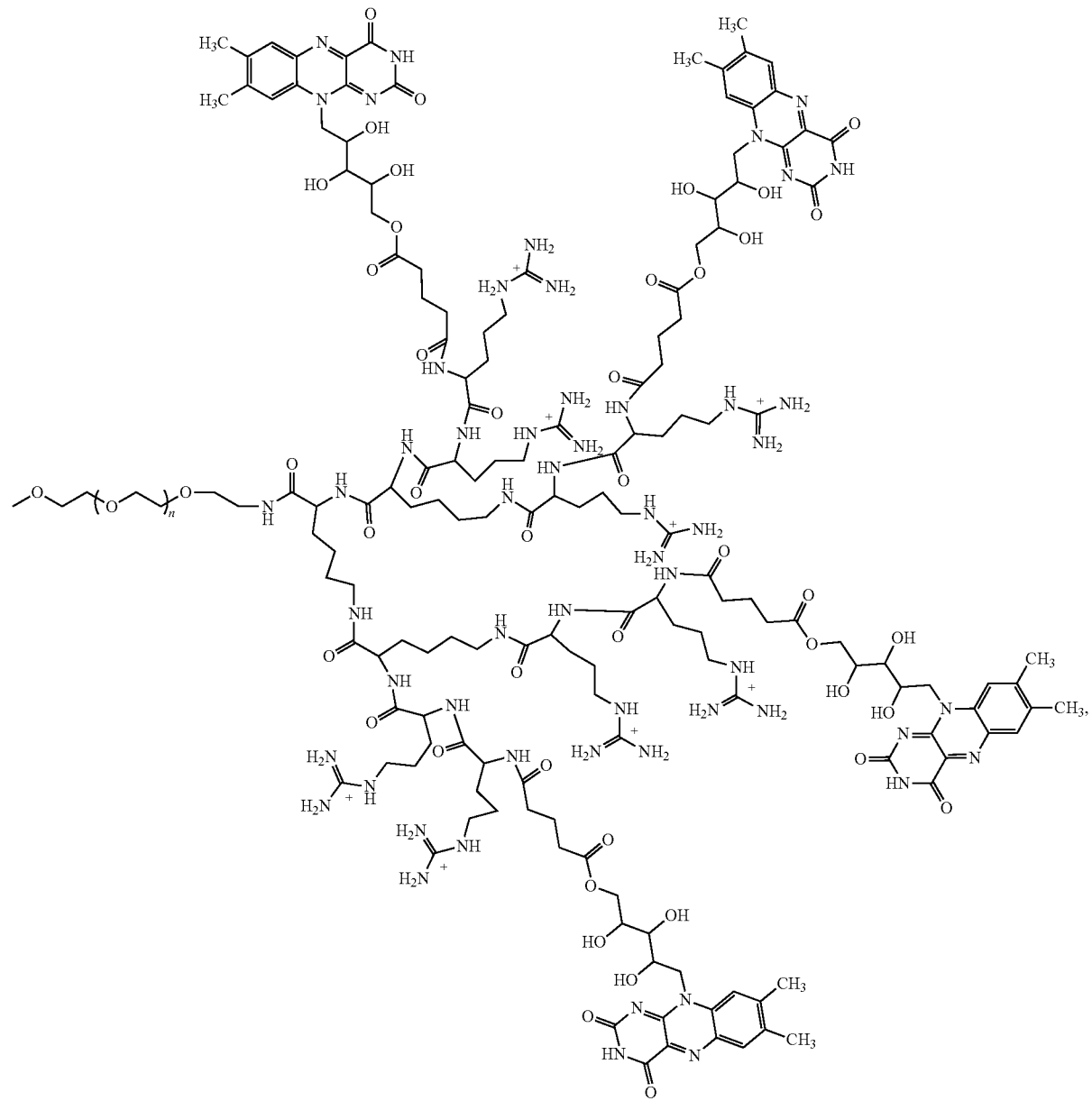

-continued
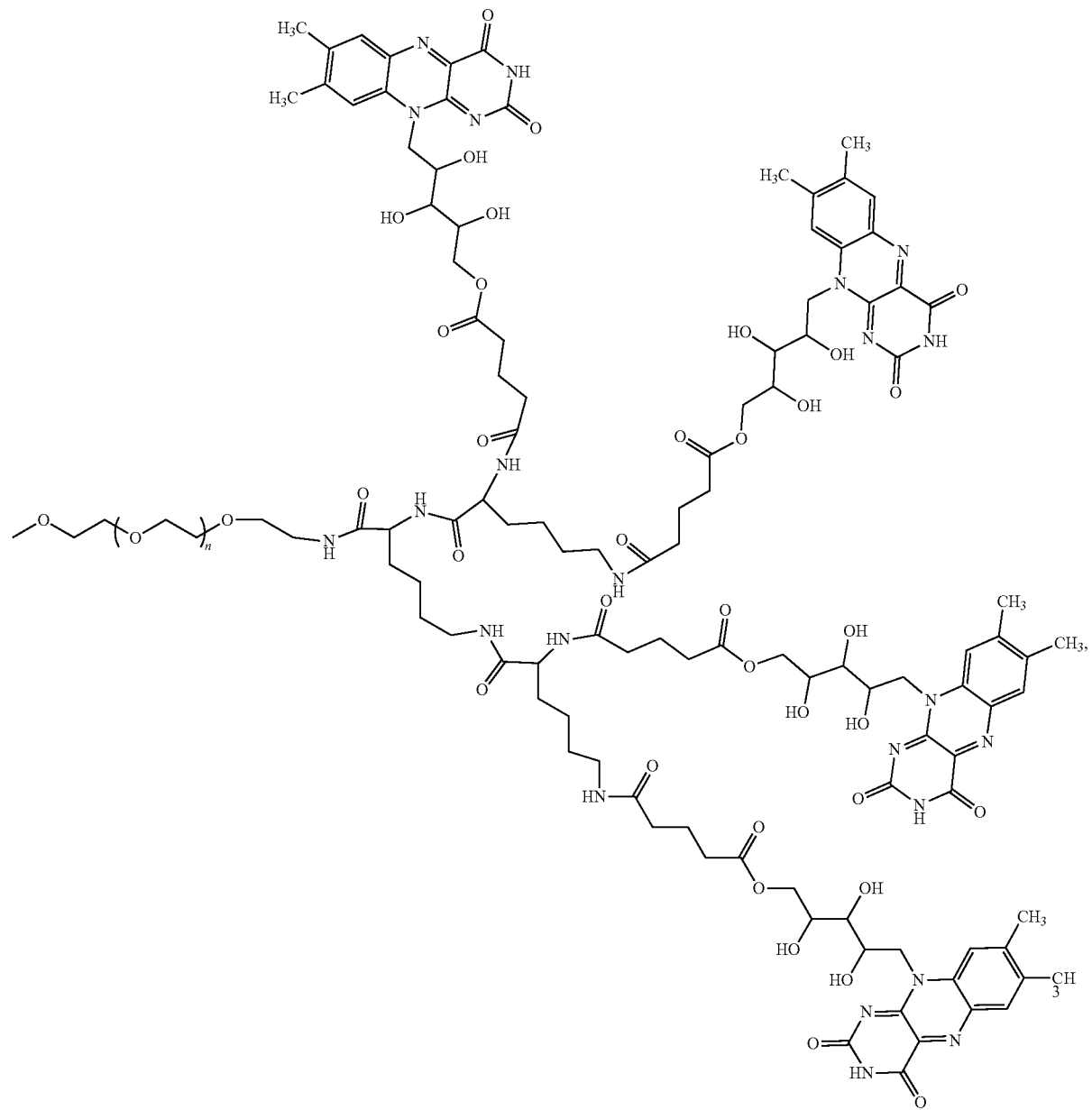

and

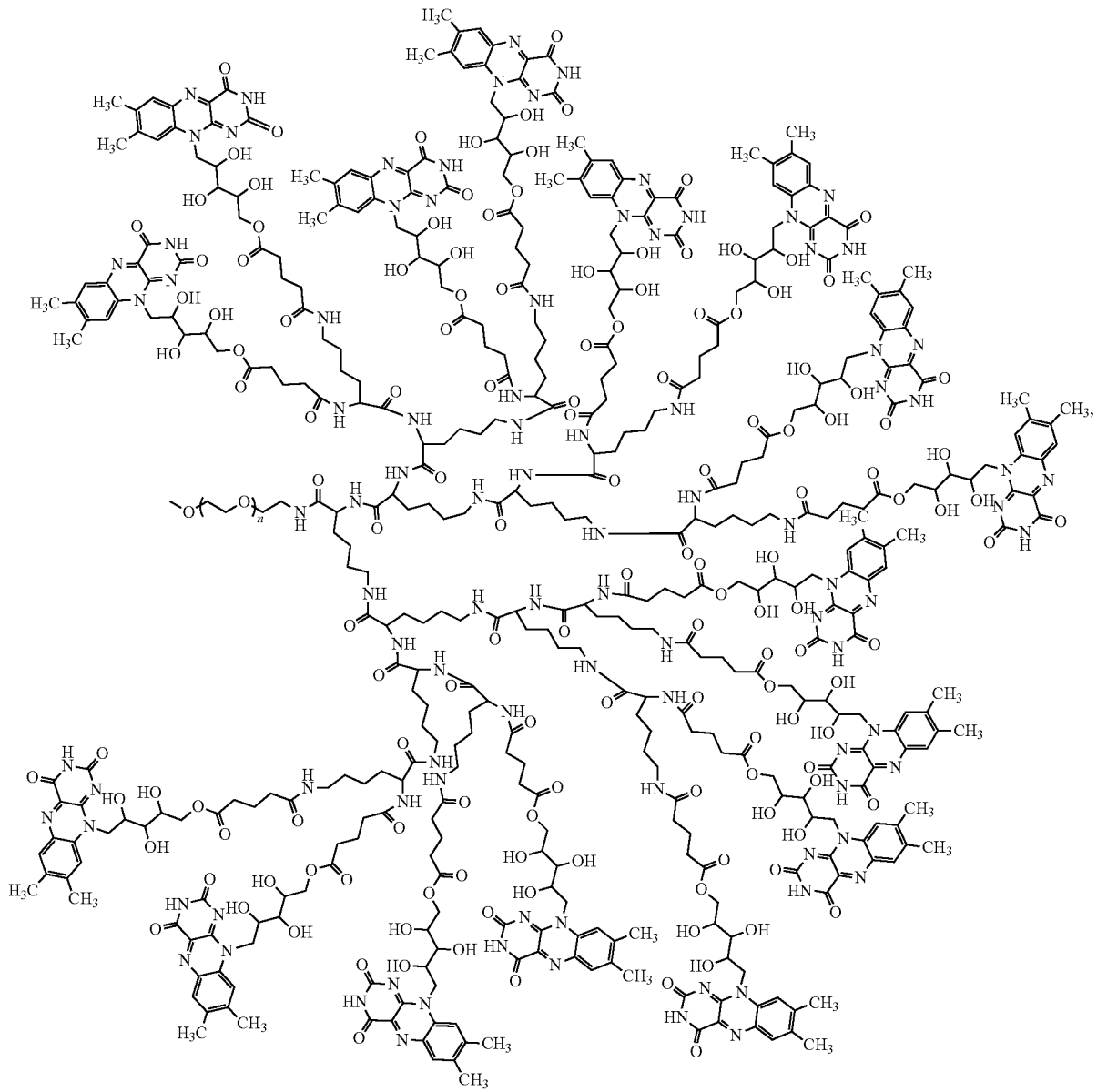

wherein n=1 to 72736.

10. The compound of claim 9, wherein the PEG group has the following structure:

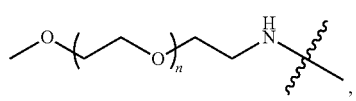

wherein n is 10-500.

11. A composition comprising one or more compounds of claim 9 and a drug selected from the group consisting of methotrexate, anthracycline, and combinations thereof.

12. The composition of claim 11, wherein the anthracycline is selected from the group consisting of daunorubicin, doxorubicin, epirubicin, idarubicin, and combinations thereof.

13. The composition of claim 11, wherein the one or more compounds are present as a nanocarrier.

14. The composition of claim 11, wherein for each
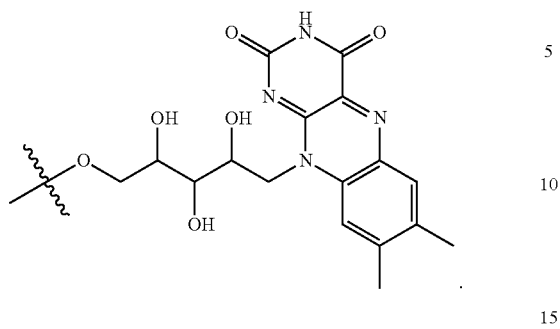
there is one methotrexate or anthracycline present.
15. The composition of claim 11, wherein the composition has a nanocarrier:methotrexate/anthracycline mass ratio of 1:1 to 1:1.6.
* * * * *